(12) United States Patent
Verheijden

(10) Patent No.: US 12,180,295 B2
(45) Date of Patent: Dec. 31, 2024

(54) HUMANIZED ANTI-SIRPα ANTIBODIES

(71) Applicant: BYONDIS B.V., Nijmegen (NL)

(72) Inventor: Gijsbertus Franciscus Maria Verheijden, Nijmegen (NL)

(73) Assignee: Byondis B.V., Nijmegen (NL)

( * ) Notice: Subject to any disclaimer, the term of this patent is extended or adjusted under 35 U.S.C. 154(b) by 833 days.

(21) Appl. No.: 17/292,182

(22) PCT Filed: Nov. 15, 2019

(86) PCT No.: PCT/EP2019/081523
§ 371 (c)(1),
(2) Date: May 7, 2021

(87) PCT Pub. No.: WO2020/099653
PCT Pub. Date: May 22, 2020

(65) Prior Publication Data
US 2021/0388107 A1 Dec. 16, 2021

(30) Foreign Application Priority Data
Nov. 15, 2018 (EP) .................................. 18206594

(51) Int. Cl.
C07K 16/28 (2006.01)
A61K 39/395 (2006.01)
A61K 45/06 (2006.01)
A61P 35/00 (2006.01)
C12N 5/10 (2006.01)
C12N 15/13 (2006.01)

(52) U.S. Cl.
CPC .......... C07K 16/2896 (2013.01); A61K 45/06 (2013.01); A61K 39/395 (2013.01); A61P 35/00 (2018.01); C07K 2317/24 (2013.01); C07K 2317/72 (2013.01); C07K 2317/732 (2013.01); C07K 2317/76 (2013.01); C07K 2317/92 (2013.01); C12N 5/10 (2013.01)

(58) Field of Classification Search
CPC .......... C07K 2317/24; C07K 2317/565; C07K 2317/72; C07K 2317/732; C07K 2317/76; C07K 2317/92; C07K 16/2803; A61K 2039/505; A61K 39/395
See application file for complete search history.

(56) References Cited

U.S. PATENT DOCUMENTS

| | | |
|---|---|---|
| 4,522,811 A | 6/1985 | Eppstein et al. |
| 4,816,567 A | 3/1989 | Cabilly et al. |
| 5,500,362 A | 3/1996 | Robinson et al. |
| 5,821,337 A | 10/1998 | Carter et al. |
| 11,274,159 B2 | 3/2022 | Verheijden et al. |
| 2003/0054415 A1 | 3/2003 | Buhring et al. |
| 2015/0166654 A1 | 6/2015 | Igawa et al. |
| 2016/0340397 A1 | 11/2016 | Ring et al. |

FOREIGN PATENT DOCUMENTS

| | | | |
|---|---|---|---|
| EP | 2474557 B1 | 7/2012 | |
| WO | WO01/40307 | 6/2001 | |
| WO | WO 2006/019447 A1 | 2/2006 | |
| WO | WO2009/131453 | 10/2009 | |
| WO | WO2010/095940 | 8/2010 | |
| WO | WO 2012/098407 A1 | 7/2012 | |
| WO | WO2013/056352 | 4/2013 | |
| WO | WO 2013/150043 | 10/2013 | |
| WO | WO 2014/127906 | 8/2014 | |
| WO | WO2015/138600 | 9/2015 | |
| WO | WO 2017/068164 | 4/2017 | |
| WO | WO2017/178653 | 10/2017 | |
| WO | WO2018/026600 | 2/2018 | |
| WO | WO2018/057669 | 3/2018 | |
| WO | WO2018/107058 | 6/2018 | |
| WO | WO2018/190719 | 10/2018 | |
| WO | WO2018/210793 | 11/2018 | |
| WO | WO 2018/210795 | 11/2018 | |
| WO | WO-2018210793 A2 * | 11/2018 | ......... A61K 39/3955 |
| WO | WO2019/023347 | 1/2019 | |

OTHER PUBLICATIONS

Maute et al., Immunooncol Technol, 2022, 13: 100070, pp. 1-13.*
Xie et al., Cell Reports Medicine, 2023, 4: 101130, pp. 1-18.*
Feng et al., Eur. J. Immunol. 2023;53:2350375, pp. 1-13.*
DiLillo and Ravetch "Differential Fc-Receptor Engagement Drives and Anti-tumor Vaccinal Effect," *Cell*, May 21, 2015, 161(5), pp. 1035-1045.
Bournazos and Ravetch, "Fcγ Receptor Function and the Design of Vaccination Strategies," *Immunity*, Aug. 15, 2017, 47(2), pp. 224-233.
Richards et al. "Optimization of antibody binding to FcγRIIa enhances macrophage phagocytosis of tumor cells," *Mol. Cancer Ther.* 2008, 7(8), pp. 2517-2527.
Hayes et al., "Fc gamma receptors: glycobiology and therapeutic prospects," *J. Inflamm. Res.* vol. 9, Nov. 16, 2016, pp. 209-219.
Tseng et al., "Anti-CD47 antibody-mediated phagocytosis of cancer by macrophages primes an effective antitumor T-cell response." *Proceedings of the National Academy of Sciences of the United States of America* vol. 110, No. 27, May 20, 2013, pp. 11103-11108.
Liu et al., "CD47 blockade triggers T cell-mediated destruction of immunogenic tumors," *Nature Med.* Oct. 2015, 21(10), 1209-1215.
Kipp Weiskopf, "Cancer immunotherapy targeting the CD47/SIRPα axis," *Eur. J. Cancer*, May 29, 2017, vol. 76, pp. 100-109.
Advani et al. "CD47 Blockade by Hu5F9-G4 and Rituximab in Non-Hodgkin's Lymphoma," *N. Engl. J. Med.* Nov. 1, 2018, 379(18), pp. 1711-1721.
Zhao et al. "CD47-signal regulatory protein-α (SIRPα) interactions form a barrier for antibody-mediated tumor cell destruction," *PNAS*, Nov. 8, 2011, 108(45), pp. 18342-18347.

(Continued)

Primary Examiner — Hong Sang
(74) Attorney, Agent, or Firm — Buscher Patent PLLC

(57) ABSTRACT

The present invention relates to humanized antibodies against SIRPα that are suitable for use in anti-cancer therapy. The invention further relates to the use of the humanized anti-SIRPα antibodies in the treatment of human solid tumours and haematological malignancies, optionally in combination with further anti-cancer therapeutics.

22 Claims, 21 Drawing Sheets
Specification includes a Sequence Listing.

(56) References Cited

OTHER PUBLICATIONS

Treffers et al. "Genetic variation of human neutrophil Fcγ receptors and SIRPα in antibody-dependent cellular cytotoxicity towards cancer cells," *Eur. J. Immunol.* Feb. 2018, 48(2), pp. 344-354.

Takenaka et al. "Polymorphism in *Sirpa* modulates engraftment of human hematopoietic stem cells," *Nature Immun.* Dec. 2007, 8(12), pp. 1313-1323.

Hatherley et al. "Polymorphisms in the Human Inhibitory Signal-regulatory Protein α Do Not Affect Binding to Its Ligand CD47," *J. Biol. Chem.* Apr. 4, 2014, 289(14), pp. 10024-10028.

Piccio et al., "Adhesion of human T cells to antigen presenting cells through SIRPβ2-CD47 interacation costimulates T-cell proliferation," *Blood*, Mar. 15, 2005, 105(6), pp. 2421-2427.

Stefanidakis et al. "Endothelial CD47 interaction with SIRPγ is required for human T-cell transendothelial migration under shear flow conditions in vitro," *Blood*, Aug. 15, 2008, 112, pp. 1280-1289.

Stites et al., "Immunoglobulin Proteins," *Basic and Clinical Immunology*, 8th edition, Chapter 6 (pp. 66-79), Appleton & Lange, Norwalk, CT, (1994).

Köhler et al. "Continuous cultures of fused cells secreting antibody of predefined specificity," *Nature* Aug. 7, 1975, vol. 256, pp. 495-497.

Liu et al., "Functional Elements on SIRPα IgV Domain Mediate Cell Surface Binding to CD47", *Journal of Molecular Biology, Academic Press, United Kingdom*, vol. 365, No. 3, Dec. 23, 2006, pp. 680-693.

Pluckthun, "Antibodies from *Escherichia coli*," *The Pharmacology of Monoclonal Antibodies*, vol. 113, Rosenburg and Moore eds., Springer-Verlag, New York, pp. 269-315 (1994).

E.S. Day et al., "Determining the affinity and stoichiometry of interactions between unmodified proteins in solution using Biacore," *Anal. Biochem.* Sep. 2013, 440, pp. 96-107.

Jones et al., "Replacing the complementarity-determining regions in a human antibody with those from a mouse," *Nature*, May 1986, 321, pp. 522-525.

Riechmann et al., "Reshaping human antibodies for therapy," *Nature*, Mar. 1988, 332, pp. 323-327.

Verhoeyen et al., "Reshaping Human Antibodies: Grafting an Antilysozyme Activity," *Science*, Mar. 1988, 239, pp. 1534-1536.

Presta, "Antibody engineering," *Curr. Op. Struct. Biol.* 1992, 2, pp. 593-596.

Vaswani et al., "Humanized antibodies as potential therapeutic drugs," *Ann. Allergy, Asthma and Immunol.*, Aug. 1998, 1, pp. 105-115.

Harris, "Production of humanized monoclonal antibodies for in vivo imaging and therapy," *Biochem. Soc. Transactions* 1995, 23, pp. 1035-1038.

Hurle et al., "Protein engineering techniques for antibody humanization," *Curr. Op. Biotech.* (1994), 5, pp. 428-433.

Chothia et al., "Canonical Structures for the Hypervariable Regions of Immunoglobulins," *J. Mol. Biol.*, Apr. 23, 1987, 196, pp. 901-917.

Lefranc et al., "IMGT, the international ImMunoGeneTics database," *Nucl. Acids Res.*, 1999, 27, pp. 209-212.

Ruiz et al., "IMGT, the international ImMunoGene Tics database," *Nucl. Acids Res.* 2000, 28, pp. 219-221.

Honegger et al., "Yet Another Numbering Scheme for Immunoglobulin Variable Domains: An Automatic Modeling and Analysis Tool," *Mol. Biol.* 2001, 309, pp. 657-670.

Dondelinger et al. "Understanding the Significance and Implications of Antibody Numbering and Antigen-Binding Surface/Residue Definition," *Frontiers in Immunology*, Oct. 2018, 9, pp. 1-15.

Matlung et al. "Neutrophils Kill Antibody-Opsonized Cancer Cells by Trogoptosis," *Cell Rep.* 2018, 23(13), pp. 3946-3959.

Bruhns et al., "Mouse and human FcR effector functions," *Immunol Rev.* 2015, 268(1), pp. 25-51.

Clynes et al., "Fc receptors are required in passive and active immunity to melanoma," *Proc. Natl. Acad. Sci.* (*USA*) Jan. 1998, 95, pp. 652-656.

Daëron, "Fc Receptor Biology," *Annu. Rev. Immunol.* 1997, 15, pp. 203-234.

Ravetch et al., "Fc Receptors," *Annu. Rev. Immunol.* 1991, 9, pp. 457-492.

Capel et al., "Heterogeneity of Human IgG Fc Receptors," *Immunomethods* 1994, 4, pp. 25-34.

De Haas et al., "Fcγ receptors of phagocytes," *J. Lab. Clin. Med.* 1995, 126, pp. 330-341.

Henikoff & Henikoff, "Amino acid substitution matrices from protein blocks," PNAS Nov. 1992, 89, pp. 10915-10919.

Gardai et al., "By Binding SIRPα or Calreticulin/CD91 Lung Collectins Act as Dual Function Surveillance Molecules to Suppress or Enhance Inflammation," *Cell*, vol. 115, Oct. 3, 2003, pp. 13-23.

Janssen et al., "Surfactant Proteins A and D Suppress Alveolar Macrophage Phagocytosis via Interaction with SIRPα" *Am. J. Respir. Crit. Care Med.*, vol. 178, 2008, pp. 158-167.

Fournier et al., "Surfactant Protein D (Sp-D) Binds to Membrane-proximal Domain (D3) of Signal Regulatory Protein α (SIRPα), a Site Distant from Binding Domain of CD47, while Also Binding to Analogous Region on Signal Regulatory Protein β (SIRPβ)," *The Journal of Biological Chemistry*, vol. 287, No. 23, Jun. 1, 2012, pp. 19386-19398.

Van den Berg et al., "A Nomenclature for Signal Regulatory Protein Family Members," *J. Immunol.*, 2005, 175(12), pp. 7788-7789.

Van Beek et al., "Signal Regulatory Proteins in the Immune System," *J. Immunol.*, 2005, 175(12), pp. 7781-7787.

Hayashi et al., "Positive Regulation of Phagocytosis by SIRPβ and Its Signaling Mechanism in Macrophages," *J. Biol. Chem.* Jul. 9, 2004, 279(28), pp. 29450-29460.

Dietrich et al., "Cutting Edge: Signal-Regulatory Protein β1 Is a DAP12-Asociated Activating Receptor Expressed in Myeloid Cells," *J. Immunol.*, 2000, 164, pp. 9-12.

Liu et al., "SIRPβ1 Is Expressed as a Disulfide-linked Homodimer in Leukocytes and Positively Regulates Neutrophil Transepithelial Migration," *J. Biol. Chem.*, Oct. 28, 2005, 280 (43), pp. 36132-36140.

Baker et al., "Immunogenicity of protein therapeutics: The key causes, consequences and challenges," *Self/Nonself*, 2010, 1(4), pp. 314-322.

Harding et al., "The immunogenicity of humanized and fully human antibodies," mAbs 2010, 2(3), pp. 256-265.

Joubert et al., "Use of In Vitro Assays to Assess Immunogenicity Risk of Antibody-Based Biotherapeutics," *PLoS.One*, Aug. 5, 2016, 11(8), pp. 1-22.

Kabat et al., "Sequences of Proteins of Immunological Interest," 5th Ed. Public Health Service, National Institutes of Health, Bethesda, MD 1991, NIH publication No. 91-3242, pp. 662, 680, 689.

A. Martin, "Protein Sequence and Structure Analysis of Antibody Variable Domains," *Antibody Engineering* vol. 2, Chapter 3, 2010, Kontermann and Dübel Eds. Springer-Verlag Berlin Heidelberg.

Lefranc, "The IMGT Unique Numbering for Immunoglobulins, T-Cell Receptors, and Ig-Like Domains," *The Immunologist* 1999, 7(4), pp. 132-136.

Yanagita et al. "Anti-SIRPα antibodies as a potential new tool for cancer immunotherapy," *JCI Insight* 2017, 2(1), pp. 1-15.

Kurlander et al., "Blockade of Fc Receptor-Mediated Binding to U-937 Cells by Murine Monoclonal Antibodies Directed Against a Variety of Surface Antigens," *J. Immunol.* Jul. 1983, 131(1), pp. 140-147.

Harrison et al., "Methods to measure the binding of therapeutic monoclonal antibodies to the human Fc receptor FcγRIII (CD16) using real time kinetic analysis and flow cytometry," *J. Pharm. Biomed. Anal.*, 2012, 63, pp. 23-28.

Vafa et al., "An engineered Fc variant of an IgC eliminates all immune effector functions via structural perturbations," *Methods*, 2014, 65, pp. 114-126.

Leoh et al., "Insights into the effector functions of human IgG3 in the context of an antibody targeting transferrin receptor 1," *Mol. Immunol.*, Oct. 2015, 67, pp. 407-415.

Parekh et al., "Development and validation of an antibody-dependent cell-mediated cytotoxicity-reporter gene assay," *mAbs* 2012, 4(3), pp. 310-318.

(56) References Cited

OTHER PUBLICATIONS

Pleass et al., "Identification of Residues in the CH2/CH3 Domain Interface of IgA Essential for Interaction with the Human Fcα Receptor (FcαR) CD89," *J. Biol. Chem.* Aug. 13, 1999, 274(33), pp. 23508-23514.

Shukla et al., "Recent advances in large-scale production of monoclonal antibodies and related proteins," *Trends in Biotechnol.* 2010, 28(5), pp. 253-261.

Sosale et al., "Marker of Self' CD47 on lentiviral vectors decreases macrophage-mediated clearance and increases delivery to SIRPA-expressing lung carcinoma tumors," *Mol. Ther. Methods Clin. Dev.* 2016, 3, pp. 1-13.

Gluzman et al., "SV40-Transformed Simian Cells Support the Replication of Early SV40 Mutants," *Cell* Jan. 1981, 23, pp. 175-182.

McMahan et al., "A novel IL-1 receptor, cloned from B cells by mammalian expression, is expressed in many cell types," *EMBO J.*, 1991, vol. 10, No. 10, pp. 2821-2832.

Chen et al., "Expression and Activation of Signal Regulatory Protein α on Astrocytomas," *Cancer Res.* Jan. 1, 2004, 64(1), pp. 117-127.

Low et al., "Future of antibody purification," *J. Chromatography B*, 2007, 848, pp. 48-63.

Shukla et al., "Downstream processing of monoclonal antibodies—Application of platform approaches," *J. Chromatography B*, 2007, 848, pp. 28-39.

Eifler et al., "Development of a Noval Affinity Chromatography Resin for Platform Purification of Lambda Fabs," *Biotechnology Progress*, 2014, 30(6), pp. 1311-1318.

Cheson et al., "Revised Recommendations of the International Working Group for Diagnosis, Standardization of Response Criteria, Treatment Outcomes, and Reporting Standards for Therapeutic Trials in Acute Myeloid Leukemia," *Journal of Clinical Oncology*, Dec. 15, 2003; 21(24), pp. 4642-4649.

Moghbel et al., "Response Assessment Criteria and Their Applications in Lymphoma: Part 1," *Journal of Nuclear Medicine*, Jun. 2016, 57(6), pp. 928-935.

Moore et al., "Apoptosis in CHO cell batch cultures: examination by flow cytometry," *Cytotechnology* 1995; 17, pp. 1-11.

Eisenhauer et al., "New response evaluation criteria in solid tumours: Revised RECIST guideline (version 1.1)," *European Journal of Cancer*, 2009; 45, pp. 228-247.

Schwartz et al., "RECIST 1.1—Standardisation and disease-specific adaptations: Perspectives from the RECIST Working Group," *European Journal of Cancer*, 2016, 62, pp. 138-145.

Baert et al., "Influence of Immunogenicity on the Long-Term Efficacy of Infliximab in Crohn's Disease," *New Engl. J. Med.* Feb. 13, 2003, 348, pp. 601-608.

Milgrom et al., "Treatment of Allergic Asthma with Monoclonal Anti-IgE Antibody," *New Engl. J. Med.*, Dec. 23, 1999, 341(26), pp. 1966-1973.

Slamon et al., "Use of Chemotherapy Plus a Monoclonal Antibody Against HER2 for Metastatic Breast Cancer that Overexpresses HER2," *New Engl. J. Med.*, Mar. 5, 2001, 344(11), pp. 783-792.

Beniaminovitz et al., "Prevention of Rejection in Cardiac Transplantation by Blockade of the Interleukin-2 Receptor with a Monoclonal Antibody," *New Engl. J. Med.*, 2000, 342(9), 613-619.

Ghosh et al., "Natalizumab for Active Crohn's Disease," *New Engl. J. Med.*, Jan. 2, 2003, 348(1), pp. 24-32.

Lipsky et al., "Infliximab and Methotrexate in the Treatment of Rheumatoid Arthritis," *New Engl. J. Med.*, Nov. 30, 2000, 343(22), pp. 1594-1602.

Yang et al., "A Randomized Trial of Bevacizumab, an Anti-Vascular Endothelial Growth Factor Antibody, for Metastatic Renal Cancer," *New Engl. J. Med.*, Jul. 31, 2003 349(5), pp. 427-434.

Herold et al., "Anti-CD3 Monoclonal Antibody in New-Onset Type 1 Diabetes Mellitus," *New Engl. J. Med.*, May 30, 2002, 346(22), pp. 1692-1698.

Liu et al., "Randomised, double-blind, placebo controlled study of interferon β-1a in relapsing-remitting multiple sclerosis analysed by area under disability/time curves," *J. Neurol. Neurosurg. Psych.*, 1999, 67, pp. 451-456.

Portielje et al., "IL-12: a promising adjuvant for cancer vaccination," *Cancer Immunol. Immunother.* 2003, 52, pp. 133-144.

Chao et al., "The CD47-SIRPα pathway in cancer immune evasion and potential therapeutic implications," *Curr. Opin. Immunol.* 2012, 24(2), 225-232.

Chao et al., "Anti-CD47 Antibody Synergizes with Rituximab to Promote Phagocytosis and Eradicate Non-Hodgkin Lymphoma," *Cell*, 142(5), Sep. 3, 2010, pp. 699-713.

Rösner et al., "Immune Effector Functions of Human IgG2 Antibodies against EGFR," *Mol Cancer Ther.* 18(1), Jan. 1, 2019, pp. 75-88 (Published online first Oct. 3, 2018).

Russ et al., "Blocking 'don't eat me' signal of CD47-SIRPα in hematological malignancies, an in-depth review," *Blood Rev.* 2018, vol. 32; pp. 480-489.

G. Brooke et al., "Human Lymphocytes Interact Directly with CD47 through a Novel Member of the Signal Regulatory Protein (SIRP) Family," *J. Immunol.* 2004, 173, pp. 2562-2570.

M. K. Leabman et al., "Effects of altered FcγR binding on antibody pharmacokinetics in cynomolgus monkeys," *mAbs*, 5:6, Nov./Dec. 2013, pp. 896-903.

Matozaki et al., "Functions and molecular mechanisms of the CD47-SIRPalpha signalling pathway," Trends in Cell Biology, Elsevier Science Ltd., vol. 19, No. 2, Feb. 2009, pp. 72-80.

P. A. Oldenborg, "Role of CD47 as a Marker of Self on Red Blood Cells," Science, vol. 288, No. 5473, Jun. 16, 2000, pp. 2051-2054.

Jiang et al., "Integrin-Associated Protein is a Ligand for the P84 Neural Adhesion Molecule," Journal of Biological Chemistry, American Society for Biochemistry and Molecular Biology, US, vol. 274, No. 2, Jan. 8, 1999, pp. 559-562.

Liu et al., "Signal Regulatory Protein (SIRPα), a Cellular Ligand for CD47, Regulates Neutrophil Transmigration," Journal of Biological Chemistry, vol. 277, No. 12, Mar. 22, 2002, pp. 10028-10036.

Motegi et al., "Role of the CD47-SHPS-1 system in regulation of cell migration," EMBO (European Molecular Biology Organization) Journal, Wiley, DE, vol. 22, No. 11, 2003 pp. 2634-2644.

Weiskopf et al., "Direct SIRPα Blockade Augments Macrophage Responses to Therapeutic Anticancer Antibodies," Blood Journal, vol. 124, No. 21, 2014, p. 2729.

Zhao et al., "CD47-signal regulatory protein-alpha (SIRPα) interactions form a barrier for antibody-mediated tumor cell destruction: Supporting Information," Proceedings of the National Academy of Sciences, Oct. 31, 2011, pp. 1-3.

Hatherley et al., "The Structure of the Macrophage Signal Regulatory Protein α (SIRPα) Inhibitory Receptor Reveals a Binding Face Reminiscent of That Used by T Cell Receptors," Journal of Biological Chemistry, vol. 282, No. 19, May 11, 2007, pp. 14567-14575.

Nettleship et al., "Crystal structure of signal regulatory protein gamma (SIRP gamma) in complex with an antibody Fab fragment," BMC Structural Biology, Biomed Central Ltd., London, GB, vol. 13, No. 1, Jul. 4, 2013, p. 3.

Lee et al., "Novel Structural Determinants on SIRPα that Mediate Binding to CD47," The Journal of Immunology, 2007, vol. 179, pp. 7741-7750.

Clackson et al., "Making antibody fragments using phage display libraries," Nature, Aug. 15, 1991, vol. 352, pp. 624-628.

Marks et al., "Human Antibodies from V-gene Libraries Displayed on Phage," J. Mol. Biol. 1991, 222, pp. 581-597.

Chothia et al., "Conformations of immunoglobulin hypervariable regions," Nature, Dec. 28, 1989, vol. 342, No. 21, pp. 877-883.

Soto-Pantoja et al., "CD47 signaling pathways controlling cellular differentiation and responses to stress," Crit. Rev. in Biochem. and Mol. Biol., Feb. 24, 2015, vol. 50, No. 3, pp. 212-230.

Barclay, A.N., et al., "The Interaction Between Signal Regulatory Protein Alpha (SIRPα) and CD47; Structure, Function, and Therapeutic Target", Annu. Rev. Immunol., 2014, vol. 32, pp. 25-50.

\* cited by examiner

HUMANIZED ANTI-SIRPα ANTIBODIES

FIELD OF THE INVENTION

The present invention relates to humanized antibodies against SIRPα and the use of these antibodies in the treatment of cancer, optionally in combination with anti-cancer therapeutics.

REFERENCE TO SEQUENCE LISTING

This application includes an electronically submitted sequence listing in .txt format. The .txt file contains a sequence listing entitled "P1729US00_ST25txt" created on Sep. 12, 2024 and is 162,646 bytes in size. The sequence listing contained in this .txt file is part of the specification and is hereby incorporated by reference herein in its entirety.

BACKGROUND OF THE INVENTION

Since the late 1990s, therapeutic antibodies that recognize antigens on tumour cells have been available for the treatment of cancer. These therapeutic antibodies can act upon malignant cells via different pathways. The signalling pathways triggered by binding of the antibody to its target on malignant cells result in inhibition of cell proliferation or in apoptosis. The Fc region of the therapeutic antibody can trigger complement dependent cytotoxicity (CDC), antibody-dependent cellular cytotoxicity (ADCC) and/or antibody-dependent cellular phagocytosis (ADCP). Another possible mechanism may be the antibody-dependent induction of a T-cell (CD8$^+$ and/or CD4$^+$) anti-tumour response (antibody-dependent antigen presentation (ADAP): DiLillo and Ravetch *Cell* 2015, 161 (5), 1035-1045; Bournazos and Ravetch *Immunity* 2017, 47 (2), 224-233). This occurs via the Fc receptors expressed on antigen presenting cells, such as for example dendritic cells. However, therapeutic antibodies are often not effective enough as monotherapy. One option to improve the efficacy of therapeutic antibodies is through improving ADCC and/or ADCP. This has for example been done by improving the affinity of the Fc region for Fcγ receptors, e.g. by amino acid substitutions (Richards et al. *Mol. Cancer Ther.* 2008, 7 (8), 2517-2527) or by influencing the glycosylation of the Fc region (Hayes et al. *J. Inflamm. Res.* 2016, 9, 209-219).

Another way of improving the ADCC and/or ADCP of a therapeutic antibody is by combining the therapeutic antibody with an antagonistic antibody against signal regulatory protein α (SIRPα) or an anti-CD47 antibody (WO2009/131453). When CD47—which has been found to be upregulated in and/or on at least several human tumour types—binds to the inhibitory immunoreceptor SIRPα expressed on monocytes, macrophages, dendritic cells and neutrophils. SIRPα transmits an inhibitory signal that prevents destruction of cancer cells by phagocytosis or other Fc-receptor-dependent cell destruction mechanisms of immune effector cells. One of the mechanisms through which anti-CD47 or anti-SIRPα antibodies are hypothesized to act is through blocking of the inhibitory signalling generated via the CD47-SIRPα axis, resulting in an increase in ADCC and/or ADCP and/or ADAP (Tjeng et al. *Proc Natl Acad Sci USA* 2013, 110(27), 11103-11108; Liu et al. *Nature Med.* 2015, 21(10), 1209-1215).

Most clinical research related to the CD47-SIRPα interaction has been focused on anti-CD47 antibodies, both as monotherapy and as therapy in combination with a therapeutic antibody (Weiskopf. *Eur. J. Cancer* 2017, 76, 100-109; Advani et al. *N. Engl. J. Med.* 2018, 379(18), 1711-1721). Research regarding anti-CD47 antibodies as anticancer therapeutics is growing, despite the fact that CD47 is widely expressed on the surface of cells in most normal tissues.

No clinical research has been conducted on anti-cancer monotherapy or combination therapy using anti-SIRPα antibodies. The majority of the work on anti-SIRPα antibodies is mechanistic research regarding the CD47-SIRPα interaction and has been performed using murine anti-SIRPα antibodies: e.g. murine 12C4 and 1.23A were reported to increase neutrophil-mediated ADCC of trastuzumab-opsonised SKBR3 cells (Zhao et al. *PNAS* 2011, 108(45), 18342-18347). WO2015/138600 discloses murine anti-human SIRPα antibody KWAR23 and its chimeric Fab fragment, which were reported to increase cetuximab-mediated phagocytosis in vitro. Humanized KWAR23 with a human IgG$_1$ Fc part comprising a N297A mutation is disclosed in WO2018/026600. WO2013/056352 discloses IgG$_4$ 29AM4-5 and other IgG$_4$ human anti-SIRPα antibodies. The IgG$_4$ 29AM4-5, dosed three times per week for four weeks at 8 mg/kg, reduced leukaemic engraftment of primary human acute myeloid leukaemia (AML) cells injected into the right femur of NOD scid gamma (NSG) mice. WO2017/178653 discloses chimeric anti-SIRPα antibody HEFLB which binds to SIRPα$_1$ and SIRPα$_{BIT}$, but not to SIRPγ. However, although the antibody retains binding to SIRPα$_{BIT}$ upon humanization, it no longer binds to SIRPα$_1$. Since for instance 51.3% of the Caucasians have at least 1 allele of SIRPα$_1$, their immune cells are (at least partly when heterozygous) unresponsive to an antibody only binding SIRPα$_{BIT}$ (Treffers et al. *Eur J Immunol.* 2018, 48 (2), 344-354). WO2018/057669 discloses humanized chicken anti-SIRPα antibodies against domain 1 of human SIRPα$_1$ and/or human SIRPα$_{BIT}$. WO2018/107058 discloses that mouse anti-SIRPα antibodies 3F9 and 9C2 do not bind to SIRPβ$_{1v1}$ and they concluded that these antibodies are therefore SIRPα-specific, with equilibrium binding constants of $1.0 \times 10^{-8}$ and $8.0 \times 10^{-8}$ M, respectively. WO2018/190719 discloses humanized anti-SIRPα antibodies that also bind to human SIRPγ, but that do not bind to human SIRPβ$_1$.

Human SIRPα is highly polymorphic in its NH$_2$-terminal ligand binding domain (Takenaka et al. *Nature Immun.* 2007, 8(12), 1313-1323): SIRPα$_{BIT}$ (v1) and SIRPα$_1$ (v2) are the two most common and most divergent (13 residues different) polymorphs and their affinities for CD47 are very similar (Hatherley et al. *J. Biol. Chem.* 2014, 289(14), 10024-10028; Treffers et al. *Eur J Immunol.* 2018, 48(2), 344-354). Other biochemically characterized human SIRP family members are SIRPβ$_1$, which does not bind CD47 and has at least two polymorphic variants (SIRPβ$_{1v1}$ and SIRPβ$_{1v2}$), and SIRPγ, which is expressed on T-cells and activated NK-cells and binds CD47 with an approximately 10-fold lower affinity as compared to SIRPα (van Beek et al. *J Immunol.* 2005, 175(12), 7781-7). The CD47-SIRPγ interaction is involved in the contact between antigen-presenting cells and T-cells, respectively, co-stimulating T-cell activation and promoting T-cell proliferation (Piccio et al. *Blood* 2005, 105, 2421-2427). Furthermore. CD47-SIRPγ interactions play a role in the transendothelial migration of T-cells (Stefanidakis et al. *Blood* 2008, 112, 1280-1289).

A disadvantage of the anti-SIRPα antibodies known in the art is that they are either (i) not specific for human SIRPα, because they bind to other human SIRP family members such as human SIRPγ, thereby possibly resulting in undesirable side effects, or (ii) they are too limited in their specificity, only binding to one of the SIRPα allelic variants—for example SIRPα$_{BIT}$ or SIRPα$_1$—thereby making them less suitable for mono- or combination therapy, since part of the human population has a SIRPα allelic variant to which the anti-SIRPα antibody does not bind. For example, prior art antibodies KWAR23, SE5A5, 29AM4-5 and 12C4 are not specific, as they also bind to human SIRPγ, which might negatively influence T-cell proliferation and recruitment. Conversely, 1.23A mAb for example is too specific and only recognizes the human SIRPα polymorphic variant SIRPα$_1$ and not the variant SIRPα$_{BIT}$, which is predominant in at least the Caucasian population (Zhao et al. *PNAS* 2011, 108(45), 18342-18347; Treffers et al. *Eur J Immunol.* 2018, 48(2), 344-354). Also humanized antibody HEFLB disclosed in WO2017/178653 is too specific, as this antibody does not bind to SIRPα$_1$ (SPR measurements; see Example section) and does not promote anti-tumour activity of immune effector cells from SIRPα$_1$ carriers, even when one allele of SIRPα$_{BIT}$ is present (FIG. 3).

Only later published WO2018/210793 discloses several antagonistic chimeric anti-SIRPα antibodies which exhibit specific binding to the two predominant SIRPα polymorphic variants SIRPα$_{BIT}$ and SIRPα$_1$, that do not bind to SIRPγ and that increase the ADCC of therapeutic antibodies (antibodies 2-9). In Table 1 of WO2018/210793, humanized variants for two of the chimeric antibodies are disclosed (antibodies 10-16).

In conclusion, there is still a need in the art for further and improved anti-SIRPα antibodies that are useful in anti-cancer therapy either alone or in combination with a further therapeutic anti-cancer antibody. More in particular, a need remains for antagonistic anti-SIRPα antibodies which have no, low, or reduced binding to human SIRPγ, thereby reducing the risk for undesirable side effects, and which anti-SIRPα antibodies bind to both human SIRPα and human SIRPα$_{BIT}$ polymorphic variants, to make them suitable for a large part of the human population, including SIRPα$_1$/SIRPα$_{BIT}$ heterozygotes, SIRPα$_{BIT}$ homozygotes and SIRPα$_1$ homozygotes. There is a need for anti-SIRPα antibodies with these characteristics and which reduce inhibitory, i.e. SHP-1 and/or SHP-2-mediated, SIRPα signalling. Such antibodies are suitable for use in anti-cancer therapy either alone or, preferably, in combination with a therapeutic anti-cancer antibody.

BRIEF DESCRIPTION OF THE INVENTION

The present invention relates to humanized antibodies against SIRPα that are suitable for use in anti-cancer therapy alone or, preferably, in combination with anti-cancer therapy such as a therapeutic anti-cancer antibody.

In a first aspect, the present invention relates to a humanized anti-SIRPα antibody or an antigen-binding fragment thereof, comprising heavy chain complementarity determining regions (HCDR) and light chain complementarity determining regions (LCDR) HCDR1, HCDR2, HCDR3, LCDR1, LCDR2 and LCDR3, wherein the antibody or the antigen-binding fragment thereof comprises:
  a. HCDR1 comprising SEQ ID NO:36;
  b. HCDR2 comprising SEQ ID NO:44;
  c. HCDR3 comprising SEQ ID NO:45;
  d. LCDR1 comprising SEQ ID NO:39;
  e. LCDR2 comprising SEQ ID NO:40; and
  f. LCDR3 comprising SEQ ID NO:41.

In a preferred embodiment, the anti-SIRPα antibody or the antigen-binding fragment thereof has one or more properties from the group consisting of: (a) the anti-SIRPα antibody or the antigen-binding fragment thereof binds human SIRPα$_1$ with a binding affinity of at least $10^{-10}$ M, preferably at least $10^{-11}$ M, as analysed by surface plasmon resonance (SPR) (preferably BiaCore™) at 25° C. using human SIRPα$_1$ extracellular domain as shown in SEQ ID NO: 51; (b) the anti-SIRPα antibody or the antigen-binding fragment thereof binds human SIRPα$_{BIT}$ with a binding affinity of at least $10^{-10}$ M, preferably at least $10^{-11}$ M, as analysed by SPR (preferably BiaCore™) at 25° C. using human SIRPα$_{BIT}$ extracellular domain as shown in SEQ ID NO:52; (c) the anti-SIRPα antibody or the antigen-binding fragment thereof binds cynomolgus monkey SIRPα with a binding affinity of at least $10^{-8}$ M, preferably at least $10^{-9}$ M, as analysed by SPR (preferably BiaCore™) at 25° C. using cynomolgus SIRPα extracellular domain as shown in SEQ ID NO:56; (d) the anti-SIRPα antibody or the antigen-binding fragment thereof does not bind human SIRPγ as measured by T-cell binding using flow cytometry, preferably using fluorescence-activated cell sorting (FACS) staining; (e) the anti-SIRPα antibody or the antigen-binding fragment thereof does not bind human SIRPγ as analysed by SPR (preferably BiaCore™) at 25° C. using human SIRPγ extracellular domain as shown in SEQ ID NO:55; and (f) the anti-SIRPα antibody or the antigen-binding fragment thereof is not immunogenic as determined by IL-2 enzyme-linked immunosorbent spot (ELISpot) and/or T-cell proliferation assay.

In a preferred embodiment, the humanized anti-SIRPα antibody or an antigen-binding fragment thereof: (a) binds human SIRPα$_1$ with a binding affinity of at least $10^{-10}$ M, preferably at least $10^{-11}$ M, as analysed by SPR (preferably BiaCore™) at 25° C. using human SIRPα$_1$ extracellular domain as shown in SEQ ID NO:51; (b) binds human SIRPα$_{BIT}$ with a binding affinity of at least $10^{-10}$ M, preferably at least $10^{-11}$ M, as analysed by SPR (preferably BiaCore™) at 25° C. using human SIRPα$_{BIT}$ extracellular domain as shown in SEQ ID NO:52; (c) blocks CD47 binding to SIRPα$_1$ and SIRPα$_{BIT}$, preferably as analysed by dissociation from captured CD47 by SPR (preferably BiaCore™), more preferably as described in Example 6; and (d) does not bind human SIRPγ as measured by T-cell flow cytometry, preferably fluorescence-activated cell sorting (FACS) staining.

In a preferred embodiment, the invention relates to a humanized anti-SIRPα antibody or an antigen-binding fragment thereof, wherein: (a) the heavy chain variable domain of the antibody comprises 4 heavy chain framework regions, HFR1 to HFR4, and 3 complementarity determining regions HCDR1 to HCDR3 that are operably linked in the order HFR1-HCDR1-HFR2-HCDR2-HFR3-HCDR3-HFR4, wherein each of the heavy chain framework regions has at least 90% amino acid identity with the framework amino acid sequence of SEQ ID NO:8 or wherein HFR1 to HFR4 differ from SEQ ID NO:8 in one or more of the amino acid substitutions as defined in Tables 8 to 11 (and correspondingly SEQ ID NO:77 to SEQ ID NO: 80, respectively); and (b) the light chain variable domain of the antibody comprises 4 light chain framework regions. LFR1 to LFR4, and 3 complementarity determining regions LCDR1 to LCDR3 that are operably linked in the order LFR1-LCDR1-LFR2-LCDR2-LFR3-LCDR3-LFR4, wherein each of the light chain framework regions has at least 90% amino acid identity with the framework amino acid sequence of SEQ ID NO:9, or wherein LFR1. LFR2 and/or LFR4 differ from SEQ ID NO:9 in one or more amino acid substitutions as defined in Tables 12 to 14 (and correspondingly SEQ ID NO:81 to SEQ ID NO:83, respectively).

In a preferred embodiment, a humanized anti-SIRPα antibody or an antigen-binding fragment thereof according to the invention, comprises a heavy chain variable region (HCVR) amino acid sequence and a light chain variable region (LCVR), wherein the anti-SIRPα antibody or the antigen-binding fragment thereof comprises the HCVR amino acid sequence of SEQ ID NO:8 and the LCVR amino acid sequence of SEQ ID NO:9.

In a preferred embodiment, a humanized anti-SIRPα antibody according to the invention, comprises a modified Fc region that exhibits reduced binding to a human Fcα or Fcγ receptor compared to the same anti-SIRPα antibody comprising a wild-type Fc region, preferably a reduction of at least 10, 20, 30, 40, 50, 60, 70, 80, 90% or a reduction of 100%. In a preferred embodiment, a modified human IgG$_1$ Fc region comprises an amino acid substitution at one or more positions selected from the group consisting of L234, L235, G237, D265, D270, N297, A327, P328, and P329 according to Eu numbering. More preferably, a modified human IgG$_1$ Fc region comprises amino acid substitutions: L234A and L235A; L234E and L235A; L234A, L235A and P329A; or L234A, L235A and P329G. More preferably the antibody comprises the amino acid substitutions L234A and L235A; or, L234E and L235A. Most preferably, the antibody comprises amino acid substitutions L234A and L235A. In a preferred embodiment, the human IgG Fc region does not comprise other amino acid substitutions.

In a second aspect, the present invention relates to a pharmaceutical composition comprising a humanized anti-SIRPα antibody, or an antigen-binding fragment thereof, according to the invention and a pharmaceutically acceptable excipient.

In a third aspect, the present invention relates to a humanized anti-SIRPα antibody, or an antigen-binding fragment thereof, according to the invention, or a pharmaceutical composition according to the invention for use as a medicament.

In a fourth aspect, the present invention relates to a humanized anti-SIRPα antibody or an antigen-binding fragment thereof according to the invention or a pharmaceutical composition according to the invention for use in the treatment of a cancer, wherein the treatment further comprises administration of a therapeutic antibody, wherein the cancer preferably is a human solid tumour or a haematological malignancy. Preferably, the therapeutic antibody is directed against a membrane-bound target on the surface of tumour cells and comprises a human Fc region that binds to activating Fc receptors present on human immune effector cells.

In a preferred embodiment, the human solid tumour is selected from the group consisting of (HER2-positive) breast cancer, (EGFR-positive) colon carcinoma. (GD2-positive) neuroblastoma, melanoma, osteosarcoma, (CD20-positive) B-cell lymphomas, (CD38-positive) multiple myeloma (CD52-positive) lymphoma, (CD33-positive) acute myeloid leukaemia (AML), chronic myeloid leukaemia (CML), chronic lymphatic leukaemia (CLL), acute lymphoblastic leukaemia (ALL), non-Hodgkin's lymphoma (NHL), including follicular lymphoma (FL) and diffuse large B-cell lymphoma (DLBCL), hepatocellular carcinoma, multiple myeloma (MM), bladder cancer, gastric cancer, ovarian cancer, head and neck cancer, pancreatic cancer, renal carcinoma, prostate cancer, hepatocellular carcinoma and lung cancer. In a preferred embodiment, the treatment comprises administration of a further anti-cancer therapeutic compound, such as for example a targeted therapeutic, preferably an immunotherapeutic agent.

In a fifth aspect, the present invention relates to a nucleic acid molecule comprising a nucleotide sequence encoding a humanized anti-SIRPα antibody or an antigen binding fragment thereof according to the invention, wherein preferably the nucleic acid molecule comprises a nucleotide sequence encoding at least one of the HCVR and the LCVR of the antibody, and wherein preferably the coding nucleotide sequence is operably linked to regulatory sequences for expression of the coding nucleotide sequence in a host cell.

In a sixth aspect, the present invention relates to a host cell comprising the nucleic acid molecule according to the invention.

DETAILED DESCRIPTION OF THE INVENTION

Definitions

Figure 1A:
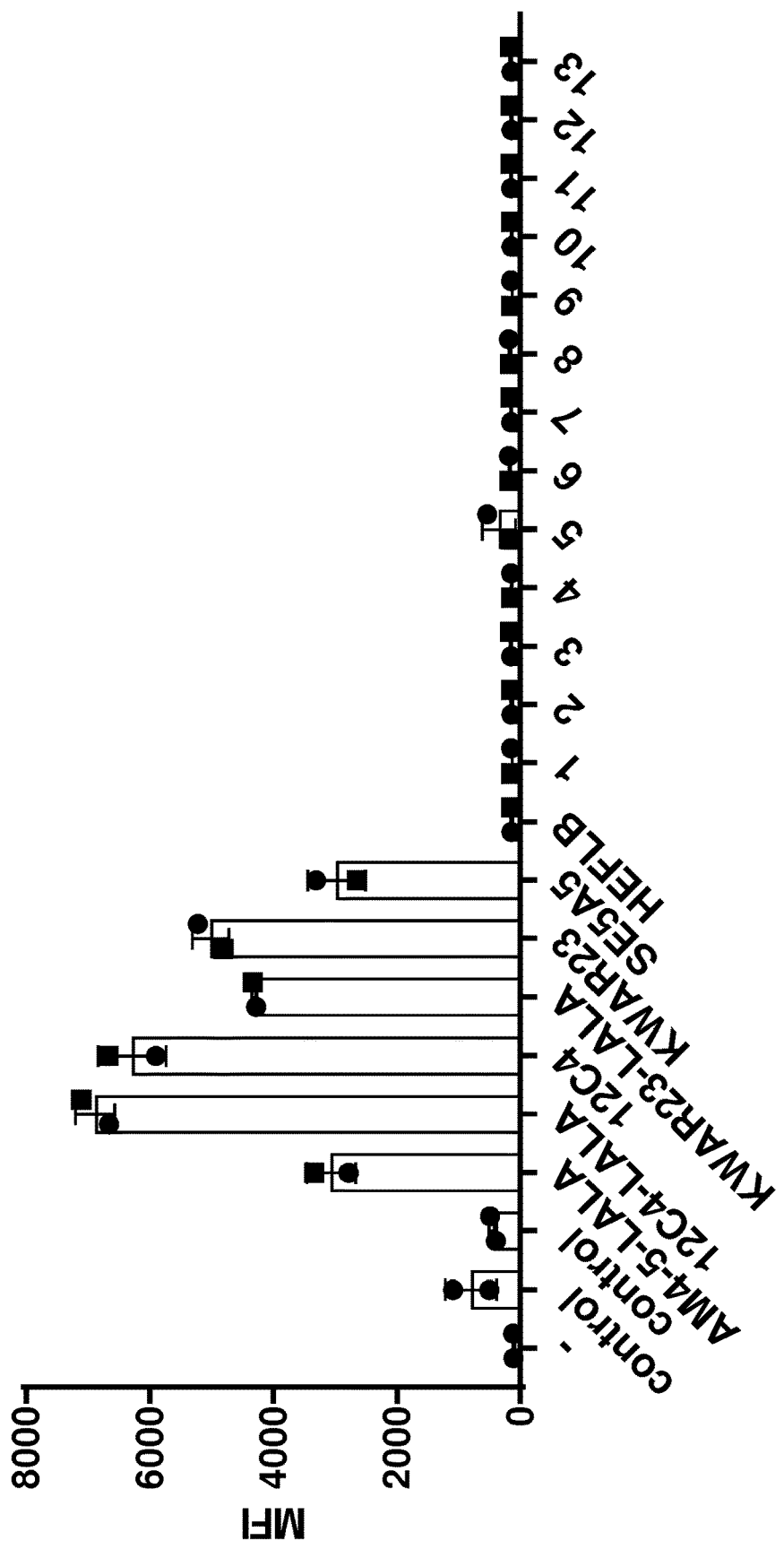
FIG. 1. Binding of antibodies to SIRPγ expressing human CD3$^+$ T-cells by flow cytometry. Data is depicted as mean fluorescence intensity (MFI) (FIG. 1a) and percentage (%) of positive cells (FIG. 1b). Symbols represent measurements from two healthy individuals.

The term "antibody" as used throughout the present specification refers to a monoclonal antibody (mAb) comprising two heavy chains and two light chains. Antibodies may be of any isotype such as IgA, IgE, IgG, or IgM antibodies. Antibodies may also be of an IgGA cross-isotype (Kelton et al. *Chemistry and Biology*, 2014, 21, 1603-1609). Preferably, the antibody is an IgG antibody, e.g. an IgG$_1$, IgG$_2$, IgG$_3$ or IgG$_4$ antibody, more preferably an IgG$_1$ or IgG$_2$ antibody. The term "immunoglobulin" (Ig) is used interchangeably with antibody herein. An antibody according to the invention preferably is a humanized or human antibody.

The basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contain 10 antigen-binding sites, while secreted IgA antibodies can polymerize to form polyvalent assemblages comprising 2-5 of the basic 4-chain units along with the J chain). In the case of IgGs, the 4-chain unit is generally about 150.000 Daltons. Each L chain is linked to an H chain by one covalent disulfide bond, while the two H chains are linked to each other by one or more disulfide bonds depending on the H chain isotype. However. IgGs may lack one or more of the disulfide bonds, while retaining their function. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Generally, the H chain comprises a hinge region, typically between the first and second constant region. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the L chain and H chain variable domains. The pairing of a VH and VL together forms a single antigen-binding site. For the structure and properties of the different classes of antibodies, see, e.g., Basic and Clinical Immunology. 8th edition. Daniel P. Stites. Abba I. Terr and Tristram G. Parslow (eds.), Appleton & Lange, Norwalk, CT, page 71 and Chapter 6 (1994).

The L chain from any vertebrate species can be assigned to one of two clearly distinct types, called kappa (κ) and lambda (λ), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The α and γ classes are further divided into subclasses on the basis of relatively minor differences in CH sequence and function, e.g., humans express the following subclasses: IgG$_1$, IgG$_2$, IgG$_3$, IgG$_4$, IgA$_1$, and IgA$_2$.

Preferably, an antibody of the invention is a humanized or human antibody. Even more preferably, the antibody is a humanized or human IgG antibody, most preferably a humanized or human IgG$_1$ mAb. The antibody may have k or A light chains, preferably κ light chains (for example as shown in SEQ ID NO:26), i.e., a humanized or human IgG$_1$-κ antibody. An antibody of the invention may comprise a constant region that is engineered, for example one or more mutations may be introduced to e.g. increase half-life and/or decrease effector function.

The terms "monoclonal antibody" and "mAb" as used herein refer to an antibody obtained from a population of substantially homogeneous antibodies, i.e., the individual antibodies comprising the population are identical except for possible naturally-occurring mutations that may be present in minor amounts. The modifier "monoclonal" is not to be construed as requiring production of the antibody by any particular method. There are several ways known in the art to generate monoclonal antibodies. For example, the monoclonal antibodies useful in the present invention may be generated by immunizing animals with a mixture of peptides representing the desired antigen. Subsequently. B-lymphocytes may be isolated and fused with myeloma cells or single B-lymphocytes may be cultivated for several days in the presence of conditioned medium and feeder cells. The myeloma or B-lymphocyte supernatants containing the produced antibodies are tested to select suitable B-lymphocytes or hybridomas. Monoclonal antibodies may be prepared from suitable hybridomas by the hybridoma methodology first described by Köhler et al. Nature 1975, 256, 495-497. Alternatively, suitable B-cells or lymphoma may be lysed. RNA may be isolated, reverse transcribed and sequenced. Antibodies may be made by recombinant DNA methods in bacterial, eukaryotic animal or plant cells (see, e.g., U.S. Pat. No. 4,816,567).

The "variable region" or "variable domain" of an antibody refers to the amino-terminal domains of the heavy or light chain of the antibody. The term "variable" refers to the fact that certain segments of the variable domains differ extensively in sequence among antibodies. The variable domain mediates antigen binding and defines specificity of a particular antibody for its particular antigen. However, the variability is not evenly distributed across the approximately 110-amino acid span of the variable domains. Instead, the variable regions consist of relatively invariant stretches called framework regions (FRs) of 15-30 amino acids separated by shorter regions of extreme variability called "hypervariable regions" (HVRs) or "complementarity determining regions" (CDRs) that are each approximately 9-12 amino acids long, but may be shorter or longer, as for example HCDR1 in the mAbs of the present invention that has a length of 5 amino acid residues. The variable domains of heavy and light chains of naturally occurring antibodies each comprise four FRs, largely adopting a β-sheet configuration, connected by three CDRs, which form loops connecting, and in some cases forming part of, the β-sheet structure. The CDRs in each chain are held together in close proximity by the FRs and, with the CDRs from the other chain, contribute to the formation of the antigen-binding site of antibodies (see Kabat et al. Sequences of Proteins of Immunological Interest. 5th Ed. Public Health Service. National Institutes of Health, Bethesda, MD. 1991). The constant domains are not involved directly in binding an antibody to an antigen, but exhibit various effector functions, such as participation of the antibody in ADCC and/or ADCP. The variable domain of the heavy chain may be referred to as "VH". The variable domain of the light chain may be referred to as "VL".

The term "antigen-binding fragment" as used throughout the present specification includes Fab, Fab', F(ab')$_2$, Fv, scFv and rIgG fragments as long as they exhibit the desired biological and/or immunological activity. The term "antigen-binding fragment" further includes a single chain (sc) antibody, a single domain (sd) antibody, a diabody, or a minibody. For example, papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having an additional few residues at the C-terminus of the CH1 domain including one or more cysteines from the antibody hinge region. Fab'-SH is the designation herein for Fab in which the cysteine residue(s) of the constant domains bear a free thiol group. F(ab')$_2$ antibody fragments originally were produced as pairs of Fab' fragments, which have hinge cysteines between them. Other chemical couplings of antibody fragments are also known. The Fc fragment comprises the C-terminal portions of both H chains held together by disulfides. The effector functions of antibodies are determined by sequences in the Fc region, which region is also the part recognized by Fc receptors (FcR) found on certain types of cells. "Fv" is the minimum antibody fragment which contains a complete antigen-recognition and -binding site. This fragment consists of a dimer of one heavy and one light chain variable region domain in tight, non-covalent association. In a single-chain Fv (scFv) species, one heavy and one light chain variable domain can be covalently linked by a flexible peptide linker such that the heavy and light chains can associate in a "dimeric" structure analogous to that in a two-chain Fv species. From the folding of these two domains emanate six hypervariable loops (3 loops each from the H and L chain) that contribute the amino acid residues for antigen binding and confer antigen-binding specificity to the antibody. However, even a single variable domain (or half of an Fv comprising only three CDRs specific for an antigen) has the ability to recognize and bind antigen, although at a lower affinity than the entire binding site. "Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994). "rIgG" refers to reduced IgG, approximately 75,000 Daltons, and may be produced by selectively reducing just the hinge region disulfide bonds, for example using a mild reducing agent such as 2-mercaptoethylamine (2-MEA).

The term "anti-SIRPα antibody" or "an antibody that binds to SIRPα" refers to an antibody that is capable of binding SIRPα with sufficient affinity such that the antibody is useful as a diagnostic and/or therapeutic agent in targeting SIRPα. Preferably, the extent of binding of an anti-SIRPα antibody to an unrelated, non-SIRP protein is less than about 10% of the binding of the antibody to SIRPα as measured, e.g., by a radioimmunoassay (RIA), surface Plasmon resonance (SPR) or enzyme-linked immunosorbent assay (ELISA). Binding to non-related targets may also be profiled using a cell microarray technology, such as for example by Retrogenix™.

An "isolated antibody" is one which has been identified and separated and/or recovered from a component of its natural environment. Contaminant components of its natural environment are materials which would interfere with therapeutic uses of the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight. (2) to a degree sufficient to obtain at least residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, an isolated antibody will be prepared by at least one purification step.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The binding affinity of a molecule X for its partner Y as used throughout the present specification, refers to the equilibrium dissociation constant (also referred to as "binding constant"; $K_D$) of a particular antigen-antibody interaction. The $K_D$ is the ratio of the rate of dissociation ($k_{off}$) to the association rate ($k_{on}$). Consequently. $K_D$ equals $k_{off}/k_{on}$ and is expressed as a molar concentration (M). It follows that the smaller the $K_D$, the stronger the affinity of binding. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following. Typically. $K_D$ values are determined by using surface plasmon resonance (SPR), typically using a biosensor system (e.g. BIAcore™) using methods known in the art (e.g. E. S. Day et al. *Anal. Biochem.* 2013, 440, 96-107), such as for example described in the Example section. Alternatively, the term "binding affinity" may also refer to the concentration of antibody that gives half-maximal binding ($EC_{50}$) determined with e.g. an ELISA assay or as determined by flow cytometry.

An antibody "which binds" an antigen of interest or antigens of interest, e.g. a SIRPα antigen target, is one that binds the antigen with sufficient affinity such that the antibody is useful as a therapeutic agent in targeting a cell or tissue expressing the antigen(s), and does not significantly cross-react with other proteins. For example, an anti-SIRPα antibody according to the present invention binds to human SIRPα—that is, at least to human SIRPα$_1$ and human SIRPα$_{BIT}$, preferably to cynomolgus SIRPα—and possibly to SIRPβ$_{1v1}$ and/or SIRPβ$_{1v2}$, whereas it does not bind to SIRPγ or unrelated proteins. In such embodiments, the extent of binding of the antibody to a "non-target" protein will preferably be less than about 10%, more preferably less than about 5%, more preferably less than about 2%, more preferably less than about 1% of the binding of the antibody to its particular target protein as determined by fluorescence activated cell sorting (FACS) analysis or radioimmunoprecipitation assay (RIPA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labelled target. In this case, specific binding is indicated if the binding of the labelled target to a probe is competitively inhibited by excess unlabelled target. The term "specific binding" or "specifically binds to" or is "specific for" particular polypeptide(s) or an epitope on particular polypeptide target(s) as used herein can be exhibited, for example, by a molecule having a $K_D$ for the target (which may be determined as described above) of at least about $10^{-7}$ M, preferably at least about $10^{-8}$ M, more preferably at least about $10^{-9}$ M, even more preferably at least about $10^{-10}$ M, even more preferably at least about $10^{-11}$ M, even more preferably at least about $10^{-12}$ M, or greater as determined by SPR at 25° C.

The term "low affinity" as used throughout the present specification is interchangeable with the phrases "does/do not bind" or "is/are not binding to", and refers to a binding affinity between an antibody and its antigen with an $EC_{50}$ larger than 1500 ng/ml as determined using an ELISA assay, and/or where limited or no specific binding is observed between the immobilized antigen and the antibody as preferably determined by SPR at 25° C., such as for example when the $K_D$ between an antibody and an antigen is higher than for example $10^{-7}$ M, higher than $10^{-6}$ M or even higher, as determined by SPR at 25° C.

The term "high affinity" as used herein refers to a binding affinity between an antibody and its antigen wherein the $K_D$ is typically less than $10^{-8}$ M, $10^{-9}$ M, $10^{-10}$ M, $10^{-11}$ M, or even lower, as determined by SPR at 25° C., as described in the Examples.

"Humanized" forms of non-human (e.g., rodent) antibodies are antibodies (e.g., non-human-human chimeric antibodies) that contain minimal sequences derived from the non-human antibody. Various methods for humanizing non-human antibodies are known in the art. For example, the antigen-binding CDRs in the variable regions (VRs) of the H chain (VH) and L chain (VL) are derived from antibodies from a non-human species, commonly mouse, rat or rabbit. These non-human CDRs are combined with human framework regions (FR1, FR2, FR3 and FR4) of the VH and VL regions, in such a way that the functional properties of the antibodies, such as binding affinity and specificity, are at least partially retained. Selected amino acids in the human FRs may be exchanged for the corresponding original non-human species amino acids to further refine antibody performance, such as to improve binding affinity, while retaining low immunogenicity. Alternatively, non-human antibodies can be humanized by modifying their amino acid sequence to increase similarity to antibody variants produced naturally in humans. For example, selected amino acids of the original non-human species FRs are exchanged for their corresponding human amino acids to reduce immunogenicity, while retaining the antibody's binding affinity. Exemplary methods for humanization of non-human antibodies are the method of Winter and co-workers (Jones et al. *Nature* 1986, 321, 522-525; Riechmann et al. *Nature* 1988, 332, 323-327; Verhoeyen et al. *Science* 1988, 239, 1534-1536), by substituting CDRs for the corresponding sequences of a human antibody.

The thus humanized variable regions will be typically combined with human constant regions. In general, the humanized antibody will comprise typically two variable domains in which all or substantially all of the CDRs correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 1986, 321, 522-525: Riechmann et al. *Nature* 1988, 332, 323-327; and Presta. *Curr. Op. Struct. Biol.* 1992, 2, 593-596. See also the following review articles and references cited therein: Vaswani and Hamilton. *Ann. Allergy. Asthma and Immunol.* 1998, 1, 105-115; Harris. *Biochem. Soc. Transactions* 1995, 23, 1035-1038; and Hurle and Gross. *Curr. Op. Biotech.* (1994), 5, 428-433.

The term "hypervariable region". "HVR", when used herein refers to the regions of an antibody variable domain which are hypervariable in sequence and/or form structurally defined loops that are responsible for antigen binding. Generally, antibodies comprise six hypervariable regions; three in the VH (H1, H2, H3), and three in the VL (L1, L2, L3). A number of hypervariable region delineations are in use and are encompassed herein. The hypervariable regions generally comprise amino acid residues from a "complementarity determining region" or "CDR" (e.g., residues 24-34 (L1), 50-56 (L2) and 89-97 (L3) in the VL, and around about 31-35 (H1), 50-65 (H2) and 95-102 (H3) in the VH when numbered in accordance with the Kabat numbering system: Kabat et al. Sequences of Proteins of Immunological Interest. 5th Ed. Public Health Service, National Institutes of Health, Bethesda, MD, 1991); and/or those residues from a "hypervariable loop" (e.g., residues 24-34 (L1), 50-56 (L2) and 89-97 (L3) in the VL, and 26-32 (H1), 52-56 (H2) and 95-101 (H3) in the VH when numbered in accordance with the Chothia numbering system: Chothia and Lesk. *J. Mol. Biol.* 1987, 196, 901-917); and/or those residues from a "hypervariable loop"/CDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system: Lefranc et al. *Nucl. Acids Res.* 1999, 27, 209-212. Ruiz et al. *Nucl. Acids Res.* 2000, 28, 219-221). Optionally, the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with Honneger and Plunkthun (*Mol. Biol.* 2001, 309, 657-670). Dondelinger et al. reviewed several of the numbering systems and their uses (Dondelinger et al. *Frontiers in Immunology*, 2018, 9, Art 2278). The HVR/CDRs of the antibodies and antigen-binding fragments of the invention are preferably defined and numbered in accordance with the Kabat numbering system.

"Framework" or "FR" residues are those variable domain residues other than the hypervariable region residues herein defined.

A "blocking" antibody or an "antagonist(ic)" antibody as used herein means an antibody which partially or fully prevents the natural ligand to bind. For example, an anti-SIRPα blocking antibody prevents CD47 to bind to SIRPα. Preferred blocking antibodies or antagonist(ic) antibodies substantially or completely inhibit the biological activity of the antigen.

The term "epitope" is the portion of a molecule that is bound by an antigen-binding protein, e.g. an antibody. The term includes any determinant capable of specifically binding to an antigen-binding protein, such as an antibody or to a T-cell receptor. An epitope can be contiguous or non-contiguous (e.g., in a polypeptide, amino acid residues that are not contiguous to one another in the polypeptide sequence but that within the context of the molecule—i.e. the tertiary structure—are bound by the antigen-binding protein). In certain embodiments, epitopes may be mimetic in that they comprise a three dimensional structure that is similar to an epitope used to generate the antigen-binding protein, yet comprise none or only some of the amino acid residues found in that epitope used to generate the antigen-binding protein. Most often, epitopes reside on proteins, but in some instances may reside on other kinds of molecules, such as nucleic acids. Epitope determinants may include chemically active surface groupings of molecules such as amino acids, sugar side chains, phosphoryl, sulfonyl or sulfate groups, and may have specific three dimensional structural characteristics, and/or specific charge characteristics. Generally, antibodies specific for a particular target antigen will preferentially recognize an epitope on the target antigen in a complex mixture of proteins and/or macromolecules. The extracellular domain of SIRPα may for example harbour epitopes in domain d1, d2 or d3.

The term "Fc region" herein is used to define a C-terminal region of an immunoglobulin heavy chain, including wild-type sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the C-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a wild-type sequence Fc region. Antibody effector functions vary with antibody isotype. Exemplary "effector functions" include complement component 1q (C1q) binding; CDC; Fc receptor binding; ADCC; ADCP; ADAP; down regulation of cell surface receptors (e.g. B-cell receptor; BCR), and B-cell activation. Such effector functions generally require the Fc region to be combined with a binding domain (e.g. an antibody variable domain) and can be assessed using various assays as disclosed, for example, in definitions herein.

A "wild-type sequence Fc region" comprises an amino acid sequence identical to the amino acid sequence of an Fc region found in nature. Wild-type sequence human Fc regions include a wild-type sequence human $IgG_1$ Fc region (non-A and A allotypes): a wild-type sequence human $IgG_2$ Fc region: a wild-type sequence human $IgG_3$ Fc region; and a wild-type sequence human $IgG_4$ Fc region as well as naturally occurring variants thereof.

A "variant Fc region" comprises an amino acid sequence which differs from that of a wild-type sequence Fc region by virtue of at least one amino acid modification, preferably one or more amino acid substitution(s). Preferably, the variant Fc region has at least one amino acid substitution compared to a wild-type sequence Fc region or to the Fc region of a parent polypeptide, e.g. from about one to about ten amino acid substitutions, and preferably from about one to about five amino acid substitutions in a wild-type sequence Fc region or in the Fc region of the parent polypeptide. The variant Fc region herein will preferably possess at least about 80% homology with a wild-type sequence Fc region and/or with an Fc region of a parent polypeptide, and most preferably at least about 90% homology therewith, more preferably at least about 95% homology therewith.

"Antibody-dependent cell-mediated cytotoxicity" (also referred to as "antibody-dependent cellular cytotoxicity") or "ADCC" refers to a form of cytotoxicity in which secreted Ig bound onto Fc receptors (FcRs) present on certain cytotoxic cells (e.g., Natural Killer (NK) cells, neutrophils, and monocytes/macrophages) enable these cytotoxic effector cells to bind specifically to an antigen-bearing target cell. The NK cells express FcγRIIIA only, whereas monocytes express FcγRI, FcγRIIA/B and FcγRIIIA. Neutrophils, which are the most abundant leukocytes in human blood, also mediate ADCC and this generally depends on FcγRIIA (Zhao et al. *Natl Acad Sci USA*. 2011, 108(45), 18342-7; Treffers et al. *Eur J Immunol*. 2018, 48(2), 344-354; Mat-lung et al. *Cell Rep*. 2018, 23(13), 3946-3959). FcR expression on haematopoietic cells is summarized in Table 2 on page 33 of Bruhns and Jönsson *Immunol Rev*. 2015, 268(1), 25-51. To assess ADCC activity of a molecule of interest, an in vitro ADCC assay, such as that described in U.S. Pat. No. 5,500,362 or 5,821,337 or such as described in the Examples may be performed. Useful effector cells for such assays include peripheral blood mononuclear cells (PBMC), containing a mixture of monocytes and NK cells, or isolated monocytes, neutrophils or NK cells. Alternatively, or additionally. ADCC activity of the molecule of interest may be assessed in vivo, e.g., in an animal model such as that disclosed in Clynes et al. *Proc. Natl. Acad. Sci.* (USA) 1998, 95, 652-656 or in well-known tumour models such as the B16F10 model described in Zhao et al. PNAS 2011, see above. "Fc receptor" or "FcR" describes a receptor that binds to the Fc region of an antibody. The preferred FcR is a wild-type sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M, in Daëron. *Annu. Rev. Immunol*. 1997, 15, 203-234). FcRs are reviewed in Ravetch and Kinet. *Annu. Rev. Immunol*. 1991, 9, 457-492; Capel et al. *Immunomethods* 1994, 4, 25-34; and de Haas et al. *J. Lab. Clin. Med*. 1995, 126, 30) 330-341. Other FcRs, including those to be identified in the future, are encompassed by the term "FcR" herein.

"Human effector cells" are leukocytes which express one or more FcRs and perform effector functions. Preferably, the cells express FcγRIIA (neutrophils or monocytes) or FcγRIIIA (NK cells or monocytes) and perform ADCC effector function. Examples of human leukocytes which mediate ADCC include PBMCs. NK cells, monocytes, macrophages, and neutrophils, with neutrophils being preferred. The effector cells may be isolated from a native source, e.g., from blood, preferably from human blood.

The term "therapeutic antibody" as used herein refers to an antibody or an antigen-binding fragment thereof as defined hereinabove, which is suitable for human therapy. Antibodies suitable for human therapy are of sufficient quality, safe and efficacious for treatment of specific human diseases. Quality may be assessed using the established guidelines for Good Manufacturing Practice: safety and efficacy are typically assessed using established guidelines of medicines regulatory authorities, e.g. the European Medicines Agency (EMA) or the United States Food and Drug Administration (FDA). These guidelines are well-known in the art. In the present specification the term "therapeutic antibody" does not include an anti-SIRPα antibody. The term "therapeutic antibody" as used herein means an anticancer antibody such as for example an anti-CD20, anti-HER2, anti-GD2, anti-EGFR or anti-CD70) antibody.

"Sequence identity" and "sequence similarity" can be determined by alignment of two amino acid sequences or two nucleotide sequences using global or local alignment algorithms, depending on the length of the two sequences. Sequences of similar lengths are preferably aligned using global alignment algorithms (e.g. Needleman and Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff. PNAS 1992, 89, 915-919). Sequence alignments and scores for percentage sequence identity may be determined using computer programs, such as the GCG Wisconsin Package. Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for water and both for protein and for DNA alignments, the default Gap opening penalty is 10.0 and the default gap extension penalty is 0.5: default scoring matrices are Blossum62 for proteins and DNAFull for DNA). When sequences have substantially different overall lengths, local alignments, such as those using the Smith Waterman algorithm, are preferred. Alternatively, percentage similarity or identity may be determined by searching against public databases, using algorithms such as FASTA. BLAST, etc.

Once two amino acid sequences are aligned using any of the above alignment programs, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Optionally, in determining the degree of amino acid similarity, so-called "conservative amino acid substitutions" may be taken into account. "Conservative amino acid substitutions" refer to the interchangeability of residues having similar side chains. For example, a group of amino acid residues with aliphatic side chains is glycine, alanine, valine, leucine and isoleucine; a group of a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Exemplary conservative substitutions for each of the naturally occurring amino acids are as follows: ala to ser; arg to lys; asn to gln or his; asp to glu; cys to ser or ala; gln to asn; glu to asp; gly to pro; his to asn or gln; ile to leu or val; leu to ile or val; lys to arg, gln or glu; met to leu or ile; phe to met, leu or tyr; ser to thr; thr to ser; trp to tyr; tyr to trp or phe; and val to ile or leu.

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and, optionally. 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The term "ADC" as used herein refers to a cytotoxic drug conjugated to a therapeutic antibody or an antigen-binding fragment thereof as defined hereinabove via a linker. The antibody or antigen-binding fragment thereof in the ADC is not an anti-SIRPα antibody. Typically, the cytotoxic drugs are highly potent, e.g. a duocarmycin, calicheamicin, pyrrolobenzodiazepine (PBD) dimer, maytansinoid or auristatin derivative. The linker may be cleavable, e.g. comprising the cleavable dipeptide valine-citrulline (vc) or valine-alanine (va), or non-cleavable, e.g. succinimidyl-4-(N-maleimidomethyl)cyclohexane-1-carboxylate (SMCC).

Antibodies of the Invention or Fragments Thereof

No approved therapeutics directed against SIRPα are currently available, although SIRPα has been shown to play an important role in tumour immune evasion mechanisms.

SIRPα (also known as CD172 antigen-like family member A, CD172a, SHPS-1, MyD-1) is a member of the family of signal regulatory proteins (SIRP), transmembrane glycoproteins with extracellular Ig-like domains present on immune effector cells. CD47 (also known as integrin-associated protein, IAP) is a ligand of SIRPα. The $NH_2$-terminal ligand binding domain of SIRPα is highly polymorphic (Takenaka et al. Nature Immun. 2007, 8(12), 1313-1323). However, this polymorphism does not influence binding to CD47 significantly. SIRPα$_{BIT}$ (v1) and SIRPα$_1$ (v2) are the two most common and most divergent (13 residues different) polymorphs (Hatherley et al. J. Biol. Chem. 2014, 289(14), 10024-10028). Besides by CD47, SIRPα can also be bound by surfactant proteins (SP-A and SP-D; Gardai et al 2003, Janssen et al. 2008, Fournier et al. 2012). In fact, CD47 can bind to SIRPα domain DI whereas SP-D can (simultaneously) bind to SIRPα domain D3. Like SIRPα, the surfactant proteins are implicated in innate immune/inflammatory responses towards e.g. apoptotic cells and microorganisms, involving macrophages and/or neutrophils. Other biochemically characterized human SIRP family members are SIRPβ$_1$, and SIRPγ. SIRP-family nomenclature is described in van den Berg et al. J Immunology 2005, 175 (12), 7788-9.

SIRPβ$_1$ (also known as CD172B) does not bind CD47 (van Beek et al. J. Immunol. 2005, 175(12), 7781-7787, 7788-7789) and at least two SIRPβ$_1$ polymorphic variants are known, SIRPβ$_{1v1}$ (ENSP00000371018) and SIRPβ$_{1v2}$ (ENSP00000279477). Although the natural ligand of SIRPβ$_1$ is yet unknown, in vitro studies using anti-SIRPβ$_1$ specific antibodies show that engagement of SIRPβ$_1$ promotes phagocytosis in macrophages by inducing the tyrosine phosphorylation of DAP12, Syk, and SLP-76, and the subsequent activation of a MEK-MAPK-myosin light chain kinase cascade (Matozaki et al. J. Biol. Chem. 2004, 279 (28), 29450-29460). Human SIRPβ$_1$ is expressed in myeloid cells, such as monocytes and granulocytes, but not in lymphocytes (Hayashi et al. J. of Biol Chem. 2004, 279(28); Dietrich et al. The Journal of Immunology 2000, 164, 9-12).

SIRPγ (also known as CD172G) is expressed on T-cells and activated NK-cells and binds CD47 with a 10-fold lower affinity as compared to SIRPα. The CD47-SIRPγ interaction is involved in the contact between antigen-presenting cells and T-cells, co-stimulating T-cell activation and promoting T-cell proliferation (Piccio et al. Blood 2005, 105, 2421-2427). Furthermore. CD47-SIRPγ interactions play a role in the transendothelial migration of T-cells (Stefanidakis et al. Blood 2008, 112, 1280-1289). WO2017/178653 discloses that due to the high similarity of sequences between SIRPα and SIRPγ, in particular in the region that interacts with CD47, the anti-SIRPα antibodies of the prior art also bind SIRPγ and have undesirable effects in humans such as inhibition of the proliferation of T-cells and a decrease of the immune response. Thus, an anti-SIRPα antibody of the invention, which does not bind to SIRPγ on T-cells, is hypothesized to have less or no inhibition of T-cell extravasation and/or less or no inhibition of transendothelial migration of T-cells as opposed to an anti-SIRPα antibody that does bind SIRPγ on T-cells.

The present invention relates to antagonistic anti-SIRPα antibodies which exhibit specific binding to at least the two predominant human SIRPα polymorphic variants SIRPα$_{BIT}$ and SIRPα$_1$. Preferably, the anti-SIRPα antibodies of the invention have reduced, low or most preferable no affinity to human SIRPγ (preferably as measured by $CD3^+$ T-cell FACS staining or surface plasmon resonance (preferably BiaCore™) according to the Example section). Preferably, the anti-SIRPα antibodies of the invention have reduced or low affinity to human SIRPβ$_{1v1}$ and/or human SIRPβ$_{1v2}$. Preferably, they increase the ADCC and/or ADCP of a therapeutic antibody. In a preferred embodiment, an anti-SIRPα antibody according to the invention also binds to cynomolgus monkey SIRPα.

Antagonistic antibodies have affinity for a specific antigen, and binding of the antibody to its antigen inhibits the function of an agonist or inverse agonist at receptors. In the present case, it is hypothesized that binding of an antagonistic anti-SIRPα antibody to SIRPα will prevent binding of CD47 to SIRPα. Antagonistic anti-SIRPα antibodies may bind to the same site where CD47 binds, i.e. an orthosteric site, preventing ligation of SIRPα by CD47 and consequently inhibiting the signalling that negatively regulates the Fc-receptor-dependent action of immune effector cells. Alternatively, antagonistic anti-SIRPα antibodies may bind in close vicinity to the site where CD47 binds, preventing interaction between CD47 and SIRPα through steric hindrance. Alternatively, an antibody distal to the CD47 interaction site May block CD47/SIRPα binding, for example by inducing a non-receptive conformation. Without wishing to be bound by any theory, it is hypothesized that blocking CD47-binding to SIRPα reduces or prevents the SIRPα signalling cascade, preferably by at least 60%, more preferably by at least 65%, at least 70%, at least 75%, most preferably by at least 80% when measured as indicated in the Examples at an anti-SIRPα antibody concentration of 3.3 µg/ml.

If an antibody binds also to other antigens than the target, such as for example to SIRPβ$_{1v1}$, SIRPβ$_{1v2}$ and SIRPγ, especially when the antibody is bound to those antigens with high affinity, such antigens may function as an antibody sink. Therefore, it is hypothesized that by minimizing off-target antibody binding, any antibody sink effect is reduced, which may result in efficacy at a lower dose or a higher effect at the same dose as compared to an antibody which further has the same characteristics.

The role of SIRPβ$_1$ is at present poorly understood. Therefore, it is preferred that an antibody of the present invention has relatively low binding affinities to both of the polymorphic variants (SIRPβ$_{1v1}$ and SIRPβ$_{1v2}$). However, it has been reported that activation of SIRPα (signalling via Immunoreceptor Tyrosine-based Inhibitory Motifs. ITIMs) and SIRPβ$_1$ (signalling via Immunoreceptor Tyrosine-based Activating Motifs. ITAMs) have opposing effects on the function of immunologic effector cells such as macrophages and PMNs/neutrophils (van Beek et al. J. Immunol. 2005, 175(12), 7781-7787, 7788-7789). Furthermore, it has been reported that triggering of the murine SIRPβ$_1$ receptor promotes phagocytosis in macrophages (Hayashi et al. *J. Biol. Chem.* 2004, 279 (28), 29450-29460). Liu et al. (*J. Biol. Chem.* 2005, 280 (43), 36132-36140) state that antibody-mediated ligation of SIRPβ$_1$ enhanced fMLP-driven PMN transepithelial migration. Without wishing to be bound by any theory, it is conceivable that anti-SIRPα blocking antibodies that also bind to SIRPβ$_1$ may have opposite effects on SIRPα and SIRPβ$_1$. In order to obtain maximal stimulation of an anti-tumour cell response, there is a need for antibodies that stimulate the activity of innate immune cells (e.g. PMNs/neutrophils and/or macrophages) by blocking SIRPα, while limiting or avoiding affecting SIRPβ$_1$ functioning, and simultaneously avoiding blocking adaptive immune cells, i.e. T-cells via binding to SIRPγ.

The antibodies of the present invention preferably have all of the following characteristics: (i) they are able to block CD47 binding to SIRPα$_{BIT}$ and SIRPα$_1$. (ii) they do not bind to human CD3$^+$ T-cells, and (iii) they are able to reduce SIRPα signalling. Preferably, they have reduced or low binding to SIRPβ$_{1v1}$ and/or SIRPβ$_{1v2}$ as measured by SPR. In contrast, known anti-SIRPα antibodies do not combine all desired specificities in a single antibody: all of the antibodies that are able to block CD47 binding to SIRPα$_{BIT}$ and SIRPα$_1$ also show binding to SIRPγ, whereas HEFLB is able to block SIRPα$_{BIT}$ without binding to SIRPγ, but does not have the ability to bind, let alone to block, SIRPα$_1$. Some other prior art antibodies that are able to bind both SIRPα$_1$ and SIRPα$_{BIT}$ without binding SIRPγ are not able to block CD47 binding to SIRPα and hence do not, or only at a high IC$_{50}$ concentration, block SIRPα signalling as measured by blocking of the recruitment of SHP-1. Despite being able to bind and block both SIRPα$_1$ and SIRPα$_{BIT}$, SE5A5 is not capable of blocking SIRPα signalling as measured by blocking of the recruitment of SHP-1. These characteristics are determined as described or referred to in the Examples.

In a first aspect, the invention provides an antibody or an antigen-binding fragment thereof that binds to SIRPα. An anti-SIRPα antibody of the invention preferably is an isolated antibody. Preferably, an anti-SIRPα antibody or an antigen-binding fragment thereof according to the invention binds to a primate SIRPα, more preferably to a human SIRPα, most preferably at least to the allelic variants SIRPα$_1$ and SIRPα$_{BIT}$. In a preferred embodiment, the antibody or antigen-binding fragment thereof has reduced binding as compared to prior art antibodies, more preferably has low binding, most preferably does not bind to SIRPγ, preferably as measured using human CD3$^+$ T-cell FACS staining according to the Examples or as Biacore experiment as shown in the Examples. Preferably, the antibody or antigen-binding fragment thereof increases the ADCC and/or ADCP of therapeutic antibodies. Preferably, an anti-SIRPα antibody of the invention increases the ADCC of 10 μg/ml of trastuzumab at 0.1 μg/ml of anti-SIRPα antibody at least 1.2; more preferably at least 1.3; more preferably at least 1.4; more preferably at least 1.5; more preferably at least 1.6; more preferably at least 1.7; more preferably at least 1.8; more preferably at least 1.9; more preferably at least 2.0; more preferably at least 2.1; more preferably at least 2.2: most preferably at least 2.3-fold as compared to trastuzumab alone, when measured using the DELFIA or $^{51}$Cr-release assay as used in the Examples.

Alternatively or in combination with any one of the other embodiments herein, in a preferred embodiment, an anti-SIRPα antibody of the invention is a humanized or human anti-SIRPα antibody and an antigen-binding fragment according to the invention is an antigen-binding fragment as defined hereinabove from a humanized or human anti-SIRPα antibody. More preferably, an anti-SIRPα antibody of the invention is a humanized anti-SIRPα antibody and an antigen-binding fragment of the invention is derived from a humanized anti-SIRPα antibody.

A humanized antibody according to the invention or an antigen-binding fragment thereof preferably elicits little to no immunogenic response against the antibody in a subject to which the antibody or fragment is administered. The original non-human antibody, for example a rodent antibody such as a mouse or a rat antibody, or a rabbit antibody or the non-human-human chimeric antibody may potentially elicit a human anti-non-human animal antibody response, in which case the humanized antibody according to the invention or antigen-binding fragment thereof elicits and/or is expected to elicit an immunogenic response at a substantially reduced level compared to the original non-human antibody or compared to the non-human-human chimeric antibody in a host subject. Preferably, the humanized antibody elicits and/or is expected to elicit a minimal or no human anti-non-human antibody response. Immunogenicity testing can be performed as known by methods in the art, such as described in Baker et al. *Immunogenicity of protein therapeutics* 2010, 1 (4), 314-322: Harding et al. *MAbs* 2010, 2(3), 256-265; or Joubert et al. *PLoS.One* 2016, 11 (8), e0159328. Most preferably, an antibody of the invention elicits a human anti-non-human animal antibody response, particularly a human anti-rabbit antibody (HARA) response, that is at or less than a clinically-acceptable level. It is further important that antibodies be humanized with retention of high affinity for the antigen and other favourable biological properties.

The CDRs may be determined using the approach of Kabat (in Kabat et al. Sequences of Proteins of Immunological Interest. 5th Ed. Public Health Service. National Institutes of Health. Bethesda. MD 1991. NIH publication no. 91-3242, pp. 662, 680, 689). Chothia (Chothia and Lesk. *J. Mol. Biol.* 1987, 196, 901-917: Antibody Engineering Vol. 2. Chapter 3 by Martin. 2010. Kontermann and Dübel Eds. Springer-Verlag Berlin Heidelberg) or IMGT (Lefranc. *The Immunologist* 1999, 7, 132-136). The CDRs of the heavy chain and the light chain as used herein are determined using Kabat and shown in the sequence listing under the SEQ ID NO as indicated in Table 1a. In the context of the present invention. Eu numbering is used for indicating the positions in the heavy chain and light chain constant regions of the antibody. The expression "Eu numbering" refers to the Eu index as in Kabat et al. Sequences of Proteins of Immunological Interest, 5th Ed. Public Health Service, National Institutes of Health, Bethesda, MD 1991, NIH publication no. 91-3242, pp. 662, 680, 689.

In a preferred embodiment, the present invention relates to an anti-SIRPα antibody, preferably a humanized anti-SIRPα antibody, or an antigen-binding fragment thereof, comprising heavy chain complementarity determining regions (HCDR) and light chain complementarity determining regions (LCDR) HCDR1. HCDR2. HCDR3. LCDR1. LCDR2 and LCDR3, selected from the group consisting of: (a) HCDR1 comprises SHGIS (SEQ ID NO: 36); HCDR2 comprises TIGTGVITYFASWAKG (SEQ ID NO:44); HCDR3 comprises GSAWNDPFDP (SEQ ID NO:45); LCDR1 comprises QASQSVYGNNDLA (SEQ ID NO: 39); LCDR2 comprises LASTLAT (SEQ ID NO:40); LCDR3 comprises LGGGDDEADNT (SEQ ID NO:41); (b) HCDR1 comprises SYVMG (SEQ ID NO:30); HCDR2 comprises IISSSGSPYYASWVNG (SEQ ID NO:31); HCDR3 comprises VGPLGVDYFNI (SEQ ID NO:32); LCDR1 comprises RASQSINSYLA (SEQ ID NO:33); LCDR2 comprises SASFLYS (SEQ ID NO:34); LCDR3 comprises QSWHYISRSYT (SEQ ID NO: 35); (c) HCDR1 comprises SHGIS (SEQ ID NO:36); HCDR2 comprises TIGTGVITYYASWAKG (SEQ ID NO:37); HCDR3 comprises GSAWNDPFDY (SEQ ID NO: 38); LCDR1 comprises QASQSVYGNNDLA (SEQ ID NO:39); LCDR2 comprises LASTLAT (SEQ ID NO:40); LCDR3 comprises LGGGDDEADNV (SEQ ID NO:46); (d) HCDR1 comprises SHGIS (SEQ ID NO:36); HCDR2 comprises TIGTGVITYYASWAKG (SEQ ID NO:37); HCDR3 comprises GSAWNDPFDY (SEQ ID NO:38); LCDR1 comprises QASQSVYGNNDLA (SEQ ID NO:39); LCDR2 comprises LASTLAT (SEQ ID NO:40); LCDR3 comprises LGGGDDEADNT (SEQ ID NO:41); and (e) HCDR1 comprises SHGIS (SEQ ID NO:36); HCDR2 comprises TIGTGGITYYASWAKG (SEQ ID NO:42); HCDR3 comprises GSAWNDPFDI (SEQ ID NO:43); LCDR1 comprises QASQSVYGNNDLA (SEQ ID NO: 39); LCDR2 comprises LASTLAT (SEQ ID NO:40); LCDR3 comprises LGGGDDEADNT (SEQ ID NO:41). More preferably, an anti-SIRPα antibody according to the invention or an antigen-binding fragment thereof comprises HCDR and LCDR selected from the group consisting of: (a) HCDR1 comprises SHGIS (SEQ ID NO:36); HCDR2 comprises TIGTGVITYFASWAKG (SEQ ID NO:44); HCDR3 comprises GSAWNDPFDP (SEQ ID NO:45); LCDR1 comprises QASQSVYGNNDLA (SEQ ID NO:39); LCDR2 comprises LASTLAT (SEQ ID NO:40); LCDR3 comprises LGGGDDEADNT (SEQ ID NO: 41); and (b) HCDR1 comprises SYVMG (SEQ ID NO:30); HCDR2 comprises IISSSGSPYYASWVNG (SEQ ID NO:31); HCDR3 comprises VGPLGVDYFNI (SEQ ID NO: 32); LCDR1 comprises RASQSINSYLA (SEQ ID NO:33); LCDR2 comprises SASFLYS (SEQ ID NO:34); LCDR3 comprises QSWHYISRSYT (SEQ ID NO:35).

Alternatively or in combination with any one of the preceding embodiments, in a preferred embodiment, an anti-SIRPα antibody or an antigen-binding fragment thereof according to the invention, has one or more of the following functional properties.

Preferably, the anti-SIRPα antibody or the antigen-binding fragment thereof binds human SIRPα$_1$ with a K$_D$ below $10^{-9}$ M, more preferably with a K$_D$ below $10^{-10}$ M, even more preferably with a K$_D$ below $10^{-11}$ M, as analysed by surface plasmon resonance (preferably BiaCore™) at 25° C. using human SIRPα$_1$ extracellular domain as shown in SEQ ID NO:51. Preferably, the anti-SIRPα antibody or the antigen-binding fragment thereof binds human SIRPα$_{BIT}$ with a K$_D$ below $10^{-9}$ M, more preferably with a K$_D$ below $10^{-10}$ M, even more preferably with a K$_D$ below $10^{-11}$ M as analysed by surface plasmon resonance (preferably BiaCore™) at 25° C. using human SIRPα$_{BIT}$ extracellular domain as shown in SEQ ID NO:52. Preferably, the anti-SIRPα antibody or the antigen-binding fragment thereof binds cynomolgus monkey SIRPα with a K$_D$ below $10^{-7}$ M, more preferably with a K$_D$ below $10^{-8}$ M, even more preferably with a K$_D$ below $10^{-9}$ M as analysed by surface plasmon resonance (preferably BiaCore™) at 25° C. using cynomolgus SIRPα extracellular domain as shown in SEQ ID NO:56. Preferably, the anti-SIRPα antibody or the antigen-binding fragment thereof does not detectably bind human SIRPγ as measured by CD3$^+$ T-cell FACS staining according to the Examples. Preferably, the anti-SIRPα antibody or the antigen-binding fragment thereof does not bind human SIRPγ as analysed by surface plasmon resonance (preferably BiaCore™) at 25° C. using human SIRPγ extracellular domain as shown in SEQ ID NO:55. Preferably, the anti-SIRPα antibody or the antigen-binding fragment thereof is not immunogenic as determined by IL-2 ELIspot and/or T-cell proliferation assay. Preferably, the anti-SIRPα antibody or the antigen-binding fragment thereof binds human SIRPβ$_{1v2}$ with moderate to low affinity as analysed by surface plasmon resonance (preferably BiaCore™) at 25° C. using human SIRPβ 1.2 extracellular domain as shown in SEQ ID NO:54. Preferably, the K$_D$ is above $10^{-10}$ M, more preferably above $10^{-9}$ M. Preferably, in combination with the moderate to low affinity binding of SIRPβ$_{1v2}$, the anti-SIRPα antibody or the antigen-binding fragment thereof binds SIRPβ$_{1v1}$ with a K$_D$ above $10^{-11}$ M, more preferably above $3\times10^{-11}$ M, even more preferably above $10^{-10}$ M, even more preferably above $10^{-9}$ M as analysed by surface plasmon resonance (preferably BiaCore™) at 25° C. using human SIRPβ$_{1v1}$ extracellular domain as shown in SEQ ID NO:53. These assays are described or referred to in the Examples.

Alternatively or in combination with any one of the preceding embodiments, in a preferred embodiment, the invention relates to an anti-SIRPα antibody or an antigen-binding fragment thereof as defined hereinabove, wherein the antibody shows specific binding to both human SIRPα$_{BIT}$ and human SIRPα$_1$ and does not detectably bind to human SIRPγ using CD3 T-cell staining and/or SPR, both as described in the Examples. In an embodiment, the anti-SIRPα antibody or an antigen-binding fragment thereof binds human SIRPα$_{BIT}$ with a K$_D$ below $10^{-9}$ M, more preferably with a K$_D$ below $10^{-10}$ M, even more preferably with a K$_D$ below $10^{-11}$ M; and binds human SIRPα$_1$ with a K$_D$ below $10^{-8}$ M, more preferably with a K$_D$ below $10^{-9}$ M, more preferably with a K$_D$ below $10^{-10}$ M, even more preferably with a K$_D$ below $10^{-11}$ M, wherein the K$_D$ is measured with SPR at 25° C. (see Examples). Preferably, the anti-SIRPα antibody of the invention or an antigen-binding fragment thereof binds to SIRPγ with a K$_D$ higher than $10^{-8}$ M, more preferably with a K$_D$ higher than $10^{-7}$ M, more preferably with a K$_D$ higher than $10^{-6}$ M, even more preferably with a K$_D$ higher than $10^{-5}$ M, most preferably, where no binding can be detected, wherein the K$_D$ is measured with SPR at 25° C. (see Examples).

Alternatively or in combination with any one of the preceding embodiments, in a preferred embodiment, an anti-SIRPα antibody or an antigen-binding fragment thereof according to the invention: (a) binds human SIRPα$_1$ with a K$_D$ below $10^{-8}$ M, more preferably with a K$_D$ below $10^{-9}$ M, more preferably with a K$_D$ below $10^{-10}$ M, even more preferably with a K$_D$ below $10^{-11}$ M, as analysed by surface plasmon resonance (SPR; preferably by BiaCore™) at 25° C. using human SIRPα$_1$ extracellular domain as shown in SEQ ID NO:51 (see Examples); (b) binds human SIRPα$_{BIT}$ with a K$_D$ below $10^{-9}$ M, more preferably with a K$_D$ below $10^{-10}$ M, even more preferably with a K$_D$ below $10^{-11}$ M as analysed by SPR (preferably by BiaCore™) at 25° C. using human SIRPα$_{BIT}$ extracellular domain as shown in SEQ ID NO:52 (see Examples); (c) blocks CD47 binding to SIRPα and SIRPα$_{BIT}$, preferably as analysed by dissociation from captured CD47 by SPR (preferably by BiaCore™), more preferably as described in Example 6; and (d) does not detectably bind human SIRPγ as measured by CD3 T-cell flow cytometry, preferably fluorescence-activated cell sorting (FACS) staining, and/or SPR, both as described in the Examples. Preferably, in combination with the previous embodiment, the anti-SIRPα antibody or the antigen-binding fragment thereof binds human SIRPβ$_{1v2}$ with moderate to low affinity as analysed by SPR (preferably by BiaCore™) at 25° C. using human SIRPβ$_{1v2}$ extracellular domain as shown in SEQ ID NO:54. Preferably, the K$_D$ is above $10^{-10}$ M, more preferably above $10^{-9}$ M. Preferably, in combination with the moderate to low affinity binding of SIRPβ$_{1v2}$, the anti-SIRPα antibody or the antigen-binding fragment thereof binds SIRPβ$_{1v1}$ with a K$_D$ above $10^{-11}$ M, more preferably above $3 \times 10^{-11}$ M, even more preferably above $10^{-10}$ M, even more preferably above $10^{-9}$ M as analysed by SPR (preferably by BiaCore™) at 25° C. using human SIRPβ$_{1v1}$ extracellular domain as shown in SEQ ID NO:53. These assays are described or referred to in the Examples.

Alternatively or in combination with any one of the preceding embodiments, in a preferred embodiment the invention relates to an anti-SIRPα antibody or an antigen-binding fragment thereof according to the invention, wherein: (a) the heavy chain variable domain of the antibody comprises 4 heavy chain framework regions. HFR1 to HFR4, and 3 complementarity determining regions HCDR1 to HCDR3 that are operably linked in the order HFR1-HCDR1-HFR2-HCDR2-HFR3-HCDR3-HFR4, wherein each of the heavy chain framework regions has at least 90%, at least 91%, at least 92%, at least 95%, at least 97%, at least 98%, at least 99% or preferably has 100% amino acid identity with the framework amino acid sequence of any one of SEQ ID NOs 1, 3-6, 8, 10-15, or wherein HFR1 to HFR4 differ from any one of SEQ ID NOs 1, 3-6, 8, 10-15 in one or more of the amino acid substitutions as defined in Tables 8 to 11; and (b) the light chain variable domain of the antibody comprises 4 light chain framework regions. LFR1 to LFR4, and 3 complementarity determining regions LCDR1 to LCDR3 that are operably linked in the order LFR1-LCDR1-LFR2-LCDR2-LFR3-LCDR3-LFR4, wherein each of the light chain framework regions has at least 90%, at least 91%, at least 92%, at least 95%, at least 97%, at least 98%, at least 99% or preferably has 100% amino acid identity with the framework amino acid sequence of any one of SEQ ID NOs 2, 7 or 9, or wherein LFR1. LFR2 and/or LFR4 differ from any one of SEQ ID NOs 2, 7 or 9 in one or more amino acid substitutions as defined in Tables 12 to 14. In a preferred embodiment, the invention relates to an anti-SIRPα antibody or an antigen-binding fragment thereof according to the invention, wherein: (a) the heavy chain variable domain of the antibody comprises 4 heavy chain framework regions. HFR1 to HFR4, and 3 complementarity determining regions HCDR1 to HCDR3 that are operably linked in the order HFR1-HCDR1-HFR2-HCDR2-HFR3-HCDR3-HFR4, wherein each of the heavy chain framework regions has at least 90%, at least 91%, at least 92%, at least 95%, at least 97%, at least 98%, at least 99% or preferably has 100% amino acid identity with the framework amino acid sequence of SEQ ID NO 8, or wherein HFR1 to HFR4 differ from SEQ ID NO 8 in one or more of the amino acid substitutions as defined in Tables 8 to 11 (corresponding to SEQ ID NO:77, SEQ ID NO:78, SEQ ID NO: 79, and SEQ ID NO:80, respectively); and (b) the light chain variable domain of the antibody comprises 4 light chain framework regions. LFR1 to LFR4, and 3 complementarity determining regions LCDR1 to LCDR3 that are operably linked in the order LFR1-LCDR1-LFR2-LCDR2-LFR3-LCDR3-LFR4, wherein each of the light chain framework regions has at least 90%, at least 91%, at least 92%, at least 95%, at least 97%, at least 98%, at least 99% or preferably has 100% amino acid identity with the framework amino acid sequence of SEQ ID NO 9, or wherein LFR1. LFR2 and/or LFR4 differ from SEQ ID NO 9 in one or more amino acid substitutions as defined in Tables 12 to 14 (corresponding to SEQ ID NO:81, SEQ ID NO:82, and SEQ ID NO:83, respectively).

Preferably, the amino acid residues that are present at each position (according to Kabat numbering) of the FR1, FR2. FR3 and FR4 of the variable domain of the heavy chain are as indicated in Tables 8 to 11 (i.e., SEQ ID NO: 77 to SEQ ID NO:80) for FR1, FR2. FR3 and FR4, respectively, or a conservative amino acid substitution thereof, and the amino acid residues that are present at each position (according to Kabat numbering) of the FR1, FR2, and FR4 of the variable domain of the light chain preferably are as indicated in Tables 12 to 14 (i.e., SEQ ID NO:81 to SEQ ID NO:83) for FR1, FR2, and FR4, respectively or a conservative amino acid substitution thereof. More preferably, however, the framework amino acid residue for any position within the framework region is selected from the amino acid residues shown in the corresponding position in Tables 8 to 14 (i.e., SEQ ID NO:77 to SEQ ID NO:83).

An anti-SIRPα antibody or an antigen-binding fragment thereof according to the invention, preferably comprises HCDR, LCDR and heavy chain and light chain framework regions selected from the group consisting of: (a) HCDR1 comprises SEQ ID NO:36; HCDR2 comprises SEQ ID NO:44; HCDR3 comprises SEQ ID NO:45; LCDR1 comprises SEQ ID NO: 39; LCDR2 comprises SEQ ID NO:40; LCDR3 comprises SEQ ID NO:41; HFR1 to HFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO:8, or wherein HFR1 to HFR4 differ from SEQ ID NO:8 in one or more amino acid substitutions as defined in Tables 8 to 11 (i.e., SEQ ID NO:77 to SEQ ID NO: 80); LFR1 to LFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO:9, or wherein LFR1. LFR2 and/or LFR4 differ from SEQ ID NO:9 in one or more amino acid substitutions as defined in Tables 12 to 14 (i.e., SEQ ID NO:81 to SEQ ID NO:83); (b) HCDR1 comprises SEQ ID NO:30; HCDR2 comprises SEQ ID NO:31; HCDR3 comprises SEQ ID NO:32; LCDR1 comprises SEQ ID NO:33; LCDR2 comprises SEQ ID NO:34; LCDR3 comprises SEQ ID NO:35; HFR1 to HFR4 having at least 90% more preferably at least 91%, more preferably at least 92%, more preferably at least 95%, more preferably at least 97%, more preferably at least 98%, more preferably at least 99% or most preferably 100% amino acid identity with the framework amino acid sequences of any one of SEQ ID NOs 1, 3, 4, 5, 14 or 15, or wherein HFR1 to HFR4 differ from any one of SEQ ID NOs 1, 3, 4, 5, 14 or 15 in one or more amino acid substitutions as defined in Tables 8 to 11 (i.e., SEQ ID NO:77 to SEQ ID NO:80); LFR1 to LFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO: 2, or wherein LFR1. LFR2 and/or LFR4 differ from SEQ ID NO:2 in one or more amino acid substitutions as defined in Tables 12 to 14 (i.e., SEQ ID NO:81 to SEQ ID NO:83); (c) HCDR1 comprises SEQ ID NO:36; HCDR2 comprises SEQ ID NO:37; HCDR3 comprises SEQ ID NO:38; LCDR1 comprises SEQ ID NO:39; LCDR2 comprises SEQ ID NO:40; LCDR3 comprises SEQ ID NO:46; HFR1 to HFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NOs 6 or 13, or wherein HFR1 to HFR4 differ from SEQ ID NOs 6 or 13 in one or more amino acid substitutions as defined in Tables 8 to 11 (i.e., SEQ ID NO:77 to SEQ ID NO:80); LFR1 to LFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO:7, or wherein LFR1. LFR2 and/or LFR4 differ from SEQ ID NO: 7 in one or more amino acid substitutions as defined in Tables 12 to 14 (i.e., SEQ ID NO:81 to SEQ ID NO:83); (d) HCDR1 comprises SEQ ID NO:36; HCDR2 comprises SEQ ID NO:37; HCDR3 comprises SEQ ID NO:38; LCDR1 comprises SEQ ID NO:39; LCDR2 comprises SEQ ID NO:40; LCDR3 comprises SEQ ID NO:41; HFR1 to HFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NOs: 6, 10 or 11, or wherein HFR1 to HFR4 differ from any one of SEQ ID NOs 6, 10 or 11 in one or more amino acid substitutions as defined in Tables 8 to 11 (i.e., SEQ ID NO:77 to SEQ ID NO:80); LFR1 to LFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO:9, or wherein LFR1. LFR2 and/or LFR4 differ from SEQ ID NO:9 in one or more amino acid substitutions as defined in Tables 12 to 14 (i.e., SEQ ID NO:81 to SEQ ID NO:83); and (e) HCDR1 comprises SEQ ID 20) NO:36; HCDR2 comprises SEQ ID NO:42; HCDR3 comprises SEQ ID NO:43; LCDR1 comprises SEQ ID NO:39; LCDR2 comprises SEQ ID NO:40; LCDR3 comprises SEQ ID NO:41; HFR1 to HFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO:12, or wherein HFR1 to HFR4 differ from SEQ ID NO:12 in one or more amino acid substitutions as defined in Tables 8 to 11 (i.e., SEQ ID NO: 77 to SEQ ID NO:80); LFR1 to LFR4 having at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO:9, or wherein LFR1. LFR2 and/or LFR4 differ from SEQ ID NO:9 in one or more amino acid substitutions as defined in Tables 12 to 14 (i.e., SEQ ID NO:81 to SEQ ID NO:83). More preferably, an anti-SIRPα antibody or an antigen-binding fragment thereof according to the invention, comprises: (a) HCDR1 comprising SEQ ID NO:36; HCDR2 comprising SEQ ID NO:44; HCDR3 comprising SEQ ID NO:45; LCDR1 comprising SEQ ID NO:39; LCDR2 comprising SEQ ID NO:40; and LCDR3 comprising SEQ ID NO:41; wherein (i) HFR1 to HFR4 have at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO: 8, or wherein HFR1 to HFR4 differ from SEQ ID NO:8 in one or more amino acid substitutions as defined in Tables 8 to 11 (i.e., SEQ ID NO:77 to SEQ ID NO:80); and (ii) LFR1 to LFR4 have at least 90%, more preferably at least 91%, more preferably at least 92%, more preferably at least 95%, more preferably at least 97%, more preferably at least 98%, more preferably at least 99% or most preferably 100% amino acid identity with the framework amino acid sequences of SEQ ID NO:9, or wherein LFR1. LFR2 and/or LFR4 differ from SEQ ID NO: 9 in one or more amino acid substitutions as defined in Tables 12 to 14 (i.e., SEQ ID NO:81 to SEQ ID NO:83).

Alternatively or in combination with a previous embodiment, in a preferred embodiment, the framework substitutions are limited to the residues provided in Tables 8 to 14 (i.e., SEQ ID NO:77 to SEQ ID NO:83). Thus, it is preferred that no substitutions are made at other locations within the framework regions and it is also preferred that substitutions are limited to the residues shown in Tables 8 to 14 (i.e., SEQ ID NO:77 to SEQ ID NO:83) or a conservative amino acid substitution thereof.

Alternatively or in combination with a previous embodiment, in a preferred embodiment an anti-SIRPα antibody according to the present invention or an antigen-binding fragment thereof comprises a HCVR and a LCVR selected from the group consisting of: (a) HCVR amino acid sequence of SEQ ID NO:8; LCVR amino acid sequence of SEQ ID NO:9; (b) HCVR amino acid sequence of SEQ ID NO:1; LCVR amino acid sequence of SEQ ID NO:2; (c) HCVR amino acid sequence of SEQ ID NO:3; LCVR amino acid sequence of SEQ ID NO:2; (d) HCVR amino acid sequence of SEQ ID NO:4; LCVR amino acid sequence of SEQ ID NO:2; (e) HCVR amino acid sequence of SEQ ID NO:5; LCVR amino acid sequence of SEQ ID NO:2; (f) HCVR amino acid sequence of SEQ ID NO:6; LCVR amino acid sequence of SEQ ID NO:7; (g) HCVR amino acid sequence of SEQ ID NO:10; LCVR amino acid sequence of SEQ ID NO:9; (h) HCVR amino acid sequence of SEQ ID NO:6; LCVR amino acid sequence of SEQ ID NO:9; (i) HCVR amino acid sequence of SEQ ID NO:11; LCVR amino acid sequence of SEQ ID NO:9; (j) HCVR amino acid sequence of SEQ ID NO: 12; LCVR amino acid sequence of SEQ ID NO:9; (k) HCVR amino acid sequence of SEQ ID NO: 13; LCVR amino acid sequence of SEQ ID NO:7; (l) HCVR amino acid sequence of SEQ ID NO:14; LCVR amino acid sequence of SEQ ID NO:2; and (m) HCVR amino acid sequence of SEQ ID NO: 15; LCVR amino acid sequence of SEQ ID NO:2. More preferably, an anti-SIRPα antibody according to the present invention or an antigen-binding fragment thereof comprises a HCVR and a LCVR selected from the group consisting of: (a) HCVR amino acid sequence of SEQ ID NO: 8 and LCVR amino acid sequence of SEQ ID NO:9; (b) HCVR amino acid sequence of SEQ ID NO:1 and LCVR amino acid sequence of SEQ ID NO:2; (c) HCVR amino acid sequence of SEQ ID NO:3 and LCVR amino acid sequence of SEQ ID NO:2; (d) HCVR amino acid sequence of SEQ ID NO:4 and LCVR amino acid sequence of SEQ ID NO:2; (e) HCVR amino acid sequence of SEQ ID NO:5 and LCVR amino acid sequence of SEQ ID NO:2; (f) HCVR amino acid sequence of SEQ ID NO:14 and LCVR amino acid sequence of SEQ ID NO: 2; and (g) HCVR amino acid sequence of SEQ ID NO: 15 and LCVR amino acid sequence of SEQ ID NO:2. Most preferably, an anti-SIRPα antibody according to the present invention or an antigen-binding fragment thereof comprises a HCVR amino acid sequence of SEQ ID NO: 8 and a LCVR amino acid sequence of SEQ ID NO:9.

Besides binding to both human (hu)SIRPα$_{BIT}$ and (hu)SIRPα$_1$, the antibodies according to the invention may also bind to cynomolgus monkey (cy)SIRPα, enabling in vivo studies in a relevant animal model. Affinity of the antibodies according to the invention for SIRPα from other species is not excluded.

Without wishing to be bound by any theory, it is believed that an antibody or antigen-binding fragment thereof according to the invention may act by one of the following. An antibody of the invention may bind to the same site where CD47 binds, preventing binding of SIRPα by CD47 and consequently inhibiting the signalling that negatively regulates the Fc-receptor-dependent action of immune effector cells.

The anti-SIRPα antibodies or antigen-binding fragments thereof according to the invention preferably are more specific than known anti-SIRPα antibodies, and show excellent affinity for both human SIRPα$_{BIT}$ and human SIRPα$_1$, while they have reduced, more preferably low affinity, even more preferably no detectable affinity for human SIRPγ, preferably as measured using human CD3$^+$ T-cell staining according to the Examples.

In some embodiments, an anti-SIRPα antibody of the invention comprises a light chain and/or a heavy chain antibody constant region. Any antibody constant regions known in the art can be used. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant region, e.g., a human alpha-, delta-, epsilon-, gamma-, or mu-type heavy chain constant region. In one embodiment, the light or heavy chain constant region is a fragment, derivative, variant, or mutein of a naturally occurring constant region.

In one particular embodiment, an anti-SIRPα antibody according to the invention comprises an Fc region that binds to activating Fc receptors present on human immune effector cells. Such an anti-SIRPα antibody may be suitable for monotherapy of SIRPα-positive tumours, preferably renal cell carcinoma or melanoma, as it can induce ADCC and/or ADCP (Yanagita et al. *JCI Insight* 2017, 2 (1), e89140). Without wishing to be bound by any theory, it is believed that destruction of cancer cells by such an antibody occurs, at least in part, through ADCC. Human immune effector cells possess a variety of activating Fc receptors, which upon ligation trigger phagocytosis, trogoptosis, perforin and granzyme release, cytokine release, ADCC, ADCP, ADAP and/or other mechanisms. Examples of these receptors are Fcγ receptors, e.g. FcγRI (CD64), FcγRIIA (CD32a), FcγRIIIA (CD16a), FcγRIIIB (CD16b), FcγRIIC (CD32c) and the Fcα receptor FcαRI (CD89). The various natural antibody isotypes bind to a variety of these receptors. E.g. IgG$_1$ binds to FcγRI, FcγRIIA, FcγRIIC, FcγRIIIA, FcγRIIIB; IgG$_2$ binds to FcγRIIA, FcγRIIC, FcγRIIIA; IgG$_3$ binds to FcγRI, FcγRIIA, FcγRIIC, FcγRIIIA, FcγRIIIB; IgG$_4$ binds to FcγRI, FcγRIIA, FcγRIIC, FcγRIIIA; and IgA binds to FcαRI.

In a preferred embodiment, an anti-SIRPα antibody according to the invention comprises an Fc region of the IgA or IgG isotype. More preferred is an anti-SIRPα antibody comprising an Fc region of the IgG$_1$, IgG$_2$, IgG$_3$ or IgG$_4$ isotype; the IgG$_1$, IgG$_2$ or IgG$_4$ isotype is even more preferred. Most preferred is an anti-SIRPα antibody comprising an Fc region of the IgG$_1$ isotype, preferably as shown in SEQ ID NO:24.

Figure 2:
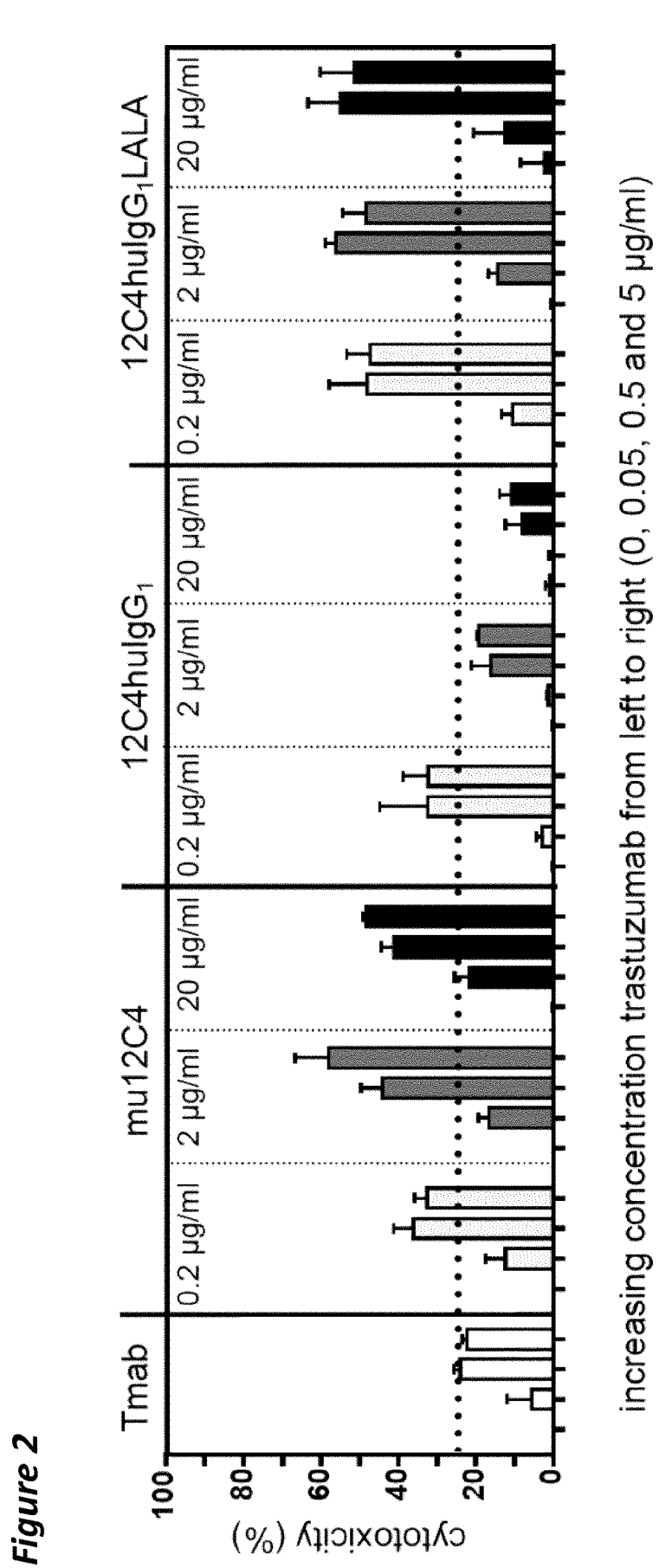
FIG. 2. Comparison of the ADCC measured in % cytotoxicity of trastuzumab (Tmab) alone, trastuzumab in combination with the murine 12C4 anti-SIRPα antibody (mu12C4), trastuzumab in combination with an antibody wherein murine 12C4 variable regions are grafted onto the human IgG$_1$ constant region (12C4huIgG$_1$), and trastuzumab in combination with an antibody wherein murine 12C4 variable regions are grafted onto the human IgG$_1$ constant region comprising the amino acid substitutions L234A and L235A (12C4huIgG$_1$LALA; also indicated as 12C4-LALA herein), measured using SKBR3 HER2-positive breast cancer cells as target cells and human neutrophils as effector cells. Neutrophils were isolated from human donors carrying two SIRPα$_{BIT}$ alleles. Increasing concentrations of trastuzumab were employed: 0, 0.05, 0.5 and 5 µg/ml, respectively, as well as increasing concentrations of each anti-SIRPα antibody (0.2, 2 and 20 µg/ml, respectively).

Although the anti-SIRPα antibodies comprising an Fc region that binds to activating Fc receptors present on human immune effector cells are suitable to treat cancers expressing CD47 in a combination therapy with a therapeutic antibody, in vitro ADCC experiments of a chimeric anti-SIRPα IgG$_1$ antibody in combination with a therapeutic antibody (trastuzumab) comprising a human Fc region that binds to activating Fc receptors present on human immune effector cells (i.e. antibodies that are able to induce ADCC and/or ADCP) did not show the increase in ADCC as had been expected on the basis of earlier results using murine antibodies (FIG. 2). Without wishing to be bound by any theory, it is believed that the Kurlander effect may occur (Kurlander *J Immunol* 1983, 131 (1), 140-147), for the anti-SIRPα antibody, which may compete with the therapeutic antibody (in this case trastuzumab) for binding to the activating Fc receptor on the immune effector cell (in this case the neutrophilic granulocyte). Thus, Fc tail of the anti-SIRPα may bind in cis to the Fc receptor on the relevant phagocytic immune effector cell e.g. granulocyte, macrophage or dendritic cell thereby reducing or preventing ADCC and/or ADCP and/or ADAP. Consequently, reduction of binding of the Fc region of the anti-SIRPα antibody to the activating Fc receptors present on human immune effector cells, for instance by modifying the Fc tail, was shown to improve ADCC by a therapeutic antibody (trastuzumab; FIG. 2). Therefore, in a preferred embodiment, the present invention relates to an anti-SIRPα antibody that exhibits reduced binding to and/or low affinity for activating Fc receptors present on human immune effector cells and that can be advantageously used in a combination therapy with a therapeutic antibody as is further explained in section "Use of the antibodies of the invention or fragments thereof". Such an anti-SIRPα antibody may comprise a native Fc region that has a low affinity for the Fc receptor, such as for example IgG$_4$ or IgG$_2$ Fc, or such an anti-SIRPα antibody may comprise a modified Fc region in which one or more amino acids have been substituted by (an) other amino acid(s) when compared to a similar unmodified Fc region. Alternatively, enzymatic deglycosylation reduces binding of the Fc to Fc gamma receptors, without requiring amino acid mutations. Reduced binding in this context means that the affinity of the anti-SIRPα antibody comprising a modified Fc region for the activating Fc receptors is less than the affinity of an anti-SIRPα antibody with the same variable regions comprising a similar unmodified Fc region. Preferably, the affinity decreases at least 2-fold, preferably at least 3-fold, preferably at least 4-fold, preferably at least 5-fold, preferably at least 10-fold, preferably at least 50-fold, preferably at least 100-fold, preferably at least 1000-fold. The binding affinity of antibodies for activating Fc receptors is typically measured using SPR or flow cytometry using methods known in the art, e.g. the method of Harrison et al. in *J. Pharm. Biomed. Anal.* 2012, 63, 23-28. Anti-SIRPα antibodies exhibiting reduced binding to or low affinity for the human Fcα or Fcγ receptor in combination with a therapeutic antibody are especially effective in cellular destruction of cancer cells by increasing ADCC and/or ADCP 25 and/or ADAP of immune effector cells. Typically, the Fc region of an anti-SIRPα antibody according to the invention is modified to reduce binding to activating Fc receptors present on human immune effector cells.

In a preferred embodiment, an anti-SIRPα antibody according to the invention comprises a modified Fc region that exhibits reduced binding to or low affinity for, preferably no binding to, a human Fcα or Fcγ receptor. For instance, IgG$_1$ binding to an Fcγ receptor can be reduced by substituting one or more IgG$_1$ amino acids selected from the group consisting of L234, L235, G237, D265, D270, N297, A327, P328, and P329 (Eu numbering); IgG$_2$ binding can be reduced by introducing e.g. one or more of the following amino acid substitutions: V234A, G237A, P238S, H268A, V309L, A330S, and/or P331S; or H268Q, V309L, A330S, and/or P331S (numbering analogue to IgG$_1$ Eu numbering) (Vafa et al. *Methods* 2014, 65, 114-126); IgG$_3$ binding can be reduced by introducing e.g. amino acid substitutions L234A and L235A, or amino acid substitutions L234A, L235A and P331S (Leoh et al. *Mol. Immunol.* 2015, 67, 407-415); and IgG$_4$ binding can be reduced by introducing e.g. amino acid substitutions S228P, F234A and/or L235A ((numbering analogue to IgG$_1$ Eu numbering) (Parekh et al. *mAbs* 2012, 4(3), 310-318). IgA binding to the Fcα receptor can be reduced by introducing e.g. one or more of the amino acid substitutions L257R, P440A, A442R, F443R, and/or P440R (sequential numbering. Pleass et al. *J. Biol. Chem.* 1999, 271(33), 23508-23514).

Preferably, an anti-SIRPα antibody according to the invention comprises a modified Fc region that exhibits reduced binding to or low affinity for, preferably no binding to, a human Fcα or Fcγ receptor compared to the same anti-SIRPα antibody comprising a wild-type Fc region. More preferably, the modified Fc region is an Fc region of the IgG isotype. Even more preferably, the modified Fc region is an Fc region of the IgG$_1$, IgG$_2$ or IgG$_4$ isotype. In a preferred embodiment, an anti-SIRPα antibody according to the invention comprises a modified human IgG$_1$ Fc region comprising one or more amino acid substitutions at one or more positions selected from the group consisting of L234, L235, G237, D265, D270, N297, A327, P328, and P329 (Eu numbering).

In a preferred embodiment, an anti-SIRPα antibody of the invention comprises a modified human IgG$_1$ Fc region comprising one or more amino acid substitutions selected from the group consisting of L234A, L234E, L235A, G237A, D265A, D265E, D265N, D270A, D270E, D270N, N297A, N297G, A327Q, P328A, P329A and P329G. More preferably, the one or more amino acid substitutions are selected from the group consisting of L234A, L234E, L235A, G237A, D265A, D265E, D265N, N297A, P328A, P329A and P329G. Alternatively preferred, the one or more amino acid substitutions are selected from the group consisting of L234A, L234E, L235A, G237A, D265A, D265E, D265N, D270A, D270E, D270N, A327Q, P328A, P329A and P329G. Even more preferably, an anti-SIRPα antibody of the invention comprises a modified human IgG$_1$ Fc region comprising one or more amino acid substitutions selected from the group consisting of L234A, L234E, L235A, G237A, D265A, D265E, D265N, P328A, P329A and P329G. In a preferred embodiment, the modified human IgG$_1$ Fc region comprises amino acid substitutions: (i) L234A and L235A; (ii) L234E and L235A; (iii) L234A, L235A and P329A; or (iv) L234A, L235A and P329G. More preferably, the modified human IgG$_1$ Fc region comprises amino acid substitutions: (i) L234A and L235A; or (ii) L234E and L235A. Most preferably, the modified human IgG$_1$ Fc region comprises amino acid substitutions L234A and L235A. In combination with any one of the previous embodiments, in a preferred embodiment the modified Fc IgG$_1$ region does not comprise either amino acid substitution N297A or N297G. More preferably, the modified Fc IgG$_1$ region does not comprise an amino acid substitution at position N297. Thus, it is preferred that the amino acid residue at position 297 according to Eu numbering is asparagine. An anti-SIRPα antibody according to this embodiment, preferably comprises a modified Fc region of the IgG$_1$ genotype as shown in SEQ ID NO: 25 (with L234A and L235A mutations shown at positions 117 and 118).

Production and Purification of the Antibodies of the Invention or Fragments Thereof Anti-SIRPα antibodies of the invention or antigen-binding fragments thereof can be prepared by any of a number of conventional techniques. They will usually be produced in recombinant expression systems, using any technique known in the art. See e.g. Shukla and Thömmes (*Trends in Biotechnol.* 2010, 28(5), 253-261). Harlow and Lane. Antibodies: A Laboratory Manual. Cold Spring Harbor Laboratory Press. Cold Spring Harbor, NY, 1988, and Sambrook and Russell. Molecular Cloning: A Laboratory Manual. 3rd edition. Cold Spring Harbor Laboratory, Cold Spring Harbor Laboratory Press, NY, 2001. Any expression system known in the art can be used to make the recombinant polypeptides of the invention. In general, host cells are transformed with a recombinant expression vector that comprises DNA encoding a desired polypeptide.

In one aspect, the invention therefore relates to a nucleic acid molecule comprising a nucleotide sequence encoding an anti-SIRPα antibody of the invention or an antigen-binding fragment thereof. One nucleotide sequence encodes a polypeptide comprising at least the variable domain of the light chain of an anti-SIRPα antibody of the invention; another nucleotide sequence encodes a polypeptide comprising at least the variable domain of the heavy chain of an anti-SIRPα antibody of the invention. Thus, in a preferred embodiment, the nucleic acid molecule comprises a nucleotide sequence encoding at least one of the HCVR and the LCVR of the antibody. A preferred nucleic acid molecule is an expression vector wherein the nucleotide sequences encoding the antibody polypeptides of the invention are operably linked to expression regulatory sequences, such as e.g. a promoter and a leader sequence (also referred to as a signal peptide, signal sequence, targeting signal, localization signal, localization sequence, transit peptide or leader peptide), for expression of the coding nucleotide sequence in a host cell. A preferred leader sequence for the heavy chain is shown in SEQ ID NO:28. A preferred leader sequence for the light chain is shown in SEQ ID NO:29. Another suitable leader sequence for use in the present invention is shown in SEQ ID NO:27.

In another aspect, the invention pertains to a host cell comprising a nucleic acid molecule as defined above in this section. The cell preferably is an isolated cell or a cultured cell. Among the host cells that may be employed are prokaryotes, yeast or higher eukaryotic cells. Prokaryotes include gram negative or gram positive organisms, for example *Escherichia coli* or bacilli. Higher eukaryotic cells include insect cells and established cell lines of mammalian origin. Examples of suitable mammalian host cell lines include Chinese Hamster Ovary (CHO) cells. COS-7 line of monkey kidney cells (Gluzman et al. *Cell* 1981, 23, 175), human embryonic kidney (HEK) 293 cells. L cells. C127 cells. 3T3 cells. HeLa cells, baby hamster kidney (BHK) cell lines, and the CVI/EBNA cell line derived from the African green monkey kidney cell line CVI as described by McMahan et al. *EMBO J.* 1991, 10, 2821. Appropriate cloning and expression vectors for use with bacterial, fungal, yeast, and mammalian cellular hosts are for example described by Pouwels et al (Cloning Vectors: A Laboratory Manual, Elsevier, New York, 1985).

The transformed cells can be cultured under conditions that promote expression of the polypeptide. Thus in one aspect, the invention relates to a method for producing an anti-SIRPα antibody of the invention or antigen-binding fragment thereof, the method comprising the step of cultivating a cell comprising at least one expression vector as defined herein, under conditions conducive to expression of the polypeptide and, optionally, recovering the polypeptide.

An anti-SIRPα antibody according to the invention or antigen-binding fragment thereof can be recovered by conventional protein purification procedures, including e.g. hydroxyapatite chromatography, gel electrophoresis, dialysis, affinity chromatography (such as for example protein A-Sepharose, protein G-Sepharose), ion exchange chromatography (such as for example anion-exchange chromatography, cation-exchange chromatography, mixed mode), or hydrophobic interaction chromatography (see e.g. Low et al. *J. Chromatography B* 2007, 848, 25 48-63; Shukla et al. *J. Chromatography B* 2007, 848, 28-39). Affinity chromatography encompasses affinity chromatography using Capture-Select™ ligands, which offer a unique affinity purification solution based on Camelid-derived single domain (VHH) antibody fragments (see e.g. Eifler et al. *Biotechnology Progress* 2014, 30(6), 1311-1318). Polypeptides contemplated for use herein include substantially homogeneous recombinant anti-SIRPα antibody polypeptides substantially free of contaminating endogenous materials.

Amino acid sequence modification(s) of the anti-SIRPα antibody of the invention or antigen-binding fragment thereof are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antibody or antigen-binding fragment thereof. Any combination of deletion, insertion, and substitution is made to achieve the final construct, provided that the final construct possesses the desired characteristics. The amino acid changes may also alter post-translational processes of the antibody or antigen-binding fragment thereof, such as changing the number or position of glycosylation sites.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody or the antigen-binding fragment thereof include the fusion with an enzyme or a polypeptide which increases the serum half-life of the antibody or antigen-binding fragment.

Another type of variant is an amino acid substitution variant. These variants have at least one amino acid residue in the antibody or the antigen-binding fragment thereof replaced by a different residue. Such substitutional mutagenesis of antibodies or antigen-binding fragments thereof include FR alterations as indicated above as well as alterations to reduce binding of the Fc region to an Fc receptor to prevent receptor activation as indicated above.

Another type of amino acid variant of the antibody alters the original glycosylation pattern of the antibody or the antigen-binding fragment thereof. By altering is meant deleting one or more carbohydrate moieties found in the antibody or the antigen-binding fragment thereof, and/or adding one or more glycosylation sites that are not present in the antibody or the antigen-binding fragment thereof. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of any of these tripeptide sequences in a polypeptide creates a potential glycosylation site. O-linked glycosylation refers to the attachment of one of the monosaccharides or monosaccharide derivatives N-acetylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody or the antigen-binding fragment thereof.

Compositions Comprising the Antibodies of the Invention or Fragments Thereof.

In another aspect, the invention relates to a pharmaceutical composition comprising an anti-SIRPα antibody of the invention or an antigen-binding fragment thereof, or a pharmaceutical derivative or prodrug thereof, together with one or more pharmaceutically acceptable excipients, such as for example a pharmaceutically acceptable carrier, an adjuvant, or a vehicle. Preferably, the invention relates to a pharmaceutical composition comprising an anti-SIRPα antibody of the invention, or an antigen-binding fragment thereof, and a pharmaceutically acceptable excipient.

Such a pharmaceutical composition is for administration to a subject. A pharmaceutical composition according to the invention can be used in the methods of treatment described hereinbelow by administration of an effective amount of the composition to a subject in need thereof. The term "subject" as used herein refers to all animals classified as mammals and includes, but is not restricted to, primates and humans. The subject is preferably a human.

The term "pharmaceutically acceptable excipient" as used herein, is intended to include any and all solvents, dispersion media, coatings, antibacterial and antifungal agents, isotonic and adsorption delaying agents, and the like, compatible with pharmaceutical administration (see e.g. Handbook of Pharmaceutical Excipients. Rowe et al. Eds. 7th edition, 2012, www.pharmpress.com). The use of such media and agents for pharmaceutically active substances is well known in the art. Except insofar as any conventional media or agent is incompatible with the active compound, use thereof in the composition is contemplated. Acceptable excipients, including carriers or stabilizers, are nontoxic to recipients at the dosages and concentrations employed, and include buffers such as phosphate, citrate, acetate, histidine, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides: proteins, such as serum albumin, gelatin, or immunoglobulins: hydrophilic polymers such as polyvinylpyrrolidone: amino acids such as glycine, glutamine, asparagine, histidine, arginine, or lysine: monosaccharides, disaccharides, and other carbohydrates including glucose, mannose, or dextrins: chelating agents such as EDTA: sugars such as sucrose, mannitol, trehalose or sorbitol; salt-forming counter ions such as sodium; metal complexes (e.g. Zn-protein complexes); and/or non-ionic surfactants such as polysorbate (e.g. TWEEN™), poloxamer (e.g. PLURONICS™), hydroxypropyl-β-cyclodextrin or polyethylene glycol (PEG).

Supplementary active compounds can also be incorporated into the pharmaceutical composition of the invention. Thus, in a particular embodiment, the pharmaceutical composition of the invention may also contain more than one active compound as necessary for the particular indication being treated, preferably those with complementary activities that do not adversely affect each other. The effective amount of such other active agent depends, among other things, on the amount of anti-SIRPα antibody of the invention or antigen-binding fragment thereof present in the pharmaceutical composition, the type of disease or disorder or treatment, etc.

In an embodiment, the anti-SIRPα antibody of the invention or the antigen-binding fragment thereof is prepared with carriers that will protect said compound against rapid elimination from the body, such as a controlled release formulation, including implants and microencapsulated delivery systems, e.g. liposomes. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions, including targeted liposomes can also be used as pharmaceutically acceptable carriers. These can be prepared according to methods known to those skilled in the art, for example, as described in U.S. Pat. No. 4,522,811 or WO2010/095940.

The administration route of the anti-SIRPα antibody of the invention, or antigen-binding fragment thereof, can be oral, parenteral, by inhalation or topical. The term "parenteral" as used herein includes intravenous, intra-arterial, intralymphatic, intraperitoneal, intramuscular, subcutaneous, rectal or vaginal administration. The intravenous forms of parenteral administration are preferred. By "systemic administration" is meant oral, intravenous, intraperitoneal and intramuscular administration. The amount of an antibody required for therapeutic or prophylactic effect will, of course, vary with the antibody chosen, the nature and severity of the condition being treated and the subject. In addition, the antibody may suitably be administered by pulse infusion, e.g., with declining doses of the antibody. Preferably, the dosing is given by injections, most preferably intravenous or subcutaneous injections, depending in part on whether the administration is brief or chronic.

Thus, in a particular embodiment, the pharmaceutical composition of the invention may be in a form suitable for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water. CremophorEM (BASF, Parsippany, NJ) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, or sodium chloride in the composition.

Prolonged absorption of the injectable compositions can be brought about by including in the composition an agent which delays absorption, for example, aluminium monostearate or gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, said pharmaceutical composition is administered via intravenous (IV) or subcutaneous (SC) route. Adequate excipients can be used, such as bulking agents, buffering agents or surfactants. The mentioned formulations will be prepared using standard methods for preparing parenterally administrable compositions as are well known in the art and described in more detail in various sources, including, for example, Remington: The Science and Practice of Pharmacy. Allen Ed. 22nd edition, 2012, www.pharmpress.com).

It is especially advantageous to formulate the pharmaceutical compositions, namely parenteral compositions, in dosage unit form to ease administration and for uniformity of dosage. Dosage unit form as used herein refers to physically discrete units suited as unitary dosages for the subject to be treated; each unit containing a predetermined quantity of active compound (anti-SIRPα antibody of the invention or antigen-binding fragment thereof) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, an effective administered amount of an anti-SIRPα antibody of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.001 to 1,000 mg/kg bodyweight/day, preferably about 0.01 to about 100 mg/kg bodyweight/day, most preferably from about 0.05 to 10 mg/kg bodyweight/day. Guidance in selecting appropriate doses of antibodies is available (see, e.g., Wawrzynczak (1996) Antibody Therapy, Bios Scientific Pub. Ltd. Oxfordshire, UK: Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) *New Engl. J. Med.* 1999, 348, 601-608; Milgrom et al. *New Engl. J. Med.* 1999, 341, 1966-1973; Slamon et al. *New Engl. J. Med.* 2001, 344, 783-792; Beniaminovitz et al. *New Engl. J. Med.* 2000, 342, 613-619; Ghosh et al. *New Engl. J. Med.* 2003, 348, 24-32; Lipsky et al. *New Engl. J. Med.* 2000, 343, 1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Antibodies or antibody fragments can be administered by continuous infusion, or by doses at intervals of, e.g., one day, one week, or 1-7 times per week. Alternatively, antibodies or antibody fragments can be administered once daily, every other day. 2-3 times weekly, once every 2 weeks, once every 3 weeks, once every 6 weeks. A preferred dose protocol is one involving the maximal dose or dose frequency that avoids significant undesirable side effects. A total or mean weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang et al. *New Engl. J. Med.* 2003 349, 427-434; Herold et al. *New Engl. J. Med.* 2002, 346, 1692-1698; Liu et al. J. Neurol. Neurosurg. Psych. 1999, 67, 451-456; Portielje et al. *Cancer Immunol. Immunother.* 2003, 52, 133-144). Preferably, the total or mean weekly dose is in the range of from 0.001 to 100 mg/kg bodyweight, preferably about 0.01 to about 50 mg/kg bodyweight, preferably about 0.05 to about 30 mg/kg bodyweight, most preferably from about 0.1 to 10 mg/kg bodyweight.

The pharmaceutical compositions can be included in a container, pack, or dispenser together with instructions for administration.

The anti-SIRPα antibodies of the present invention or antigen-binding fragments thereof are preferably used in combination with a therapeutic antibody as will be detailed more in the following section and possibly in combination with other drugs. The therapeutic antibody may form part of the same composition, or be provided as a separate composition for administration at the same time or at a different time. Alternatively or in combination with any of the previous embodiments, any other drugs may form part of the same composition or be provided as a separate composition for administration at the same time or at a different time.

Preferably, a pharmaceutical composition of the invention is in the form of a lyophilized cake (lyophilized powders), which requires (aqueous) dissolution (i.e. reconstitution) before intravenous administration, or of a frozen (aqueous) solution, which requires thawing before administration. Most preferably, the pharmaceutical composition is in the form of a lyophilized cake. Suitable pharmaceutically acceptable excipients for inclusion into the pharmaceutical composition (before freeze-drying) in accordance with the present invention include buffer solutions (e.g. citrate, acetate, histidine or succinate containing salts in water), lyoprotectants (e.g. sucrose, trehalose), tonicity modifiers (e.g. sodium chloride), surfactants (e.g. polysorbate or hydroxypropyl-β-cyclodextrin), and bulking agents (e.g. mannitol, glycine). Excipients used for freeze-dried protein formulations are selected for their ability to prevent protein denaturation during the freeze-drying process as well as during storage.

Use of the Antibodies of the Invention or Fragments Thereof

The anti-SIRPα antibodies, antigen-binding fragments thereof and pharmaceutical compositions of the invention will be useful in the treatment of diseases, conditions and indications where SIRPα is expressed or where SIRPα and CD47 are expressed, preferably overexpressed, in particular for the treatment of CD47-expressing cancer.

Thus, in a further aspect, the present invention relates to an anti-SIRPα antibody of the invention or an antigen-binding fragment thereof, or a pharmaceutical composition of the invention, for use as a medicament.

In another aspect, the present invention relates to an anti-SIRPα antibody of the invention or an antigen-binding fragment thereof, or a pharmaceutical composition of the invention for use in the treatment of a cancer, preferably in the treatment of CD47-expressing cancer.

CD47 has been found to be expressed on several human tumour types, including acute myeloid leukaemia (AML), breast cancer, chronic myeloid leukaemia (CML), chronic lymphatic leukaemia (CLL), acute lymphoblastic leukaemia (ALL), non-Hodgkin's lymphoma (NHL), including follicular lymphoma (FL) and diffuse large B-cell lymphoma (DLBCL), hepatocellular carcinoma, multiple myeloma (MM), bladder cancer, colon cancer, gastric cancer, ovarian cancer, head and neck cancer, neuroblastoma, melanoma, osteosarcoma, pancreatic cancer, renal carcinoma, prostate cancer, hepatocellular carcinoma, lung cancer and other solid tumours (Chao et al. *Curr Opin Immunol.* 2012, 24 (2), 225-232; Chao et al. *Cell* 2010, 142 (5), 699-713: Rösner et al. Mol Cancer Ther. 2018). Increased expression has been observed for several of these tumours as compared to their normal cell counterparts (Russ et al. *Blood Rev.* 2018, doi: 10.1016/j.blre.2018.04.005). It has been hypothesized that—along with other hypothesized CD47-mechanisms—CD47 upregulation in tumour cells enables the tumours to escape innate immune system surveillance through evasion of phagocytosis (Chao et al. *Curr Opin Immunol.* 2012, 24 (2), 225-232).

Interestingly. Yanagita et al. reported that human renal cell carcinoma and melanoma highly express SIRPα (Yanagita et al. *JCI Insight* 2017, 2(1), e89140). In addition, SIRPα expression has been found on some neuroblastoma cells and in acute myeloid leukaemia (AML). Sosale et al. reported SIRPα expression in lung carcinoma and glioblastoma (Sosale et al. *Mol. Ther. Methods Clin. Dev.* 2016, 3, 16080). Chen et al. reported SIRPα expression on astrocytoma and glioblastoma (Chen et al. *Cancer Res* 2004, 64(1), 117-127).

Mesothelioma and B-cell lymphoma can also be SIRPα-positive. Thus, in another aspect, the present invention relates to an anti-SIRPα antibody of the invention or an antigen-binding fragment thereof or a pharmaceutical composition of the invention for use in the treatment of a disease, condition or indication where SIRPα is expressed, in particular in the treatment of SIRPα-expressing cancer, such as for example human renal cell carcinoma and melanoma, but also in autoimmune disease such as for example in rheumatoid arthritis, multiple sclerosis and perhaps granulomatosis with polyangiitis (GPA), microscopic polyangiitis (MPA) and pemphigus vulgaris (PV). Anti-SIRPα antibodies could also increase efficacy of another antibody in diseases whether this latter antibody is used to deplete pathogenic or infected cells. For a SIRPα-expressing tumour, an anti-SIRPα antibody of the invention comprising wild-type human Fc may be suitable as monotherapy. In one embodiment, the invention relates to an anti-SIRPα antibody comprising an Fc region that binds to activating Fc receptors present on human immune effector cells for use in the treatment of SIRPα-positive human solid tumours and haematological malignancies, preferably renal cell carcinoma or malignant melanoma. Preferably, the Fc region that binds to activating Fc receptors present on human immune effector cells is of the IgA or IgG isotype. More preferred is an anti-SIRPα antibody comprising an Fc region of the $IgG_1$, $IgG_2$, $IgG_3$ or $IgG_4$ isotype; the $IgG_1$, $IgG_2$ or $IgG_4$ isotype is even more preferred. Most preferred is an anti-SIRPα antibody comprising an Fc region of the $IgG_1$ isotype.

As indicated above, anti-SIRPα antibodies of the invention or antigen-binding fragments thereof wherein preferably the Fc effector function is partly or completely disrupted, can be used to improve the effector functions-such as for example increase ADCC—of a therapeutic antibody. Preferably, a cancer to be treated with such an antibody of the invention or antigen-binding fragment thereof and a therapeutic antibody does not express SIRPα. Such a method of treatment is preferably combined with one or more further anti-cancer therapies. An anti-SIRPα antibody comprising a modified Fc region that exhibits reduced binding to a human Fcα or Fcγ receptor, when compared to the same anti-SIRPα antibody comprising a wild-type Fc region as described hereinabove was found to enhance the in vitro ADCC of a therapeutic antibody using neutrophils as effector cells. The antibodies 1-13 provided in the Examples show a dose-dependent increase in the in vitro ADCC using neutrophils of heterozygous $SIRPα_1/SIRPα_{BIT}$ donors. Preferred antibodies are the ones that increase in vitro ADCC using neutrophils to the best extent while preferably not showing signs of immunogenicity in vitro using T-cell proliferation assay and/or IL-2 ELIspot. Most preferred are antibodies 1-6, 12 and 13, preferably antibody 6.

Preferably, the therapeutic antibody is an antibody approved by a medicines regulatory authority, such as the European Medicines Agency (EMA) or Food and Drug Administration (FDA). Online databases of most Regulatory Authorities can be consulted to find whether an antibody is approved.

Typically, the therapeutic antibody for use in combination with an anti-SIRPα antibody according to the invention (preferably with reduced binding of its Fc region) or an antigen-binding fragment thereof, is a monospecific or bispecific antibody or antibody fragment comprising at least one of an HCVR and a LCVR binding to a target selected from the group consisting of annexin Al, AMHR2, AXL, BCMA, B7H3, B7H4, CA6, CA9, CA15-3, CA19-9, CA27-29, CA125, CA242, CCR2, CCR4, CCR5, CD2, CD4, CD16, CD19, CD20, CD22, CD27, CD30, CD33, CD37, CD38, CD40, CD44, CD47, CD52, CD56, CD70, CD74, CD79. CD98, CD115, CD123, CD138, CD203c, CD303, CD333, CEA, CEACAM, CLCA-1, CLL-1, c-MET, Cripto, CTLA-4, DLL3, EGFL, EGFR, EPCAM, EPh (e.g. EphA2 or EphB3), endothelin B receptor (ETBR), FAP, FcRL5 (CD307), FGF, FGFR (e.g. FGFR3), FOLR1, fucosyl-GM1, GCC, GD2, GPNMB, gp100, HER2, HER3, HMW-MAA, integrin α (e.g. αvβ3 and αvβ5), IGF1R, IL1RAP, kappa myeloma antigen, TM4SF1 (or L6 antigen). Lewis A like carbohydrate, Lewis X, Lewis Y, LIV1, mesothelin, MUC1, MUC16, NaPi2b, Nectin-4, PD-1, PD-L1, prolactin receptor, PSMA, PTK7, SLC44A4, STEAP-1, 5T4 antigen (or TPBG, trophoblast glycoprotein), TF (tissue factor), Thomsen-Friedenreich antigen (TF-Ag), Tag72, TNF, TNFR, TROP2, VEGF, VEGFR, and VLA.

Non-limiting examples of cancers that express such a target are: (HER2-positive) breast cancer, (EGFR-positive) colon carcinoma, (GD2-positive) neuroblastoma, melanoma, osteosarcoma, (CD20)-positive B-cell lymphomas. (CD38-positive) multiple myeloma (CD52-positive) lymphoma, and (CD33-positive) acute myeloid leukaemia (AML).

Preferred is a monospecific therapeutic antibody. More preferred is a therapeutic antibody against a membrane-bound target on the surface of tumour cells.

In a preferred embodiment, a therapeutic antibody against a membrane-bound target on the surface of tumour cells comprises a human Fc region that binds to activating Fc receptors present on human immune effector cells. Via binding to these activating Fc receptors, described hereinabove, a therapeutic antibody comprising a human Fc region that binds to activating Fc receptors present on human immune effector cells can induce ADCC and/or ADCP. Therapeutic antibodies of the human IgG, IgE, or IgA isotype comprise a human Fc region that binds to activating Fc receptors present on human immune effector cells.

A preferred therapeutic antibody for use according to the invention is a therapeutic antibody of the IgG or IgA isotype. More preferred is a therapeutic antibody of the IgG isotype, such as $IgG_1$, $IgG_2$, $IgG_3$, and $IgG_4$ antibodies. Even more preferred is a therapeutic antibody of the $IgG_1$ or $IgG_2$ isotype. Most preferred is a therapeutic antibody of the $IgG_1$ isotype.

Suitable therapeutic antibodies for use in combination with an anti-SIRPα antibody according to the invention or an antigen-binding fragment thereof include alemtuzumab (for example in the treatment of multiple sclerosis), obinutuzumab (for example in treatment of CLL, FL), ofatuzumab (for example in treatment of MM), daratumumab (for example in treatment of MM), trastuzumab (for example in treatment of HER-2 overexpressing breast cancer, gastric cancer, gastroesophageal junction adenocarcinoma), dinutuximab (for example in treatment of neuroblastoma, paediatric patients), panitumumab, cetuximab (for example in treatment of head&neck cancer, colorectal cancer), rituximab, ofatumumab (for example in treatment of NHL, CLL, FL, DLBCL), ublituximab, margetuximab, pertuzumab, veltuzumab, brentuximab, elotuzumab, ibritumomab, ifabotuzumab, farletuzumab, otiertuzumab, carotuximab, epratuzumab, inebilizumab, lumretuzumab, mogamulizumab, leukotuximab, isatuximab, oportuzumab, ensituximab, cemiplimab, nivolumab, pembrolizumab, durvalumab, avelumab, atezolizumab, spartalizumab, tislelizumab, camrelizumab, sintilimab, cemiplimab. Such therapeutic antibodies can also be provided as part of an antibody-drug conjugate (ADC). Suitable ADCs for use in combination with an anti-SIRPα antibody according to the invention or an antigen-binding fragment thereof include, but are not limited to, trastuzumab duocarmazine, trastuzumab deruxtecan, trastuzumab emtansine, gemtuzumab ozogamicin, inotuzumab ozogamicin, polatuzumab vedotin, naratuximab emtansine, ibritumomab tiuxetan and brentuximab vedotin.

The antibodies of the invention or antigen-binding fragments thereof and the therapeutic antibody may be in the same formulation or may be administered in different formulations. Administration can be concurrent or sequential, and may be effective in either order.

Thus, in a preferred embodiment, the present invention relates to an anti-SIRPα antibody of the invention or an antigen-binding fragment thereof for use in the treatment of human solid tumours and haematological malignancies in combination with the use of a therapeutic antibody against a membrane-bound target on the surface of tumour cells, which comprises a human Fc region that binds to activating Fc receptors present on human immune effector cells, wherein the anti-SIRPα antibody comprises a modified Fc region that exhibits reduced binding to a human Fcα or Fcγ receptor, when compared to the same anti-SIRPα antibody comprising a wild-type Fc region, preferably a modified human $IgG_1$ Fc region comprising one or more amino acid substitutions at positions selected from the group consisting of: L234, L235, G237, D265, D270, N297, A327, P328, and P329 (Eu numbering).

Alternatively or in combination with any of the other embodiments, in an embodiment, the present invention relates to a use of an anti-SIRPα antibody of the invention or an antigen-binding fragment thereof or a pharmaceutical composition of the invention for the manufacture of a medicament for the treatment of a disease, condition or indication where CD47 is expressed, preferably overexpressed, in particular in the treatment of cancer. For illustrative, non-limitative, cancers to be treated according to the invention: see hereinabove. In a preferred embodiment, the anti-SIRPα antibody of the invention or the antigen-binding fragment thereof or the pharmaceutical composition of the invention are for concurrent or sequential administration with a therapeutic antibody as described above.

Alternatively or in combination with any of the other embodiments, in an embodiment, the present invention relates to a use of an anti-SIRPα antibody of the invention or an antigen-binding fragment thereof or a pharmaceutical composition of the invention for the manufacture of a medicament for the treatment of a SIRPα-expressing cancer, such as human renal cell carcinoma or melanoma. In a preferred embodiment, the anti-SIRPα antibody of the invention or the antigen-binding fragment thereof or the pharmaceutical composition of the invention are for concurrent or sequential administration with a therapeutic antibody as described above.

Alternatively or in combination with any of the other embodiments, in an embodiment, the present invention relates to a method for treating cancer, specifically a cancer of which the tumour cells express CD47 or SIRPα, which method comprises administering to a subject in need of said treatment a therapeutically effective amount of an anti-SIRPα antibody of the invention or an antigen-binding fragment thereof, or a pharmaceutical composition according to the invention. In a particular embodiment, said cancer is a cancer characterized by tumour cells expressing CD47, potentially overexpressing CD47. For illustrative, non-limitative. CD47-expressing cancers to be treated according to the invention: see hereinabove. In an alternative embodiment, the SIRPα expressing cancer is a human renal cell carcinoma or melanoma or neuroblastoma or acute myeloid leukaemia (AML).

It is preferred that an anti-SIRPα antibody of the invention or an antigen-binding fragment thereof or a composition of the invention inhibits the growth of tumour cells expressing CD47 when used in combination with a therapeutic antibody. "Inhibiting the growth of tumour cells expressing CD47" or "growth inhibition" is where a measurable growth inhibition of cancer cells (expressing or overexpressing CD47) is achieved. Preferred growth inhibitory anti-SIRPα antibodies inhibit growth of CD47-expressing tumour cells by greater than 20%, preferably from about 20% to about 50%, and even more preferably, by greater than 50% (e.g., from about 50% to about 100%) as compared to the appropriate control, the control typically being tumour cells not treated with the antibody being tested. In one embodiment, growth inhibition can be measured at an antibody concentration of about 0.1 to 30 mg/ml or about 0.5 nM to 200 nM in cell culture, where the growth inhibition is determined 1-10 days after exposure of the tumour cells to the antibody. Growth inhibition of tumour cells in vivo can be determined in various ways such as for example is described in EP2474557B1. The antibody is growth inhibitory in vivo if administration of the anti-SIRPα antibody at about 1 mg/kg to about 100 mg/kg bodyweight results in reduction in tumour size or tumour cell proliferation within about 5 days to 3 months from the first administration of the antibody, preferably within about 5 to 30 days.

An antibody which "induces cell death" is one which causes a viable cell to become non-viable. The cell is one which expresses CD47. Cell death in vitro may be determined in the absence of complement and immune effector cells to distinguish cell death induced by ADCC. Thus, the assay for cell death may be performed using heat inactivated serum (i.e., in the absence of complement) in the absence of immune effector cells. To determine whether the antibody is able to induce cell death, loss of membrane integrity as evaluated by uptake of propidium iodide (PI), trypan blue (see Moore et al. *Cytotechnology* 1995; 17, 1-11), or 7-AAD can be assessed relative to untreated cells or loss of cell viability can be evaluated (tetrazolium reduction, resazurin reduction, protease markers, and ATP detection).

The expression "therapeutically effective amount" means an amount effective in treating cancer, as previously defined: said amount can be an amount sufficient to effect a desired response, or to ameliorate a symptom or sign, e.g., of metastasis or primary tumour progression, size, or growth. A therapeutically effective amount for a particular subject may vary depending on factors such as the condition being treated, the overall health of the subject, the method, route, and dose of administration and the severity of side effects. Response evaluation criteria have been described (RECIST; Eisenhauer et al. *European Journal of Cancer* 2009; 45, 228-247; Schwartz et al. *European Journal of Cancer* 2016; 62, 138-145; Cheson et al. *Journal of Clinical Oncology* 2003; 21(24), 4642-4649; Moghbel et al. *Journal of Nuclear Medicine* 2016, 57(6), 928-935; references included by reference in their entirety). Preferably, the effect will result in tumour stasis (i.e. no reduction but a status quo), a reduction in the number of lesions or a reduction in tumour size of at least about 10%, preferably at least 20%, 30%, 50%, 70%, or even 90% or more as compared to the baseline tumour size, preferably a reduction of at least 30%, at least 40%, at least 50%, at least 60%, at least 70%, at least 80%, at least 90% in the sum of diameters of target lesions, taking as a reference the baseline sum diameters. When in combination, a therapeutically effective amount is in ratio to a combination of components and the effect is not limited to individual components alone. A therapeutically effective amount will modulate the symptoms preferably by at least about 10%; preferably by at least about 20%; preferably at least about 30%; or more preferably at least about 50%. Alternatively, modulation of migration will mean that the migration or trafficking of various cell types is affected. Such will result in, e.g., statistically significant and quantifiable, changes in the numbers of cells being affected. This may be a decrease in the numbers of target cells being attracted within a time period or target area. Rate of primary tumour progression, size, dissemination or growth may also be monitored.

In a preferred embodiment, the present invention relates to an anti-SIRPα antibody or antigen-binding fragment thereof or pharmaceutical composition as described hereinabove for use in the treatment of a CD47 expressing disease, condition or indication, in particular a cancer, more in particular a human solid tumour or haematological malignancy, in combination with the use of a therapeutic antibody and further in combination with one or more other anti-cancer therapies. Suitable other anti-cancer therapies include, but are not limited to surgery, chemotherapy, radiation therapy, hormonal therapy, and small-molecule targeted therapy, such as for example angiogenesis inhibitors. The anti-SIRPα antibody or antigen-binding fragment thereof or pharmaceutical composition as described hereinabove may be for concomitant or sequential use in the treatment of human solid tumours and haematological malignancies in combination with the use of one or more other anti-cancer therapies. In particular, the anti-SIRPα antibody or antigen-binding fragment thereof or pharmaceutical composition as described hereinabove may be for use in the treatment of human solid tumours and haematological malignancies after the use of one or more other anti-cancer therapies.

Preferably, the present invention relates to an anti-SIRPα antibody or antigen-binding fragment thereof or pharmaceutical composition as described hereinabove for use in the treatment of a CD47 expressing disease, condition or indication, in combination with the use of one or more further anti-cancer therapeutic compounds. An "anti-cancer therapeutic compound" as used herein is intended not to include a therapeutic antibody. A therapeutic antibody is defined hereinabove. Thus, the anti-SIRPα antibody or antigen-binding fragment thereof or pharmaceutical composition as described hereinabove, preferably in combination with a therapeutic antibody as defined above, may be for use in the treatment of human solid tumours and haematological malignancies before, after or simultaneously with the use of one or more other anti-cancer therapeutic compounds.

Suitable anti-cancer therapeutic compounds include a cytotoxic agent, i.e. a substance that inhibits or prevents the function of cells and/or causes destruction of cells. The term is intended to include chemotherapeutic agents, i.e., chemical compounds useful in the treatment of cancer, radiation therapeutics, such as radioactive isotopes, hormonal therapeutics, targeted therapeutics and immunotherapeutic agents. Suitable chemotherapeutic agents include alkylating agents, such as nitrogen mustards, nitrosoureas, tetrazines and aziridines; anti metabolites, such as anti-folates, fluoropyrimidines, deoxynucleoside analogues and thiopurines; anti-microtubule agents, such as *vinca* alkaloids and taxanes; topoisomerase I and II inhibitors; and cytotoxic antibiotics, such as anthracyclines and bleomycins. For example, the chemotherapy regimen may be selected from the group consisting of CHOP (cyclophosphamide, doxorubicin (also called hydroxyl daunorubicin), vincristine (also called oncovin) and prednisone), ICE (idarubicin, cytarabine and etoposide), mitoxantrone, cytarabine, DVP (daunorubicin, vincristine and prednisone), ATRA (all-trans retinoic acid), idarubicin, Hoelzer chemotherapy regimen, ABVD (bleomycin, dacarbazine, doxorubicin and vincristine), CEOP (cyclophosphamide, epirubicin, vincristine and prednisolone), 2-CdA (2-chlorodeoxyadenosine), FLAG & IDA (fludarabine, cytarabine, filgastrim and idarubicin) (with or without subsequent G-CSF (granulocyte-colony stimulating factor) or GM-CSF treatment), VAD (vincristine, doxorubicin and dexamethasone), M & P (melphalan and prednisone), C (cyclophosphamide)-Weekly, ABCM (adriamycin, bleomycin, cyclophosphamide and mitomycin-C), MOPP (mechlorethamine, vincristine, prednisone and procarbazine) and DHAP (dexamethasone, cytarabine and cisplatin). A preferred chemotherapeutic regimen is CHOP. Suitable radiation therapeutics include radioisotopes, such as $^{131}$I-metaiodobenzylguanidine (MIBG), $^{32}$P as sodium phosphate, $^{223}$Ra chloride, $^{89}$Sr chloride and $^{153}$Sm diamine tetramethylene phosphonate (EDTMP). Suitable agents to be used as hormonal therapeutics include inhibitors of hormone synthesis, such as aromatase inhibitors and GnRH analogues; and hormone receptor antagonists, such as selective oestrogen receptor modulators and antiandrogens. A targeted therapeutic as used herein is a therapeutic that interferes with specific proteins involved in tumourigenesis and proliferation and may be a small molecule drug; or a peptide or peptide derivative. Examples of targeted small molecule drugs include mTOR inhibitors, such as everolimus, temsirolimus and rapamycin; kinase inhibitors, such as imatinib, dasatinib and nilotinib; VEGF inhibitors, such as sorafenib and regorafenib; and EGFR/HER2 inhibitors such as gefitinib, lapatinib and erlotinib. Examples of peptide or peptide derivative targeted therapeutics include proteasome inhibitors, such as bortezomib and carfilzomib. Immunotherapeutic agents include agents that induce, enhance or suppress an immune response, such as cytokines (IL-2 and IFN-α); immunomodulatory imide drugs, such as thalidomide, lenalidomide and pomalidomide; therapeutic cancer vaccines, such as talimogene laherparepvec; cell based immunotherapeutic agents, such as dendritic cell vaccines, adoptive T-cells and chimeric antigen receptor-modified T-cells); or immunotoxins, such as moxetumomab pasudotox.

Any of the above mentioned therapeutic methods described above may be applied to any subject in need of such therapy, including, for example, mammals, preferably primates, including for example non-human primates, and most preferably, humans.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following Examples are offered for illustrative purposes only, and are not intended to limit the scope of the present invention in any way.

EXAMPLES

1. Transient Expression of Antibodies a) Preparation of cDNA Constructs and Expression Vectors The heavy chain variable region (HCVR) amino acid sequences of the antibodies were each joined at the N-terminus to a leader sequence (SEQ ID NO:28 for antibodies 1-13), and at the C-terminus to the constant domain of a human IgG$_1$ HC LALA according to SEQ ID NO:25 (in silico). The HCVR amino acid sequences of antibodies 12C4, 12C4-LALA, 29AM4-5-LALA or KWAR23-LALA, were each joined at the N-terminus to a HAVT20 leader sequence (SEQ ID NO:27) and at the C-terminus to the constant domain of a human IgG$_1$ HC LALA according to SEQ ID NO:25 or a wild-type human IgG$_1$ HC (SEQ ID NO:24). KWAR23 has the standard adalimumab constant domain of the heavy chain, but lacks the LALA mutation. HEFLB heavy chain is an IgG$_4$ and was used as disclosed SEQ ID NO:42 of WO 2017/178653. The resulting amino acid sequences were back-translated into a cDNA sequence codon-optimized for expression in human cells (*Homo sapiens*). Similarly, the cDNA sequence for the LC of the construct (light chain variable region: LCVR) was obtained by joining the sequences of a leader sequence (SEQ ID NO:29 for antibodies 1-13, SEQ ID NO:27 for 12C4, 12C4-LALA, 29AM4-5-LALA, KWAR23, KWAR23-LALA and (humanized) HEFLB) to the LCVR of antibodies 1-13, 12C4, 12C4-LALA, 29AM4-5-LALA, KWAR23, KWAR23-LALA and (humanized) HEFLB at the N-terminus and at the C-terminus to a human antibody κ light chain constant region (SEQ ID NO:26). The HCVR and LCVR sequences according to Table 1a-c were used. Anti-SIRPα antibody SE5A5 (mouse IgG$_{1κ}$) was obtained from Biolegend (San Diego, USA; Purified anti-human CD172a/b (SIRPα/β antibody)). The cDNA constructs and expression vectors for the comparative anti-SIRPα antibodies provided in Table 1c and the isotype controls provided in Table 1d were made similarly.

Table 1a presents (i) the HCDR1, HCDR2, HCDR3, LCDR1, LCDR2, LCDR3 amino acid sequences (SEQ ID NOs) that are comprised in the heavy chain and the light chain in each of the humanized anti-SIRPα antibodies 1-13, and (ii) the amino acid sequences of each of the HCVR and LCVR including the CDRs of humanized anti-SIRPα antibodies 1-13.

| Antibody | HCVR | HCDR1 | HCDR2 | HCDR3 | LCVR | LCDR1 | LCDR2 | LCDR3 |
|---|---|---|---|---|---|---|---|---|
| | | SEQ ID NO: | | | | SEQ ID NO: | | |
| 1 | SEQ ID NO: 1 | 30 | 31 | 32 | SEQ ID NO: 2 | 33 | 34 | 35 |
| 2 | SEQ ID NO: 3 | 30 | 31 | 32 | SEQ ID NO: 2 | 33 | 34 | 35 |
| 3 | SEQ ID NO: 4 | 30 | 31 | 32 | SEQ ID NO: 2 | 33 | 34 | 35 |
| 4 | SEQ ID NO: 5 | 30 | 31 | 32 | SEQ ID NO: 2 | 33 | 34 | 35 |
| 5 | SEQ ID NO: 6 | 36 | 37 | 38 | SEQ ID NO: 7 | 39 | 40 | 46 |
| 6 | SEQ ID NO: 8 | 36 | 44 | 45 | SEQ ID NO: 9 | 39 | 40 | 41 |
| 7 | SEQ ID NO: 10 | 36 | 37 | 38 | SEQ ID NO: 9 | 39 | 40 | 41 |
| 8 | SEQ ID NO: 6 | 36 | 37 | 38 | SEQ ID NO: 9 | 39 | 40 | 41 |
| 9 | SEQ ID NO: 11 | 36 | 37 | 38 | SEQ ID NO: 9 | 39 | 40 | 41 |
| 10 | SEQ ID NO: 12 | 36 | 42 | 43 | SEQ ID NO: 9 | 39 | 40 | 41 |
| 11 | SEQ ID NO: 13 | 36 | 37 | 38 | SEQ ID NO: 7 | 39 | 40 | 46 |
| 12 | SEQ ID NO: 14 | 30 | 31 | 32 | SEQ ID NO: 2 | 33 | 34 | 35 |
| 13 | SEQ ID NO: 15 | 30 | 31 | 32 | SEQ ID NO: 2 | 33 | 34 | 35 |

Table 1b presents the HC and LC of control antibodies.

| Reference antibody | HC SEQ ID NO: | LC SEQ ID NO: |
|---|---|---|
| 12C4 (IgG$_1$) | 16 | 17 |
| 29AM4-5-LALA (IgG$_1$) | 18 | 19 |
| 12C4-LALA (IgG$_1$) | 20 | 21 |
| KWAR23-LALA (chimeric IgG$_1$, LALA) | 22 | 23 |
| KWAR23 (mouse IgG$_{2a}$) | 47 | 48 |
| HEFLB (humanized IgG$_4$)* | 49 | 50 |

*HEFLB is an IgG$_4$ antibody, thus the heavy chain variable domain is not joined to an IgG$_1$ backbone, but to an IgG$_4$ Fc sequence (WO 2017/178653).

Table 1c presents the amino acid sequences of the HC and LC of further comparative anti-SIRPα antibodies. These antibodies were selected from WO2018/190719, WO2018/057669, WO2019/023347, WO2018/107058 and WO01/40307.

| Reference antibody | HC SEQ ID NO: | LC SEQ ID NO: | Description |
|---|---|---|---|
| 1H9 | 57 | 58 | 1H9 humanized IgG$_1$-kappa, HC-N297A |
| 40A-1 | 59 | 60 | 40AVH2VL4 humanized IgG$_1$-kappa, HC-N297A |
| 40A-2 | 61 | 62 | 40AVH2VL4 humanized IgG$_2$-kappa, HC-A378S |
| AB3-LALA | 63 | 64 | AB3 chicken-human chimeric IgG$_1$-kappa, LALA |
| AB25-LALA | 65 | 66 | AB25 humanized IgG$_1$-kappa, LALA |
| AB115-LALA | 67 | 68 | AB115 human IgG$_1$-kappa, LALA |

-continued

| Reference antibody | HC SEQ ID NO: | LC SEQ ID NO: | Description |
|---|---|---|---|
| AB119-LALA | 69 | 70 | AB119 human IgG$_1$-kappa, LALA |
| AB136-LALA | 71 | 72 | AB136 human IgG$_1$-kappa, LALA |
| 3F9-LALA | 73 | 74 | 3F9 mouse-human chimeric IgG$_1$-kappa, LALA |
| 7H9-LALA | 75 | 76 | 7H9 mouse-human chimeric IgG$_1$-kappa, LALA |

All reference antibodies HC and LC sequences comprise as a leader sequence the HAVT20 leader sequence of SEQ ID NO: 27. The leader sequence is expressed and is needed for transport out of the cell, during which process it is cut off. Table 1d presents the list of isotype control antibodies

| Reference antibody | Description |
|---|---|
| iso1-LALA | humanized IgG$_1$-kappa, LALA |
| iso2 | humanized IgG$_1$-kappa, HC-N297A |
| iso3 | humanized IgG$_2$-kappa, HC-A378S |
| iso4 | mouse IgG$_{2a}$, wt |
| iso5 | humanized IgG$_4$ |
| iso6 | humanized IgG$_1$ |
| iso7* | Purified Mouse IgG$_1$, κ, BioLegend |
| iso8 | humanized IgG$_4$-kappa, HC-S228P, L445P |

*iso7 was obtained from BioLegend (cat#400102).

b) Vector Construction and Cloning Strategy

For expression of the antibody chains a mammalian expression vector was used (pcDNA3.4; ThermoFisher), which contains a CMV: TKpA expression cassette. The final vectors containing either the HC or the LC expression cassette (CMV:HC: TKpA and CMV: LC-TKpA, respectively) were transferred to and expanded in E. coli NEB 5-α cells. Large-scale production of the final expression vectors for transfection was performed using Maxi- or Megaprep kits (Qiagen).

c) Transient Expression in Mammalian Cells

Commercially available Expi293F cells (Thermo Fisher) were transfected with the expression vectors using the ExpiFectamine transfection agent according to the manufacturer's instructions as follows: 75×10$^7$ cells were seeded in 300 ml FortiCHO medium, 300 µg of the expression vector was combined with 800 µl of ExpiFectamine transfection agent and added to the cells. One day after transfection, 1.5 ml Enhancer 1 and 15 ml Enhancer 2 were added to the culture. Six days post transfection, the cell culture supernatant was harvested by centrifugation at 4,000 g for 15 min and filtering the clarified harvest over PES bottle filters/MF 75 filters (Nalgene). Antibodies were purified by affinity chromatography.

2. Antibody Binding and Specificity

Experimental

Surface Plasmon Resonance (SPR) assay: Affinity analysis was performed by single cycle kinetics analysis on a Surface Plasmon Resonance apparatus (BiaCore™ T200 system, GE Life Sciences) at 25° C. Biotinylated SIRP antigens (SEQ ID NOs: 51-56) were captured on the surface of a chip suitable for biotinylated molecules (Sensor Chip CAP, GE Life Sciences) by injecting 5 µg/ml of the SIRP antigen in running buffer (10 mM HEPES buffer at pH 7.4 with 150 mM NaCl, 3 mM EDTA and 0.005% v/v polyoxyethylene (20) sorbitan monolaurate (Surfactant P20) for 60 sec at 10 µl/min after injection of a 20× diluted (in running buffer) biotin CAPture reagents (GE Life Sciences) for 60 sec at 10 µl/min. Baseline stabilization was set at 1 min after which five increasing concentrations of an anti-SIRP antibody in running buffer were injected. For each step an association time of 150 sec was used, followed by a dissociation time of 600 sec after the highest concentration only, all at a flow rate of 30 µl/min. Regeneration was performed with 6 M guanidine-HCl, 0.25 M NaOH solution (120 sec with flow rate of 30 µl/min). Double blank subtraction was performed on the observed sensorgrams using a non anti-SIRP (blank) immobilized reference flow channel and running buffer injection. Sensorgrams were fitted with a 1:1 Langmuir model for all tested anti-SIRP antibodies. The kinetic parameters (association rate [$k_a$], dissociation rate [$k_d$] and binding constant, also referred to as equilibrium dissociation constant or binding affinity [$K_D$]) were calculated using BiaCore™ T200 evaluation software (v3.1).

Flow Cytometry assay: U937 cells (human monocytic cell line) endogenously expressing human SIRPα$_{BIT}$ antigen and cells derived from a non-engineered subclone that has been screened and isolated from CHO-S Chinese hamster ovary cells (ExpiCHO-S) cells expressing either one of human SIRPα$_1$, SIRPα$_{BIT}$ or cySIRPα antigen (100,000 cells/well in a 96-well plate) were washed three times with ice-cold FACS buffer (1×PBS (LONZA) containing 0.1% v/w BSA (Sigma-Aldrich. St. Louis, MO) and 0.02% v/w NaN$_3$ (Sigma-Aldrich), followed by the addition of a concentration range of each primary mAb (50 µl/well) diluted in ice-cold FACS buffer. After an incubation time of 30 min at 4° C. the cells were washed three times with ice-cold FACS buffer and 50 µl/well secondary mAb (for human antibodies. AffiniPure F(ab')$_2$ fragment Goat-anti-human IgG-APC, 1:6.000 dilution, Jackson Immuno Research was added and for mouse antibodies. AffiniPure Fab fragment Goat Anti-Mouse IgG (H+L)-Alexa Fluor 488, 1:1,000 dilution, Jackson Immuno Research was added). After 30 min at 4° C. cells were washed twice and resuspended in 150 µl FACS buffer. Fluorescence intensities were determined by flow cytometry (BD FACSVerse, Franklin Lakes, NJ) and indicated as the median fluorescence intensity (MFI-Median) for U937 cells and the mean fluorescence intensity (MFI-Mean) for ExpiCHO-S cells. Curves were fitted by nonlinear regression using the sigmoidal dose-response equation with variable slope (four parameters) in GraphPad Prism (version 7.02 for Windows. GraphPad. San Diego, CA). EC$_{50}$ values were calculated as the concentration in µg/ml that gives a response half way between bottom and top of the curve, when using a 4-parameter logistic fit.

Results

SPR assay: The $K_D$ (i.e. binding constant, also referred to as 'equilibrium dissociation constant' or 'binding affinity') values for binding to human SIRPα$_1$ (huSIRPα$_1$), human SIRPα$_{BIT}$ (huSIRPα$_{BIT}$), cynomolgus monkey SIRPα (cySIRPα), human SIRPγ (huSIRPγ), human SIRPβ$_{1v1}$ (huSIRPβ$_{1v1}$) and human SIRPβ$_{1v2}$ (huSIRPβ$_{1v2}$) of antibodies 1-13 and reference antibodies are summarized in Table 2. Antibodies 1-13 bind to both huSIRPα$_{BIT}$ and huSIRPα$_1$, and do not bind to huSIRPγ. Some of antibodies 1-13, for example antibody 6, occasionally show weak association with SIRPγ, but with a very low response unit (RU), which appears to be irrelevant as shown in the cellular binding experiments in the Examples below. Humanized HEFLB recognizes only the huSIRPα$_{BIT}$ variant and not huSIRPα$_1$ and huSIRPγ and cySIRPα. KWAR23, 29AM4-5, SE5A5 and 12C4 antibodies bind to all SIRP variants, including huSIRPγ.

TABLE 2

Binding affinities ($K_D$ in M) of anti-SIRPα antibodies to human SIRPα$_1$, human SIRPα$_{BIT}$, human SIRPγ, human SIRPβ$_{1v1}$, human SIRPβ$_{1v2}$ and cynomolgus monkey SIRPα measured by SPR

| Antibody | huSIRPα$_1$ | huSIRPα$_{BIT}$ | cySIRPα | huSIRPγ | huSIRPβ$_{1v2}$ | huSIRPβ$_{1v1}$ |
|---|---|---|---|---|---|---|
| 12C4 | 9.72E−11 | <1.0E−11 | <1.0E−11 | <1.0E−11 | <1.0E−11 | 1.01E−10 |
| 29AM4-5-LALA | 2.29E−11 | <1.0E−11 | 2.21E−11 | 4.45E−10 | 8.54E−11 | 6.01E−11 |
| 12C4-LALA | 1.01E−10 | <1.0E−11 | <1.0E−11 | <1.0E−11 | <1.0E−11 | 1.13E−10 |
| KWAR23-LALA | 1.25E−11 | <1.0E−11 | <1.0E−11 | <1.0E−11 | <1.0E−11 | 3.20E−11 |
| KWAR23 | 1.44E−11 | <1.0E−11 | <1.0E−11 | <1.0E−11 | <1.0E−11 | 3.56E−11 |
| HEFLB | n.r. | 1.28E−11 | n.r. | 1.74E−08# | 2.16E−10 | 1.61E−10 |
| SE5A5 | 1.54E−11 | 7.98E−10 | 1.80E−09 | 2.66E−09 | 2.87E−10 | 3.82E−11 |
| 1 | 1.49E−09 | <1.0E−11 | 1.87E−09 | n.r. | 2.42E−09 | n.r. |
| 2 | 1.34E−09 | <1.0E−11 | 2.27E−09 | n.r. | 2.54E−09 | n.r. |
| 3 | 9.08E−10 | <1.0E−11 | 1.66E−09 | n.r. | 1.92E−09 | n.r. |
| 4 | 1.38E−09 | <1.0E−11 | 1.94E−09 | n.r. | 2.34E−09 | n.r. |
| 5 | <1.0E−11 | 1.42E−10 | 7.62E−08# | n.r. | 2.97E−09 | 5.93E−10 |
| 6 | <1.0E−11 | <1.0E−11 | 4.56E−09 | n.r. | 2.01E−09 | 7.43E−11 |
| 7 | 1.71E−11 | 3.78E−10 | n.r. | n.r. | n.r. | 1.65E−09 |
| 8 | <1.0E−11 | 1.52E−10 | 1.88E−09# | n.r. | 1.84E−09 | 6.61E−10 |
| 9 | 1.91E−11 | 3.65E−10 | n.r. | n.r. | n.r. | 1.44E−09 |
| 10 | 6.72E−10 | 5.10E−09# | n.r. | n.r. | n.r. | 1.29E−08 |
| 11 | 3.49E−11 | 2.12E−10 | n.r. | n.r. | n.r. | 2.01E−09 |
| 12 | 1.38E−09 | <1.0E−11 | 1.53E−09 | n.r. | 1.94E−09 | n.r. |
| 13 | 1.41E−09 | <1.0E−11 | 2.05E−09 | n.r. | 2.78E−09 | n.r. |

The $K_D$ values of huSIRPα$_1$ and huSIRPα$_{BIT}$ were obtained from a concentration series 1.56-6.25-25-100-400 ng/ml. The $K_D$ values of cySIRPα, huSIRPγ, huSIRPβ$_{1v1}$ and huSIRPβ$_{1v2}$ were obtained from a concentration series 6.25-25-100-400-1600 ng/ml. n.r.: no response or below a 10 response unit (RU) cut-off of the calculated $R_{max}$. When <1.0E−11 M is given as $K_D$ value the sample could not be accurately determined because the affinity is outside the instrument range or the calculated $K_D$ was around 1.0E−11 M, but surface saturation was seen. A $K_D$ value of <1.0E−11 M means high affinity. # means sub-optimal fit to a 1:1 Langmuir model was observed.

Flow Cytometry assay: The binding of various antibodies to huSIRPα$_1$, huSIRPα$_{BIT}$, and/or cySIRPα expressed on cells was determined by flow cytometry. The binding is indicated as EC$_{50}$ values, i.e. the antibody concentration in μg/ml that gives a response half way between bottom and top of the curve, which are shown in Table 3. Antibodies 1-13 bind to huSIRPα$_{BIT}$ (either transiently expressed in ExpiCHO-S cells or endogenously expressed in U937 cells) and huSIRPα$_1$. Antibodies 1-4, 6, 12, 13 bind to cySIRPα in the low μg/ml range. These antibodies also bind, with the same EC$_{50}$ value range (low μg/ml), to U937 cells endogenously expressing huSIRPα$_{BIT}$. Reference antibodies KWAR23, KWAR23huIgG$_1$LALA, 12C4huIgG$_1$LALA, 12ChuIgG$_1$, 29AM4-5huIgG$_1$LALA and HEFLB show similar binding to huSIRPα$_{BIT}$ expressed on U937 cells. HEFLB does not bind to huSIRPα$_1$ and cySIRPα.

TABLE 3

Cellular binding of anti-SIRPα antibodies to U937 cells endogenously expressing human SIRPα$_{BIT}$ and to ExpiCHO-S cells transiently transfected with either human SIRPα$_1$, human SIRPα$_{BIT}$ or cynomolgus monkey SIRPα

| Antibody | U937 cells (huSIRPα$_{BIT}$) EC$_{50}$ (μg/ml) | ExpiCHO-S (huSIRPα$_1$) EC$_{50}$ (μg/ml) | ExpiCHO-S (huSIRPα$_{BIT}$) EC$_{50}$ (μg/ml) | ExpiCHO-S (cySIRPα) EC$_{50}$ (μg/ml) |
|---|---|---|---|---|
| 1 | 0.09 | 0.28 | 0.30 | 0.12 |
| 2 | 0.10 | 0.32 | 0.31 | 0.12 |
| 3 | 0.12 | 0.40 | 0.28 | 0.15 |
| 4 | 0.10 | 0.38 | 0.36 | 0.14 |
| 5 | 1.60 | 0.22 | 0.12 | 1.91 |
| 6 | 0.14 | 0.24 | 0.18 | 0.13 |
| 7 | 3.55 | 0.20 | 0.20 | 5.35 |
| 8 | 1.04 | 0.17 | 0.14 | 2.44 |
| 9 | 2.78 | 0.19 | 0.11 | >10 |
| 10 | 7.11 | 0.10 | 0.30 | >10 |
| 11 | 3.73 | 0.11 | 0.08 | 6.30 |
| 12 | 0.08 | 0.27 | 0.26 | 0.23 |
| 13 | 0.08 | 0.27 | 0.28 | 0.11 |
| 12C4 | 0.07 | 0.12 | 0.36 | 0.16 |
| 29AM4-5-LALA | 0.17 | 0.09 | 0.12 | 0.13 |
| 12C4-LALA | 0.04 | 0.11 | 0.17 | 0.22 |
| KWAR23-LALA | 0.07 | 0.19 | 0.19 | 0.27 |
| KWAR23 | 0.14 | 0.08 | 0.10 | 0.08 |
| HEFLB | 0.25 | >30 | 0.15 | >30 |
| SE5A5 | 1.48 | 0.09 | 0.62 | 0.05 |

3. Human SIRPγ Binding-T-Cells FACS Staining

Experimental

Flow Cytometry assay: Peripheral mononuclear cells (PBMC) were isolated from fresh blood of healthy individuals using Percoll gradient. Cells were washed in HEPES+ buffer (132 mM NaCl, 6 mM KCl, 1 mM CaCl$_2$, 1 mM MgSO$_4$, 1.2 mM potassium phosphate, 20 mM HEPES, 5.5 mM glucose and 0.5% (w/v) human serum albumin, pH 7.4) and resuspended in a concentration of 1×10$^6$/ml in FACS buffer (PBS+human albumin 1% buffer w/v, Human Albuman 200 g/ml, Sanquin Plasma Products B.V., Amsterdam, Netherlands), spun down and resuspended in PBS+20% normal goat-serum (NGS). Cells (200,000 cells/well in a 96-well plate) were subsequently incubated in the presence of tested antibodies or control conditions with secondary antibodies only (secondary goat anti-human IgG Alexa 633 F(ab')$_2$ fragment, dilution 1:1000, Jackson Immuno Research, and secondary goat anti-mouse IgG Alexa 633 F(ab')$_2$ fragment, dilution 1:250, Invitrogen) for 30 min on ice. After that, cells were washed with FACS buffer and resuspended in a mixture of anti-human CD3 FITC antibody (dilution 1:100, Invitrogen) with respective secondary antibody (either anti-human or anti-mouse) and incubated for 30 min in the dark on ice. Afterwards the cells were washed with FACS buffer and resuspended in 150 µl of FACS buffer and fluorescence intensities were determined by flow cytometry (LSRII HTS or LSRFortessa, BD Biosciences, CA, USA) and indicated as the median fluorescence intensity (MFI-Median) and percentage of positive cells.

Results

Figure 1B:
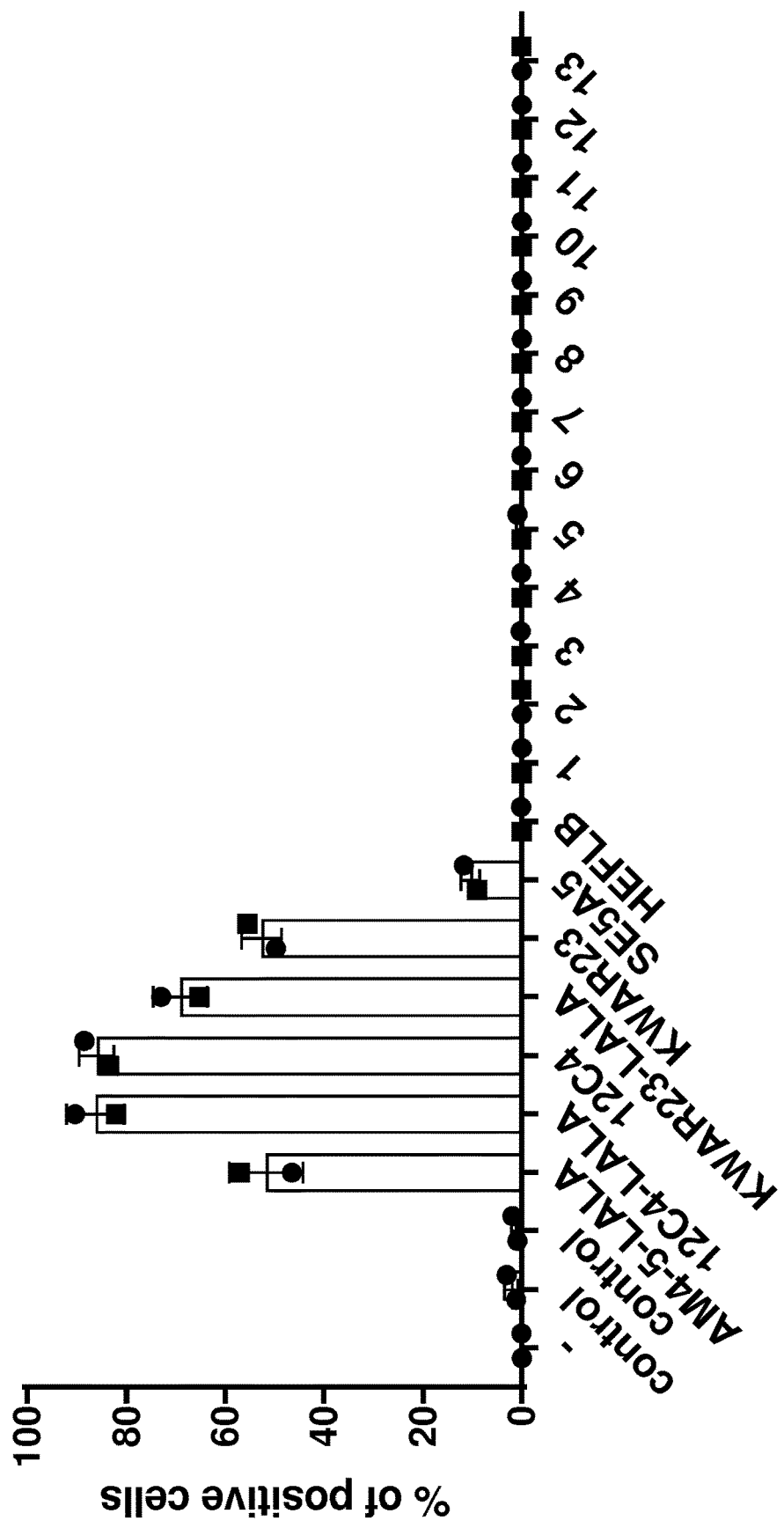

Binding of antibodies to SIRPγ expressing CD3$^+$ T-cells is shown in FIG. 1 (mean fluorescence intensity (FIG. 1a); percentage of positive cells (FIG. 1b)). All reference antibodies, except for humanized HEFLB showed binding to SIRPγ. Antibodies 1-13 did not show binding to human CD3' T-cells, confirming no binding of SIRPγ in a cell-based environment.

4. Characterization of Comparative Anti-SIRPα Antibodies

Experimental

Flow Cytometry assay: U937 cells (human monocytic cell line) endogenously expressing human SIRPα$_{BIT}$ antigen and cells derived from a non-engineered subclone that has been screened and isolated from CHO-S Chinese hamster ovary cells (ExpiCHO-S) cells transiently expressing either human SIRPα$_1$ or SIRPα$_{BIT}$ antigen (100,000 cells/well in a 96-well plate) were washed twice with ice-cold FACS buffer (1×PBS (LONZA) containing 0.1% v/w BSA (Sigma-Aldrich, St. Louis, MO) and 0.02% v/w NaN$_3$ (Sigma-Aldrich), followed by the addition of a concentration range of each primary antibody (50 µl/well) diluted in ice-cold FACS buffer. After an incubation time of 30 min at 4° C., the cells were washed twice with ice-cold FACS buffer. Then, 50 µl/well secondary mAb was added (AffiniPure™ F(ab')$_2$ fragment Goat-anti-human IgG-APC, 1:6,000 dilution, Jackson Immuno Research). After 30 min at 4° C., cells were washed twice and resuspended in 150 µl FACS buffer. Fluorescence intensities were determined by flow cytometry with the FACSVerse (BD Biosciences) and indicated as the median fluorescence intensity (MFI-Median) for U937 cells and the mean fluorescence intensity (MFI-Mean) for ExpiCHO-S cells. Curves were fitted by nonlinear regression with a variable slope (four parameters) in GraphPad Prism (version 7.02 for Windows, GraphPad, San Diego, CA). EC$_{50}$ values were calculated as the concentration in µg/ml that gives a response half way between bottom and top of the curve, when using a 4-parameter logistic fit.

Surface Plasmon Resonance (SPR) assay; Affinity analysis was performed by single cycle kinetics analysis on a BiaCore™ T200 instrument (GE life Sciences) at 25° C. AVI-tagged biotinylated SIRP antigens were captured using the Biotin CAPture kit (GE life Sciences). The streptavidin surface was prepared by injection of biotin capture reagent. Subsequently biotinylated SIRP variants were injected in running buffer (10 mM HEPES buffer at pH 7.4 with 150 mM NaCl, 3 mM EDTA and 0.005% v/v Surfactant P20) to a capture level of approximately 40-50 response units (RU). After a 1 min baseline stabilization, five increasing concentrations of the anti-SIRPα antibodies were injected with an association time of 150 sec. The dissociation was observed for 600 sec, both at a flow rate of 30 µl/min. The concentration range was chosen around the expected K$_D$. Regeneration was performed according to the manufacturer's protocol with 6M guanidine-HCl, 0.25M NaOH solution. Double reference subtraction was performed on the obtained sensorgrams using a (biotin capture reagent bound) reference flow channel and a running buffer injection. Sensorgrams were fitted with a 1:1 Langmuir model for all tested anti-SIRP antibodies. The kinetic parameters ($k_a$, $k_d$ and $K_D$) were calculated using the BiaCore™ T200 evaluation software (v3.1), huSIRPβ$_{1v1}$ and huSIRPβ$_{1v2}$ were tested in their monomeric form. Estimated K$_D$s are within the tested concentration range. When <1.0E$^{-11}$ is the reported K$_D$ value, the affinity could not accurately be determined because the kinetic parameters are outside the instruments specifications.

Results

Flow cytometry assay: A comparison of SIRPα antibodies for binding to huSIRPα$_1$ and huSIRPα$_{BIT}$ expressed on cells was determined by flow cytometry. The binding is indicated as an EC$_{50}$ value in Table 4. All antibodies tested here show binding to huSIRPα$_{BIT}$ (either transiently expressed in ExpiCHO-S cells or endogenously expressed in U937 cells) and huSIRPα$_1$. While most antibodies display an EC$_{50}$ value in the low µg/ml range, AB115-LALA, 3F9-LALA and 7H9-LALA show an EC$_{50}$ value that is greater than 1 µg/ml for binding to U937 cells. In addition, 3F9-LALA binds to huSIRPα$_1$ and huSIRPα$_{BIT}$ expressed on ExpiCHO-S cells with an EC$_{50}$ value greater than 1 µg/ml. Of note, corresponding isotype controls do not show binding to any of these cells.

TABLE 4

Cellular binding of anti-SIRPα antibodies to U937 cells endogenously expressing human SIRPα$_{BIT}$ and to ExpiCHO-S cells transiently transfected with either human SIRPα$_1$ or human SIRPα$_{BIT}$.

| Antibody | U937 cells (huSIRPα$_{BIT}$) EC$_{50}$ (µg/ml) | ExpiCHO-S (huSIRPα$_1$) EC$_{50}$ (µg/ml) | ExpiCHO-S (huSIRPα$_{BIT}$) EC$_{50}$ (µg/ml) |
|---|---|---|---|
| 6 | 0.09 | 0.06 | 0.01 |
| KWAR23-LALA | 0.07 | 0.14 | 0.16 |
| 1H9 | 0.05 | 0.04 | 0.08 |
| 40A-1 | 0.23 | 0.09 | 0.16 |
| 40A-2 | 0.24 | 0.14 | 0.12 |
| AB3-LALA | 0.06 | 0.09 | 0.13 |
| AB25-LALA | 0.08 | 0.18 | 0.10 |
| AB115-LALA | 1.43 | 0.37 | 0.48 |
| AB119-LALA | 0.04 | 0.10 | 0.07 |
| AB136-LALA | 0.39 | 0.12 | 0.18 |
| 3F9-LALA | 3.24 | 1.49 | 1.88 |
| 7H9-LALA | 1.08 | 0.49 | 0.52 |

SPR assay: A comparison of SIRPα antibodies for selectivity to human SIRPβ-variants β$_{1v1}$ and β$_{1v2}$ was performed using SPR and results are summarized in Table 5. Except for 3F9-LALA, all antibodies recognized huSIRPβ$_{1v1}$. All tested antibodies bind huSIRPβ$_{1v2}$, with antibody 6 having the highest K$_D$ and thus the lowest affinity. Of note, corresponding isotype controls do not show binding to huSIRPβ$_{1v1}$ and to huSIRPβ$_{1v2}$.

TABLE 5

Binding affinities (K$_D$ in M) of anti-SIRPα antibodies to human SIRPβ$_{1v1}$ and human SIRPβ$_{1v2}$ as measured by SPR.

| Antibody | huSIRPβ$_{1v1}$ | huSIRPβ$_{1v1}$ |
|---|---|---|
| 6 | 1.48E−10 | 3.20E−09 |
| KWAR23-LALA | 1.83E−11 | 2.52E−11 |
| 1H9 | 2.08E−11 | 2.40E−11 |
| 40A-1 | 7.15E−09 | 7.44E−11 |
| 40A-2 | 9.70E−09 | 1.88E−10 |
| AB3-LALA | 2.12E−11 | <1E−11 |

TABLE 5-continued

Binding affinities ($K_D$ in M) of anti-SIRPα antibodies to human SIRPβ$_{1v1}$ and human SIRPβ$_{1v2}$ as measured by SPR.

| Antibody | huSIRPβ$_{1v1}$ | huSIRPβ$_{1v1}$ |
|---|---|---|
| AB25-LALA | <1E−11 | <1E−11 |
| AB115-LALA | <1E−11 | <1E−11 |
| AB119-LALA | <1E−11 | 1.28E−11 |
| AB136-LALA | 1.71E−10 | 2.02E−10 |
| 3F9-LALA | no binding | 3.80E−10 |
| 7H9-LALA | 3.36E−10 | 3.99E−10 |
| KWAR23 | 1.47E−11 | 2.74E−11 |
| 12C4 | 1.06E−10 | 4.90E−11 |
| 29AM4-5-LALA | 1.05E−10 | 1.53E−10 |
| 12C4-LALA | 1.11E−10 | 5.11E−11 |
| HEFLB | 2.20E−10 | 3.46E−10 |
| SE5A5 | 6.31E−11 | 3.58E−10 |

5. Binding of Anti-SIRPα Antibodies to Primary Cells: Granulocytes, Monocytes and T-Cells Experimental Flow Cytometry assay, whole blood staining: Heparinized whole blood samples were obtained from healthy donors (Sanquin blood bank Nijmegen, the Netherlands) and were stored overnight at room temperature. Whole blood samples were lysed with 1× BD FACS™ Lysing Solution (349202, BD Biosciences)) for 15 min at room temperature and washed with FACS buffer (PBS containing 0.1% BSA and 2 mM EDTA), $1.5 \times 10^5$ cells per well were stained with 50 μl per well anti-SIRPα antibodies (concentration range starting from 10 μg/ml or 90 μg/ml with a 3.16× dilution) in 96-well microtiter plates (353910, Falcon) for 30 min at 4° C. After washing with FACS buffer, cells were incubated with a cocktail of 1:800 diluted anti-human CD3-PB clone UCHT1 (558117, BD Biosciences), 1:800 diluted anti-human CD14-FITC clone MφP9 (345784. BD Biosciences) and 1:6000 diluted APC-labelled goat anti-human IgG F(ab')$_2$ secondary antibody (109-136-098. Jackson ImmunoResearch) in FACS buffer for 30 min at 4° C. After washing with FACS buffer, cells were mixed by vortexing to avoid cell aggregation and incubated with 50 μl per well BD Cytofix™ Fixation Buffer (4.2% PFA) (554655. BD Biosciences) for 15 min at room temperature and washed prior to analysis. Samples were collected with FACSVerse (BD Biosciences) and analysed in FlowJo Software (BD Biosciences). Granulocytes were gated based on FSC-A/SSC-A, followed by CD14 gating. T-cells and monocytes were first gated based on FSC-A/SSC-A. T-cells were then identified as CD3$^+$CD14$^−$ cells and monocytes as CD14$^+$CD3$^−$ cells.

Flow Cytometry assay, binding to isolated T-cells: T-cells were isolated by negative selection (11344D Dynabeads Untouched Human T Cell Kit. ThermoFisher Scientific) from peripheral blood mononuclear cells (PBMC) of healthy individuals (Sanquin blood bank Nijmegen, the Netherlands). Cells were washed in HEPES+ buffer (132 mM NaCl, 6 mM KCl, 1 mM CaCl$_2$), 1 mM MgSO$_4$, 1.2 mM potassium phosphate, 20 mM HEPES, 5.5 mM glucose and 0.5% (w/v) human serum albumin, pH 7.4) and resuspended in a concentration of $1 \times 10^6$/ml in isolation buffer (PBS+ human albumin 1% buffer w/v. Human Albuman 200 g/ml.

Sanquin Plasma Products B.V., Amsterdam, Netherlands), spun down and resuspended in FACS buffer (1×PBS (LONZA) containing 0.1% v/w BSA (Sigma-Aldrich, St. Louis, MO) and 0.02% v/w NaN$_3$ (Sigma-Aldrich). Cells (100.000 cells/well in a 96-well plate) were washed with ice-cold FACS buffer followed by the addition of a concentration range of each primary mAb (50 μl/well) diluted in ice-cold FACS buffer. After an incubation time of 30 min at 4° C. the cells were washed two times with ice-cold FACS buffer; next 50 μl/well secondary antibody was added (for human antibodies. AffiniPure™ F(ab')$_2$ fragment Goat-anti-human IgG-APC. 1:6,000 dilution. Jackson Immuno Research; for mouse antibodies. AffiniPure™ Fab fragment Goat Anti-Mouse IgG (H+L)-Alexa Fluor 488, 1:1,000 dilution, Jackson Immuno Research). After 30 min at 4° C. cells were washed twice and resuspended in 150 μl FACS buffer. Fluorescence intensities were determined by flow cytometry with the FACSVerse (BD Biosciences) and indicated as the mean fluorescence intensity (MFI-Mean). Curves were fitted by nonlinear regression with variable slope (four parameters) in GraphPad Prism (version 7.02 for Windows. GraphPad. San Diego, CA). EC$_{50}$ values were calculated as the concentration in μg/ml that gives a response half way between bottom and top of the curve, when using a 4-parameter logistic fit.

Results

Flow Cytometry assay, whole blood staining: The binding of various SIRPα antibodies to primary cells was determined by flow cytometry. Dose-response curves for a representative healthy heterozygous SIRPα$_1$/SIRPα$_{BIT}$ donor are shown in FIG. 10a-d. It should be noted that the exact height of the response is not necessarily a characteristic of the SIRPα antibody as this can also depend on the secondary antibody. Instead, EC$_{50}$ values are independent of the detection antibody and should therefore be compared. A summary of the EC$_{50}$ values is depicted in Table 6. All antibodies show binding to granulocytes and monocytes of heterozygous SIRPα$_{BIT}$/SIRPα$_1$ donors, though exact EC$_{50}$ values are varying. Except for HEFLB, all antibodies also show binding to granulocytes and CD14+ monocytes of the homozygous SIRPα$_1$ donor with fluctuating EC$_{50}$ values. These data are in line with the SPR and cellular data of Tables 2 and 3, where HEFLB also lacks binding to SIRPα$_1$. Circulating CD3$^+$ T-cells in the human blood do not express SIRPα or SIRPβ but only SIRPγ, and therefore CD3$^+$ T-cell binding can be interpreted as SIRPγ binding. While most antibodies show binding to CD3$^+$ T-cells, antibody 6, AB3-LALA, 3F9-LALA, 7H9-LALA and HEFLB do not show binding to CD3$^+$ T-cells. In this whole blood staining assay, AB136-LALA shows binding to T-cells at higher antibody concentrations. This appears to be in alignment with the disclosure in WO2018/057669 that Ab136 binds to SIRPγ, but with a low $K_D$.

TABLE 6

Cellular binding of anti-SIRPα antibodies to granulocytes, CD14+ monocytes and CD3+ T-cells in whole blood of healthy heterozygous SIRPα$_1$/SIRPα$_{BIT}$ donors (α1/αBIT) or a homozygous SIRPα$_1$/SIRPα$_1$ donor (α1/α1).

| | Granulocytes EC$_{50}$ (μg/ml) | | | CD14+ Monocytes EC$_{50}$ (μg/ml) | | | CD3+ T-cells (human ab) EC$_{50}$ (μg/ml) | | |
|---|---|---|---|---|---|---|---|---|---|
| Antibody | Donor #1 α1/αBIT | Donor #2 α1/αBIT | Donor #3 α1/α1 | Donor #1 α1/αBIT | Donor #2 α1/αBIT | Donor #3 α1/α1 | Donor #1 α1/αBIT | Donor #2 α1/αBIT | Donor #3 α1/α1 |
| 6 | 0.03 | 0.03 | 0.02 | 0.03 | 0.03 | 0.02 | >10 | >10 | >10 |
| KWAR23-LALA | 0.03 | 0.04 | 0.02 | 0.01 | 0.02 | 0.01 | 0.01 | 0.01 | 0.003 |
| 1H9 | 0.02 | 0.04 | 0.01 | 0.01 | 0.03 | 0.01 | * | * | * |
| 40A-1 | 0.07 | 0.06 | 0.02 | 0.05 | 0.05 | 0.03 | 0.03 | 0.03 | 0.02 |
| AB3-LALA | 0.01 | 0.02 | 0.01 | 0.01 | 0.02 | 0.01 | >10 | >10 | >10 |
| AB25-LALA | 0.02 | 0.06 | 0.03 | 0.02 | 0.06 | 0.03 | # | 0.06 | 0.03 |
| AB115-LALA | 0.73 | 0.35 | 0.18 | 0.61 | 0.36 | 0.21 | 0.15 | 0.09 | 0.10 |
| AB119-LALA | 0.01 | 0.01 | 0.005 | 0.01 | 0.01 | 0.003 | 0.01 | 0.01 | 0.005 |
| AB136-LALA | * | * | * | * | * | * | * | * | * |
| 3F9-LALA | 0.83 | 0.51 | ~0.12^ | 0.48 | 0.51 | ~0.11 | >10 | >10 | >10 |
| 7H9-LALA | 0.10 | 0.08 | 0.04 | 0.10 | 0.09 | 0.04 | >10 | >10 | >10 |
| 29AM4-5-LALA | 0.03 | 0.05 | 0.04 | 0.02 | 0.03 | 0.02 | 0.07 | 0.32 | 0.12 |
| 12C4-LALA | 0.02 | 0.03 | 0.10 | 0.01 | 0.02 | 0.19 | * | * | * |
| HEFLB | 0.02 | 0.17 | >10 | 0.02 | 0.15 | >10 | >10 | >10 | >10 |

Figure 11:
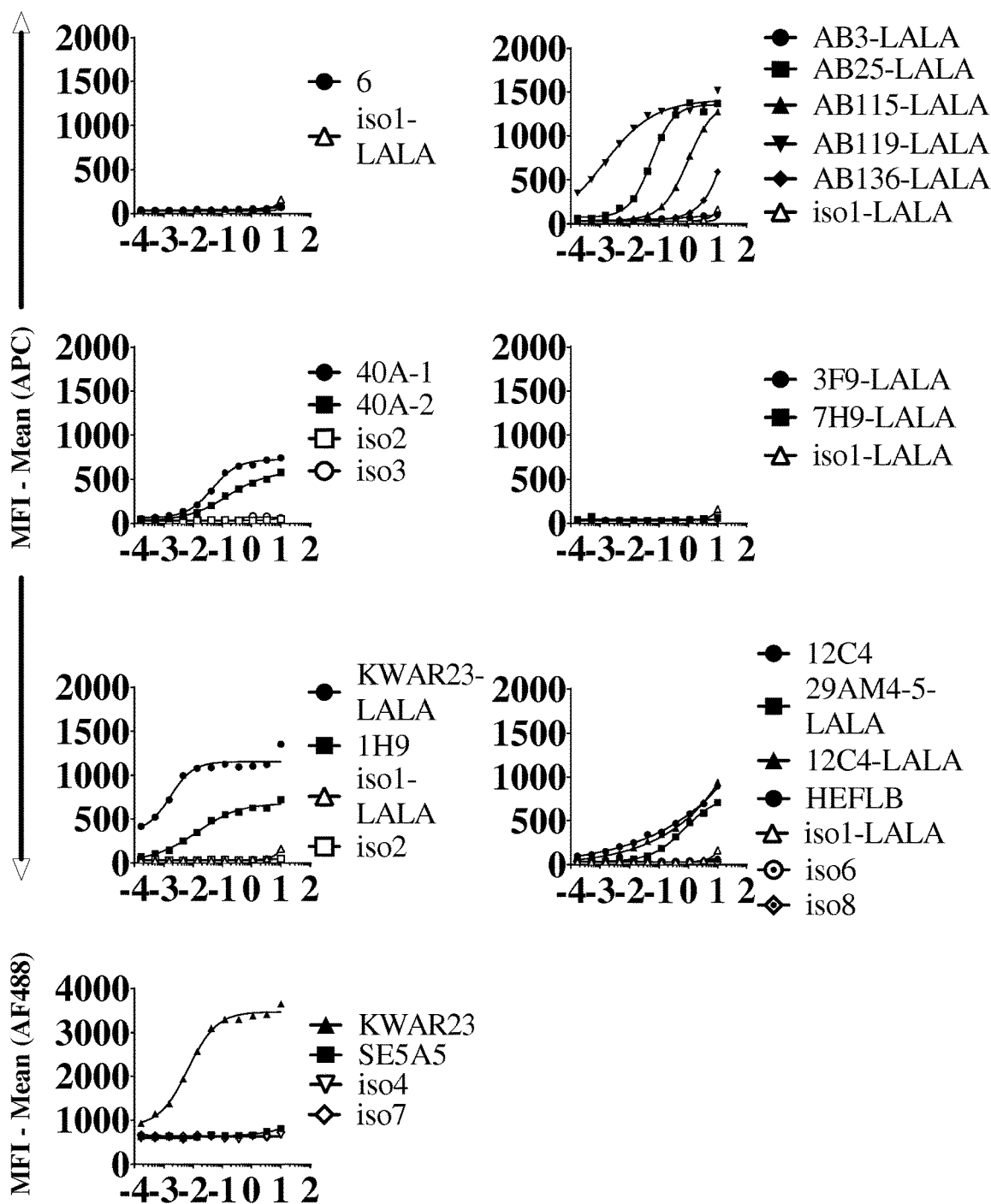
FIG. 11. Binding of indicated anti-SIRPα antibodies to SIRPγ expressing human CD3 T-cells isolated from buffy coats of a healthy donor as determined by flow cytometry. The relevant isotype control for each anti-SIRPα antibody is provided in each graph. Data is depicted as mean fluorescence intensity (MFI).

>10 = EC$_{50}$ > than 10 μg/ml
# = Excluded, resulted in an abnormal binding profile
^ = Dose-response curve is observed; however, the values are below isotype control
* = Incomplete curve (saturation not reached)
~ = Ambiguous fitting Flow Cytometry assay, binding to isolated T-cells: To confirm SIRPγ-dependent T-cell binding of various antibodies using another approach, isolated primary T-cells (in absence of SIRPα- or SIRPβ-positive myeloid cells) were stained with the panel of antibodies. Results are shown in FIG. 11. While most antibodies bind to T-cells, antibody 6, AB3-LALA, 3F9-LALA, 7H9-LALA, SE5A5 and HEFLB do not show binding to T-cells. Again, AB136-LALA shows binding at high antibody concentrations.

Thus, the Examples above show that the affinity of antibody 6 for huSIRPβ$_{1v2}$ is lower than that of any of the comparative anti-SIRPα antibodies tested in the extensive panel listed above. Also, the affinity of non T-cell binding antibody 6 to SIRPβ$_{1v1}$ was comparable to that of AB136-LALA, 7H9-LALA and HEFLB that also have low/no affinity for SIRPγ and lower than that of AB3 and SE5A5 that also have low/no affinity for SIRPγ.

In aggregate, antibody 6 has a high potency of binding to both SIRPα-alleles while simultaneously showing relatively low or absent binding to the other non-inhibitory SIRP-family members SIRPβ$_{1v1}$, SIRPβ$_{1v2}$ and SIRPγ.

6. CD47 Blocking Ability

Experimental

CD47 blocking ability: To assess the ability of anti-SIRPα antibodies to block either SIRPα$_1$ or SIRPα$_{BIT}$ binding to CD47, SIRPα$_1$ or SIRPα$_{BIT}$ was pre-incubated with anti-SIRPα antibody and then dissociation from captured CD47 was tested. Briefly, AVI-tagged biotinylated CD47-Fc was captured using the Biotin CAPture kit (GE life Sciences). The streptavidin surface was prepared by injection of biotin capture reagent. Subsequently, biotinylated CD47-Fc was injected in running buffer (10 mM HEPES buffer at pH 7.4 with 150 mM NaCl, 3 mM EDTA and 0.005% v/v Surfactant P20) to a capture level of approximately 1000 RU. A mixture containing a fivefold molar excess of antibody and either 10 μg/ml SIRPα$_1$ or 10 μg/ml SIRPα$_{BIT}$ was pre-incubated for 30 min at ambient temperature and injected over the CD47-Fc surface for 120 sec at 5 μl/min. The dissociation was observed for 300 sec prior to regeneration with 6 M guanidine-HCl, 0.25 M NaOH (3:1), according to the manufacturer's instructions. Characterization of a blocking/non-blocking antibody was done by visual assessment after double reference subtraction.

Results

CD47 blocking ability: The capacity of SIRPα-targeting antibodies to block CD47 binding was studied using SPR (Table 7). While most antibodies, including antibody 6, block the CD47-SIRPα$_{BIT}$ and CD47-SIRPα$_1$ interaction, AB3-LALA, AB136-LALA, 3F9-LALA and 7H9-LALA do not block CD47-SIRPα$_{BIT}$ and CD47-SIRPα$_1$ interaction and are thus non-blocking. In addition, HEFLB only blocks the interaction of CD47-SIRPα$_{BIT}$, but not that of CD47-SIRPα$_1$, consistent with the lack of recognition of SIRPα$_1$ by HEFLB.

TABLE 7

Characterization of SIRPα-antibodies for blocking the CD47-SIRPα$_{BIT}$ and CD47-SIRPα$_1$ interactions.

| Antibody | huSIRPα$_1$ | huSIRPα$_{BIT}$ |
|---|---|---|
| 6 | yes | yes |
| KWAR23-LALA | yes | yes |
| 1H9 | yes | yes |
| 40A-1 | yes | yes |
| 40A-2 | yes | yes |
| AB3-LALA | no | no |
| AB25-LALA | yes | yes |
| AB115-LALA | yes | yes |
| AB119-LALA | yes | yes |
| AB136-LALA | no | no |
| 3F9-LALA | no | no |
| 7H9-LALA | no | no |
| KWAR23 | yes | yes |
| 12C4 | yes | yes |
| 29AM4-5-LALA | yes | yes |
| 12C4-LALA | yes | yes |
| HEFLB | no | yes |
| SE5A5 | yes | yes |

7. Ability to Block SHP-1 Recruitment
Experimental

SIRPα$_{BIT}$ signalling was analysed using the PathHunter Enzyme Fragment Complementation technology from DiscoverX®. In this assay, CD47-deficient Jurkat cells are genetically engineered to over-express SIRPα$_{BIT}$+ tagged with Prolink (PK) and Enzyme Acceptor (EA) fused to the SH2 domain of the signalling protein SHP-1. When these Jurkat SIRPα$_{BIT}$ signalling cells are incubated with cells that express CD47 (CD47 ligand cells), SHP-1 and SIRPα$_{BIT}$ will interact resulting in the complementation of PK and EA. This creates an active β-galactosidase enzyme that can cleave a substrate to generate a chemiluminescent signal. This system can be used to study the ability of SIRPα-targeting antibodies to antagonize SHP-1 recruitment to SIRPα. The Jurkat SIRPα$_{BIT}$ signalling cells were incubated with a concentration range of anti-SIRPα antibody in combination with CD47 ligand cells. Jurkat E6.1 cells were used as CD47 ligand cells and the assay was performed in 384 wells plate format. First. 12.5 µl Jurkat SIRPα$_{BIT}$ signalling cell suspension (0.8 million cells/ml) were added to each well followed by 2.5 µl of a concentration range of anti-SIRPα antibody solution (11× concentrated). The assay was started by adding 12.5 µl CD47 ligand cell suspension at the EC$_{80}$ (1.6 million Jurkat E6.1 cells/ml). Plates were incubated for 4 hours at 37° C. and 5% CO$_2$. After incubation. 2 µl of 2× diluted reagents A (DiscoverX detection kit, in PBS containing 0.1% BSA) were added. Plates were incubated 30 min on a shaker (300 rpm), in the dark, at room temperature. Then. 10 µl of 2× diluted reagents B (DiscoverX detection kit, in PBS containing 0.1% BSA) were added. Plates were incubated for 1 hour on a shaker (300 rpm) in the dark, at room temperature. Luminescence was measured at 0.1 sec/well integration time with the Envision® system (Perkin Elmer). All cell suspensions were prepared in cell plating medium (DiscoverX), the antibody dilutions in PBS containing 0.1% BSA (Sigma). Graphs were analysed in GraphPad Prism 8 software. The % of maximal signal was determined as follows: (relative luminescence units (RLU)/RLU of maximal stimulation (no antibody)*100). Efficacy levels were calculated as followed: 100%−'% of maximum signal' of 3.3 µg/ml compound value.

Results

Figure 12A:
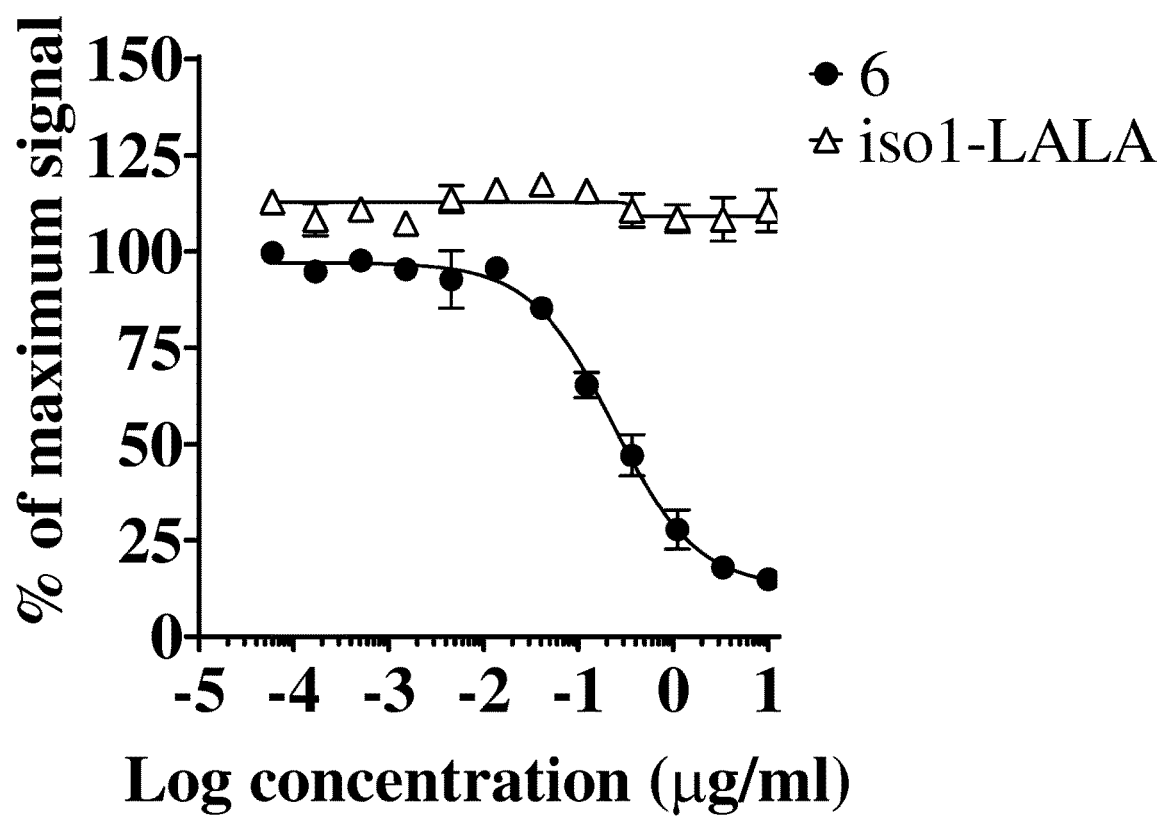
FIG. 12a. SHP-1 recruitment to SIRPα as measured by relative luminescence units (RLU) using Jurkat SIRPα$_{BIT}$ signalling cells with Jurkat E6.1 cells as CD47 ligand cells, in absence or presence of a concentration range of antibody 6 or an isotype control. The % of maximum signal was determined as follows: (RLU/RLU of maximal stimulation (no antibody)*100). Results are shown as mean+/−SEM of two independent experiments.
Figure 12B:
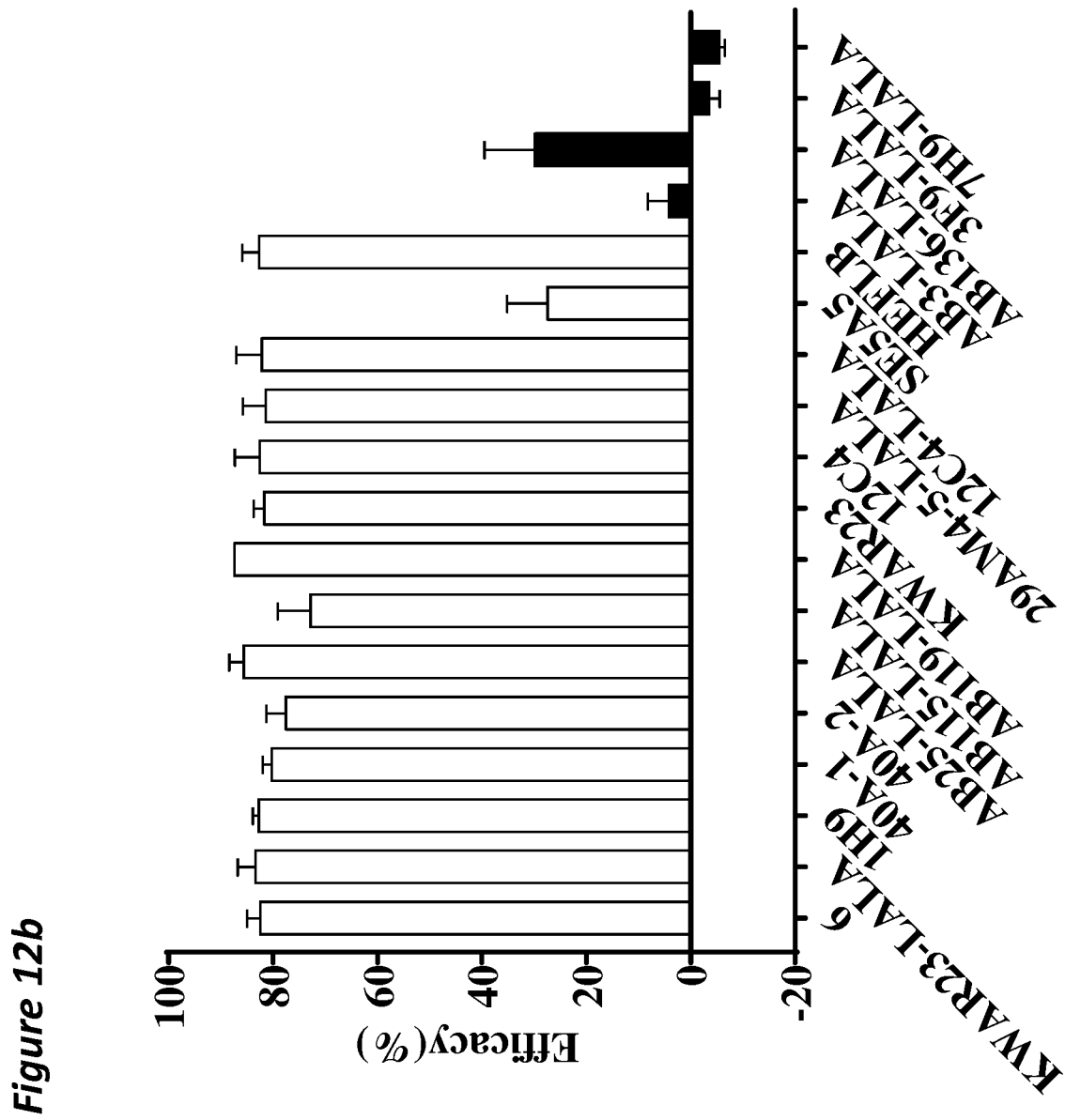
FIG. 12b. Efficacy levels of indicated anti-SIRPα antibodies at 3.3 μg/ml for inhibiting SIRPα$_{BIT}$ signalling as measured with Jurkat SIRPα$_{BIT}$ signalling cells and Jurkat E6.1 cells as CD47 ligand cells. Efficacy levels were calculated as followed: 100%−'% of maximum signal' of 3.3 μg/ml compound value. Results are shown as mean+/−SEM of two independent experiments.

Activation of SIRPα leads to a well-characterized inhibitory signal cascade. Upon binding of CD47, the cytoplasmic domain immunoreceptor tyrosine-based inhibition motifs (ITIMs) of SIRPα become phosphorylated, leading to the recruitment and activation of Src homology region 2 domain-containing phosphatase-1 (SHP-1). SHP-1 mediates inhibitory signalling through protein dephosphorylation of specific substrates, including the activating FcγRs. This leads to dampening of the immune response. The ability of SIRPα-targeting antibodies to inhibit SIRPα-mediated signalling was studied using the CD47-deficient Jurkat SIRPα$_{BIT}$ signalling cells. When these cells are incubated with CD47-containing Jurkat E6.1 cells. SHP-1 is recruited to SIRPα$_{BIT}$ resulting in a chemiluminescent signal. Antibody 6 is able to antagonize this signal in a dose-dependent manner (FIG. 12a). Other SIRPα-targeting antibodies were tested at a fixed dose (3.3 µg/ml) for their ability to antagonize SIRPα$_{BIT}$ signalling (FIG. 12b). Except for SE5A5, the efficacy for inhibiting SIRPα$_{BIT}$ signalling is similar for all CD47-SIRPα blocking antibodies (depicted in white bars). The non-blocking antibodies AB3-LALA. AB136-LALA, 3F9-LALA and 7H9-LALA (depicted in black bars) display a lower or absent signal inhibitory efficacy compared to the blocking antibodies, and thus appear less or not capable of antagonizing SIRPα-mediated signalling.

In aggregate, antibody 6 blocks binding of CD47 to both SIRPα-alleles and in contrast to the non-blocking antibodies, this leads to a high inhibition of down-stream signalling.

8. Antibody Dependent Cellular Cytotoxicity (ADCC)
Experimental

DELFIA® cytotoxicity assay (non-radioactive assay): Neutrophils of donors heterozygous for SIRPα$_1$ and SIRPα$_{BIT}$ were isolated and cultured according to the method in Zhao et al. *PNAS* 2011, 108(45), 18342-18347. Freshly isolated neutrophils were cultured overnight with human G-CSF (10 ng/ml) and IFNγ (50 ng/ml). Antibody Dependent Cellular Cytotoxicity (ADCC) was determined using the non-radioactive Europium TDA (EuTDA) cytotoxicity assay (DELFIA®, PerkinElmer). SKBR3 (human HER2-positive breast cancer cell line) cells were used as target cells and labelled with bis(acetoxymethyl)2,2':6',2"-terpyridine-6,6"-dicarboxylate) (BATDA reagent, DELFIA) for 5 min at 37° C. After 2 washes with PBS, $5 \times 10^3$ target cells per well were incubated in IMDM culture medium supplemented with 10% (v/v) ultra-low IgG foetal bovine serum (FBS, Gibco) for 4 hours at 37° C. and 5% CO$_2$ in a 96-well U-bottom plate together with neutrophils in an effector to target cell ratio of 50:1 in the presence of the appropriate antibodies. After the incubation, supernatant was harvested and added to europium solution (DELFIA, PerkinElmer) and europium 2,2':6',2"-terpyridine-6,6"-dicarboxylic acid (EuTDA) fluorescence was determined using a spectrofluorometer (Envision, PerkinElmer). The percentage of cytotoxicity was calculated as [(experimental release-spontaneous release)/(total release-spontaneous release)]×100%. All conditions were measured in duplicate and/or triplicate.

$^{51}$Cr Release Assay (Radioactive Assay):

Neutrophils of donors homozygous for either SIRPα$_1$ or SIRPα$_{BIT}$ were isolated according to the method in Zhao et al. *PNAS* 2011, 108(45), 18342-18347. For all $^{51}$Cr release assay experiments, except for those presented in FIG. 2, freshly isolated neutrophils were cultured for 100 min with 10 ng/ml of human GM-CSF. Antibody Dependent Cellular Cytotoxicity (ADCC) was determined using the $^{51}$Cr release assay. SKBR3 (human breast cancer cell line) cells were used as target cells and labelled with 100 µCi $^{51}$Cr (PerkinElmer) for 90 min at 37° C. After 2 washes with PBS, $5 \times 10^3$ target cells per well were incubated in IMDM culture medium supplemented with 10% (v/v) foetal calf serum for 4 hours at 37° C. and 5% CO$_2$ in a 96-well U-bottom plate together with neutrophils in an effector to target cell ratio of 50:1 in the presence of the appropriate antibodies. After the incubation, supernatant was harvested and analysed for radioactivity in a gamma counter (Wallac). The percentage of cytotoxicity was calculated as [(experimental release-spontaneous release)/(total release-spontaneous release)]×100%. All conditions were measured in duplicate and/or triplicate.

Results

Humanization of 12C4 Resulted in Loss of ADCC, which was Recovered by Reduced Effector Function in the IgG$_1$ Constant Region:

FIG. 2 shows the results of the ADCC assay as cytotoxicity in % as measured by a $^{51}$Cr release assay. The % cytotoxicity measured on SKBR3 cells using neutrophils from homozygous SIRPα$_{BIT}$ donors as effector cells and trastuzumab alone is less than the % cytotoxicity of trastuzumab in combination with the murine 12C4 antibody (mu12C4). Trastuzumab in combination with an antibody wherein 12C4 variable regions are grafted onto a human IgG$_1$ constant region (12C4huIgG$_1$) shows similar % cytotoxicity as compared to trastuzumab alone at low concentrations of 12C4huIgG$_1$. At higher concentrations 12C4huIgG$_1$, a decrease in % cytotoxicity is observed. Trastuzumab in combination with an antibody wherein 12C4 variable regions are grafted onto a human IgG$_1$ constant region comprising amino acid substitutions L234A and L235A (12C4huIgG$_1$LALA) shows increased % cytotoxicity compared to the % cytotoxicity of trastuzumab alone, and increased % cytotoxicity compared to the combination of 0.2 µg/ml 12C4huIgG$_1$ and trastuzumab.

Figure 3:
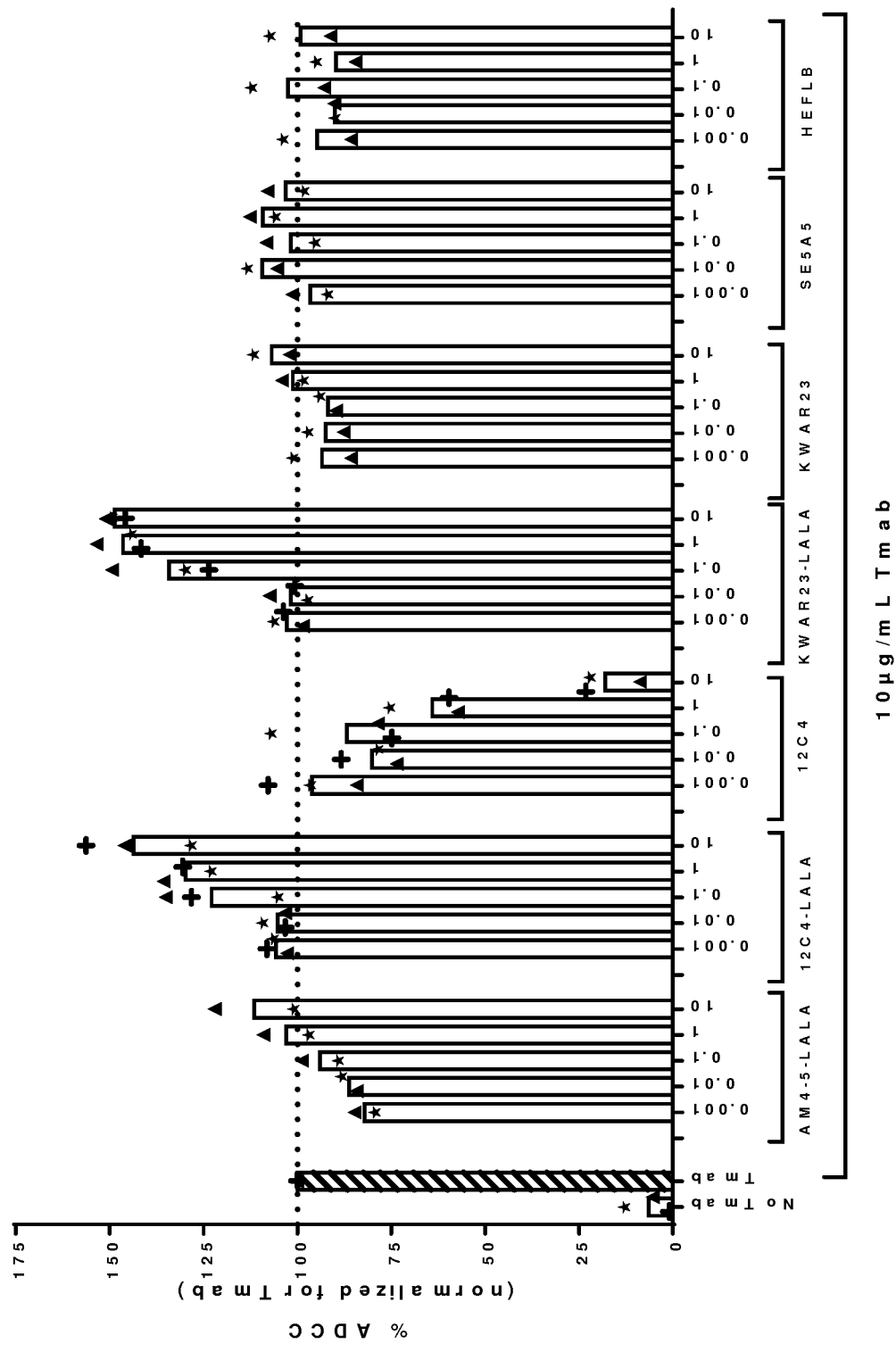
FIG. 3. Neutrophil-mediated ADCC towards trastuzumab (Tmab: 10 µg/ml) opsonized SKBR3 cells in combination with prior art based anti-SIRPα antibodies at various concentrations (µg/ml; dose response curves). Neutrophils were isolated from heterozygous human donors carrying one SIRPα$_1$ and one SIRPα$_{BIT}$ allele. Each individual neutrophil donor is indicated by a symbol. Columns are the average of all donors. As controls, untreated cells and cells treated with 10 µg/ml trastuzumab were used. Data is normalized for response to trastuzumab (set to 100%). Experiment was performed with neutrophils stimulated O/N with G-CSF and IFNγ. Cytotoxicity was measured with DELFIA cytotoxicity assay.
Figure 4:
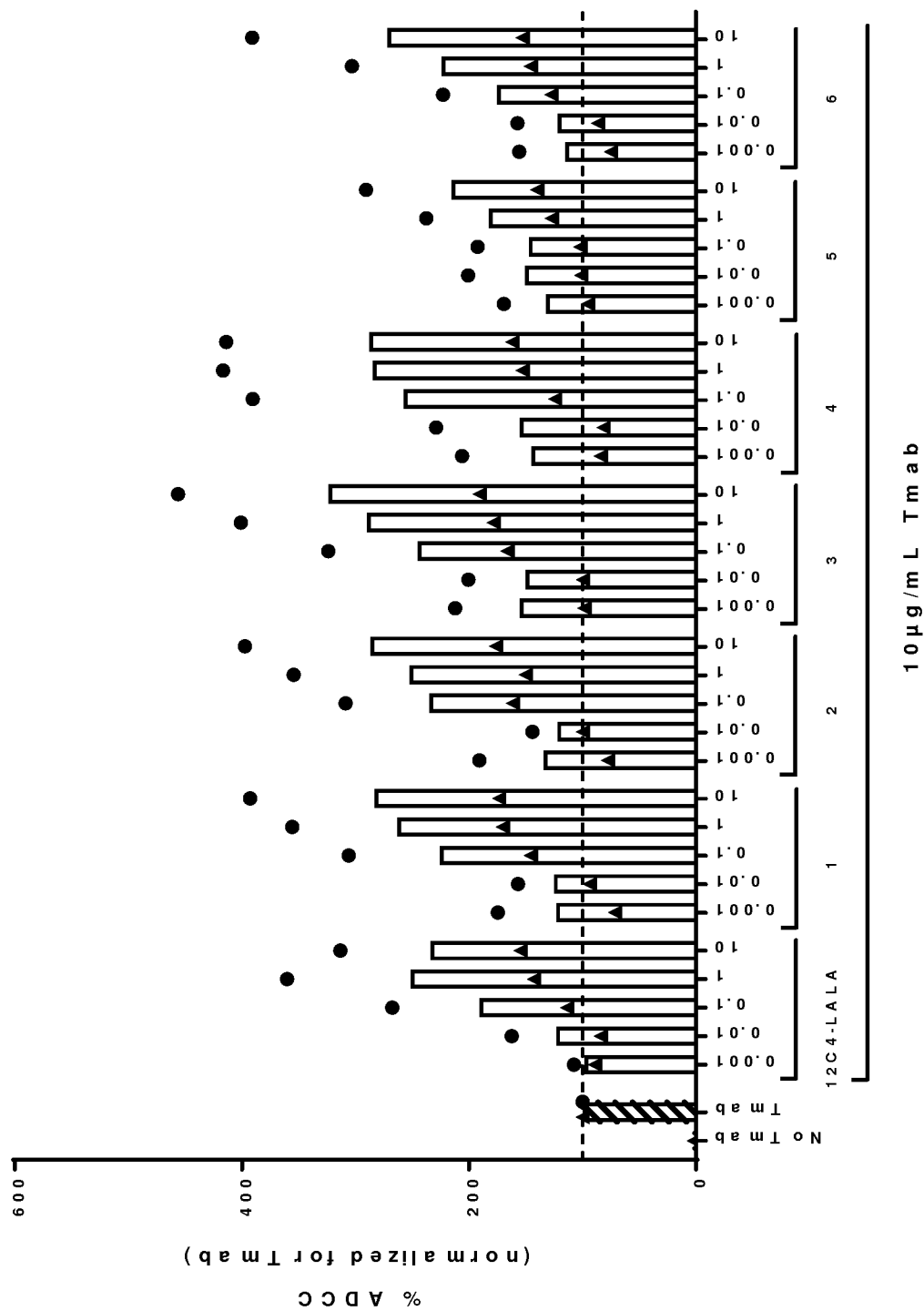
FIG. 4. Neutrophil-mediated ADCC towards trastuzumab (Tmab: 10 µg/ml) opsonized SKBR3 cells in combination with anti-SIRPα antibodies 1-6 of the invention, having a human IgG$_1$ constant region comprising the amino acid substitutions L234A and L235A, at various concentrations (µg/ml; dose response curves). Neutrophils were isolated from human donors carrying one SIRPα$_1$ and one SIRPα$_{BIT}$ allele. Each individual neutrophil donor is indicated by a symbol. Columns are the average of all donors. As controls, untreated cells and cells treated with 10 µg/ml trastuzumab were used. Data is normalized for response to trastuzumab (set to 100%). Experiment was performed with neutrophils stimulated O/N with G-CSF and IFNγ. Cytotoxicity was measured with DELFIA cytotoxicity assay.
Figure 5:
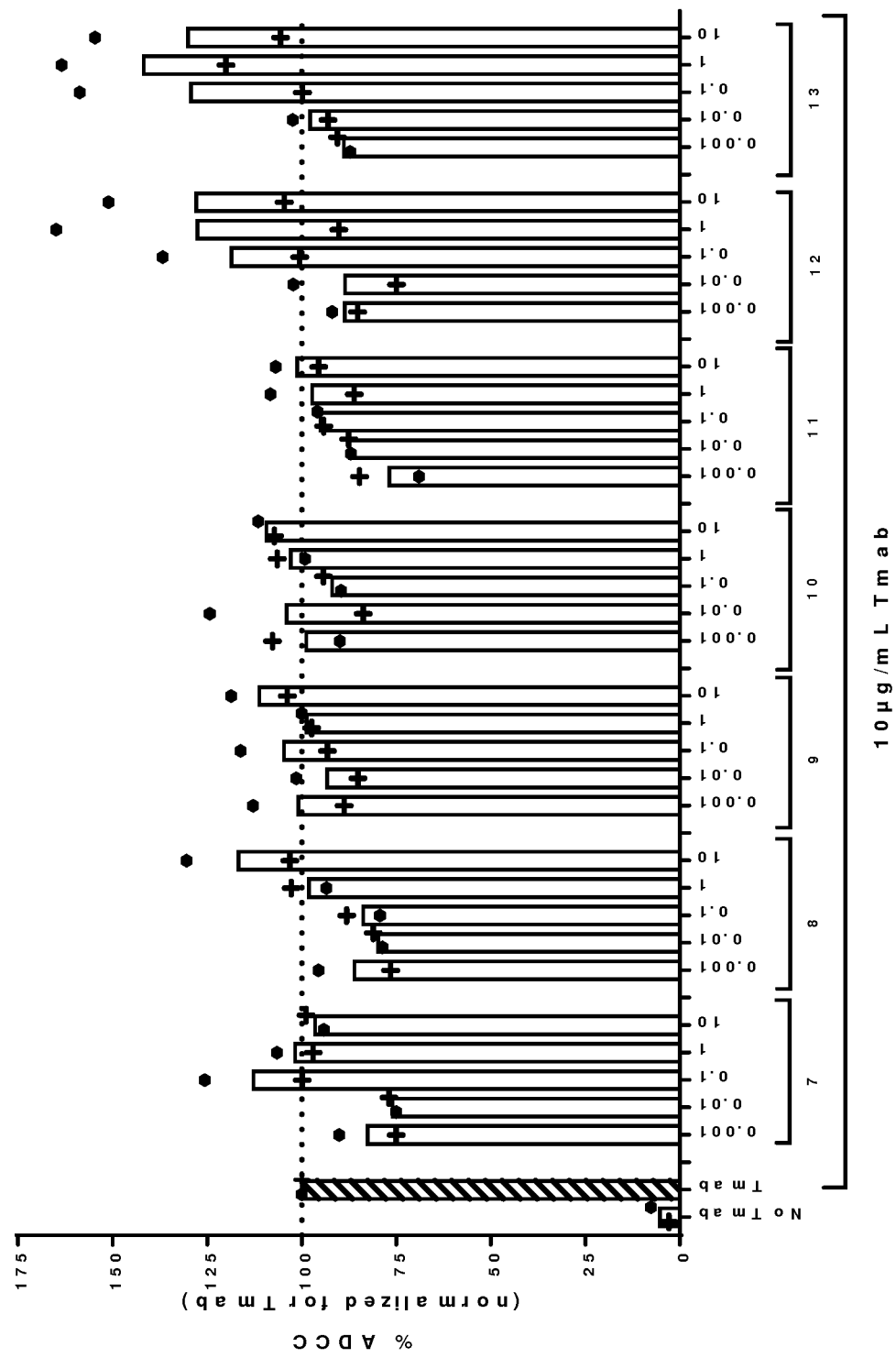
FIG. 5. Neutrophil-mediated ADCC towards trastuzumab (Tmab: 10 µg/ml) opsonized SKBR3 cells in combination with anti-SIRPα antibodies 7-13 of the invention, having a human IgG$_1$ constant region comprising the amino acid substitutions L234A and L235A, at various concentrations (μg/ml; dose response curves). Neutrophils were isolated from human donors carrying one SIRPα$_1$ and one SIRPα$_{BIT}$ allele. Each individual neutrophil donor is indicated by a symbol. Columns are the average of all donors. Data is normalized for response to trastuzumab (set to 100%). Experiment was performed with neutrophils stimulated O/N with G-CSF and IFNγ. Cytotoxicity was measured with DELFIA cytotoxicity assay.
Figure 6:
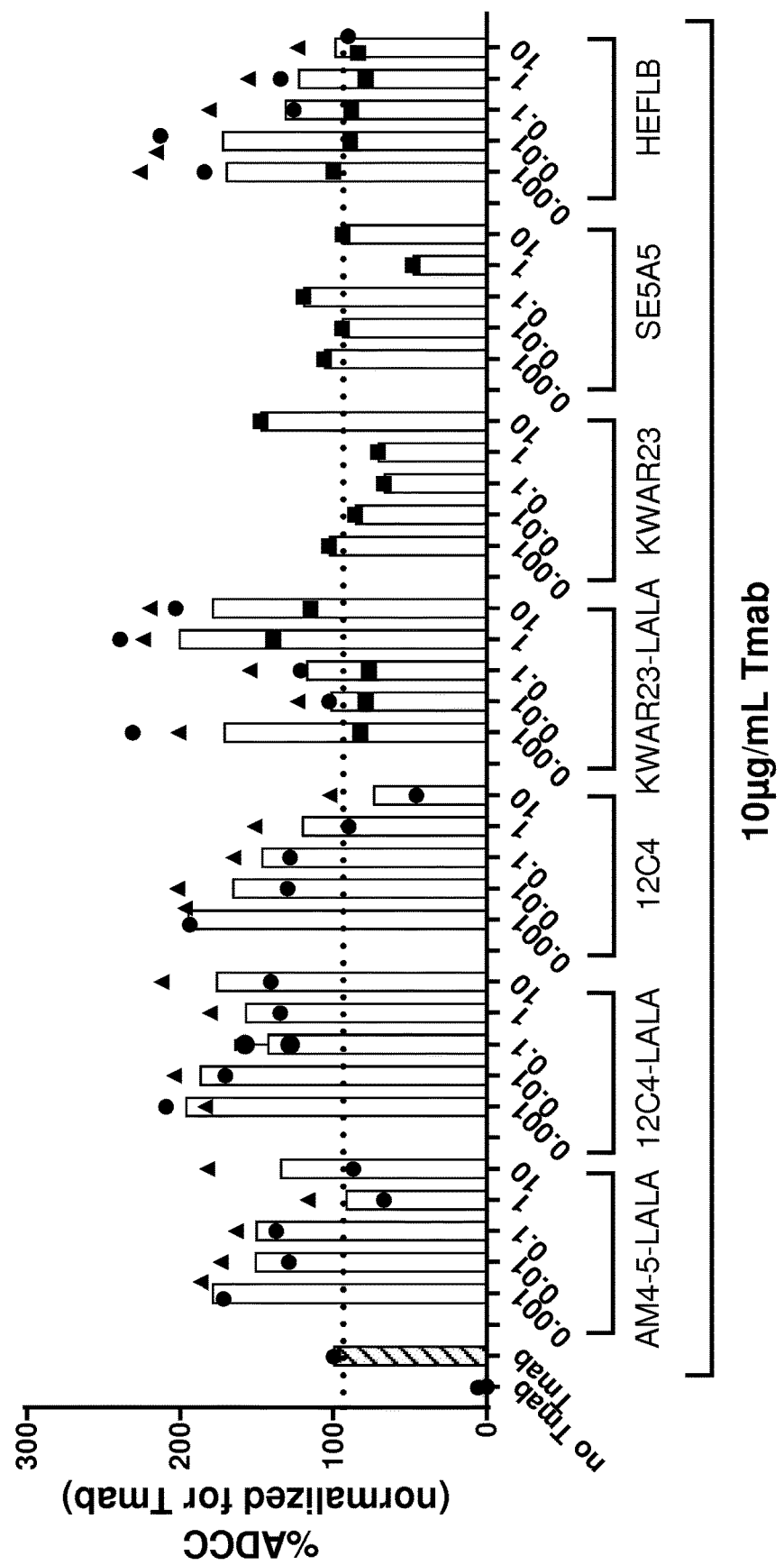
FIG. 6. Neutrophil-mediated ADCC towards trastuzumab (Tmab: 10 μg/ml) opsonized SKBR3 cells in combination with prior art based anti-SIRPα antibodies at various concentrations (μg/ml; dose response curves). Neutrophils were isolated from human donors carrying two SIRPα$_1$ alleles. Each individual neutrophil donor is indicated by a symbol. Columns are the average of all donors. As controls, untreated cells and cells treated with 10 μg/ml trastuzumab were used. Data is normalized for response to trastuzumab (set to 100%). Experiment was performed with neutrophils stimulated for 100 min with GM-CSF and cytotoxicity was measured as $^{51}$Cr release assay.
Figure 7:
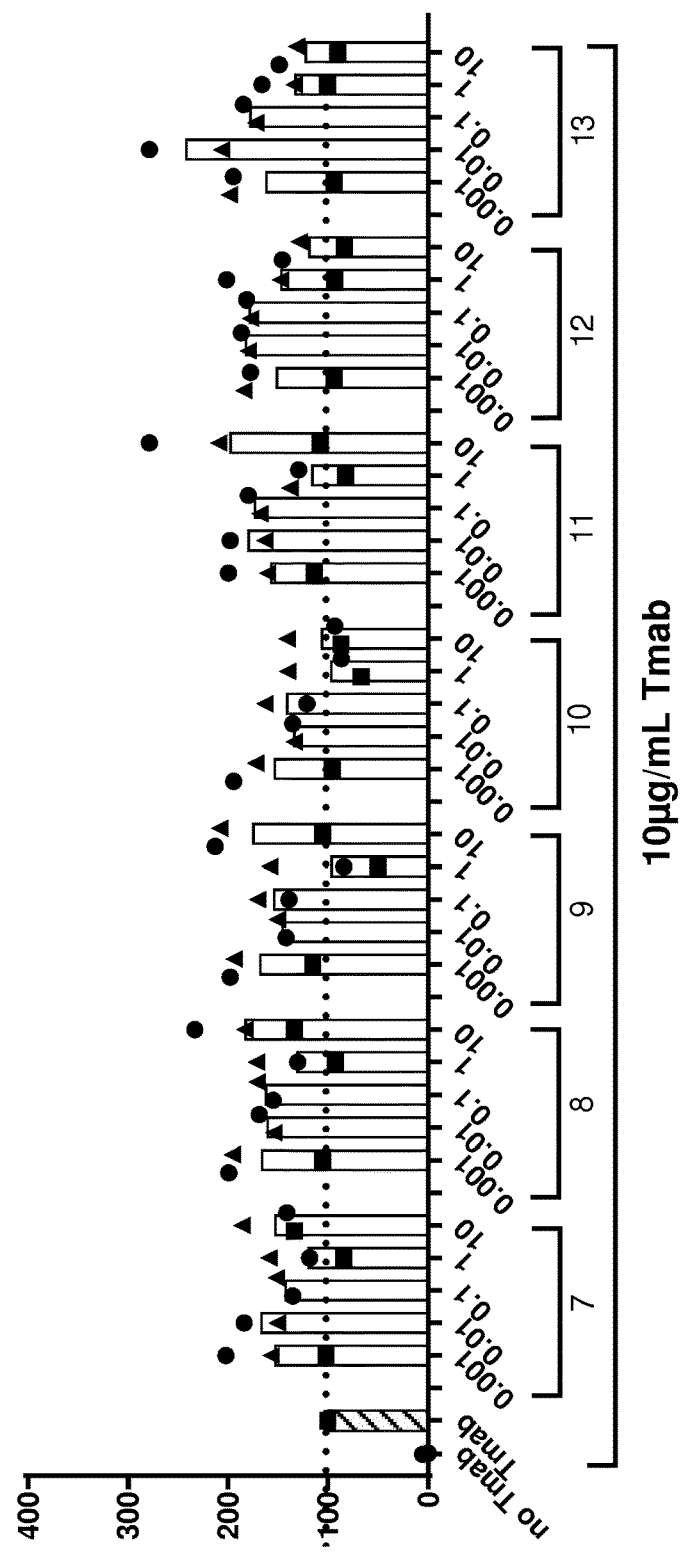
FIG. 7. Neutrophil-mediated ADCC towards trastuzumab (Tmab: 10 μg/ml) opsonized SKBR3 cells in combination with anti-SIRPα antibodies 7-13 of the invention, having a human IgG$_1$ constant region comprising the amino acid substitutions L234A and L235A, at various concentrations (μg/ml; dose response curves). Neutrophils were isolated from human donors carrying two SIRPα$_1$ alleles. Each individual neutrophil donor is indicated by a symbol. Columns are the average of all donors. As controls, untreated cells and cells treated with 10 μg/ml trastuzumab were used. Data is normalized for response to trastuzumab (set to 100%). Experiment was performed with neutrophils stimulated for 100 min with GM-CSF and cytotoxicity was measured as $^{51}$Cr release assay.
Figure 8:
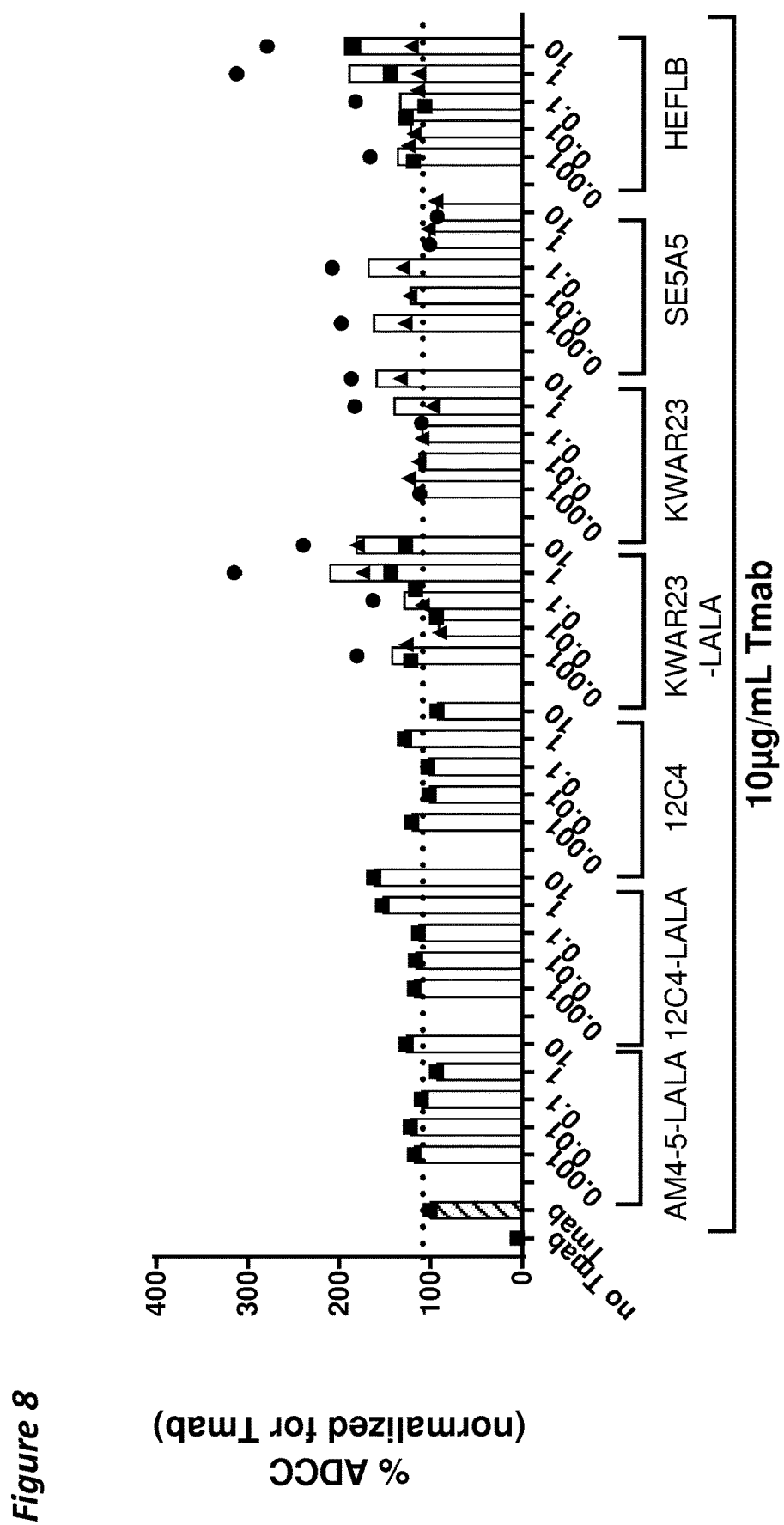
FIG. 8. Neutrophil-mediated ADCC towards trastuzumab (Tmab: 10 μg/ml) opsonized SKBR3 cells in combination with prior art based anti-SIRPα antibodies at various concentrations (μg/ml; dose response curves). Neutrophils were isolated from human donors carrying two SIRPα$_{BIT}$ alleles. Each individual neutrophil donor is indicated by a symbol. Columns are the average of all donors. As controls, untreated cells and cells treated with 10 μg/ml trastuzumab were used. Data is normalized for response to trastuzumab (set to 100%). Experiment was performed with neutrophils stimulated for 100 min with GM-CSF and cytotoxicity was measured as $^{51}$Cr release assay.
Figure 9:
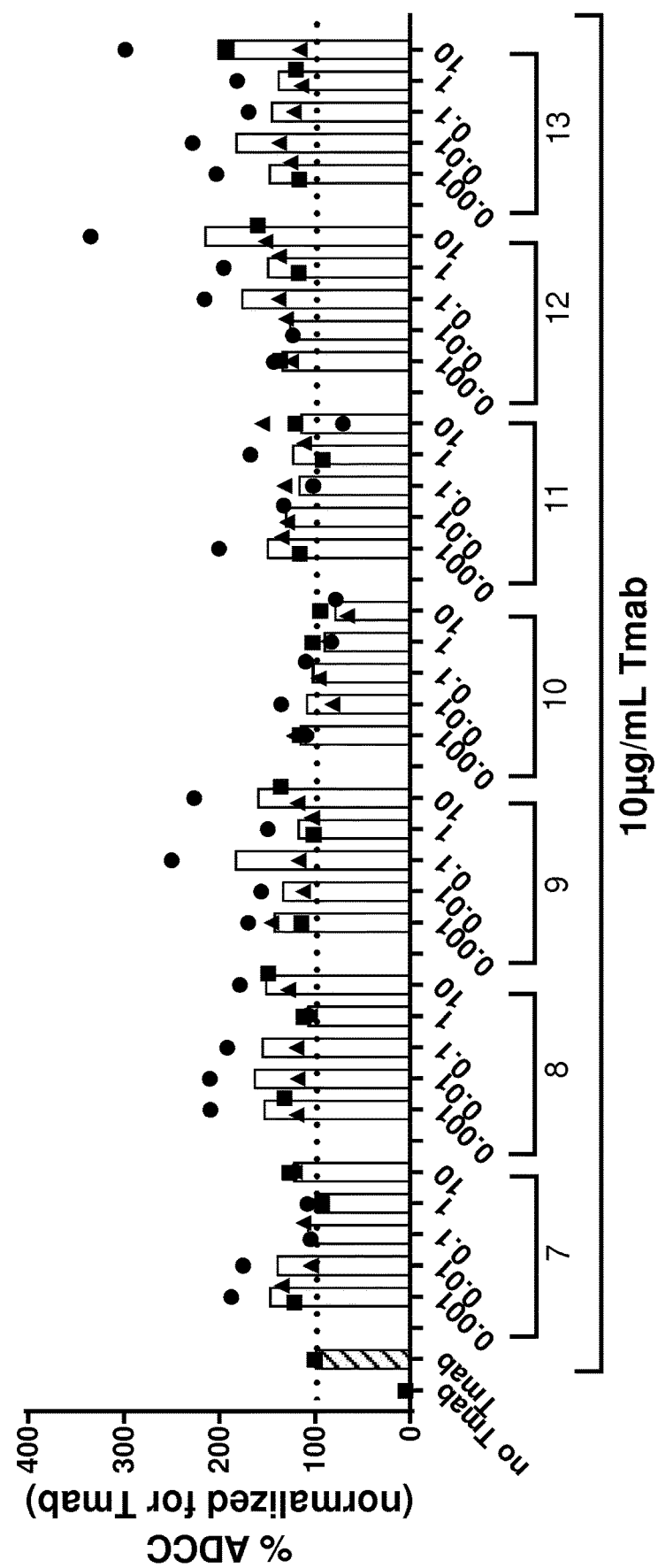
FIG. 9. Neutrophil-mediated ADCC towards trastuzumab (Tmab: 10 μg/ml) opsonized SKBR3 cells in combination with anti-SIRPα antibodies 1-6 of the invention, having a human IgG$_1$ constant region comprising the amino acid substitutions L234A and L235A, at various concentrations (μg/ml; dose response curves). Neutrophils were isolated from human donors carrying two SIRPα$_{BIT}$ alleles. Each individual neutrophil donor is indicated by a symbol. Columns are the average of all donors. As controls, untreated cells and cells treated with 10 μg/ml trastuzumab were used. Data is normalized for response to trastuzumab (set to 100%). Experiment was performed with neutrophils stimulated for 100 min with GM-CSF and cytotoxicity was measured as $^{51}$Cr release assay.
Figure 10A:
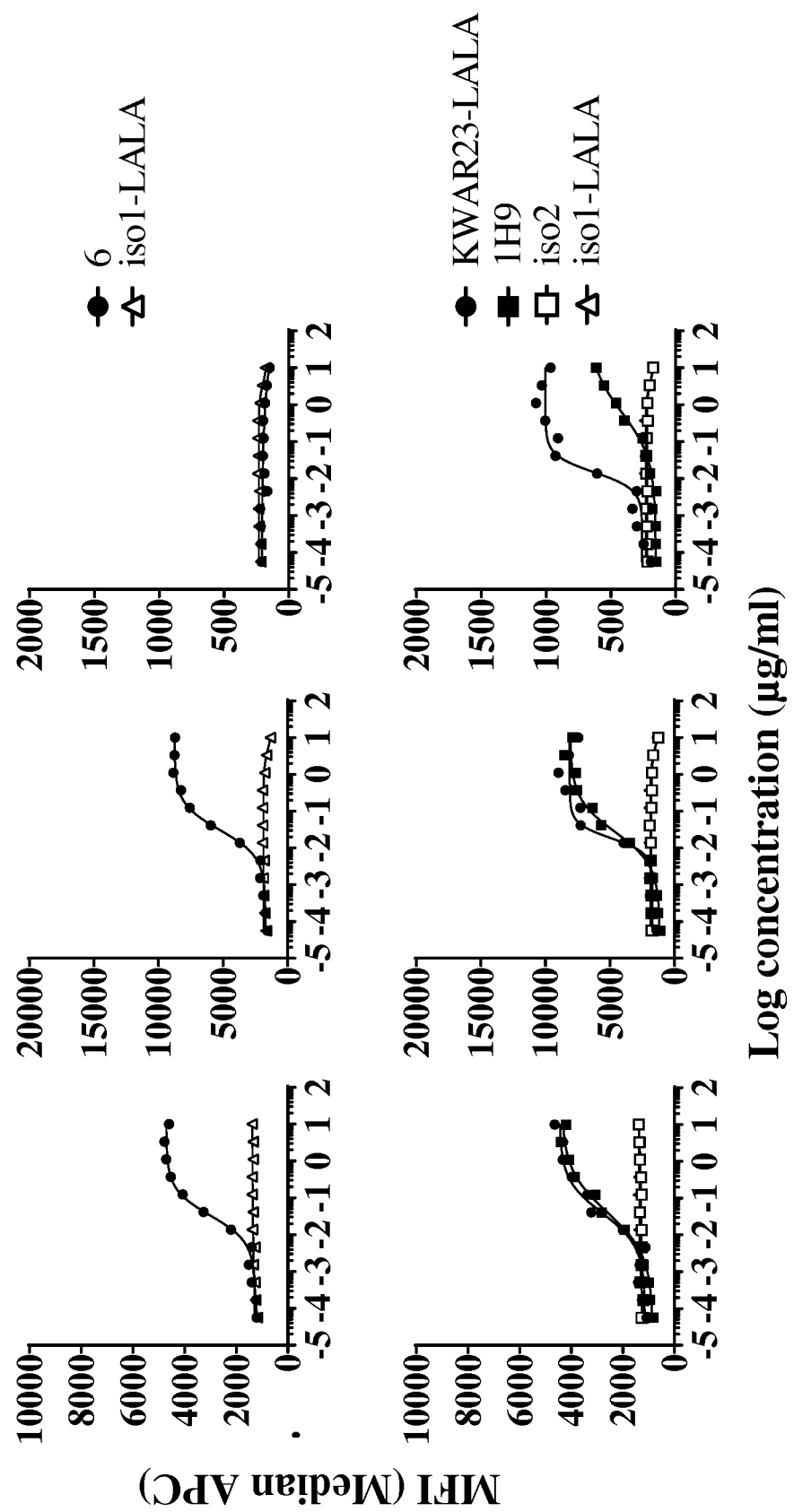
FIG. 10a-d. Binding of indicated anti-SIRPα antibodies to granulocytes (left panels), CD14 monocytes (middle panels) and CD3$^+$ T-cells (right panels) as determined by flow cytometry in whole blood of a representative healthy heterozygous SIRPα/SIRPα$_{BIT}$ donor. The relevant isotype control for each anti-SIRPα antibody is provided in each graph. Data is depicted as median fluorescence intensity (MFI).
Figure 10B:
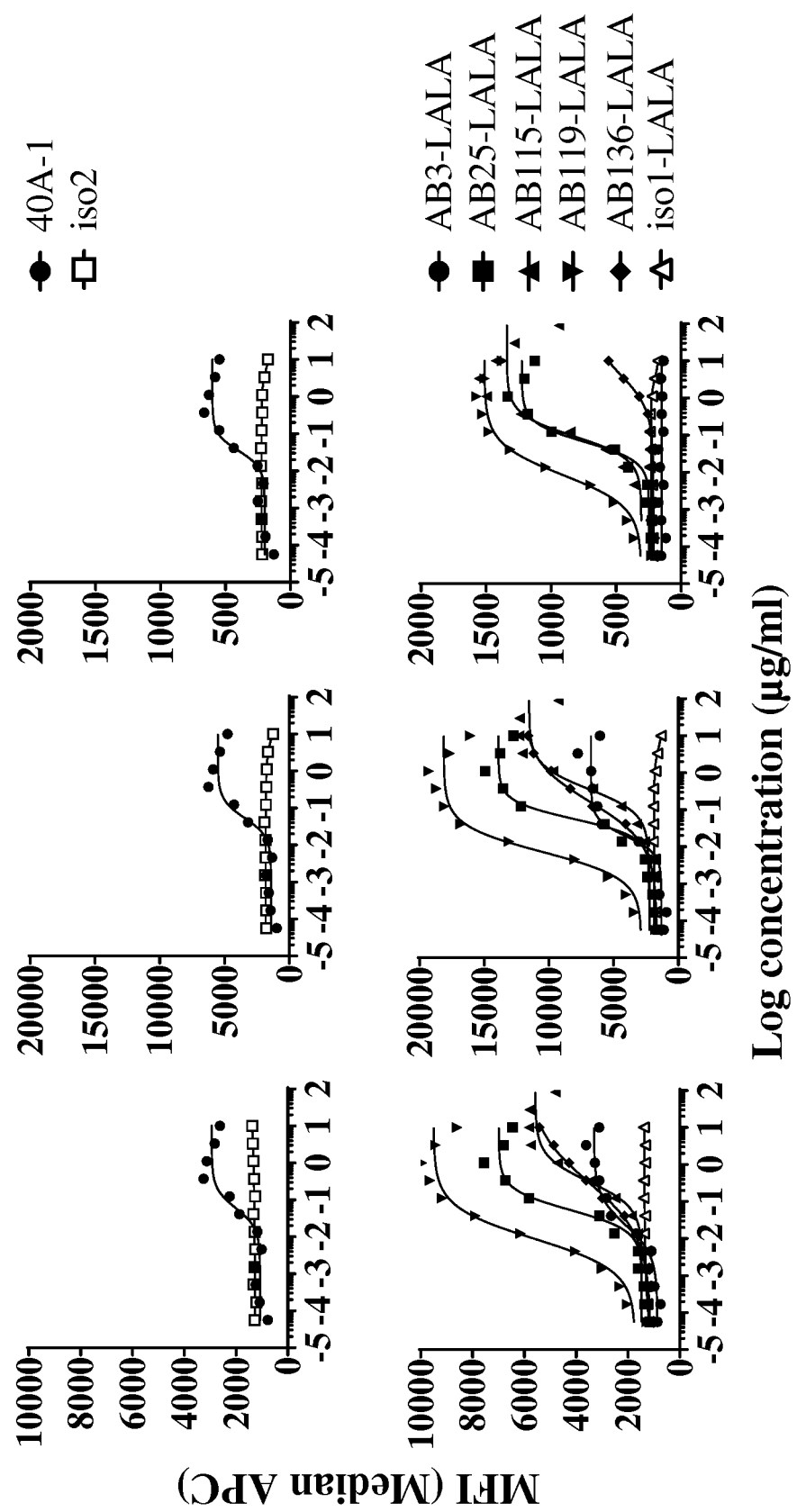
Figure 10C:
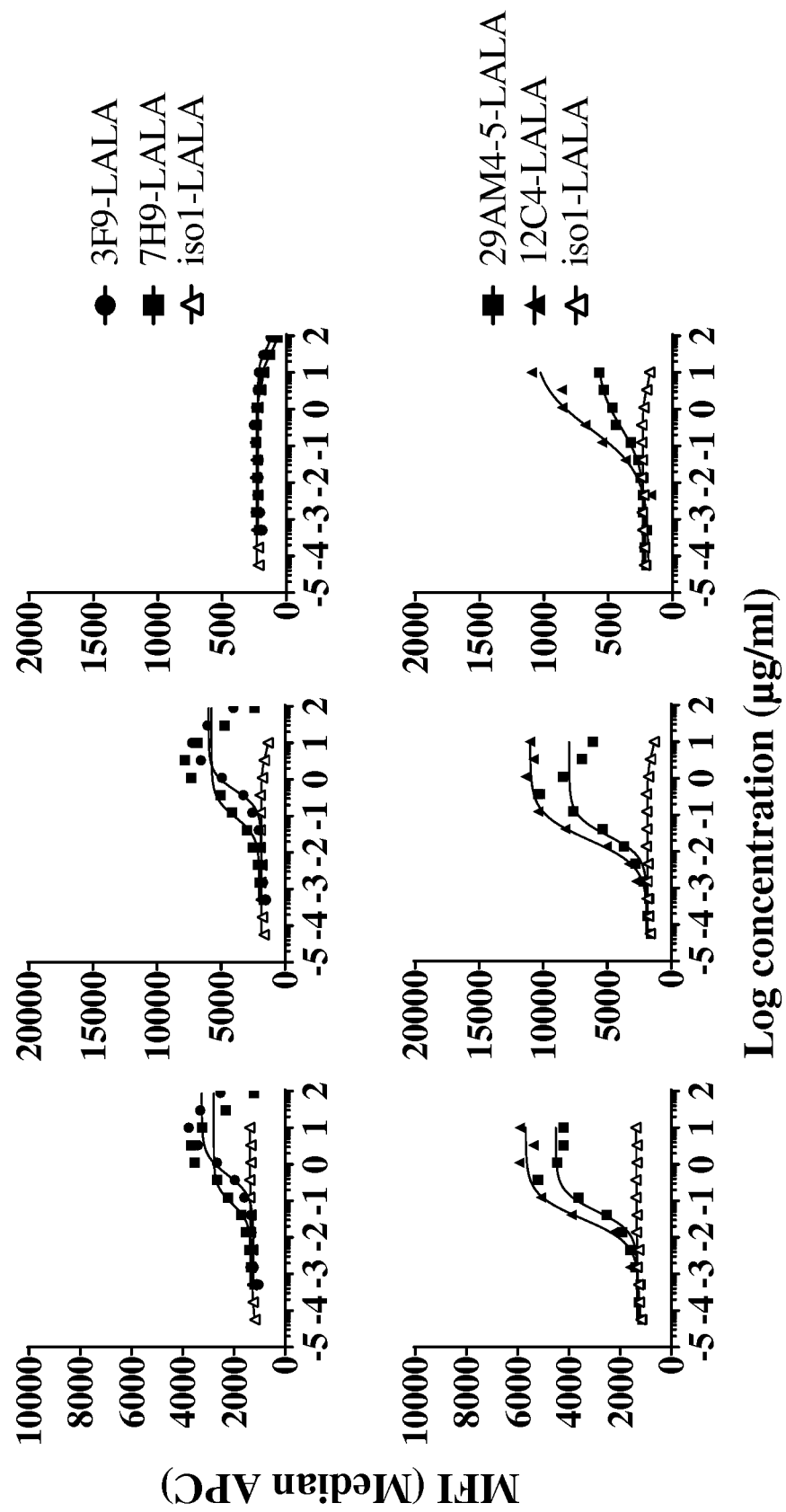
Figure 10D:
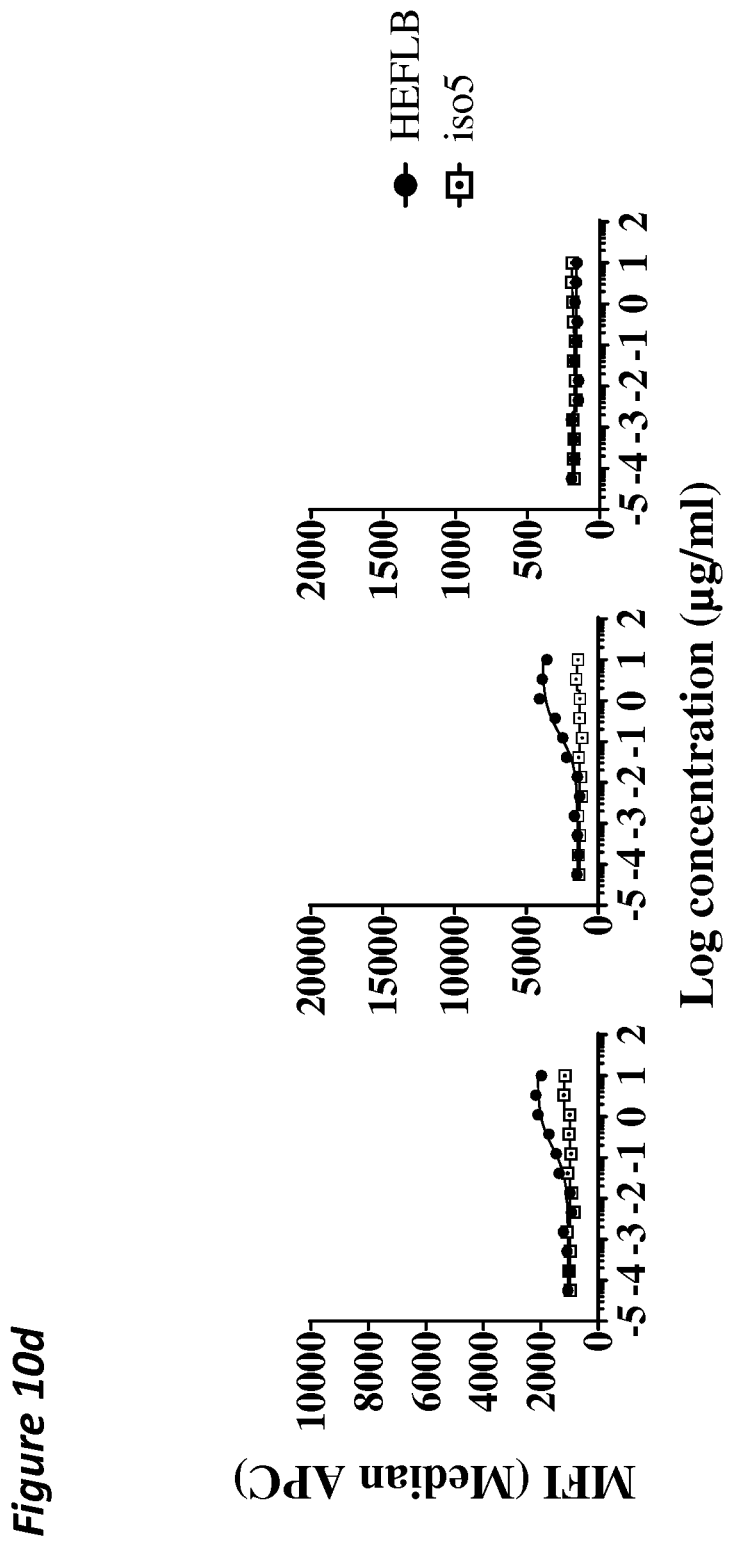

Dose-Dependent Increase in Trastuzumab Mediated ADCC:

The percentage ADCC/cytotoxicity of trastuzumab (10 µg/ml) in the presence of antibody 1-13—having a human IgG$_1$ constant region comprising the amino acid substitutions L234A and L235A (LALA)—or in the presence of reference antibody, at various concentrations (µg/ml; dose response curves) on SRBR3 HER2-positive breast cancer cells is shown in FIGS. 3-9. For antibodies 1-13 the ADCC dose-dependently increased in heterozygous SIRPα$_1$/SIRPβ$_{BIT}$ donors (FIGS. 4 and 5), whereas a dose-dependent decrease is seen for 12C4huIgG$_1$, no clear effect is seen for humanized HEFLB, minimal effects are seen for KWAR23huIgG$_1$ and SE5A5 and a dose-dependent increase is seen for KWAR23-LALA reference antibody in heterozygous donors (FIG. 3). Antibodies 7-13 and the reference antibodies were also tested on homozygous SIRPα$_1$ or SIRPα$_{BIT}$ backgrounds (FIGS. 6-9). All antibodies appeared to show more variable results.

9. Immunogenicity

CD4$^+$ T-cell epitopes are important drivers of immunogenicity (anti-drug antibodies) in vivo. An ex vivo T-cell assay was used to detect T-cell responses against T-cell epitopes in anti-SIRPα antibody 6. Antibody 6 was sent for immunogenicity assessment using EpiScreen™ time course T-cell assay for their ability to induce CD4' T-cell responses at Abzena (Cambridge, UK). PBMC from a cohort of 50 healthy donors representing the European and North American population (based on HLA allotypes) were incubated with the test samples. T-cell responses were measured using proliferation assays ([$^3$H]-thymidine uptake) and cytokine secretion assays (IL-2 ELISpot). Antibody 6 was found not immunogenic in a combination of T-cell proliferation assay and IL-2 ELISpot.

10. Antibody Dependent Cellular Cytotoxicity (ADCC); Comparative Example

Experimental

Figure 13A:
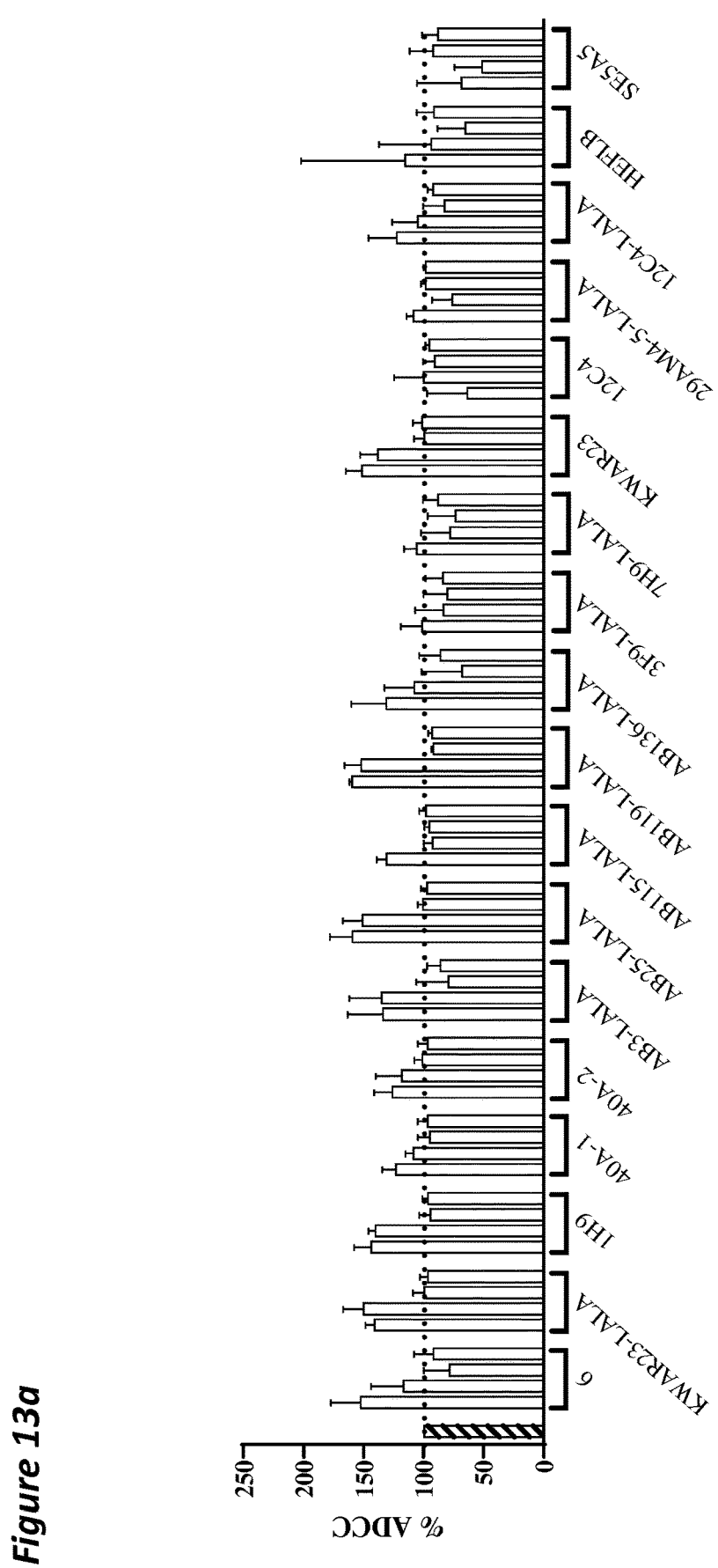
FIG. 13a-b. Neutrophil-mediated ADCC towards trastuzumab (10 μg/ml) opsonized SKBR3 cells in combination with anti-SIRPα antibody 6 of the invention and indicated reference antibodies. Neutrophils were isolated from human donors carrying two SIRPα$_{BIT}$ alleles, carrying two SIRPα$_1$ alleles or carrying one SIRPα$_{BIT}$ and one SIRPα$_1$ allele. Columns are the average of all donors+/−SEM. As controls, untreated cells and cells treated with 10 μg/ml trastuzumab were used. For each antibody, dose response curves were made at 10, 1, 0.1 and 0.01 μg/ml (from left to right). Antibody 6 and reference antibodies are shown in panel (a); Isotype controls are shown in panel (b). Data is normalized for response to trastuzumab (set to 100%). Experiment was performed as indicated in Experimental section 10.
Figure 13B:
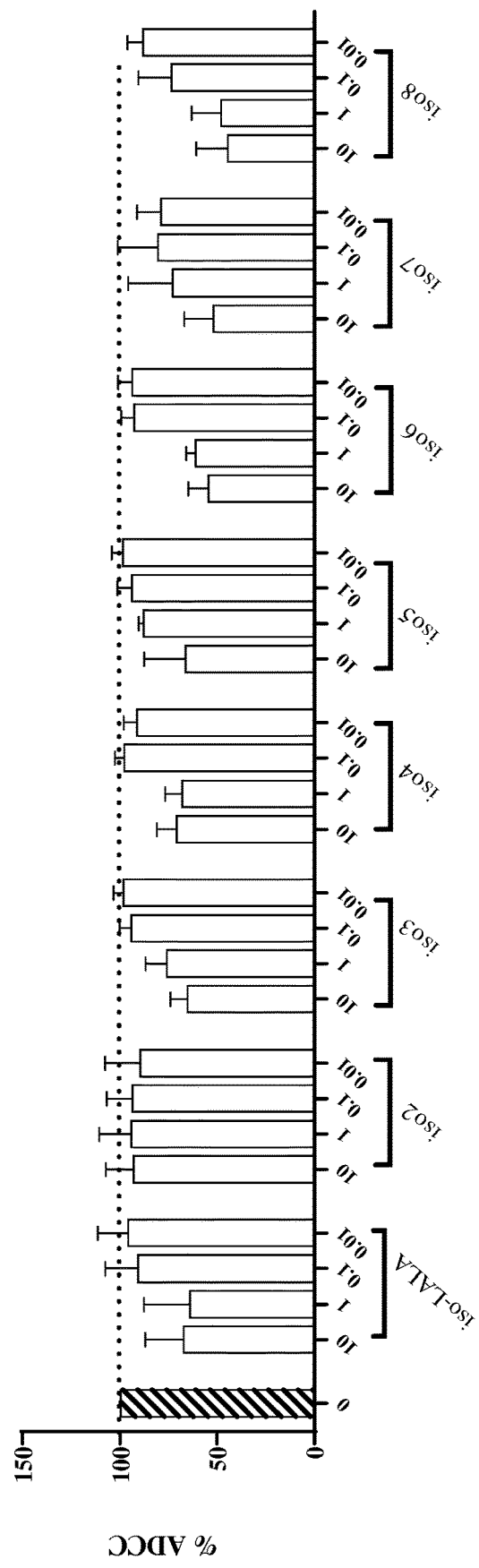

Human neutrophils of donors homozygous for either SIRPα$_1$ or SIRPα$_{BIT}$, or heterozygous for both alleles were isolated according to the method in Zhao et al. *PNAS* 2011, 108(45), 18342-18347. Neutrophils were then stimulated with 10 ng/ml of granulocyte-monocyte colony stimulating factor (GM-CSF, Peprotech) for 30 min. Antibody Dependent Cell Cytotoxicity (ADCC) was determined using the $^{51}$Cr release assay (PerkinElmer) according to the method in Zhao et al. *PNAS* 2011, 108(45), 18342-18347. Briefly, SKBR3 (human breast cancer cell line) or A431 (skin epidermoid carcinoma cell line) cells were used as target cells and labelled with 100 µCi $^{51}$Cr (Perkin-Elmer) for 90 min at 37° C. After 2 washes with PBS, 5×10$^3$ target cells per well were opsonized with trastuzumab (10 µg/ml final concentration for SKBR3), or cetuximab (5 µg/ml final concentration for A431) and incubated in IMDM culture medium supplemented with 20% (v/v) low IgG foetal bovine serum (FBS) for 4 hours at 37° C. and 5% CO$_2$ in a 96-well U-bottom plate together with neutrophils in an effector to target cell ratio of 50:1 in the presence of a dose-response range of the antibodies indicated in FIGS. 13-14. After the incubation, supernatant was harvested, transferred to LumaPlates (Perkin Elmer) and analysed for radioactivity in a MicroBeta counter (Perkin Elmer). The percentage of cytotoxicity was calculated as [(experimental release-spontaneous release)/(total release-spontaneous release)]×100%. All conditions were measured in duplicate or triplicate.

Results

Figure 14A:
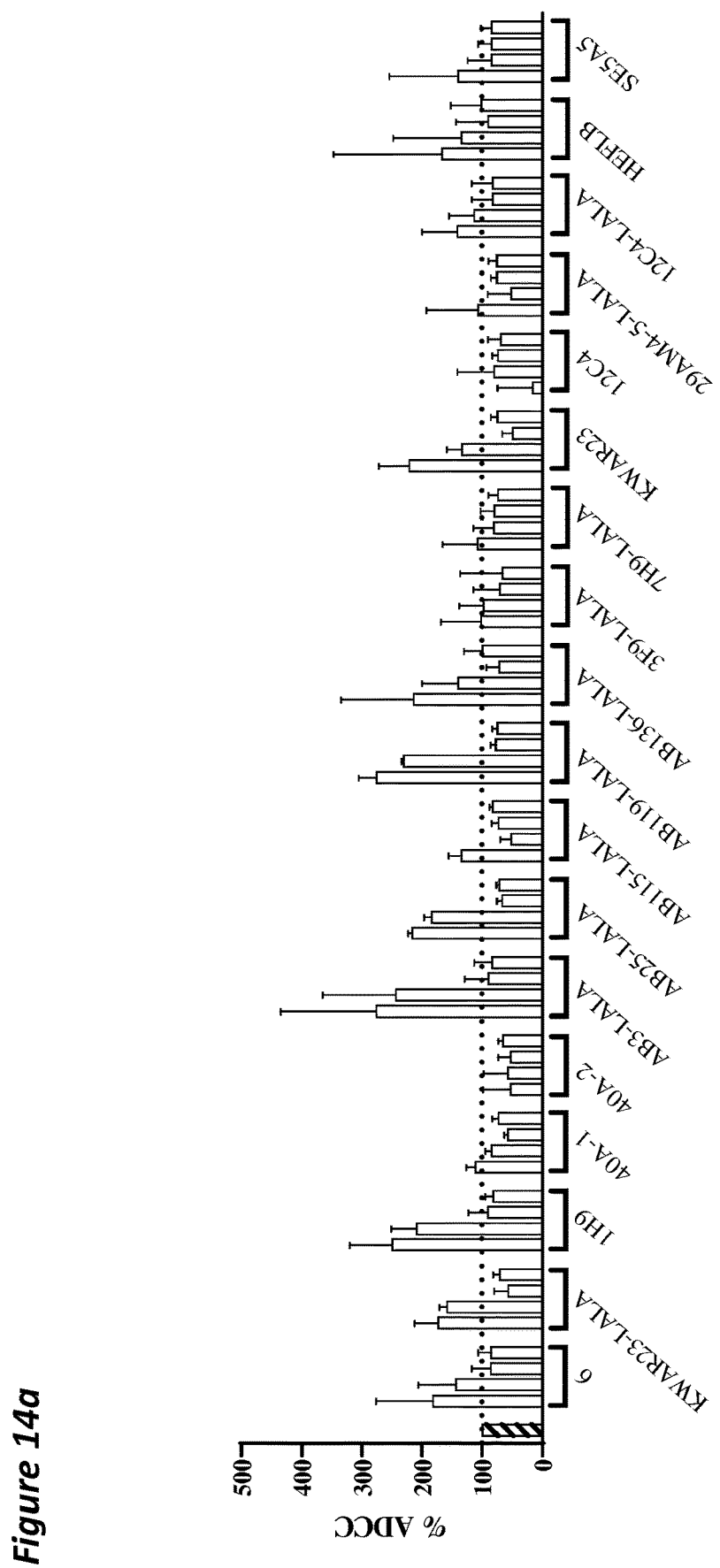
FIG. 14a-b. Neutrophil-mediated ADCC towards cetuximab (5 μg/ml) opsonized A431 cells in combination with anti-SIRPα antibody 6 of the invention and indicated reference antibodies. Neutrophils were isolated from human donors carrying two SIRPα$_{BIT}$ alleles, carrying two SIRPα$_1$ alleles or carrying one SIRPα$_{BIT}$ and one SIRPα$_1$ allele. Columns are the average of all donors. As controls, untreated cells and cells treated with 5 μg/ml cetuximab were used. For each antibody, dose response curves were made at 10, 1, 0.1 and 0.01 μg/ml (from left to right). Antibody 6 and reference antibodies are shown in panel (a): Isotype controls are shown in panel (b). Data is normalized for response to cetuximab (set to 100%). Experiment was performed as indicated in Experimental section 10.
Figure 14B:
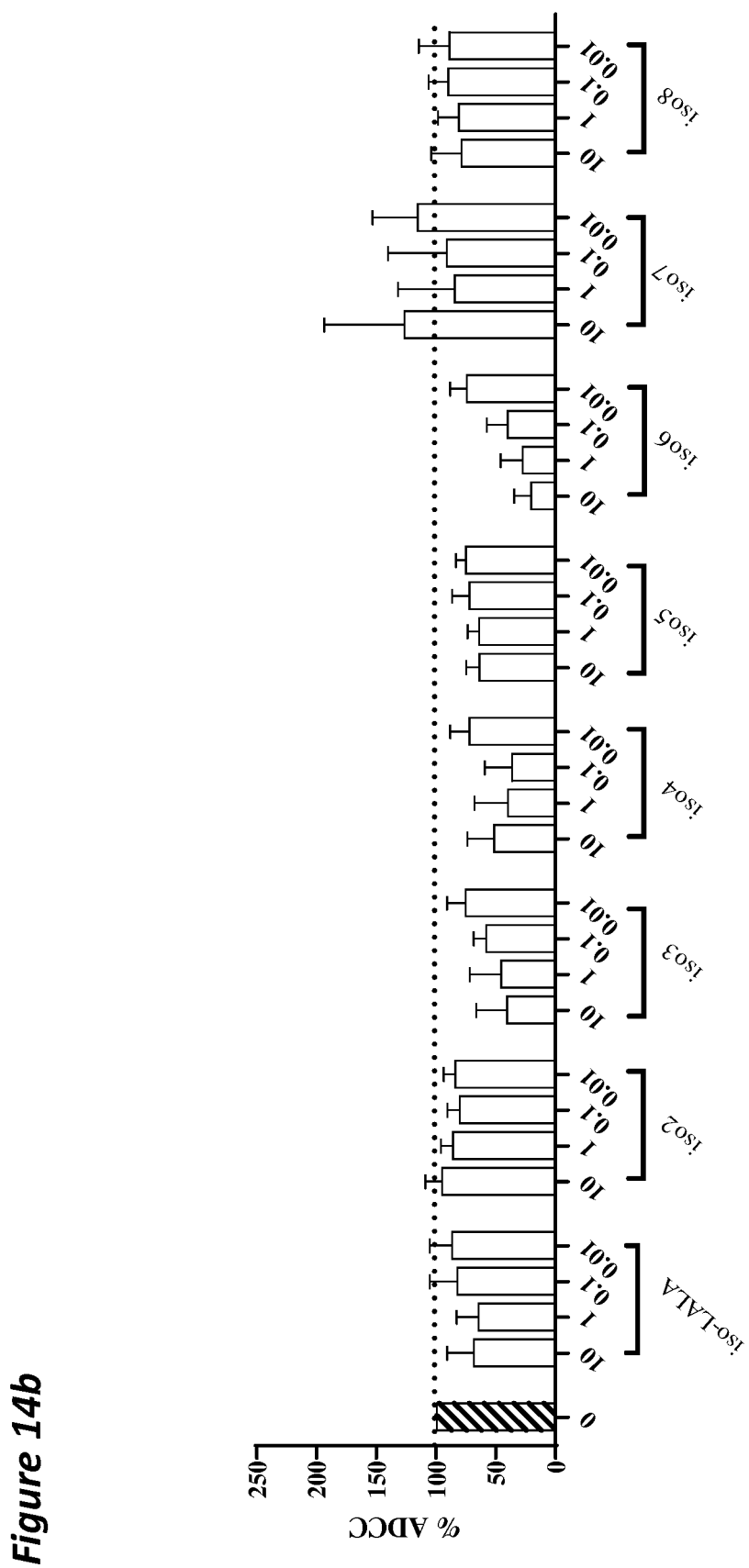

Antibody Dependent Cell Cytotoxicity (ADCC); The effect of anti-SIRPα antibodies was tested in ADCC experiments using GM-CSF activated primary human neutrophils as effector cells and different combinations of cancer-targeting therapeutic antibodies and tumour target cells (FIGS. 13a-b, 14a-b). The latter included HER2-expressing SKBR3 breast cancer cells in combination with trastuzumab (FIG. 13) and EGFR-expressing A431 carcinoma cells in combination with cetuximab (FIG. 14). The results demonstrate that antibody 6 was able to enhance neutrophil ADCC of both cancer-targeting antibody-target cancer cell combinations. Similar findings were obtained for several other anti-SIRPα antibodies, but not for e.g. 40A-1, 40A-2, 3F9-LALA, 7H9-LALA, 12C4, 29AM4-5-LALA, SE5A5.

In aggregate, antibody 6 is the only antibody with relatively low or absent affinity for the non-inhibitory SIRP-family members SIRPβ$_{1v1}$, SIRPβ$_{1v2}$ and SIRPγ, that in functional assays effectively inhibits down-stream signalling while simultaneously displaying enhanced ADCC in both SIRPα$_{BIT}$ and SIRPα$_1$ genotypes.

Sequence listings, antibodies 1-13 have underlined CDR1, CDR2 and CDR3 amino acid sequences in heavy chain (HC) and light chain (LC) variable region (VR) amino acid sequences (VR residues determined according to the method of Kabat; numbering of the sequences is sequentially, not according to the numbering of Kabat)

```
(HCVR; mAb 1)                                                                SEQ ID NO: 1

1 VQLVESGGRL GQPGTPLTLS CTVSGFSLSS YVMGWFRQAP GKGLEYIGII

51 SSSGSPYYAS WVNGRFTISK TSTTMDLKMN SLRSEDTATY FCARVGPLGV

101 DYFNIWGPGT LVTVSS (LCVR; mAb 1, 2, 3, 4, 12, 13)                                               SEQ ID NO: 2

1 DIQMTQSPSS LSASVGDRVT ITCRASQSIN SYLAWYQQKP GKAPKLLIYS

51 ASFLYSGVPS RFSGSGSGTD FTLTISSLQP EDFATYYCQS WHYISRSYTF

101 GQGTKVEIK
```

-continued (HCVR; mAb 2)  SEQ ID NO: 3

1 VQLVESGGRL VQPGTPLTLS CTVSGFSLSS YVMGWFRQAP GKGLEYIGII

51 SSSGSPYYAS WVNGRFTISK TSTTMDLKMN SLRSEDTATY FCARVGPLGV

101 DYFNIWGPGT LVTVSS (HCVR; mAb 3)  SEQ ID NO: 4

1 VQLVESGGRL GQPGTSLTLS CTVSGFSLSS YVMGWFRQAP GKGLEYIGII

51 SSSGSPYYAS WVNGRFTISK TSTTMDLKMN SPTTEDTATY FCARVGPLGV

101 DYFNIWGPGT LVTVSS (HCVR; mAb 4)  SEQ ID NO: 5

1 VQLVESGGRL GQPGTSLTLS CTVSGFSLSS YVMGWFRQAP GKGLEYIGII

51 SSSGSPYYAS WVNGRFTISK TSTTMDLKMN SLRSEDTATY FCARVGPLGV

101 DYFNIWGPGT LVTVSS (HCVR; mAb 5, 8)  SEQ ID NO: 6

1 RQLVESGGGL VQPGGSLRLS CAASGFSLSS HGISWVRQAP GKGLEYIGTI

51 GTGVITYYAS WAKGRFTGSK TSSTAYLQMT SLRAEDTAVY YCARGSAWND

101 PFDYWGQGTL VTVSS (LCVR; mAb 5, 11)  SEQ ID NO: 7

1 DIEMTQSPSS VSASVGDRVT LTCQASQSVY GNNDLAWYQQ KPGQAPKLLI

51 YLASTLATGV PSRFSGSGSG TDFTLTISSL QPEDFATYYC LGGGDDEADN

101 VFGGGTKVEI K (HCVR; mAb 6)  SEQ ID NO: 8

1 RQLVESGGGL VQPGGSLRLS CTASGFSLSS HGISWVRQAP GKGLEYIGTI

51 GTGVITYFAS WAKGRFTGSK TSSTAYMELS SLRSEDTAVY FCARGSAWND

101 PFDPWGQGTL VTVSS (LCVR; mAb 6, 7, 8, 9, 10)  SEQ ID NO: 9

1 DIVMTQSPSS LSASVGDRVT ITCQASQSVY GNNDLAWYQQ KPGQAPKLLI

51 YLASTLATGV PSRFSGSGSG TDFTLTISSL QPEDFATYYC LGGGDDEADN

101 TFGQGTKVEI K (HCVR; mAb 7)  SEQ ID NO: 10

1 RQLVESGGGL VQPGGSLRLS CAASGFSLSS HGISWVRQAP GKGLEWVGTI

51 GTGVITYYAS WAKGRFTGSK TSSTAYLQMT SLRAEDTAVY YCARGSAWND

101 PFDYWGQGTL VTVSS (HCVR; mAb 9)  SEQ ID NO: 11

1 RQLVESGGGL VQPGGSLRLS CAASGFSLSS HGISWVRQAP GKGLEWVGTI

51 GTGVITYYAS WAKGRFTGSK TSSTAYLQMT SLRSEDTAVY YCARGSAWND

101 PFDYWGQGTL VTVSS (HCVR; mAb 10)  SEQ ID NO: 12

1 RQLVESGGGL VQPGGSLRLS CAASGFSLSS HGISWVRQAP GKGLEWVGTI

51 GTGGITYYAS WAKGRFTGSK TSSTAYMELS SLRAEDTAVY YCARGSAWND

101 PFDIWGQGTL VTVSS (HCVR; mAb 11)

SEQ ID NO: 13

```
  1 RQLVESGGGL VQPGGSLRLS CAASGFSLSS HGISWVRQAP GKGLEWVGTI
 51 GTGVITYYAS WAKGRFTGSK TSSTAYLQMT SLRAEDTAVY YCARGSAWND
101 PFDYWGQGTL VTVSS
```

(HCVR; mAb 12)

SEQ ID NO: 14

```
  1 QSVEESGGRL GQPGTPLTLS CTVSGFSLSS YVMGWFRQAP GKGLEYIGII
 51 SSSGSPYYAS WVNGRFTISK TSTTMDLKMN SLRSEDTATY FCARVGPLGV
101 DYFNIWGPGT LVTVSS
```

(HCVR; mAb 13)

SEQ ID NO: 15

```
  1 VQLVESGGRL VQPGTPLTLS CTVSGFSLSS YVMGWFRQAP GKGLEYIGII
 51 SSSGSPYYAS WVNGRFTISK TSTTMDLKMN SPTTEDTATY FCARVGPLGV
101 DYFNIWGPGT LVTVSS
```

(HC; 12C4)

SEQ ID NO: 16

```
  1 EVKLEESGGG LMQPGGSMKL SCVASGFTFS NYWMNWVRQS PEKGLEWVAE
 51 IRLKSNNYAT HYAESVKGRF TISRDDSKSS VYLQMNNLRA EDTGIYYCIR
101 DYDYDAYFDY WGQGTTLTVS SASTKGPSVF PLAPSSKSTS GGTAALGCLV
151 KDYFPEPVTV SWNSGALTSG VHTFPAVLQS SGLYSLSSVV TVPSSSLGTQ
201 TYICNVNHKP SNTKVDKKVE PKSCDKTHTC PPCPAPELLG GPSVFLFPPK
251 PKDTLMISRT PEVTCVVVDV SHEDPEVKFN WYVDGVEVHN AKTKPREEQY
301 NSTYRVVSVL TVLHQDWLNG KEYKCKVSNK ALPAPIEKTI SKAKGQPREP
351 QVYTLPPSRD ELTKNQVSLT CLVKGFYPSD IAVEWESNGQ PENNYKTTPP
401 VLDSDGSFFL YSKLTVDKSR WQQGNVFSCS VMHEALHNHY TQKSLSLSPG
451 K
```

(LC; 12C4)

SEQ ID NO: 17

```
  1 DIVLTQSPAS LAVSLGQRAT ISCRASKSVS TSGYNYMYWY QQKPGQPPKL
 51 LIYLASNLES GVPARFSGSG SGTDFTLNIH PVEEEDAATY YCQHSGELPY
101 TFGGGTKLEI KRTVAAPSVF IFPPSDEQLK SGTASVVCLL NNFYPREAKV
151 QWKVDNALQS GNSQESVTEQ DSKDSTYSLS STLTLSKADY EKHKVYACEV
201 THQGLSSPVT KSFNRGEC
```

(HC; 29AM4-5-LALA)

SEQ ID NO: 18

```
  1 EVQLVESGGG LVQPGGSLRL SCAASGFNIS YYFIHWVRQA PGKGLEWVAS
 51 VYSSFGYTYY ADSVKGRFTI SADTSKNTAY LQMNSLRAED TAVYYCARFT
101 FPGLFDGFFG AYLGSLDYWG QGTLVTVSSA STKGPSVFPL APSSKSTSGG
151 TAALGCLVKD YFPEPVTVSW NSGALTSGVH TFPAVLQSSG LYSLSSVVTV
201 PSSSLGTQTY ICNVNHKPSN TKVDKKVEPK SCDKTHTCPP CPAPEAAGGP
251 SVFLFPPKPK DTLMISRTPE VTCVVVDVSH EDPEVKFNWY VDGVEVHNAK
301 TKPREEQYNS TYRVVSVLTV LHQDWLNGKE YKCKVSNKAL PAPIEKTISK
```

```
351  AKGQPREPQV YTLPPSRDEL TKNQVSLTCL VKGFYPSDIA VEWESNGQPE

401  NNYKTTPPVL DSDGSFFLYS KLTVDKSRWQ QGNVFSCSVM HEALHNHYTQ

451  KSLSLSPGK (LC; 29AM4-5-LALA)                                              SEQ ID NO: 19

1  DIQMTQSPSS LSASVGDRVT ITCRASQSVS SAVAWYQQKP GKAPKLLIYS

51  ASSLYSGVPS RFSGSRSGTD FTLTISSLQP EDFATYYCQQ AVNWVGALVT

101  FGQGTKVEIK RTVAAPSVFI FPPSDEQLKS GTASVVCLLN NFYPREAKVQ

151  WKVDNALQSG NSQESVTEQD SKDSTYSLSS TLTLSKADYE KHKVYACEVT

201  HQGLSSPVTK SFNRGEC (HC; 12C4-LALA)                                                 SEQ ID NO: 20

1  EVKLEESGGG LMQPGGSMKL SCVASGFTFS NYWMNWVRQS PEKGLEWVAE

51  IRLKSNNYAT HYAESVKGRF TISRDDSKSS VYLQMNNLRA EDTGIYYCIR

101  DYDYDAYFDY WGQGTTLTVS SASTKGPSVF PLAPSSKSTS GGTAALGCLV

151  KDYFPEPVTV SWNSGALTSG VHTFPAVLQS SGLYSLSSVV TVPSSSLGTQ

201  TYICNVNHKP SNTKVDKKVE PKSCDKTHTC PPCPAPEAAG GPSVFLFPPK

251  PKDTLMISRT PEVTCVVVDV SHEDPEVKFN WYVDGVEVHN AKTKPREEQY

301  NSTYRVVSVL TVLHQDWLNG KEYKCKVSNK ALPAPIEKTI SKAKGQPREP

351  QVYTLPPSRD ELTKNQVSLT CLVKGFYPSD IAVEWESNGQ PENNYKTTPP

401  VLDSDGSFFL YSKLTVDKSR WQQGNVFSCS VMHEALHNHY TQKSLSLSPG

451  K (LC; 12C4-LALA)                                                 SEQ ID NO: 21

1  DIVLTQSPAS LAVSLGQRAT ISCRASKSVS TSGYNYMYWY QQKPGQPPKL

51  LIYLASNLES GVPARFSGSG SGTDFTLNIH PVEEEDAATY YCQHSGELPY

101  TFGGGTKLEI KRTVAAPSVF IFPPSDEQLK SGTASVVCLL NNFYPREAKV

151  QWKVDNALQS GNSQESVTEQ DSKDSTYSLS STLTLSKADY EKHKVYACEV

201  THQGLSSPVT KSFNRGEC (HC; KWAR23-LALA)                                               SEQ ID NO: 22

1  EVQLQQSGAE LVKPGASVKL SCTASGFNIK DYYIHWVQQR TEQGLEWIGR

51  IDPEDGETKY APKFQDKATI TADTSSNTAY LHLSSLTSED TAVYYCARWG

101  AYWGQGTLVT VSSASTKGPS VFPLAPSSKS TSGGTAALGC LVKDYFPEPV

151  TVSWNSGALT SGVHTFPAVL QSSGLYSLSS VVTVPSSSLG TQTYICNVNH

201  KPSNTKVDKK VEPKSCDKTH TCPPCPAPEA AGGPSVFLFP PKPKDTLMIS

251  RTPEVTCVVV DVSHEDPEVK FNWYVDGVEV HNAKTKPREE QYNSTYRVVS

301  VLTVLHQDWL NGKEYKCKVS NKALPAPIEK TISKAKGQPR EPQVYTLPPS

351  RDELTKNQVS LTCLVKGFYP SDIAVEWESN GQPENNYKTT PPVLDSDGSF

401  FLYSKLTVDK SRWQQGNVFS CSVMHEALHN HYTQKSLSLS PGK (LC; KWAR23-LALA)                                               SEQ ID NO: 23

1  QIVLTQSPAI MSASPGEKVT LTCSASSSVS SSYLYWYQQK PGSSPKLWIY

51  STSNLASGVP ARFSGSGSGT SYSLTISSME AEDAASYFCH QWSSYPRTFG
```

```
101 AGTKLELKRT VAAPSVFIFP PSDEQLKSGT ASVVCLLNNF YPREAKVQWK

151 VDNALQSGNS QESVTEQDSK DSTYSLSSTL TLSKADYEKH KVYACEVTHQ

201 GLSSPVTKSF NRGEC
```

(human IgG₁ antibody HC constant region)  SEQ ID NO: 24

```
  1 ASTKGPSVFP LAPSSKSTSG GTAALGCLVK DYFPEPVTVS WNSGALTSGV

51 HTFPAVLQSS GLYSLSSVVT VPSSSLGTQT YICNVNHKPS NTKVDKKVEP

101 KSCDKTHTCP PCPAPELLGG PSVFLFPPKP KDTLMISRTP EVTCVVVDVS

151 HEDPEVKFNW YVDGVEVHNA KTKPREEQYN STYRVVSVLT VLHQDWLNGK

201 EYKCKVSNKA LPAPIEKTIS KAKGQPREPQ VYTLPPSRDE LTKNQVSLTC

251 LVKGFYPSDI AVEWESNGQP ENNYKTTPPV LDSDGSFFLY SKLTVDKSRW

301 QQGNVFSCSV MHEALHNHYT QKSLSLSPGK
```

(human IgG₁ antibody HC constant region LALA mutant (mutations underlined))  SEQ ID NO: 25

```
  1 ASTKGPSVFP LAPSSKSTSG GTAALGCLVK DYFPEPVTVS WNSGALTSGV

51 HTFPAVLQSS GLYSLSSVVT VPSSSLGTQT YICNVNHKPS NTKVDKKVEP

101 KSCDKTHTCP PCPAPEAAGG PSVFLFPPKP KDTLMISRTP EVTCVVVDVS

151 HEDPEVKFNW YVDGVEVHNA KTKPREEQYN STYRVVSVLT VLHQDWLNGK

201 EYKCKVSNKA LPAPIEKTIS KAKGQPREPQ VYTLPPSRDE LTKNQVSLTC

251 LVKGFYPSDI AVEWESNGQP ENNYKTTPPV LDSDGSFFLY SKLTVDKSRW

301 QQGNVFSCSV MHEALHNHYT QKSLSLSPGK
```

(human antibody LC κ constant region)  SEQ ID NO: 26

```
  1 RTVAAPSVFI FPPSDEQLKS GTASVVCLLN NFYPREAKVQ WKVDNALQSG

51 NSQESVTEQD SKDSTYSLSS TLTLSKADYE KHKVYACEVT HQGLSSPVTK

101 SFNRGEC
```

(HAVT20 leader sequence 12C4/12C4-LALA/29AM4-5 LALA/KWAR23/KWAR23-LALA/HEFLB)  SEQ ID NO: 27

```
  1 MACPGFLWAL VISTCLEFSM A
```

(leader sequence heavy chains mAb 1-13)  SEQ ID NO: 28

```
  1 MGWTLVFLFL LSVTAGVHS
```

(leader sequence light chains mAb 1-13)  SEQ ID NO: 29

```
  1 MVSSAQFLGL LLLCFQGTRC
```

(HCDR1; mAb 1, 2, 3, 4, 12 and 13)  SEQ ID NO: 30

```
  1 SYVMG
```

(HCDR2; mAb 1, 2, 3, 4, 12 and 13)  SEQ ID NO: 31

```
  1 IISSSGSPYY ASWVNG
```

(HCDR3; mAb 1, 2, 3, 4, 12 and 13)  SEQ ID NO: 32

```
  1 VGPLGVDYFN I
```

(LCDR1; mAb 1, 2, 3, 4, 12 and 13)  SEQ ID NO: 33

```
  1 RASQSINSYL A
```

(LCDR2; mAb 1, 2, 3, 4, 12 and 13)  SEQ ID NO: 34

```
  1 SASFLYS
```

(LCDR3; mAb 1, 2, 3, 4, 12 and 13)

```
                                                            SEQ ID NO: 35
  1 QSWHYISRSY T (HCDR1; mAb 5-11)
                                                            SEQ ID NO: 36
  1 SHGIS (HCDR2; mAb 5, 7, 8, 9, 11)
                                                            SEQ ID NO: 37
  1 TIGTGVITYY ASWAKG (HCDR3; mAb 5, 7, 8, 9, 11)
                                                            SEQ ID NO: 38
  1 GSAWNDPFDY (LCDR1; mAb 5-11)
                                                            SEQ ID NO: 39
  1 QASQSVYGNN DLA (LCDR2; mAb 5-11)
                                                            SEQ ID NO: 40
  1 LASTLAT (LCDR3; mAb 6-10)
                                                            SEQ ID NO: 41
  1 LGGGDDEADN T (HCDR2; mAb 10)
                                                            SEQ ID NO: 42
  1 TIGTGGITYY ASWAKG (HCDR3; mAb 10)
                                                            SEQ ID NO: 43
  1 GSAWNDPFDI (HCDR2; mAb 6)
                                                            SEQ ID NO: 44
  1 TIGTGVITYF ASWAKG (HCDR3; mAb 6)
                                                            SEQ ID NO: 45
  1 GSAWNDPFDP (LCDR3; mAb 5, 11)
                                                            SEQ ID NO: 46
  1 LGGGDDEADN V (HC; KWAR23)
                                                            SEQ ID NO: 47
  1 EVQLQQSGAE LVKPGASVKL SCTASGFNIK DYYIHWVQQR TEQGLEWIGR
 51 IDPEDGETKY APKFQDKATI TADTSSNTAY LHLSSLTSED TAVYYCARWG
101 AYWGQGTLVT VSSAKTTAPS VYPLAPVCGD TTGSSVTLGC LVKGYFPEPV
151 TLTWNSGSLS SGVHTFPAVL QSDLYTLSSS VTVTSSTWPS QSITCNVAHP
201 ASSTKVDKKI EPRGPTIKPC PPCKCPAPNL LGGPSVFIFP PKIKDVLMIS
251 LSPIVTCVVV DVSEDDPDVQ ISWFVNNVEV HTAQTQTHRE DYNSTLRVVS
301 ALPIQHQDWM SGKEFKCKVN NKDLPAPIER TISKPKGSVR APQVYVLPPP
351 EEEMTKKQVT LTCMVTDFMP EDIYVEWTNN GKTELNYKNT EPVLDSDGSY
401 FMYSKLRVEK KNWVERNSYS CSVVHEGLHN HHTTKSFSRT PGK (LC; KWAR23)
                                                            SEQ ID NO: 48
  1 QIVLTQSPAI MSASPGEKVT LTCSASSSVS SSYLYWYQQK PGSSPKLWIY
 51 STSNLASGVP ARFSGSGSGT SYSLTISSME AEDAASYFCH QWSSYPRTFG
101 AGTKLELKRA DAAPTVSIFP PSSEQLTSGG ASVVCFLNNF YPKDINVKWK
```

-continued

```
151 IDGSERQNGV LNSWTDQDSK DSTYSMSSTL TLTKDEYERH NSYTCEATHK

201 TSTSPIVKSF NRNEC
```

(HC; HEFLB)                                                              SEQ ID NO: 49

```
  1 EVQLVQSGAE VKKPGESLRI SCKASGYSFT SYWVHWVRQM PGKGLEWMGN

51 IDPSDSDTHY SPSFQGHVTL SVDKSISTAY LQLSSLKASD TAMYYCVRGG

101 TGTLAYFAYW GQGTLVTVSS ASTKGPSVFP LAPCSRSTSE STAALGCLVK

151 DYFPEPVTVS WNSGALTSGV HTFPAVLQSS GLYSLSSVVT VPSSSLGTKT

201 YTCNVDHKPS NTKVDKRVES KYGPPCPPCP APEFLGGPSV FLFPPKPKDT

251 LMISRTPEVT CVVVDVSQED PEVQFNWYVD GVEVHNAKTK PREEQFNSTY

301 RVVSVLTVLH QDWLNGKEYK CKVSNKGLPS SIEKTISKAK GQPREPQVYT

351 LPPSQEEMTK NQVSLTCLVK GFYPSDIAVE WESNGQPENN YKTTPPVLDS

401 DGSFFLYSRL TVDKSRWQEG NVFSCSVMHE ALHNHYTQKS LSLSPGK
```

(LC; HEFLB)                                                              SEQ ID NO: 50

```
  1 DVVMTQSPLS LPVTLGQPAS ISCRSSQSLV HSYGNTYLYW FQQRPGQSPR

51 LLIYRVSNRF SGVPDRFSGS GSGTDFTLKI SRVEAEDVGV YYCFQGTHVP

101 YTFGGGTKVE IKRTVAAPSV FIFPPSDEQL KSGTASVVCL LNNFYPREAK

151 VQWKVDNALQ SGNSQESVTE QDSKDSTYSL SSTLTLSKAD YEKHKVYACE

201 VTHQGLSSPV TKSFNRGEC
```

(human SIRPα₁ extracellular domain 1-370, Avi-FXa-Fc tag)                SEQ ID NO: 51

MEPAGPAPGRLGPLLCLLLAASCAWSGVAGEEELQVIQPDKSVSVAAGESAILHCTVTSLIP

VGPIQWFRGAGPARELIYNQKEGHFPRVTTVSESTKRENMDFSISISNITPADAGTYYCVKF

RKGSPDTEFKSGAGTELSVRAKPSAPVVSGPAARATPQHTVSFTCESHGFSPRDITLKWFKN

GNELSDFQTNVDPVGESVSYSIHSTAKVVLTREDVHSQVICEVAHVTLQGDPLRGTANLSET

IRVPPTLEVTQQPVRAENQVNVTCQVRKFYPQRLQLTWLENGNVSRTETASTVTENKDGTYN

WMSWLLVNVSAHRDDVKLTCQVEHDGQPAVSKSHDLKVSAHPKEQGSNTAAENTGSNERN*GG*

*GLNDIFEAQKIEWHEIEGRDKTHTCPPCPAPELLGGPSVFLFPPKPKDTLMISRTPEVTCVV*

*VDVSHEDPEVKFNWYVDGVEVHNAKTKPREEQYNSTYRVVSVLTVLHQDWLNGKEYKCKVSN*

*KALPAPIEKTISKAKGQPREPQVYTLPPSREEMTKNQVSLTCLVKGFYPSDIAVEWESNGQP*

*ENNYKTTPPVLDSDGSFFLYSKLTVDKSRWQQGNVFSCSVMHEALHNHYTQKSLSLSPGK*

(human SIRPα_{BIT}, extracellular domain 1-370, Avi-FXa-Fc tag)          SEQ ID NO: 52

MEPAGPAPGRLGPLLCLLLAASCAWSGVAGEEELQVIQPDKSVLVAAGETATLRCTATSLIP

VGPIQWFRGAGPGRELIYNQKEGHFPRVTTVSDLTKRNNMDFSIRIGNITPADAGTYYCVKF

RKGSPDDVEFKSGAGTELSVRAKPSAPVVSGPAARATPQHTVSFTCESHGFSPRDITLKWFK

NGNELSDFQTNVDPVGESVSYSIHSTAKVVLTREDVHSQVICEVAHVTLQGDPLRGTANLSE

TIRVPPTLEVTQQPVRAENQVNVTCQVRKFYPQRLQLTWLENGNVSRTETASTVTENKDGTY

NWMSWLLVNVSAHRDDVKLTCQVEHDGQPAVSKSHDLKVSAHPKEQGSNTAAENTGSNERNG

*GGLNDIFEAQKIEWHEIEGRDKTHTCPPCPAPELLGGPSVFLFPPKPKDTLMISRTPEVTCV*

*VVDVSHEDPEVKFNWYVDGVEVHNAKTKPREEQYNSTYRVVSVLTVLHQDWLNGKEYKCKVS*

| | |
|---|---|
| NKALPAPIEKTISKAKGQPREPQVYTLPPSREEMTKNQVSLTCLVKGFYPSDIAVEWESNGQ | |
| PENNYKTTPPVLDSDGSFFLYSKLTVDKSRWQQGNVFSCSVMHEALHNHYTQKSLSLSPGK | |
| (human SIRPβ1v1, extracellular domain, Avi-FXa-Fc tag) | SEQ ID NO: 53 |
| MPVPASWPHLPSPFLLMTLLLGRLTGVAGEDELQVIQPEKSVSVAAGESATLRCAMTSLIPV | |
| GPIMWFRGAGAGRELIYNQKEGHFPRVTTVSELTKRNNLDFSISISNITPADAGTYYCVKFR | |
| KGSPDDVEFKSGAGTELSVRAKPSAPVVSGPAVRATPEHTVSFTCESHGFSPRDITLKWFKN | |
| GNELSDFQTNVDPAGDSVSYSIHSTARVVLTRGDVHSQVICEIAHITLQGDPLRGTANLSEA | |
| IRVPPTLEVTQQPMRAENQANVTCQVSNFYPRGLQLTWLENGNVSRTETASTLIENKDGTYN | |
| WMSWLLVNTCAHRDDVVLTCQVEHDGQQAVSKSYALEISAHQKEHGSDITHEAALAPTAPLG | |
| GGLNDIFEAQKIEWHEIEGRDKTHTCPPCPAPELLGGPSVFLFPPKPKDTLMISRTPEVTCV | |
| VVDVSHEDPEVKFNWYVDGVEVHNAKTKPREEQYNSTYRVVSVLTVLHQDWLNGKEYKCKVS | |
| NKALPAPIEKTISKAKGQPREPQVYTLPPSREEMTKNQVSLTCLVKGFYPSDIAVEWESNGQ | |
| PENNYKTTPPVLDSDGSFFLYSKLTVDKSRWQQGNVFSCSVMHEALHNHYTQKSLSLSPGK | |
| (human SIRPß1v2, extracellular domain, Avi-FXa-Fc tag) | SEQ ID NO: 54 |
| MPVPASWPHLPSPFLLMTLLLGRLTGVAGEEELQVIQPDKSISVAAGESATLHCTVTSLIPV | |
| GPIQWFRGAGPGRELIYNQKEGHFPRVTTVSDLTKRNNMDFSIRISNITPADAGTYYCVKFR | |
| KGSPDHVEFKSGAGTELSVRAKPSAPVVSGPAARATPQHTVSFTCESHGFSPRDITLKWFKN | |
| GNELSDFQTNVDPAGDSVSYSIHSTAKVVLTREDVHSQVICEVAHVTLQGDPLRGTANLSET | |
| IRVPPTLEVTQQPVRAENQVNVTCQVRKFYPQRLQLTWLENGNVSRTETASTLTENKDGTYN | |
| WMSWLLVNVSAHRDDVKLTCQVEHDGQPAVSKSHDLKVSAHPKEQGSNTAPGPALASAAPLG | |
| GGLNDIFEAQKIEWHEIEGRDKTHTCPPCPAPELLGGPSVFLFPPKPKDTLMISRTPEVTCV | |
| VVDVSHEDPEVKFNWYVDGVEVHNAKTKPREEQYNSTYRVVSVLTVLHQDWLNGKEYKCKVS | |
| NKALPAPIEKTISKAKGQPREPQVYTLPPSREEMTKNQVSLTCLVKGFYPSDIAVEWESNGQ | |
| PENNYKTTPPVLDSDGSFFLYSKLTVDKSRWQQGNVFSCSVMHEALHNHYTQKSLSLSPGK | |
| (human SIRPγ, extracellular domain, Avi-FXa-Fc tag) | SEQ ID NO: 55 |
| MPVPASWPHPPGPFLLLTLLLGLTEVAGEEELQMIQPEKLLLVTVGKTATLHCTVTSLLPVG | |
| PVLWFRGVGPGRELIYNQKEGHFPRVTTVSDLTKRNNMDFSIRISSITPADVGTYYCVKFRK | |
| GSPENVEFKSGPGTEMALGAKPSAPVVLGPAARTTPEHTVSFTCESHGFSPRDITLKWFKNG | |
| NELSDFQTNVDPTGQSVAYSIRSTARVVLDPWDVRSQVICEVAHVTLQGDPLRGTANLSEAI | |
| RVPPTLEVTQQPMRVGNQVNVTCQVRKFYPQSLQLTWSENGNVCQRETASTLTENKDGTYNW | |
| TSWFLVNISDQRDDVVLTCQVKHDGQLAVSKRLALEVTVHQKDQSSDATPKGQDNSADIQHS | |
| GGRSSLEGPRFEGKPIPNPLLGLDSTRTGGGGLNDIFEAQKIEWHEIEGRDKTHTCPPCPAP | |
| ELLGGPSVFLFPPKPKDTLMISRTPEVTCVVVDVSHEDPEVKFNWYVDGVEVHNAKTKPREE | |
| QYNSTYRVVSVLTVLHQDWLNGKEYKCKVSNKALPAPIEKTISKAKGQPREPQVYTLPPSRE | |
| EMTKNQVSLTCLVKGFYPSDIAVEWESNGQPENNYKTTPPVLDSDGSFFLYSKLTVDKSRWQ | |
| QGNVFSCSVMHEALHNHYTQKSLSLSPGK | |
| (cynomolgus monkey SIRPα, extracellular domain, Avi-FXa-Fc tag) | SEQ ID NO: 56 |
| MEPAGPAPGRLGPLLCLLLTASCAWSGVLGEEELQVIQPEKSVSVAAGDSATLNCTVSSLIP | |
| VGPIQWFRGAGPGRELIYNLKEGHFPRVTAVSDPTKRNNMDFSIRISNITPADAGTYYCVKF | |
| RKGSPDVELKSGAGTELSVRAKPSAPVVSGPAVRATAEHTVSFTCESHGFSPRDITLKWFKN | |
| GNELSDVQTNVDPAGKSVSYSIRSTARVLLTRRDVHSQVICEVAHVTLQGDPLRGTANLSEA | |

```
IRVPPFLEVTQQSMRADNQVNVTCQVTKFYPQRLQLTWLENGNVSRTEMASALPENKDGTYN

WTSWLLVNVSAHRDDVKLTCQVEHDGQPAVNKSFSVKVSAHPKEQGSNTAAENTGTNERNGG

GLNDIFEAQKIEWHEIEGRDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKVSN

KALPAPIEKTISKAKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHYTQKSLSLSPGK
```

(HC; 1H9; including leader sequence [underlined]; constant region [italic])

SEQ ID NO: 57

```
MACPGFLWALVISTCLEFSMAQVQLVQSGAEVKKPGASVKVSCKASGYTFTSYWITWVKQAP

GQGLEWIGDIYPGSGSTNHIEKFKSKATLTVDTSISTAYMELSRLRSDDTAVYYCATGYGSS

YGYFDYWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSCDKTH

TCPPCPAPELLGGPSVFLFPPKPKDTLMISRTPEVTCVVVDVSHEDPEVKFNWYVDGVEVHN

AKTKPREEQYASTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKL

TVDKSRWQQGNVFSCSVMHEALHNHYTQKSLSLSPGK
```

(LC; 1H9; including leader sequence [underlined]; constant region [italic])

SEQ ID NO: 58

```
MACPGFLWALVISTCLEFSMADIQMTQSPSSLSASVGDRVTITCRASENIYSYLAWYQQKPG

KAPKLLIYTAKTLAEGVPSRFSGSGSGTDFTLTISSLQPEDFATYYCQHQYGPPFTFGQGTK

LEIKRTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC
```

(HC; 40A-1; including leader sequence [underlined]; constant region [italic])

SEQ ID NO: 59

```
MACPGFLWALVISTCLEFSMAQVQLVQSGAEVKKPGASVKVSCKASGYTFTSYWITWVKQAP

GQGLEWIGDIYPGSGSTNHIEKFKSKATLTVDTSISTAYMELSRLRSDDTAVYYCATGYGSS

YGYFDYWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKKVEPKSCDKTH

TCPPCPAPELLGGPSVFLFPPKPKDTLMISRTPEVTCVVVDVSHEDPEVKFNWYVDGVEVHN

AKTKPREEQYASTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKL

TVDKSRWQQGNVFSCSVMHEALHNHYTQKSLSLSPGK
```

(LC; 40A-1; including leader sequence [underlined]; constant region [italic])

SEQ ID NO: 60

```
MACPGFLWALVISTCLEFSMADIQMTQSPSSLSASVGDRVTITCRASQDIGSRLNWLQQKPG

KAPKRLIYATSSLDSGVPSRFSGSGSGTEFTLTISSLQPEDFATYYCLQYASSPFTFGGGTK

VEIKRTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC
```

(HC; 40A-2; including leader sequence [underlined]; constant region [italic])

SEQ ID NO: 61

```
MACPGFLWALVISTCLEFSMAEVQLVQSGAEVVKPGASVKLSCKASGSTFTSYWMHWVKQAP

GQGLEWIGAIYPVNSDTTYNQKFKGKATLTVDKSASTAYMELSSLRSEDTAVYYCTRSFYYS

LDAAWFVYWGQGTLVTVSSASTKGPSVFPLAPCSRSTSESTAALGCLVKDYFPEPVTVSWNS

GALTSGVHTFPAVLQSSGLYSLSSVVTVPSSNFGTQTYTCNVDHKPSNTKVDKTVERKCCVE

CPPCPAPPVAGPSVFLFPPKPKDTLMISRTPEVTCVVVDVSHEDPEVQFNWYVDGVEVHNAK
```

-continued

*TKPREEQFNSTFRVVSVLTVVHQDWLNGKEYKCKVSNKGLPAPIEKTISKTKGQPREPQVYT*

*LPPSREEMTKNQVSLTCLVKGFYPSDIAVEWESNGQPENNYKTTPPMLDSDGSFFLYSKLTV*

*DKSRWQQGNVFSCSVMHEALHNHYTQKSLSLSPGK*

(LC; 40A-2; including leader sequence [underlined]; constant region [italic])
SEQ ID NO: 62

<u>MACPGFLWALVISTCLEFSMA</u>DIQMTQSPSSLSASVGDRVTITCRASQDIGSRLNWLQQKPG

KAPKRLIYATSSLDSGVPSRFSGSGSGTEFTLTISSLQPEDFATYYCLQYASSPFTFGGGTK

VEIKR*TVAAPSVFIFPPSDEQLKSGTASVVCLLNNFYPREAKVQWKVDNALQSGNSQESVTE*

*QDSKDSTYSLSSTLTLSKADYEKHKVYACEVTHQGLSSPVTKSFNRGEC*

(HC; AB3-LALA; including leader sequence [underlined]; constant region [italic])
SEQ ID NO: 63

<u>MACPGFLWALVISTCLEFSMA</u>AVTLDESGGGLQTPGGALSLVCKASGFIFSDYGMNWVRQAP

GKGLEFVAQITSGSRTYYGAAVKGRATISRDNRQSTVKLQLNNLRAEDTGIYFCARDFGSGV

GSIDAWGNGTEVIVSS*ASTKGPSVFPLAPSSKSTSGGTAALGCLVKDYFPEPVTVSWNSGAL*

*TSGVHTFPAVLQSSGLYSLSSVVTVPSSSLGTQTYICNVNHKPSNTKVDKKVEPKSCDKTHT*

*CPPCPAPEAAGGPSVFLFPPKPKDTLMISRTPEVTCVVVDVSHEDPEVKFNWYVDGVEVHNA*

*KTKPREEQYNSTYRVVSVLTVLHQDWLNGKEYKCKVSNKALPAPIEKTISKAKGQPREPQVY*

*TLPPSRDELTKNQVSLTCLVKGFYPSDIAVEWESNGQPENNYKTTPPVLDSDGSFFLYSKLT*

*VDKSRWQQGNVFSCSVMHEALHNHYTQKSLSLSPGK*

(LC; AB3-LALA; including leader sequence [underlined]; constant region [italic])
SEQ ID NO: 64

<u>MACPGFLWALVISTCLEFSMA</u>ALTQPASVSANLGGTVKITCSGSRGRYGWYQQRSPGSAPVT

VIYRDNQRPSNIPSRFSSSTSGSTSTLTITGVQADDESVYFCGSYDGSIDIFGAGTTLTVLR

*TVAAPSVFIFPPSDEQLKSGTASVVCLLNNFYPREAKVQWKVDNALQSGNSQESVTEQDSKD*

*STYSLSSTLTLSKADYEKHKVYACEVTHQGLSSPVTKSFNRGEC*

(HC; AB25-LALA; including leader sequence [underlined]; constant region [italic])
SEQ ID NO: 65

<u>MACPGFLWALVISTCLEFSMA</u>DVQLVESGGGVVRPGESLRLSCEASGFTFSSNAMSWVRQAP

GKGLEWVAGISSGSDTYYGDSVKGRLTISRDNSKNILYLQMNSLTAEDTAVYYCARETWNHL

FDYWGLGTLVTVSS*ASTKGPSVFPLAPSSKSTSGGTAALGCLVKDYFPEPVTVSWNSGALTS*

*GVHTFPAVLQSSGLYSLSSVVTVPSSSLGTQTYICNVNHKPSNTKVDKKVEPKSCDKTHTCP*

*PCPAPEAAGGPSVFLFPPKPKDTLMISRTPEVTCVVVDVSHEDPEVKFNWYVDGVEVHNAKT*

*KPREEQYNSTYRVVSVLTVLHQDWLNGKEYKCKVSNKALPAPIEKTISKAKGQPREPQVYTL*

*PPSRDELTKNQVSLTCLVKGFYPSDIAVEWESNGQPENNYKTTPPVLDSDGSFFLYSKLTVD*

*KSRWQQGNVFSCSVMHEALHNHYTQKSLSLSPGK*

(LC; AB25-LALA; including leader sequence [underlined]; constant region [italic])
SEQ ID NO: 66

<u>MACPGFLWALVISTCLEFSMA</u>SYELTQPPSVSVSPGQTARITCSGGSYSSYYYAWYQQKPGQ

APVTLIYSDDKRPSNIPERFSGSSSGTTVTLTISGVQAEDEADYYCGGYDQSSYTNPFGGGT

KLTVLR*TVAAPSVFIFPPSDEQLKSGTASVVCLLNNFYPREAKVQWKVDNALQSGNSQESVT*

*EQDSKDSTYSLSSTLTLSKADYEKHKVYACEVTHQGLSSPVTKSFNRGEC*

(HC; AB115-LALA; including leader sequence [underlined]; constant region [italic])
SEQ ID NO: 67

<u>MACPGFLWALVISTCLEFSMA</u>VQLVESGGGVVRPGESLRLSCAASGFSFSSYAMNWVRQAPG

EGLEWVSRINSGGGGTDYAESVKGRFTISRDNSENTLYLQMNSLRAEDTAVYYCAKQYDWNS

FFDYWGLGALVTVSS*ASTKGPSVFPLAPSSKSTSGGTAALGCLVKDYFPEPVTVSWNSGALT*

*SGVHTFPAVLQSSGLYSLSSVVTVPSSSLGTQTYICNVNHKPSNTKVDKKVEPKSCDKTHTC*

-continued

*PPCPAPEAAGGPSVFLFPPKPKDTLMISRTPEVTCVVVDVSHEDPEVKFNWYVDGVEVHNAK*

*TKPREEQYNSTYRVVSVLTVLHQDWLNGKEYKCKVSNKALPAPIEKTISKAKGQPREPQVYT*

*LPPS<u>R</u>DELTKNQVSLTCLVKGFYPSDIAVEWESNGQPENNYKTTPPVLDSDGSFFLYSKLTV*

*DKSRWQQGNVFSCSVMHEALHNHYTQKSLSLSPGK*

(LC; AB115-LALA; including leader sequence [underlined]; constant region [italic])
SEQ ID NO: 68

<u>MACPGFLWALVISTCLEFSMA</u>ETVLTQSPATLSVSPGERATLSCRASQTVGSKLAWHQQKPG

QAPRLLIYDATNRATGISDRFSGSGSGTDFTLTISSLQTEDSAVYYCQQYYYWPPYRFGGGT

KVEIKR*TVAAPSVFIFPPSDEQLKSGTASVVCLLNNFYPREAKVQWKVDNALQSGNSQESVT*

*EQDSKDSTYSLSSTLTLSKADYEKHKVYACEVTHQGLSSPVTKSFNRGEC*

(HC; AB119-LALA; including leader sequence [underlined]; constant region [italic])
SEQ ID NO: 69

<u>MACPGFLWALVISTCLEFSMA</u>VQLLESGGGVVQPGGSLRLSCAASGFSFSNFAMTWVRQAPG

EGLEWVSTIGSGDTYYADSVKGRFTISRDNSKNTLYLQMNSLRAEDTAVYYCAKDSTVSWSG

DFFDYWGLGTLVTVSS*ASTKGPSVFPLAPSSKSTSGGTAALGCLVKDYFPEPVTVSWNSGAL*

*TSGVHTFPAVLQSSGLYSLSSVVTVPSSSLGTQTYICNVNHKPSNTKVDKKVEPKSCDKTHT*

*CPPCPAPEAAGGPSVFLFPPKPKDTLMISRTPEVTCVVVDVSHEDPEVKFNWYVDGVEVHNA*

*KTKPREEQYNSTYRVVSVLTVLHQDWLNGKEYKCKVSNKALPAPIEKTISKAKGQPREPQVY*

*TLPPSRDELTKNQVSLTCLVKGFYPSDIAVEWESNGQPENNYKTTPPVLDSDGSFFLYSKLT*

*VDKSRWQQGNVFSCSVMHEALHNHYTQKSLSLSPGK*

(LC; AB119-LALA; including leader sequence [underlined]; constant region [italic])
SEQ ID NO: 70

<u>MACPGFLWALVISTCLEFSMA</u>EIVLTQSPATLSVSPGERATFSCRASQNVKNDLAWYQQRPG

QAPRLLIYAARIRETGIPERFSGSGSGTEFTLTITSLQSEDFAVYYCQQYYDWPPFTFGGGT

KVEIKR*TVAAPSVFIFPPSDEQLKSGTASVVCLLNNFYPREAKVQWKVDNALQSGNSQESVT*

*EQDSKDSTYSLSSTLTLSKADYEKHKVYACEVTHQGLSSPVTKSFNRGEC*

(HC; AB136-LALA; including leader sequence [underlined]; constant region [italic])
SEQ ID NO: 71

<u>MACPGFLWALVISTCLEFSMA</u>DVQLVESGGGVVRPGESLRLSCAASGFTFSSYDMNWVRQAP

GEGLEWVSLISGSGEIIYYADSVKGRFTISRDNSKNTLYLQMNSLRAEDTAVYYCAKENNRY

RFFDDWGLGTLVTVSS*ASTKGPSVFPLAPSSKSTSGGTAALGCLVKDYFPEPVTVSWNSGAL*

*TSGVHTFPAVLQSSGLYSLSSVVTVPSSSLGTQTYICNVNHKPSNTKVDKKVEPKSCDKTHT*

*CPPCPAPEAAGGPSVFLFPPKPKDTLMISRTPEVTCVVVDVSHEDPEVKFNWYVDGVEVHNA*

*KTKPREEQYNSTYRVVSVLTVLHQDWLNGKEYKCKVSNKALPAPIEKTISKAKGQPREPQVY*

*TLPPSRDELTKNQVSLTCLVKGFYPSDIAVEWESNGQPENNYKTTPPVLDSDGSFFLYSKLT*

*VDKSRWQQGNVFSCSVMHEALHNHYTQKSLSLSPGK*

(LC; AB136-LALA; including leader sequence [underlined]; constant region [italic])
SEQ ID NO: 72

<u>MACPGFLWALVISTCLEFSMA</u>ETVLTQSPGTLTLSPGERATLTCRASQSVYTYLAWYQEKPG

QAPRLLIYGASSRATGIPDRFSGSGSGTEFTLTISSLQSEDFAVYYCQQYYDRPPLTFGGGT

KVEIKR*TVAAPSVFIFPPSDEQLKSGTASVVCLLNNFYPREAKVQWKVDNALQSGNSQESVT*

*EQDSKDSTYSLSSTLTLSKADYEKHKVYACEVTHQGLSSPVTKSFNRGEC*

(HC; 3F9-LALA; including leader sequence [underlined]; constant region [italic])
SEQ ID NO: 73

<u>MACPGFLWALVISTCLEFSMA</u>EVKLVESGGGLVKPGGSLKLSCAASGFTFSSYAMSWVRQTP

EKRLEWVATISDYGGSYTYYPDSVKGRFTISRDNAKYTLYLQMSSLRSEDTALYYCARPPYD

-continued

DYYGGFAYWGQGTLVTVSAA*STKGPSVFPLAPSSKSTSGGTAALGCLVKDYFPEPVTVSWNS*

*GALTSGVHTFPAVLQSSGLYSLSSVVTVPSSSLGTQTYICNVNHKPSNTKVDKKVEPKSCDK*

*THTCPPCPAPEAAGGPSVFLFPPKPKDTLMISRTPEVTCVVVDVSHEDPEVKFNWYVDGVEV*

*HNAKTKPREEQYNSTYRVVSVLTVLHQDWLNGKEYKCKVSNKALPAPIEKTISKAKGQPREP*

*QVYTLPPSRDELTKNQVSLTCLVKGFYPSDIAVEWESNGQPENNYKTTPPVLDSDGSFFLYS*

*KLTVDKSRWQQGNVFSCSVMHEALHNHYTQKSLSLSPGK*

(LC; 3F9-LALA; including leader sequence [underlined]; constant region [italic])

SEQ ID NO: 74

<u>MACPGFLWALVISTCLEFSMAD</u>IVLTQSPASLAVSLGQRATISCRASKSVSSSGYSYMHWYQ

QKPGQPPKLLIYLASNLESGVPARFSGSGSGTDFTLNIHPVEEEDAATYYCQHNRELPCTFG

GGTKLEIKR*TVAAPSVFIFPPSDEQLKSGTASVVCLLNNFYPREAKVQWKVDNALQSGNSQE*

*SVTEQDSKDSTYSLSSTLTLSKADYEKHKVYACEVTHQGLSSPVTKSFNRGEC*

(HC; 7H9-LALA; including leader sequence [underlined]; constant region [italic])

SEQ ID NO: 75

<u>MACPGFLWALVISTCLEFSMAD</u>VQLQESGPGLVKPSQSLSLTCTVTGFSISRGYDWHWIRHF

PGNILEWMGYITYSGISNYNPSLKSRISITHDTSKNHFFLRLNSVTAEDTATYYCARGGGAW

FTYWGQGTLVTVSAA*STKGPSVFPLAPSSKSTSGGTAALGCLVKDYFPEPVTVSWNSGALTS*

*GVHTFPAVLQSSGLYSLSSVVTVPSSSLGTQTYICNVNHKPSNTKVDKKVEPKSCDKTHTCP*

*PCPAPEAAGGPSVFLFPPKPKDTLMISRTPEVTCVVVDVSHEDPEVKFNWYVDGVEVHNAKT*

*KPREEQYNSTYRVVSVLTVLHQDWLNGKEYKCKVSNKALPAPIEKTISKAKGQPREPQVYTL*

*PPSRDELTKNQVSLTCLVKGFYPSDIAVEWESNGQPENNYKTTPPVLDSDGSFFLYSKLTVD*

*KSRWQQGNVFSCSVMHEALHNHYTQKSLSLSPGK*

(LC; 7H9-LALA; including leader sequence [underlined]; constant region [italic])

SEQ ID NO: 76

<u>MACPGFLWALVISTCLEFSMAD</u>IVMTQSPATLSVTPGDRVSLSCRASQSISDSLHWYHQKSH

ESPRLLIKYASQSISGIPSRFSAGGSGSDFTLTINSVEPEDVGVYYCQNGHSLPWTFGGGTK

LEIKR*TVAAPSVFIFPPSDEQLKSGTASVVCLLNNFYPREAKVQWKVDNALQSGNSQESVTE*

*QDSKDSTYSLSSTLTLSKADYEKHKVYACEVTHQGLSSPVTKSFNRGEC*

TABLE 8

Examples of amino acid residue substitutions in heavy chain FR1 (SEQ ID NO: 77)

| 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|----|----|----|----|----|----|----|----|----|----|----|----|----|----|----|----|----|----|----|----|----|
| V | Q | L | V | E | S | G | G | R  | L  | V  | Q  | P  | G  | T  | S  | L  | T  | L  | S  | C  | T  | V  | S  | G  | F  | S  | L  | S  |
| R | S | V | E |   |   |   |   | G  |    | G  |    |    |    | G  | P  |    | R  |    |    |    | A  | A  |    |    |    |    |    |    |
| Q |   |   |   |   |   |   |   |    |    |    |    |    |    |    |    |    |    |    |    |    |    |    |    |    |    |    |    |    |

TABLE 9

Examples of amino acid residue substitutions in heavy chain FR2 (SEQ ID NO: 78)

| 36 | 37 | 38 | 39 | 40 | 41 | 42 | 43 | 44 | 45 | 46 | 47 | 48 | 49 |
|----|----|----|----|----|----|----|----|----|----|----|----|----|----|
| W  | F  | R  | Q  | A  | P  | G  | K  | G  | L  | E  | Y  | I  | G  |
|    | V  |    |    |    |    |    |    |    |    |    |    | W  | V  |

TABLE 10

Examples of amino acid residue substitutions in heavy chain FR379 (SEQ ID NO: 79)

| 66 | 67 | 68 | 69 | 70 | 71 | 72 | 73 | 74 | 75 | 76 | 77 | 78 | 79 | 80 | 81 | 82 | 82A | 83 | 84 | 85 | 86 | 87 | 88 | 89 | 90 | 91 | 92 | 93 | 94 |
|----|----|----|----|----|----|----|----|----|----|----|----|----|----|----|----|----|-----|----|----|----|----|----|----|----|----|----|----|----|----|
| R | F | T | I | S | K | T | S | T | T | M | D | L | K | M | N | S | L | R | S | E | D | T | A | T | Y | F | C | A | R |
|   |   |   | G |   |   |   |   | S |   |   | A | Y | M | Q | T |   | P | T |   |   |   |   |   |   | V | Y |   |   |   |
|   |   |   |   |   |   |   |   |   |   |   |   |   | E |   | S |   |   | A |   |   |   |   |   |   |   |   |   |   |   |

TABLE 11

Examples of amino acid residue substitutions in heavy chain FR4
(SEQ ID NO: 80)

| 103 | 104 | 105 | 106 | 107 | 108 | 109 | 110 | 111 | 112 | 113 |
|-----|-----|-----|-----|-----|-----|-----|-----|-----|-----|-----|
| W | G | P | G | T | L | V | T | V | S | S |
|   |   | Q |   |   |   |   |   |   |   |   |

TABLE 12

Examples of amino acid residue substitutions in light chain FR1 (SEQ ID NO: 81)

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|----|----|----|----|----|----|----|----|----|----|----|----|----|----|
| D | I | Q | M | T | Q | S | P | S | S | L | S | A | S | V | G | D | R | V | T | I | T | C |
|   |   | E |   |   |   |   |   |   |   | V |   |   |   |   |   |   |   |   |   | L |   |   |
|   |   | V |   |   |   |   |   |   |   |   |   |   |   |   |   |   |   |   |   |   |   |   |

TABLE 13

Examples of amino acid residue substitutions in light chain FR2
(SEQ ID NO: 82)

| 35 | 36 | 37 | 38 | 39 | 40 | 41 | 42 | 43 | 44 | 45 | 46 | 47 | 48 | 49 |
|----|----|----|----|----|----|----|----|----|----|----|----|----|----|----|
| W | Y | Q | Q | K | P | G | K | A | P | K | L | L | I | Y |
|   |   |   |   |   |   |   | Q |   |   |   |   |   |   |   |

TABLE 14

Examples of amino acid residue substitutions in light chain FR4
(SEQ ID NO: 83)

| 98 | 99 | 100 | 101 | 102 | 103 | 104 | 105 | 106 | 107 |
|----|----|-----|-----|-----|-----|-----|-----|-----|-----|
| F | G | Q | G | T | K | V | E | I | K |
|   |   | G |   |   |   |   |   |   |   |

The invention claimed is:

1. A humanized anti-SIRPα antibody or an antigen-binding fragment thereof, comprising heavy chain complementarity determining regions (HCDR) and light chain complementarity determining regions (LCDR) HCDR1, HCDR2, HCDR3, LCDR1, LCDR2 and LCDR3, wherein the antibody or the antigen-binding fragment thereof comprises:
   a. HCDR1 comprising SEQ ID NO:36;
   b. HCDR2 comprising SEQ ID NO:44;
   c. HCDR3 comprising SEQ ID NO:45;
   d. LCDR1 comprising SEQ ID NO:39;
   e. LCDR2 comprising SEQ ID NO:40; and
   f. LCDR3 comprising SEQ ID NO:41.

2. The humanized anti-SIRPα antibody or the antigen-binding fragment thereof according to claim 1, wherein the anti-SIRPα antibody or the antigen-binding fragment thereof has one or more properties from the group consisting of:
   a. the anti-SIRPα antibody or the antigen-binding fragment thereof binds human SIRPα$_1$ with a binding affinity of at least $10^{-10}$ M, as analysed by surface plasmon resonance at 25° C. using human SIRPα$_1$ extracellular domain as shown in SEQ ID NO:51;
   b. the anti-SIRPα antibody or the antigen-binding fragment thereof binds human SIRPα$_{BIT}$ with a binding affinity of at least $10^{-10}$ M, as analysed by surface plasmon resonance at 25° C. using human SIRPα$_{BIT}$ extracellular domain as shown in SEQ ID NO:52;
   c. the anti-SIRPα antibody or the antigen-binding fragment thereof binds cynomolgus monkey SIRPα with a binding affinity of at least $10^{-8}$ M, as analysed by surface plasmon resonance at 25° C. using cynomolgus SIRPα extracellular domain as shown in SEQ ID NO:56;
   d. the anti-SIRPα antibody or the antigen-binding fragment thereof does not bind human SIRPγ as measured by T-cell binding using flow cytometry;
   e. the anti-SIRPα antibody or the antigen-binding fragment thereof does not bind human SIRPγ as analysed by surface plasmon resonance at 25° C. using human SIRPγ extracellular domain as shown in SEQ ID NO:55; and
   f. the anti-SIRPα antibody or the antigen-binding fragment thereof is not immunogenic as determined by IL-2 enzyme-linked immunosorbent spot (ELISpot) and/or T-cell proliferation assay.

3. The humanized anti-SIRPα antibody or the antigen-binding fragment thereof according to claim 1, wherein:
   a. the anti-SIRPα antibody or the antigen-binding fragment thereof binds human SIRPα$_1$ with a binding affinity of at least $10^{-10}$ M, as analysed by surface plasmon resonance at 25° C. using human SIRPα$_1$ extracellular domain as shown in SEQ ID NO:51;
   b. the anti-SIRPα antibody or the antigen-binding fragment thereof binds human SIRPα$_{BIT}$ with a binding affinity of at least $10^{-10}$ M, as analysed by surface plasmon resonance at 25° C. using human SIRPα$_{BIT}$ extracellular domain as shown in SEQ ID NO:52;
   c. blocks CD47 binding to SIRPα$_1$ and SIRPα$_{BIT}$ as analysed by dissociation from captured CD47 by surface plasmon resonance; and
   d. the anti-SIRPα antibody or the antigen-binding fragment thereof does not bind human SIRPγ as measured by T-cell flow cytometry staining.

4. The humanized anti-SIRPα antibody or the antigen-binding fragment thereof according to claim 3, wherein:
   a. the anti-SIRPα antibody or the antigen-binding fragment thereof binds human SIRPα$_1$ with a binding affinity of at least $10^{-11}$ M, as analysed by surface plasmon resonance at 25° C. using human SIRPα$_1$ extracellular domain as shown in SEQ ID NO:51;
   b. the anti-SIRPα antibody or the antigen-binding fragment thereof binds human SIRPα$_{BIT}$ with a binding affinity of at least $10^{-11}$ M, as analysed by surface plasmon resonance at 25° C. using human SIRPα$_{BIT}$ extracellular domain as shown in SEQ ID NO:52;
   c. blocks CD47 binding to SIRPα$_1$ and SIRPα$_{BIT}$ as analysed by dissociation from captured CD47 by surface plasmon resonance; and
   d. the anti-SIRPα antibody or the antigen-binding fragment thereof does not bind human SIRPγ as measured by T-cell flow cytometry staining.

5. The humanized anti-SIRPα antibody or the antigen-binding fragment thereof according to claim 1, comprising:
   a. a heavy chain variable domain which comprises 4 heavy chain framework regions, HFR1 to HFR4, and the 3 complementarity determining regions HCDR1 to HCDR3 that are operably linked in the order HFR1-HCDR1-HFR2-HCDR2-HFR3-HCDR3-HFR4, wherein each of the heavy chain framework regions has at least 90% amino acid sequence identity with the corresponding framework amino acid sequence of SEQ ID NO:8, or wherein HFR1 to HFR4 differ from SEQ ID NO:8 in one or more of the amino acid substitutions as defined in SEQ ID NO:77, SEQ ID NO:78, SEQ ID NO:79, and SEQ ID NO:80, respectively; and b. a light chain variable domain which comprises 4 light chain framework regions, LFR1 to LFR4, and the 3 complementarity determining regions LCDR1 to LCDR3 that are operably linked in the order LFR1-LCDR1-LFR2-LCDR2-LFR3-LCDR3-LFR4, wherein each of the light chain framework regions has at least 90% amino acid sequence identity with the corresponding framework amino acid sequence of SEQ ID NO: 9, or wherein LFR1, LFR2 and/or LFR4 differ from SEQ ID NO:9 in one or more acid substitutions as defined in SEQ ID NO:81, SEQ ID NO: 82, and SEQ ID NO:83, respectively.

6. The humanized anti-SIRPα antibody according to claim 5, comprising a modified human IgG$_1$ Fc region, comprising an amino acid substitution at one or more positions of a wild-type human IgG1 Fc region selected from the group consisting of L234, L235, G237, D265, D270, N297, A327, P328, and P329 according to Eu numbering.

7. The humanized anti-SIRPα antibody or the antigen-binding fragment thereof according to claim 1, comprising a heavy chain variable region (HCVR) and a light chain variable region (LCVR), wherein the antibody or the antigen-binding fragment thereof comprises the HCVR amino acid sequence of SEQ ID NO:8 and the LCVR amino acid sequence of SEQ ID NO:9.

8. The humanized anti-SIRPα antibody according to claim 7, comprising a modified human IgG$_1$ Fc region, comprising an amino acid substitution at one or more positions of a wild-type human IgG1 Fc region selected from the group consisting of L234, L235, G237, D265, D270, N297, A327, P328, and P329 according to Eu numbering.

9. The humanized anti-SIRPα antibody according to claim 8, comprising the amino acid substitutions L234A and L235A; L234E and L235A; L234A, L235A and P329A; or L234A, L235A and P329G.

10. The humanized anti-SIRPα antibody according to claim 1, comprising a modified Fc region that exhibits reduced binding to a human Fcα or Fcγ receptor compared to the same anti-SIRPα antibody comprising a wild-type Fc region.

11. The humanized anti-SIRPα antibody according to claim 1, comprising a modified human IgG$_1$ Fc region, comprising an amino acid substitution at one or more positions of a wild-type human IgG1 Fc region selected from the group consisting of L234, L235, G237, D265, D270, N297, A327, P328, and P329 according to Eu numbering.

12. The humanized anti-SIRPα antibody according to claim 11 comprising the amino acid substitutions L234A and L235A; L234E and L235A; L234A, L235A and P329A; or L234A, L235A and P329G.

13. A pharmaceutical composition comprising the humanized anti-SIRPα antibody or antigen-binding fragment thereof according to claim 1 and a pharmaceutically acceptable excipient.

14. A method of treating cancer, which comprises administering to a patient in need of such treatment an effective amount of (i) the humanized anti-SIRPα antibody or antigen-binding fragment thereof according to claim 1, and (ii) a therapeutic antibody, wherein the cancer is a human solid tumour or a hematological malignancy.

15. The method according to claim 14, wherein said cancer comprises tumour cells; and said therapeutic antibody (i) is directed against a membrane-bound target on the surface of the tumour cells and (ii) comprises a human Fc region that binds to activating Fc receptors present on human immune effector cells.

16. The method according to claim 15, wherein the cancer is selected from the group consisting of breast cancer, colon carcinoma, neuroblastoma, melanoma, osteosarcoma, B-cell lymphomas, lymphoma, acute myeloid leukaemia, chronic myeloid leukaemia, chronic lymphatic leukaemia, acute lymphoblastic leukaemia, non-Hodgkin's lymphoma, including follicular lymphoma and diffuse large B-cell lymphoma, hepatocellular carcinoma, multiple myeloma, bladder cancer, gastric cancer, ovarian cancer, head and neck cancer, pancreatic cancer, renal carcinoma, prostate cancer, hepatocellular carcinoma and lung cancer.

17. The method according to claim 16, which further comprises administering a further anti-cancer therapeutic compound.

18. The method according to claim 17, wherein the further anti-cancer therapeutic compound is a targeted therapeutic agent.

19. The method according to claim 14, wherein said (i) anti-SIRPα antibody or the antigen-binding fragment thereof and (ii) therapeutic antibody are administered sequentially.

20. The method according to claim 14, wherein said anti-SIRPα antibody or the antigen-binding fragment thereof, has a partly or completely disrupted Fc effector function.

21. A nucleic acid molecule comprising a nucleotide sequence encoding the humanized anti-SIRPα antibody according to claim 1.

22. A host cell comprising the nucleic acid molecule according to claim 21.

* * * * *

SEQUENCE LISTING

```
<160> NUMBER OF SEQ ID NOS: 83

<210> SEQ ID NO 1
<211> LENGTH: 116
<212> TYPE: PRT
<213> ORGANISM: Artificial Sequence
<220> FEATURE:
<223> OTHER INFORMATION: humanized HCVR

<400> SEQUENCE: 1

Val Gln Leu Val Glu Ser Gly Gly Arg Leu Gly Gln Pro Gly Thr Pro
1               5                   10                  15

Leu Thr Leu Ser Cys Thr Val Ser Gly Phe Ser Leu Ser Ser Tyr Val
            20                  25                  30

Met Gly Trp Phe Arg Gln Ala Pro Gly Lys Gly Leu Glu Tyr Ile Gly
        35                  40                  45

Ile Ile Ser Ser Ser Gly Ser Pro Tyr Tyr Ala Ser Trp Val Asn Gly
    50                  55                  60

Arg Phe Thr Ile Ser Lys Thr Ser Thr Thr Met Asp Leu Lys Met Asn
```

```
                    65                  70                  75                  80
Ser Leu Arg Ser Glu Asp Thr Ala Thr Tyr Phe Cys Ala Arg Val Gly
                    85                  90                  95

Pro Leu Gly Val Asp Tyr Phe Asn Ile Trp Gly Pro Gly Thr Leu Val
                100                 105                 110

Thr Val Ser Ser
        115

<210> SEQ ID NO 2
<211> LENGTH: 109
<212> TYPE: PRT
<213> ORGANISM: Artificial Sequence
<220> FEATURE:
<223> OTHER INFORMATION: humanized LCVR

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
                20                  25                  30

Leu Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Trp His Tyr Ile Ser Arg
                85                  90                  95

Ser Tyr Thr Phe Gly Gln Gly Thr Lys Val Glu Ile Lys
                100                 105

<210> SEQ ID NO 3
<211> LENGTH: 116
<212> TYPE: PRT
<213> ORGANISM: Artificial Sequence
<220> FEATURE:
<223> OTHER INFORMATION: humanized HCVR

<400> SEQUENCE: 3

Val Gln Leu Val Glu Ser Gly Gly Arg Leu Val Gln Pro Gly Thr Pro
1               5                   10                  15

Leu Thr Leu Ser Cys Thr Val Ser Gly Phe Ser Leu Ser Ser Tyr Val
                20                  25                  30

Met Gly Trp Phe Arg Gln Ala Pro Gly Lys Gly Leu Glu Tyr Ile Gly
                35                  40                  45

Ile Ile Ser Ser Gly Ser Pro Tyr Tyr Ala Ser Trp Val Asn Gly
        50                  55                  60

Arg Phe Thr Ile Ser Lys Thr Ser Thr Met Asp Leu Lys Met Asn
65                  70                  75                  80

Ser Leu Arg Ser Glu Asp Thr Ala Thr Tyr Phe Cys Ala Arg Val Gly
                85                  90                  95

Pro Leu Gly Val Asp Tyr Phe Asn Ile Trp Gly Pro Gly Thr Leu Val
                100                 105                 110

Thr Val Ser Ser
        115

<210> SEQ ID NO 4
<211> LENGTH: 116
```

```
<212> TYPE: PRT
<213> ORGANISM: Artificial Sequence
<220> FEATURE:
<223> OTHER INFORMATION: humanized HCVR

<400> SEQUENCE: 4
```

Val Gln Leu Val Glu Ser Gly Gly Arg Leu Gly Gln Pro Gly Thr Ser
1               5                   10                  15

Leu Thr Leu Ser Cys Thr Val Ser Gly Phe Ser Leu Ser Ser Tyr Val
            20                  25                  30

Met Gly Trp Phe Arg Gln Ala Pro Gly Lys Gly Leu Glu Tyr Ile Gly
        35                  40                  45

Ile Ile Ser Ser Ser Gly Ser Pro Tyr Tyr Ala Ser Trp Val Asn Gly
50                  55                  60

Arg Phe Thr Ile Ser Lys Thr Ser Thr Thr Met Asp Leu Lys Met Asn
65                  70                  75                  80

Ser Pro Thr Thr Glu Asp Thr Ala Thr Tyr Phe Cys Ala Arg Val Gly
                85                  90                  95

Pro Leu Gly Val Asp Tyr Phe Asn Ile Trp Gly Pro Gly Thr Leu Val
            100                 105                 110

Thr Val Ser Ser
            115

```
<210> SEQ ID NO 5
<211> LENGTH: 116
<212> TYPE: PRT
<213> ORGANISM: Artificial Sequence
<220> FEATURE:
<223> OTHER INFORMATION: humanized HCVR

<400> SEQUENCE: 5
```

Val Gln Leu Val Glu Ser Gly Gly Arg Leu Gly Gln Pro Gly Thr Ser
1               5                   10                  15

Leu Thr Leu Ser Cys Thr Val Ser Gly Phe Ser Leu Ser Ser Tyr Val
            20                  25                  30

Met Gly Trp Phe Arg Gln Ala Pro Gly Lys Gly Leu Glu Tyr Ile Gly
        35                  40                  45

Ile Ile Ser Ser Ser Gly Ser Pro Tyr Tyr Ala Ser Trp Val Asn Gly
50                  55                  60

Arg Phe Thr Ile Ser Lys Thr Ser Thr Thr Met Asp Leu Lys Met Asn
65                  70                  75                  80

Ser Leu Arg Ser Glu Asp Thr Ala Thr Tyr Phe Cys Ala Arg Val Gly
                85                  90                  95

Pro Leu Gly Val Asp Tyr Phe Asn Ile Trp Gly Pro Gly Thr Leu Val
            100                 105                 110

Thr Val Ser Ser
            115

```
<210> SEQ ID NO 6
<211> LENGTH: 115
<212> TYPE: PRT
<213> ORGANISM: Artificial Sequence
<220> FEATURE:
<223> OTHER INFORMATION: humanized HCVR

<400> SEQUENCE: 6
```

Arg Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser His Gly

```
            20                  25                  30
Ile Ser Trp Val Arg Gln Ala Pro Gly Lys Gly Leu Glu Tyr Ile Gly
            35                  40                  45

Thr Ile Gly Thr Gly Val Ile Thr Tyr Tyr Ala Ser Trp Ala Lys Gly
        50                  55                  60

Arg Phe Thr Gly Ser Lys Thr Ser Ser Thr Ala Tyr Leu Gln Met Thr
 65                  70                  75                  80

Ser Leu Arg Ala Glu Asp Thr Ala Val Tyr Tyr Cys Ala Arg Gly Ser
                85                  90                  95

Ala Trp Asn Asp Pro Phe Asp Tyr Trp Gly Gln Gly Thr Leu Val Thr
            100                 105                 110

Val Ser Ser
        115

<210> SEQ ID NO 7
<211> LENGTH: 111
<212> TYPE: PRT
<213> ORGANISM: Artificial Sequence
<220> FEATURE:
<223> OTHER INFORMATION: humanized LCVR

<400> SEQUENCE: 7

Asp Ile Glu Met Thr Gln Ser Pro Ser Ser Val Ser Ala Ser Val Gly
 1               5                  10                  15

Asp Arg Val Thr Leu Thr Cys Gln Ala Ser Gln Ser Val Tyr Gly Asn
            20                  25                  30

Asn Asp Leu Ala Trp Tyr Gln Gln Lys Pro Gly Gln Ala Pro Lys Leu
        35                  40                  45

Leu Ile Tyr Leu Ala Ser Thr Leu Ala Thr Gly Val Pro Ser Arg Phe
    50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Leu Gly Gly Gly Asp Asp
                85                  90                  95

Glu Ala Asp Asn Val Phe Gly Gly Gly Thr Lys Val Glu Ile Lys
            100                 105                 110

<210> SEQ ID NO 8
<211> LENGTH: 115
<212> TYPE: PRT
<213> ORGANISM: Artificial Sequence
<220> FEATURE:
<223> OTHER INFORMATION: humanized HCVR

<400> SEQUENCE: 8

Arg Gln Leu Val Glu Ser Gly Gly Gly Leu Val Gln Pro Gly Gly Ser
 1               5                  10                  15

Leu Arg Leu Ser Cys Thr Ala Ser Gly Phe Ser Leu Ser Ser His Gly
            20                  25                  30

Ile Ser Trp Val Arg Gln Ala Pro Gly Lys Gly Leu Glu Tyr Ile Gly
            35                  40                  45

Thr Ile Gly Thr Gly Val Ile Thr Tyr Phe Ala Ser Trp Ala Lys Gly
        50                  55                  60

Arg Phe Thr Gly Ser Lys Thr Ser Ser Thr Ala Tyr Met Glu Leu Ser
 65                  70                  75                  80

Ser Leu Arg Ser Glu Asp Thr Ala Val Tyr Phe Cys Ala Arg Gly Ser
                85                  90                  95
```

Ala Trp Asn Asp Pro Phe Asp Pro Trp Gly Gln Gly Thr Leu Val Thr
            100                 105                 110

Val Ser Ser
        115

<210> SEQ ID NO 9
<211> LENGTH: 111
<212> TYPE: PRT
<213> ORGANISM: Artificial Sequence
<220> FEATURE:
<223> OTHER INFORMATION: humanized LCVR

<400> SEQUENCE: 9

Asp Ile Val Met Thr Gln Ser Pro Ser Ser Leu Ser Ala Ser Val Gly
1               5                   10                  15

Asp Arg Val Thr Ile Thr Cys Gln Ala Ser Gln Ser Val Tyr Gly Asn
            20                  25                  30

Asn Asp Leu Ala Trp Tyr Gln Gln Lys Pro Gly Gln Ala Pro Lys Leu
        35                  40                  45

Leu Ile Tyr Leu Ala Ser Thr Leu Ala Thr Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Asp Asp Asp
                85                  90                  95

Glu Ala Asp Asn Thr Phe Gly Gln Gly Thr Lys Val Glu Ile Lys
            100                 105                 110

<210> SEQ ID NO 10
<211> LENGTH: 115
<212> TYPE: PRT
<213> ORGANISM: Artificial Sequence
<220> FEATURE:
<223> OTHER INFORMATION: humanized HCVR

<400> SEQUENCE: 10

Arg Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser His Gly
            20                  25                  30

Ile Ser Trp Val Arg Gln Ala Pro Gly Lys Gly Leu Glu Trp Val Gly
        35                  40                  45

Thr Ile Gly Thr Gly Val Ile Thr Tyr Tyr Ala Ser Trp Ala Lys Gly
    50                  55                  60

Arg Phe Thr Gly Ser Lys Thr Ser Ser Thr Ala Tyr Leu Gln Met Thr
65                  70                  75                  80

Ser Leu Arg Ala Glu Asp Thr Ala Val Tyr Tyr Cys Ala Arg Gly Ser
                85                  90                  95

Ala Trp Asn Asp Pro Phe Asp Tyr Trp Gly Gln Gly Thr Leu Val Thr
            100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: humanized HCVR

<400> SEQUENCE: 11

Arg Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser His Gly
            20                  25                  30

Ile Ser Trp Val Arg Gln Ala Pro Gly Lys Gly Leu Glu Trp Val Gly
        35                  40                  45

Thr Ile Gly Thr Gly Val Ile Thr Tyr Tyr Ala Ser Trp Ala Lys Gly
50                  55                  60

Arg Phe Thr Gly Ser Lys Thr Ser Ser Thr Ala Tyr Leu Gln Met Thr
65                  70                  75                  80

Ser Leu Arg Ser Glu Asp Thr Ala Val Tyr Tyr Cys Ala Arg Gly Ser
                85                  90                  95

Ala Trp Asn Asp Pro Phe Asp Tyr Trp Gly Gln Gly Thr Leu Val Thr
            100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: humanized HCVR

<400> SEQUENCE: 12

Arg Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser His Gly
            20                  25                  30

Ile Ser Trp Val Arg Gln Ala Pro Gly Lys Gly Leu Glu Trp Val Gly
        35                  40                  45

Thr Ile Gly Thr Gly Gly Ile Thr Tyr Tyr Ala Ser Trp Ala Lys Gly
50                  55                  60

Arg Phe Thr Gly Ser Lys Thr Ser Ser Thr Ala Tyr Met Glu Leu Ser
65                  70                  75                  80

Ser Leu Arg Ala Glu Asp Thr Ala Val Tyr Tyr Cys Ala Arg Gly Ser
                85                  90                  95

Ala Trp Asn Asp Pro Phe Asp Ile Trp Gly Gln Gly Thr Leu Val Thr
            100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: humanized HCVR

<400> SEQUENCE: 13

Arg Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser His Gly
            20                  25                  30

Ile Ser Trp Val Arg Gln Ala Pro Gly Lys Gly Leu Glu Trp Val Gly
        35                  40                  45

```
Thr Ile Gly Thr Gly Val Ile Thr Tyr Tyr Ala Ser Trp Ala Lys Gly
            50                  55                  60

Arg Phe Thr Gly Ser Lys Thr Ser Ser Thr Ala Tyr Leu Gln Met Thr
 65                  70                  75                  80

Ser Leu Arg Ala Glu Asp Thr Ala Val Tyr Tyr Cys Ala Arg Gly Ser
                 85                  90                  95

Ala Trp Asn Asp Pro Phe Asp Tyr Trp Gly Gln Gly Thr Leu Val Thr
             100                 105                 110

Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: humanized HCVR

<400> SEQUENCE: 14

Gln Ser Val Glu Glu Ser Gly Gly Arg Leu Gly Gln Pro Gly Thr Pro
 1               5                   10                  15

Leu Thr Leu Ser Cys Thr Val Ser Gly Phe Ser Leu Ser Ser Tyr Val
             20                  25                  30

Met Gly Trp Phe Arg Gln Ala Pro Gly Lys Gly Leu Glu Tyr Ile Gly
             35                  40                  45

Ile Ile Ser Ser Ser Gly Ser Pro Tyr Tyr Ala Ser Trp Val Asn Gly
            50                  55                  60

Arg Phe Thr Ile Ser Lys Thr Ser Thr Thr Met Asp Leu Lys Met Asn
 65                  70                  75                  80

Ser Leu Arg Ser Glu Asp Thr Ala Thr Tyr Phe Cys Ala Arg Val Gly
                 85                  90                  95

Pro Leu Gly Val Asp Tyr Phe Asn Ile Trp Gly Pro Gly Thr Leu Val
             100                 105                 110

Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: humanized HCVR

<400> SEQUENCE: 15

Val Gln Leu Val Glu Ser Gly Gly Arg Leu Val Gln Pro Gly Thr Pro
 1               5                   10                  15

Leu Thr Leu Ser Cys Thr Val Ser Gly Phe Ser Leu Ser Ser Tyr Val
             20                  25                  30

Met Gly Trp Phe Arg Gln Ala Pro Gly Lys Gly Leu Glu Tyr Ile Gly
             35                  40                  45

Ile Ile Ser Ser Ser Gly Ser Pro Tyr Tyr Ala Ser Trp Val Asn Gly
            50                  55                  60

Arg Phe Thr Ile Ser Lys Thr Ser Thr Thr Met Asp Leu Lys Met Asn
 65                  70                  75                  80

Ser Pro Thr Thr Glu Asp Thr Ala Thr Tyr Phe Cys Ala Arg Val Gly
                 85                  90                  95

Pro Leu Gly Val Asp Tyr Phe Asn Ile Trp Gly Pro Gly Thr Leu Val
             100                 105                 110
```

Thr Val Ser Ser
        115

<210> SEQ ID NO 16
<211> LENGTH: 451
<212> TYPE: PRT
<213> ORGANISM: Artificial Sequence
<220> FEATURE:
<223> OTHER INFORMATION: heavy chain 12C4

<400> SEQUENCE: 16

Glu Val Lys Leu Glu Glu Ser Gly Gly Gly Leu Met Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ile Arg Asp Tyr Asp Tyr Asp Ala Tyr Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

```
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 17
<211> LENGTH: 218
<212> TYPE: PRT
<213> ORGANISM: Artificial Sequence
<220> FEATURE:
<223> OTHER INFORMATION: light chain 12C4

<400> SEQUENCE: 17

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Asn Tyr Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 18
<211> LENGTH: 459
<212> TYPE: PRT
<213> ORGANISM: Artificial Sequence
```

<220> FEATURE:
<223> OTHER INFORMATION: heavy chain 29AM4-5 LALA mutant

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Tyr
            20                  25                  30

Phe Ile His Trp Val Arg Gln Ala Pro Gly Lys Gly Leu Glu Trp Val
        35                  40                  45

Ala Ser Val Tyr Ser Ser Phe Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Thr Phe Pro Gly Leu Phe Asp Gly Phe Phe Gly Ala Tyr
            100                 105                 110

Leu Gly Ser Leu Asp Tyr Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400
```

```
Asn Asn Tyr Lys Thr Thr Pro Pro Val Leu Asp Ser Asp Gly Ser Phe
            405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
    450                 455

<210> SEQ ID NO 19
<211> LENGTH: 217
<212> TYPE: PRT
<213> ORGANISM: Artificial Sequence
<220> FEATURE:
<223> OTHER INFORMATION: light chain 29AM4-5 LALA mutant

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Asn Trp Val Gly
                85                  90                  95

Ala Leu Val Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 20
<211> LENGTH: 451
<212> TYPE: PRT
<213> ORGANISM: Artificial Sequence
<220> FEATURE:
<223> OTHER INFORMATION: heavy chain 12C4 LALA mutant

<400> SEQUENCE: 20

Glu Val Lys Leu Glu Glu Ser Gly Gly Gly Leu Met Gln Pro Gly Gly
1               5                   10                  15

Ser Met Lys Leu Ser Cys Val Ala Ser Gly Phe Thr Phe Ser Asn Tyr
```

```
              20                  25                  30
Trp Met Asn Trp Val Arg Gln Ser Pro Glu Lys Gly Leu Glu Trp Val
             35                  40                  45

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Ile Arg Asp Tyr Asp Tyr Asp Ala Tyr Phe Asp Tyr Trp Gly
                100                 105                 110

Gln Gly Thr Thr Leu Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
                210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445
```

Pro Gly Lys
    450

<210> SEQ ID NO 21
<211> LENGTH: 218
<212> TYPE: PRT
<213> ORGANISM: Artificial Sequence
<220> FEATURE:
<223> OTHER INFORMATION: light chain 12C4 LALA mutant

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Asn Tyr Met Tyr Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 22
<211> LENGTH: 443
<212> TYPE: PRT
<213> ORGANISM: Artificial Sequence
<220> FEATURE:
<223> OTHER INFORMATION: heavy chain KWAR23 LALA mutant

<400> SEQUENCE: 22

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
50                  55                  60

Gln Asp Lys Ala Thr Ile Thr Ala Asp Thr Ser Ser Asn Thr Ala Tyr

```
                65                  70                  75                  80
Leu His Leu Ser Ser Leu Thr Ser Glu Asp Thr Ala Val Tyr Tyr Cys
                        85                  90                  95

Ala Arg Trp Gly Ala Tyr Trp Gly Gln Gly Thr Leu Val Thr Val Ser
                100                 105                 110

Ser Ala Ser Thr Lys Gly Pro Ser Val Phe Pro Leu Ala Pro Ser Ser
                115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                    165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
                195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                    245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
                275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                    325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                    405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
    435                 440

<210> SEQ ID NO 23
<211> LENGTH: 215
<212> TYPE: PRT
<213> ORGANISM: Artificial Sequence
<220> FEATURE:
<223> OTHER INFORMATION: light chain KWAR23 LALA mutant
```

```
<400> SEQUENCE: 23

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Ser
            20                  25                  30

Tyr Leu Tyr Trp Tyr Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 24
<211> LENGTH: 330
<212> TYPE: PRT
<213> ORGANISM: Homo sapiens

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 330
<212> TYPE: PRT
<213> ORGANISM: Artificial Sequence
<220> FEATURE:
<223> OTHER INFORMATION: human IgG1 antibody heavy chain constant region
      LALA mutant

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

-continued

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 107
<212> TYPE: PRT
<213> ORGANISM: Homo sapiens

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 21
<212> TYPE: PRT
<213> ORGANISM: Artificial Sequence
<220> FEATURE:
<223> OTHER INFORMATION: HAVT20 leader sequence

<400> SEQUENCE: 27

Met Ala Cys Pro Gly Phe Leu Trp Ala Leu Val Ile Ser Thr Cys Leu
1               5                   10                  15

Glu Phe Ser Met Ala
            20

<210> SEQ ID NO 28
<211> LENGTH: 19

```
<212> TYPE: PRT
<213> ORGANISM: Artificial Sequence
<220> FEATURE:
<223> OTHER INFORMATION: heavy chain leader sequence

<400> SEQUENCE: 28

Met Gly Trp Thr Leu Val Phe Leu Phe Leu Leu Ser Val Thr Ala Gly
1               5                   10                  15

Val His Ser

<210> SEQ ID NO 29
<211> LENGTH: 20
<212> TYPE: PRT
<213> ORGANISM: Artificial Sequence
<220> FEATURE:
<223> OTHER INFORMATION: light chain leader sequence

<400> SEQUENCE: 29

Met Val Ser Ser Ala Gln Phe Leu Gly Leu Leu Leu Leu Cys Phe Gln
1               5                   10                  15

Gly Thr Arg Cys
            20

<210> SEQ ID NO 30
<211> LENGTH: 5
<212> TYPE: PRT
<213> ORGANISM: Artificial Sequence
<220> FEATURE:
<223> OTHER INFORMATION: heavy chain CDR1

<400> SEQUENCE: 30

Ser Tyr Val Met Gly
1               5

<210> SEQ ID NO 31
<211> LENGTH: 16
<212> TYPE: PRT
<213> ORGANISM: Artificial Sequence
<220> FEATURE:
<223> OTHER INFORMATION: heavy chain CDR2

<400> SEQUENCE: 31

Ile Ile Ser Ser Ser Gly Ser Pro Tyr Tyr Ala Ser Trp Val Asn Gly
1               5                   10                  15

<210> SEQ ID NO 32
<211> LENGTH: 11
<212> TYPE: PRT
<213> ORGANISM: Artificial Sequence
<220> FEATURE:
<223> OTHER INFORMATION: heavy chain CDR3

<400> SEQUENCE: 32

Val Gly Pro Leu Gly Val Asp Tyr Phe Asn Ile
1               5                   10

<210> SEQ ID NO 33
<211> LENGTH: 11
<212> TYPE: PRT
<213> ORGANISM: Artificial Sequence
<220> FEATURE:
<223> OTHER INFORMATION: light chain CDR1

<400> SEQUENCE: 33

Arg Ala Ser Gln Ser Ile Asn Ser Tyr Leu Ala
1               5                   10
```

```
<210> SEQ ID NO 34
<211> LENGTH: 7
<212> TYPE: PRT
<213> ORGANISM: Artificial Sequence
<220> FEATURE:
<223> OTHER INFORMATION: light chain CDR2

<400> SEQUENCE: 34

Ser Ala Ser Phe Leu Tyr Ser
1               5

<210> SEQ ID NO 35
<211> LENGTH: 11
<212> TYPE: PRT
<213> ORGANISM: Artificial Sequence
<220> FEATURE:
<223> OTHER INFORMATION: light chain CDR3

<400> SEQUENCE: 35

Gln Ser Trp His Tyr Ile Ser Arg Ser Tyr Thr
1               5                   10

<210> SEQ ID NO 36
<211> LENGTH: 5
<212> TYPE: PRT
<213> ORGANISM: Artificial Sequence
<220> FEATURE:
<223> OTHER INFORMATION: heavy chain CDR1

<400> SEQUENCE: 36

Ser His Gly Ile Ser
1               5

<210> SEQ ID NO 37
<211> LENGTH: 16
<212> TYPE: PRT
<213> ORGANISM: Artificial Sequence
<220> FEATURE:
<223> OTHER INFORMATION: heavy chain CDR2

<400> SEQUENCE: 37

Thr Ile Gly Thr Gly Val Ile Thr Tyr Tyr Ala Ser Trp Ala Lys Gly
1               5                   10                  15

<210> SEQ ID NO 38
<211> LENGTH: 10
<212> TYPE: PRT
<213> ORGANISM: Artificial Sequence
<220> FEATURE:
<223> OTHER INFORMATION: heavy chain CDR3

<400> SEQUENCE: 38

Gly Ser Ala Trp Asn Asp Pro Phe Asp Tyr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: light chain CDR1

<400> SEQUENCE: 39

Gln Ala Ser Gln Ser Val Tyr Gly Asn Asn Asp Leu Ala
1               5                   10
```

<210> SEQ ID NO 40
<211> LENGTH: 7
<212> TYPE: PRT
<213> ORGANISM: Artificial Sequence
<220> FEATURE:
<223> OTHER INFORMATION: light chain CDR2

<400> SEQUENCE: 40

Leu Ala Ser Thr Leu Ala Thr
1               5

<210> SEQ ID NO 41
<211> LENGTH: 11
<212> TYPE: PRT
<213> ORGANISM: Artificial Sequence
<220> FEATURE:
<223> OTHER INFORMATION: light chain CDR3

<400> SEQUENCE: 41

Leu Gly Gly Gly Asp Asp Glu Ala Asp Asn Thr
1               5                   10

<210> SEQ ID NO 42
<211> LENGTH: 16
<212> TYPE: PRT
<213> ORGANISM: Artificial Sequence
<220> FEATURE:
<223> OTHER INFORMATION: heavy chain CDR2

<400> SEQUENCE: 42

Thr Ile Gly Thr Gly Gly Ile Thr Tyr Tyr Ala Ser Trp Ala Lys Gly
1               5                   10                  15

<210> SEQ ID NO 43
<211> LENGTH: 10
<212> TYPE: PRT
<213> ORGANISM: Artificial Sequence
<220> FEATURE:
<223> OTHER INFORMATION: heavy chain CDR3

<400> SEQUENCE: 43

Gly Ser Ala Trp Asn Asp Pro Phe Asp Ile
1               5                   10

<210> SEQ ID NO 44
<211> LENGTH: 16
<212> TYPE: PRT
<213> ORGANISM: Artificial Sequence
<220> FEATURE:
<223> OTHER INFORMATION: heavy chain CDR2

<400> SEQUENCE: 44

Thr Ile Gly Thr Gly Val Ile Thr Tyr Phe Ala Ser Trp Ala Lys Gly
1               5                   10                  15

<210> SEQ ID NO 45
<211> LENGTH: 10
<212> TYPE: PRT
<213> ORGANISM: Artificial Sequence
<220> FEATURE:
<223> OTHER INFORMATION: heavy chain CDR3

<400> SEQUENCE: 45

Gly Ser Ala Trp Asn Asp Pro Phe Asp Pro
1               5                   10

```
<210> SEQ ID NO 46
<211> LENGTH: 11
<212> TYPE: PRT
<213> ORGANISM: Artificial Sequence
<220> FEATURE:
<223> OTHER INFORMATION: light chain CDR3

<400> SEQUENCE: 46

Leu Gly Gly Gly Asp Glu Ala Asp Asn Val
1               5                   10

<210> SEQ ID NO 47
<211> LENGTH: 443
<212> TYPE: PRT
<213> ORGANISM: Mus musculus

<400> SEQUENCE: 47

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ser Ala Lys Thr Thr Ala Pro Ser Val Tyr Pro Leu Ala Pro Val Cys
        115                 120                 125

Gly Asp Thr Thr Gly Ser Ser Val Thr Leu Gly Cys Leu Val Lys Gly
    130                 135                 140

Tyr Phe Pro Glu Pro Val Thr Leu Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Thr Ser Ser Thr Trp Pro Ser Gln Ser
            180                 185                 190

Ile Thr Cys Asn Val Ala His Pro Ala Ser Ser Thr Lys Val Asp Lys
        195                 200                 205

Lys Ile Glu Pro Arg Gly Pro Thr Ile Lys Pro Cys Pro Pro Cys Lys
    210                 215                 220

Cys Pro Ala Pro Asn Leu Leu Gly Gly Pro Ser Val Phe Ile Phe Pro
225                 230                 235                 240

Pro Lys Ile Lys Asp Val Leu Met Ile Ser Leu Ser Pro Ile Val Thr
                245                 250                 255

Cys Val Val Val Asp Val Ser Glu Asp Asp Pro Asp Val Gln Ile Ser
            260                 265                 270

Trp Phe Val Asn Asn Val Glu Val His Thr Ala Gln Thr Gln Thr His
        275                 280                 285

Arg Glu Asp Tyr Asn Ser Thr Leu Arg Val Val Ser Ala Leu Pro Ile
    290                 295                 300

Gln His Gln Asp Trp Met Ser Gly Lys Glu Phe Lys Cys Lys Val Asn
305                 310                 315                 320
```

```
Asn Lys Asp Leu Pro Ala Pro Ile Glu Arg Thr Ile Ser Lys Pro Lys
            325                 330                 335

Gly Ser Val Arg Ala Pro Gln Val Tyr Val Leu Pro Pro Glu Glu
            340                 345                 350

Glu Met Thr Lys Lys Gln Val Thr Leu Thr Cys Met Val Thr Asp Phe
            355                 360                 365

Met Pro Glu Asp Ile Tyr Val Glu Trp Thr Asn Asn Gly Lys Thr Glu
    370                 375                 380

Leu Asn Tyr Lys Asn Thr Glu Pro Val Leu Asp Ser Asp Gly Ser Tyr
385                 390                 395                 400

Phe Met Tyr Ser Lys Leu Arg Val Glu Lys Lys Asn Trp Val Glu Arg
                405                 410                 415

Asn Ser Tyr Ser Cys Ser Val Val His Glu Gly Leu His Asn His His
                420                 425                 430

Thr Thr Lys Ser Phe Ser Arg Thr Pro Gly Lys
                435                 440

<210> SEQ ID NO 48
<211> LENGTH: 215
<212> TYPE: PRT
<213> ORGANISM: Mus musculus

<400> SEQUENCE: 48

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 49
<211> LENGTH: 447
<212> TYPE: PRT
```

<213> ORGANISM: Artificial Sequence
<220> FEATURE:
<223> OTHER INFORMATION: heavy chain humanized HEFLB

<400> SEQUENCE: 49

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Leu Ala Tyr Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 50
<211> LENGTH: 219
<212> TYPE: PRT
<213> ORGANISM: Artificial Sequence
<220> FEATURE:
<223> OTHER INFORMATION: light chain humanized HEFLB

<400> SEQUENCE: 50

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 51
<211> LENGTH: 618
<212> TYPE: PRT
<213> ORGANISM: Artificial Sequence
<220> FEATURE:
<223> OTHER INFORMATION: human SIRPalpha1 extracellular domain 1-370,
      Avi-FXa-Fc tag

<400> SEQUENCE: 51

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30
```

-continued

```
Glu Leu Gln Val Ile Gln Pro Asp Lys Ser Val Ser Val Ala Ala Gly
             35                  40                  45

Glu Ser Ala Ile Leu His Cys Thr Val Thr Ser Leu Ile Pro Val Gly
 50                  55                  60

Pro Ile Gln Trp Phe Arg Gly Ala Gly Pro Ala Arg Glu Leu Ile Tyr
 65                  70                  75                  80

Asn Gln Lys Glu Gly His Phe Pro Arg Val Thr Thr Val Ser Glu Ser
                 85                  90                  95

Thr Lys Arg Glu Asn Met Asp Phe Ser Ile Ser Ile Ser Asn Ile Thr
                100                 105                 110

Pro Ala Asp Ala Gly Thr Tyr Tyr Cys Val Lys Phe Arg Lys Gly Ser
                115                 120                 125

Pro Asp Thr Glu Phe Lys Ser Gly Ala Gly Thr Glu Leu Ser Val Arg
                130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
                180                 185                 190

Phe Gln Thr Asn Val Asp Pro Val Gly Glu Ser Val Ser Tyr Ser Ile
                195                 200                 205

His Ser Thr Ala Lys Val Val Leu Thr Arg Glu Asp Val His Ser Gln
                210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
                260                 265                 270

Gln Val Arg Lys Phe Tyr Pro Gln Arg Leu Gln Leu Thr Trp Leu Glu
                275                 280                 285

Asn Gly Asn Val Ser Arg Thr Glu Thr Ala Ser Thr Val Thr Glu Asn
                290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
                340                 345                 350

Lys Glu Gln Gly Ser Asn Thr Ala Ala Glu Asn Thr Gly Ser Asn Glu
                355                 360                 365

Arg Asn Gly Gly Gly Leu Asn Asp Ile Phe Glu Ala Gln Lys Ile Glu
                370                 375                 380

Trp His Glu Ile Glu Gly Arg Asp Lys Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
                420                 425                 430

Val Val Val Asp Val Ser His Glu Asp Pro Glu Val Lys Phe Asn Trp
                435                 440                 445
```

-continued

```
Tyr Val Asp Gly Val Glu Val His Asn Ala Lys Thr Lys Pro Arg Glu
    450                 455                 460

Glu Gln Tyr Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Ala Leu Pro Ala Pro Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Thr Cys Leu Val Lys Gly Phe Tyr
530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys
    610                 615

<210> SEQ ID NO 52
<211> LENGTH: 619
<212> TYPE: PRT
<213> ORGANISM: Artificial Sequence
<220> FEATURE:
<223> OTHER INFORMATION: human SIRPalphaBIT, extracellular domain 1-370,
      Avi-FXa-Fc tag

<400> SEQUENCE: 52

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190
```

```
Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
            245                 250                 255

Glu Val Thr Gln Gln Pro Val Arg Ala Glu Asn Gln Val Asn Val Thr
        260                 265                 270

Cys Gln Val Arg Lys Phe Tyr Pro Gln Arg Leu Gln Leu Thr Trp Leu
    275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
            325                 330                 335

Gly Gln Pro Ala Val Ser Lys Ser His Asp Leu Lys Val Ser Ala His
        340                 345                 350

Pro Lys Glu Gln Gly Ser Asn Thr Ala Ala Glu Asn Thr Gly Ser Asn
    355                 360                 365

Glu Arg Asn Gly Gly Leu Asn Asp Ile Phe Glu Ala Gln Lys Ile
370                 375                 380

Glu Trp His Glu Ile Glu Gly Arg Asp Lys Thr His Thr Cys Pro Pro
385                 390                 395                 400

Cys Pro Ala Pro Glu Leu Leu Gly Gly Pro Ser Val Phe Leu Phe Pro
            405                 410                 415

Pro Lys Pro Lys Asp Thr Leu Met Ile Ser Arg Thr Pro Glu Val Thr
        420                 425                 430

Cys Val Val Val Asp Val Ser His Glu Asp Pro Glu Val Lys Phe Asn
    435                 440                 445

Trp Tyr Val Asp Gly Val Glu Val His Asn Ala Lys Thr Lys Pro Arg
    450                 455                 460

Glu Glu Gln Tyr Asn Ser Thr Tyr Arg Val Val Ser Val Leu Thr Val
465                 470                 475                 480

Leu His Gln Asp Trp Leu Asn Gly Lys Glu Tyr Lys Cys Lys Val Ser
            485                 490                 495

Asn Lys Ala Leu Pro Ala Pro Ile Glu Lys Thr Ile Ser Lys Ala Lys
        500                 505                 510

Gly Gln Pro Arg Glu Pro Gln Val Tyr Thr Leu Pro Pro Ser Arg Glu
    515                 520                 525

Glu Met Thr Lys Asn Gln Val Ser Leu Thr Cys Leu Val Lys Gly Phe
530                 535                 540

Tyr Pro Ser Asp Ile Ala Val Glu Trp Glu Ser Asn Gly Gln Pro Glu
545                 550                 555                 560

Asn Asn Tyr Lys Thr Thr Pro Pro Val Leu Asp Ser Asp Gly Ser Phe
            565                 570                 575

Phe Leu Tyr Ser Lys Leu Thr Val Asp Lys Ser Arg Trp Gln Gln Gly
        580                 585                 590

Asn Val Phe Ser Cys Ser Val Met His Glu Ala Leu His Asn His Tyr
    595                 600                 605
```

```
Thr Gln Lys Ser Leu Ser Leu Ser Pro Gly Lys
    610                 615
```

<210> SEQ ID NO 53
<211> LENGTH: 619
<212> TYPE: PRT
<213> ORGANISM: Artificial Sequence
<220> FEATURE:
<223> OTHER INFORMATION: human SIRPbeta1v1, extracellular domain, Avi-FXa-Fc tag

<400> SEQUENCE: 53

```
Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Arg Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
        195                 200                 205

His Ser Thr Ala Arg Val Val Leu Thr Arg Gly Asp Val His Ser Gln
    210                 215                 220

Val Ile Cys Glu Ile Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
                245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
        275                 280                 285

Asn Gly Asn Val Ser Arg Thr Glu Thr Ala Ser Thr Leu Ile Glu Asn
    290                 295                 300

Lys Asp Gly Thr Tyr Asn Trp Met Ser Trp Leu Leu Val Asn Thr Cys
305                 310                 315                 320

Ala His Arg Asp Asp Val Val Leu Thr Cys Gln Val Glu His Asp Gly
                325                 330                 335

Gln Gln Ala Val Ser Lys Ser Tyr Ala Leu Glu Ile Ser Ala His Gln
            340                 345                 350
```

```
Lys Glu His Gly Ser Asp Ile Thr His Glu Ala Ala Leu Ala Pro Thr
            355                 360                 365

Ala Pro Leu Gly Gly Gly Leu Asn Asp Ile Phe Glu Ala Gln Lys Ile
        370                 375                 380

Glu Trp His Glu Ile Glu Gly Arg Asp Lys Thr His Thr Cys Pro Pro
385                 390                 395                 400

Cys Pro Ala Pro Glu Leu Leu Gly Gly Pro Ser Val Phe Leu Phe Pro
                405                 410                 415

Pro Lys Pro Lys Asp Thr Leu Met Ile Ser Arg Thr Pro Glu Val Thr
            420                 425                 430

Cys Val Val Val Asp Val Ser His Glu Asp Pro Glu Val Lys Phe Asn
        435                 440                 445

Trp Tyr Val Asp Gly Val Glu Val His Asn Ala Lys Thr Lys Pro Arg
    450                 455                 460

Glu Glu Gln Tyr Asn Ser Thr Tyr Arg Val Val Ser Val Leu Thr Val
465                 470                 475                 480

Leu His Gln Asp Trp Leu Asn Gly Lys Glu Tyr Lys Cys Lys Val Ser
                485                 490                 495

Asn Lys Ala Leu Pro Ala Pro Ile Glu Lys Thr Ile Ser Lys Ala Lys
            500                 505                 510

Gly Gln Pro Arg Glu Pro Gln Val Tyr Thr Leu Pro Pro Ser Arg Glu
        515                 520                 525

Glu Met Thr Lys Asn Gln Val Ser Leu Thr Cys Leu Val Lys Gly Phe
    530                 535                 540

Tyr Pro Ser Asp Ile Ala Val Glu Trp Glu Ser Asn Gly Gln Pro Glu
545                 550                 555                 560

Asn Asn Tyr Lys Thr Thr Pro Pro Val Leu Asp Ser Asp Gly Ser Phe
                565                 570                 575

Phe Leu Tyr Ser Lys Leu Thr Val Asp Lys Ser Arg Trp Gln Gln Gly
            580                 585                 590

Asn Val Phe Ser Cys Ser Val Met His Glu Ala Leu His Asn His Tyr
        595                 600                 605

Thr Gln Lys Ser Leu Ser Leu Ser Pro Gly Lys
    610                 615

<210> SEQ ID NO 54
<211> LENGTH: 619
<212> TYPE: PRT
<213> ORGANISM: Artificial Sequence
<220> FEATURE:
<223> OTHER INFORMATION: human SIRPbeta1v2, extracellular domain,
      Avi-FXa-Fc tag

<400> SEQUENCE: 54

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Glu Glu
            20                  25                  30

Leu Gln Val Ile Gln Pro Asp Lys Ser Ile Ser Val Ala Ala Gly Glu
        35                  40                  45

Ser Ala Thr Leu His Cys Thr Val Thr Ser Leu Ile Pro Val Gly Pro
    50                  55                  60

Ile Gln Trp Phe Arg Gly Ala Gly Pro Gly Arg Glu Leu Ile Tyr Asn
65                  70                  75                  80

Gln Lys Glu Gly His Phe Pro Arg Val Thr Thr Val Ser Asp Leu Thr
```

-continued

```
                85                  90                  95
Lys Arg Asn Asn Met Asp Phe Ser Ile Arg Ile Ser Asn Ile Thr Pro
                100                 105                 110
Ala Asp Ala Gly Thr Tyr Tyr Cys Val Lys Phe Arg Lys Gly Ser Pro
                115                 120                 125
Asp His Val Glu Phe Lys Ser Gly Ala Gly Thr Glu Leu Ser Val Arg
            130                 135                 140
Ala Lys Pro Ser Ala Pro Val Val Ser Gly Pro Ala Ala Arg Ala Thr
145                 150                 155                 160
Pro Gln His Thr Val Ser Phe Thr Cys Glu Ser His Gly Phe Ser Pro
                    165                 170                 175
Arg Asp Ile Thr Leu Lys Trp Phe Lys Asn Gly Asn Glu Leu Ser Asp
                180                 185                 190
Phe Gln Thr Asn Val Asp Pro Ala Gly Asp Ser Val Ser Tyr Ser Ile
            195                 200                 205
His Ser Thr Ala Lys Val Val Leu Thr Arg Glu Asp Val His Ser Gln
        210                 215                 220
Val Ile Cys Glu Val Ala His Val Thr Leu Gln Gly Asp Pro Leu Arg
225                 230                 235                 240
Gly Thr Ala Asn Leu Ser Glu Thr Ile Arg Val Pro Pro Thr Leu Glu
                    245                 250                 255
Val Thr Gln Gln Pro Val Arg Ala Glu Asn Gln Val Asn Val Thr Cys
                260                 265                 270
Gln Val Arg Lys Phe Tyr Pro Gln Arg Leu Gln Leu Thr Trp Leu Glu
            275                 280                 285
Asn Gly Asn Val Ser Arg Thr Glu Thr Ala Ser Thr Leu Thr Glu Asn
        290                 295                 300
Lys Asp Gly Thr Tyr Asn Trp Met Ser Trp Leu Leu Val Asn Val Ser
305                 310                 315                 320
Ala His Arg Asp Asp Val Lys Leu Thr Cys Gln Val Glu His Asp Gly
                    325                 330                 335
Gln Pro Ala Val Ser Lys Ser His Asp Leu Lys Val Ser Ala His Pro
                340                 345                 350
Lys Glu Gln Gly Ser Asn Thr Ala Pro Gly Pro Ala Leu Ala Ser Ala
            355                 360                 365
Ala Pro Leu Gly Gly Leu Asn Asp Ile Phe Glu Ala Gln Lys Ile
        370                 375                 380
Glu Trp His Glu Ile Glu Gly Arg Asp Lys Thr His Thr Cys Pro Pro
385                 390                 395                 400
Cys Pro Ala Pro Glu Leu Leu Gly Gly Pro Ser Val Phe Leu Phe Pro
                    405                 410                 415
Pro Lys Pro Lys Asp Thr Leu Met Ile Ser Arg Thr Pro Glu Val Thr
                420                 425                 430
Cys Val Val Val Asp Val Ser His Glu Asp Pro Glu Val Lys Phe Asn
            435                 440                 445
Trp Tyr Val Asp Gly Val Glu Val His Asn Ala Lys Thr Lys Pro Arg
        450                 455                 460
Glu Glu Gln Tyr Asn Ser Thr Tyr Arg Val Val Ser Val Leu Thr Val
465                 470                 475                 480
Leu His Gln Asp Trp Leu Asn Gly Lys Glu Tyr Lys Cys Lys Val Ser
                    485                 490                 495
Asn Lys Ala Leu Pro Ala Pro Ile Glu Lys Thr Ile Ser Lys Ala Lys
                500                 505                 510
```

```
Gly Gln Pro Arg Glu Pro Gln Val Tyr Thr Leu Pro Pro Ser Arg Glu
            515                 520                 525

Glu Met Thr Lys Asn Gln Val Ser Leu Thr Cys Leu Val Lys Gly Phe
    530                 535                 540

Tyr Pro Ser Asp Ile Ala Val Glu Trp Glu Ser Asn Gly Gln Pro Glu
545                 550                 555                 560

Asn Asn Tyr Lys Thr Thr Pro Pro Val Leu Asp Ser Asp Gly Ser Phe
                565                 570                 575

Phe Leu Tyr Ser Lys Leu Thr Val Asp Lys Ser Arg Trp Gln Gln Gly
            580                 585                 590

Asn Val Phe Ser Cys Ser Val Met His Glu Ala Leu His Asn His Tyr
        595                 600                 605

Thr Gln Lys Ser Leu Ser Leu Ser Pro Gly Lys
    610                 615

<210> SEQ ID NO 55
<211> LENGTH: 649
<212> TYPE: PRT
<213> ORGANISM: Artificial Sequence
<220> FEATURE:
<223> OTHER INFORMATION: human SIRPgamma, extracellular domain,
      Avi-FXa-Fc tag

<400> SEQUENCE: 55

Met Pro Val Pro Ala Ser Trp Pro His Pro Gly Pro Phe Leu Leu
1               5                   10                  15

Leu Thr Leu Leu Leu Gly Leu Thr Glu Val Ala Gly Glu Glu Glu Leu
            20                  25                  30

Gln Met Ile Gln Pro Glu Lys Leu Leu Leu Val Thr Val Gly Lys Thr
        35                  40                  45

Ala Thr Leu His Cys Thr Val Thr Ser Leu Leu Pro Val Gly Pro Val
    50                  55                  60

Leu Trp Phe Arg Gly Val Gly Pro Gly Arg Glu Leu Ile Tyr Asn Gln
65                  70                  75                  80

Lys Glu Gly His Phe Pro Arg Val Thr Thr Val Ser Asp Leu Thr Lys
                85                  90                  95

Arg Asn Asn Met Asp Phe Ser Ile Arg Ile Ser Ser Ile Thr Pro Ala
            100                 105                 110

Asp Val Gly Thr Tyr Tyr Cys Val Lys Phe Arg Lys Gly Ser Pro Glu
        115                 120                 125

Asn Val Glu Phe Lys Ser Gly Pro Gly Thr Glu Met Ala Leu Gly Ala
    130                 135                 140

Lys Pro Ser Ala Pro Val Val Leu Gly Pro Ala Ala Arg Thr Thr Pro
145                 150                 155                 160

Glu His Thr Val Ser Phe Thr Cys Glu Ser His Gly Phe Ser Pro Arg
                165                 170                 175

Asp Ile Thr Leu Lys Trp Phe Lys Asn Gly Asn Glu Leu Ser Asp Phe
            180                 185                 190

Gln Thr Asn Val Asp Pro Thr Gly Gln Ser Val Ala Tyr Ser Ile Arg
        195                 200                 205

Ser Thr Ala Arg Val Val Leu Asp Pro Trp Asp Val Arg Ser Gln Val
    210                 215                 220

Ile Cys Glu Val Ala His Val Thr Leu Gln Gly Asp Pro Leu Arg Gly
225                 230                 235                 240

Thr Ala Asn Leu Ser Glu Ala Ile Arg Val Pro Pro Thr Leu Glu Val
```

```
                    245                 250                 255
Thr Gln Gln Pro Met Arg Val Gly Asn Gln Val Asn Val Thr Cys Gln
            260                 265                 270

Val Arg Lys Phe Tyr Pro Gln Ser Leu Gln Leu Thr Trp Ser Glu Asn
        275                 280                 285

Gly Asn Val Cys Gln Arg Glu Thr Ala Ser Thr Leu Thr Glu Asn Lys
    290                 295                 300

Asp Gly Thr Tyr Asn Trp Thr Ser Trp Phe Leu Val Asn Ile Ser Asp
305                 310                 315                 320

Gln Arg Asp Asp Val Val Leu Thr Cys Gln Val Lys His Asp Gly Gln
                325                 330                 335

Leu Ala Val Ser Lys Arg Leu Ala Leu Glu Val Thr Val His Gln Lys
            340                 345                 350

Asp Gln Ser Ser Asp Ala Thr Pro Lys Gly Gln Asp Asn Ser Ala Asp
        355                 360                 365

Ile Gln His Ser Gly Gly Arg Ser Ser Leu Glu Gly Pro Arg Phe Glu
    370                 375                 380

Gly Lys Pro Ile Pro Asn Pro Leu Leu Gly Leu Asp Ser Thr Arg Thr
385                 390                 395                 400

Gly Gly Gly Gly Leu Asn Asp Ile Phe Glu Ala Gln Lys Ile Glu Trp
                405                 410                 415

His Glu Ile Glu Gly Arg Asp Lys Thr His Thr Cys Pro Pro Cys Pro
            420                 425                 430

Ala Pro Glu Leu Leu Gly Gly Pro Ser Val Phe Leu Phe Pro Pro Lys
        435                 440                 445

Pro Lys Asp Thr Leu Met Ile Ser Arg Thr Pro Glu Val Thr Cys Val
    450                 455                 460

Val Val Asp Val Ser His Glu Asp Pro Glu Val Lys Phe Asn Trp Tyr
465                 470                 475                 480

Val Asp Gly Val Glu Val His Asn Ala Lys Thr Lys Pro Arg Glu Glu
                485                 490                 495

Gln Tyr Asn Ser Thr Tyr Arg Val Val Ser Val Leu Thr Val Leu His
            500                 505                 510

Gln Asp Trp Leu Asn Gly Lys Glu Tyr Lys Cys Lys Val Ser Asn Lys
        515                 520                 525

Ala Leu Pro Ala Pro Ile Glu Lys Thr Ile Ser Lys Ala Lys Gly Gln
    530                 535                 540

Pro Arg Glu Pro Gln Val Tyr Thr Leu Pro Pro Ser Arg Glu Glu Met
545                 550                 555                 560

Thr Lys Asn Gln Val Ser Leu Thr Cys Leu Val Lys Gly Phe Tyr Pro
                565                 570                 575

Ser Asp Ile Ala Val Glu Trp Glu Ser Asn Gly Gln Pro Glu Asn Asn
            580                 585                 590

Tyr Lys Thr Thr Pro Pro Val Leu Asp Ser Asp Gly Ser Phe Phe Leu
        595                 600                 605

Tyr Ser Lys Leu Thr Val Asp Lys Ser Arg Trp Gln Gln Gly Asn Val
    610                 615                 620

Phe Ser Cys Ser Val Met His Glu Ala Leu His Asn His Tyr Thr Gln
625                 630                 635                 640

Lys Ser Leu Ser Leu Ser Pro Gly Lys
                645

<210> SEQ ID NO 56
```

<211> LENGTH: 618
<212> TYPE: PRT
<213> ORGANISM: Artificial Sequence
<220> FEATURE:
<223> OTHER INFORMATION: cynomolgus monkey SIRPalpha, extracellular
      domain, Avi-FXa-Fc tag

<400> SEQUENCE: 56

Met Glu Pro Ala Gly Pro Ala Pro Gly Arg Leu Gly Pro Leu Leu Cys
1               5                   10                  15

Leu Leu Leu Thr Ala Ser Cys Ala Trp Ser Gly Val Leu Gly Glu Glu
                20                  25                  30

Glu Leu Gln Val Ile Gln Pro Glu Lys Ser Val Ser Val Ala Ala Gly
            35                  40                  45

Asp Ser Ala Thr Leu Asn Cys Thr Val Ser Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Leu Lys Glu Gly His Phe Pro Arg Val Thr Ala Val Ser Asp Pro
                85                  90                  95

Thr Lys Arg Asn Asn Met Asp Phe Ser Ile Arg Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Val Glu Leu Lys Ser Gly Ala Gly Thr Glu Leu Ser Val Arg
130                 135                 140

Ala Lys Pro Ser Ala Pro Val Val Ser Gly Pro Ala Val Arg Ala Thr
145                 150                 155                 160

Ala Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Val Gln Thr Asn Val Asp Pro Ala Gly Lys Ser Val Ser Tyr Ser Ile
        195                 200                 205

Arg Ser Thr Ala Arg Val Leu Leu Thr Arg Arg Asp Val His Ser Gln
210                 215                 220

Val Ile Cys Glu Val Ala His Val Thr Leu Gln Gly Asp Pro Leu Arg
225                 230                 235                 240

Gly Thr Ala Asn Leu Ser Glu Ala Ile Arg Val Pro Pro Phe Leu Glu
                245                 250                 255

Val Thr Gln Gln Ser Met Arg Ala Asp Asn Gln Val Asn Val Thr Cys
            260                 265                 270

Gln Val Thr Lys Phe Tyr Pro Gln Arg Leu Gln Leu Thr Trp Leu Glu
        275                 280                 285

Asn Gly Asn Val Ser Arg Thr Glu Met Ala Ser Ala Leu Pro Glu Asn
290                 295                 300

Lys Asp Gly Thr Tyr Asn Trp Thr Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Asn Lys Ser Phe Ser Val Lys Val Ser Ala His Pro
            340                 345                 350

Lys Glu Gln Gly Ser Asn Thr Ala Ala Glu Asn Thr Gly Thr Asn Glu
        355                 360                 365

Arg Asn Gly Gly Gly Leu Asn Asp Ile Phe Glu Ala Gln Lys Ile Glu

```
                370                 375                 380
Trp His Glu Ile Glu Gly Arg Asp Lys Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
                420                 425                 430

Val Val Val Asp Val Ser His Glu Asp Pro Glu Val Lys Phe Asn Trp
                435                 440                 445

Tyr Val Asp Gly Val Glu Val His Asn Ala Lys Thr Lys Pro Arg Glu
            450                 455                 460

Glu Gln Tyr Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Ala Leu Pro Ala Pro Ile Glu Lys Thr Ile Ser Lys Ala Lys Gly
                500                 505                 510

Gln Pro Arg Glu Pro Gln Val Tyr Thr Leu Pro Pro Ser Arg Glu Glu
                515                 520                 525

Met Thr Lys Asn Gln Val Ser Leu Thr Cys Leu Val Lys Gly Phe Tyr
                530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
                595                 600                 605

Gln Lys Ser Leu Ser Leu Ser Pro Gly Lys
            610                 615

<210> SEQ ID NO 57
<211> LENGTH: 471
<212> TYPE: PRT
<213> ORGANISM: Artificial Sequence
<220> FEATURE:
<223> OTHER INFORMATION: heavy chain 1H9 including leader sequence

<400> SEQUENCE: 57

Met Ala Cys Pro Gly Phe Leu Trp Ala Leu Val Ile Ser Thr Cys Leu
1               5                   10                  15

Glu Phe Ser Met Ala Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Ser Tyr Trp Ile Thr Trp Val Lys Gln Ala Pro Gly Gln
        50                  55                  60

Gly Leu Glu Trp Ile Gly Asp Ile Tyr Pro Gly Ser Gly Ser Thr Asn
65                  70                  75                  80

His Ile Glu Lys Phe Lys Ser Lys Ala Thr Leu Thr Val Asp Thr Ser
                85                  90                  95

Ile Ser Thr Ala Tyr Met Glu Leu Ser Arg Leu Arg Ser Asp Asp Thr
                100                 105                 110

Ala Val Tyr Tyr Cys Ala Thr Gly Tyr Gly Ser Ser Tyr Gly Tyr Phe
```

```
            115                 120                 125
Asp Tyr Trp Gly Gln Gly Thr Leu Val Thr Val Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Ala Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 58
<211> LENGTH: 235
<212> TYPE: PRT
<213> ORGANISM: Artificial Sequence
<220> FEATURE:
<223> OTHER INFORMATION: light chain 1H9 including leader sequence

<400> SEQUENCE: 58

Met Ala Cys Pro Gly Phe Leu Trp Ala Leu Val Ile Ser Thr Cys Leu
```

```
1               5                    10                   15
Glu Phe Ser Met Ala Asp Ile Gln Met Thr Gln Ser Pro Ser Ser Leu
                20                   25                   30

Ser Ala Ser Val Gly Asp Arg Val Thr Ile Thr Cys Arg Ala Ser Glu
            35                   40                   45

Asn Ile Tyr Ser Tyr Leu Ala Trp Tyr Gln Gln Lys Pro Gly Lys Ala
        50                   55                   60

Pro Lys Leu Leu Ile Tyr Thr Ala Lys Thr Leu Ala Glu Gly Val Pro
65                   70                   75                   80

Ser Arg Phe Ser Gly Ser Gly Ser Gly Thr Asp Phe Thr Leu Thr Ile
                85                   90                   95

Ser Ser Leu Gln Pro Glu Asp Phe Ala Thr Tyr Tyr Cys Gln His Gln
            100                  105                  110

Tyr Gly Pro Pro Phe Thr Phe Gly Gln Gly Thr Lys Leu Glu Ile Lys
        115                  120                  125

Arg Thr Val Ala Ala Pro Ser Val Phe Ile Phe Pro Pro Ser Asp Glu
130                  135                  140

Gln Leu Lys Ser Gly Thr Ala Ser Val Val Cys Leu Leu Asn Asn Phe
145                  150                  155                  160

Tyr Pro Arg Glu Ala Lys Val Gln Trp Lys Val Asp Asn Ala Leu Gln
                165                  170                  175

Ser Gly Asn Ser Gln Glu Ser Val Thr Glu Gln Asp Ser Lys Asp Ser
            180                  185                  190

Thr Tyr Ser Leu Ser Ser Thr Leu Thr Leu Ser Lys Ala Asp Tyr Glu
        195                  200                  205

Lys His Lys Val Tyr Ala Cys Glu Val Thr His Gln Gly Leu Ser Ser
210                  215                  220

Pro Val Thr Lys Ser Phe Asn Arg Gly Glu Cys
225                  230                  235

<210> SEQ ID NO 59
<211> LENGTH: 471
<212> TYPE: PRT
<213> ORGANISM: Artificial Sequence
<220> FEATURE:
<223> OTHER INFORMATION: heavy chain 40A-1 including leader sequence

<400> SEQUENCE: 59

Met Ala Cys Pro Gly Phe Leu Trp Ala Leu Val Ile Ser Thr Cys Leu
1               5                    10                   15

Glu Phe Ser Met Ala Gln Val Gln Leu Val Gln Ser Gly Ala Glu Val
                20                   25                   30

Lys Lys Pro Gly Ala Ser Val Lys Val Ser Cys Lys Ala Ser Gly Tyr
            35                   40                   45

Thr Phe Thr Ser Tyr Trp Ile Thr Trp Val Lys Gln Ala Pro Gly Gln
        50                   55                   60

Gly Leu Glu Trp Ile Gly Asp Ile Tyr Pro Gly Ser Gly Ser Thr Asn
65                   70                   75                   80

His Ile Glu Lys Phe Lys Ser Lys Ala Thr Leu Thr Val Asp Thr Ser
                85                   90                   95

Ile Ser Thr Ala Tyr Met Glu Leu Ser Arg Leu Arg Ser Asp Asp Thr
            100                  105                  110

Ala Val Tyr Tyr Cys Ala Thr Gly Tyr Gly Ser Ser Tyr Gly Tyr Phe
        115                  120                  125

Asp Tyr Trp Gly Gln Gly Thr Leu Val Thr Val Ser Ser Ala Ser Thr
```

-continued

```
            130                 135                 140
Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Ala Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 60
<211> LENGTH: 235
<212> TYPE: PRT
<213> ORGANISM: Artificial Sequence
<220> FEATURE:
<223> OTHER INFORMATION: light chain 40A-1 including leader sequence

<400> SEQUENCE: 60

Met Ala Cys Pro Gly Phe Leu Trp Ala Leu Val Ile Ser Thr Cys Leu
1               5                   10                  15

Glu Phe Ser Met Ala Asp Ile Gln Met Thr Gln Ser Pro Ser Ser Leu
```

```
            20                  25                  30
Ser Ala Ser Val Gly Asp Arg Val Thr Ile Thr Cys Arg Ala Ser Gln
        35                  40                  45

Asp Ile Gly Ser Arg Leu Asn Trp Leu Gln Gln Lys Pro Gly Lys Ala
    50                  55                  60

Pro Lys Arg Leu Ile Tyr Ala Thr Ser Ser Leu Asp Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Glu Asp Phe Ala Thr Tyr Tyr Cys Leu Gln Tyr
            100                 105                 110

Ala Ser Ser Pro Phe Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 61
<211> LENGTH: 469
<212> TYPE: PRT
<213> ORGANISM: Artificial Sequence
<220> FEATURE:
<223> OTHER INFORMATION: heavy chain 40A-2 including leader sequence

<400> SEQUENCE: 61

Met Ala Cys Pro Gly Phe Leu Trp Ala Leu Val Ile Ser Thr Cys Leu
1               5                   10                  15

Glu Phe Ser Met Ala Glu Val Gln Leu Val Gln Ser Gly Ala Glu Val
                20                  25                  30

Val Lys Pro Gly Ala Ser Val Lys Leu Ser Cys Lys Ala Ser Gly Ser
        35                  40                  45

Thr Phe Thr Ser Tyr Trp Met His Trp Val Lys Gln Ala Pro Gly Gln
    50                  55                  60

Gly Leu Glu Trp Ile Gly Ala Ile Tyr Pro Val Asn Ser Asp Thr Thr
65                  70                  75                  80

Tyr Asn Gln Lys Phe Lys Gly Lys Ala Thr Leu Thr Val Asp Lys Ser
                85                  90                  95

Ala Ser Thr Ala Tyr Met Glu Leu Ser Ser Leu Arg Ser Glu Asp Thr
            100                 105                 110

Ala Val Tyr Tyr Cys Thr Arg Ser Phe Tyr Tyr Ser Leu Asp Ala Ala
        115                 120                 125

Trp Phe Val Tyr Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
```

```
                145                 150                 155                 160
        Thr Ser Glu Ser Thr Ala Ala Leu Gly Cys Leu Val Lys Asp Tyr Phe
                        165                 170                 175

Pro Glu Pro Val Thr Val Ser Trp Asn Ser Gly Ala Leu Thr Ser Gly
                        180                 185                 190

Val His Thr Phe Pro Ala Val Leu Gln Ser Ser Gly Leu Tyr Ser Leu
                        195                 200                 205

Ser Ser Val Val Thr Val Pro Ser Ser Asn Phe Gly Thr Gln Thr Tyr
                210                 215                 220

Thr Cys Asn Val Asp His Lys Pro Ser Asn Thr Lys Val Asp Lys Thr
        225                 230                 235                 240

Val Glu Arg Lys Cys Cys Val Glu Cys Pro Pro Cys Pro Ala Pro Pro
                        245                 250                 255

Val Ala Gly Pro Ser Val Phe Leu Phe Pro Pro Lys Pro Lys Asp Thr
                        260                 265                 270

Leu Met Ile Ser Arg Thr Pro Glu Val Thr Cys Val Val Val Asp Val
                        275                 280                 285

Ser His Glu Asp Pro Glu Val Gln Phe Asn Trp Tyr Val Asp Gly Val
                290                 295                 300

Glu Val His Asn Ala Lys Thr Lys Pro Arg Glu Glu Gln Phe Asn Ser
        305                 310                 315                 320

Thr Phe Arg Val Val Ser Val Leu Thr Val Val His Gln Asp Trp Leu
                        325                 330                 335

Asn Gly Lys Glu Tyr Lys Cys Lys Val Ser Asn Lys Gly Leu Pro Ala
                        340                 345                 350

Pro Ile Glu Lys Thr Ile Ser Lys Thr Lys Gly Gln Pro Arg Glu Pro
                        355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
        385                 390                 395                 400

Val Glu Trp Glu Ser Asn Gly Gln Pro Glu Asn Asn Tyr Lys Thr Thr
                        405                 410                 415

Pro Pro Met Leu Asp Ser Asp Gly Ser Phe Phe Leu Tyr Ser Lys Leu
                        420                 425                 430

Thr Val Asp Lys Ser Arg Trp Gln Gln Gly Asn Val Phe Ser Cys Ser
                        435                 440                 445

Val Met His Glu Ala Leu His Asn His Tyr Thr Gln Lys Ser Leu Ser
                450                 455                 460

Leu Ser Pro Gly Lys
        465

<210> SEQ ID NO 62
<211> LENGTH: 235
<212> TYPE: PRT
<213> ORGANISM: Artificial Sequence
<220> FEATURE:
<223> OTHER INFORMATION: light chain 40A-2 including leader sequence

<400> SEQUENCE: 62

Met Ala Cys Pro Gly Phe Leu Trp Ala Leu Val Ile Ser Thr Cys Leu
        1               5                   10                  15

Glu Phe Ser Met Ala Asp Ile Gln Met Thr Gln Ser Pro Ser Ser Leu
                        20                  25                  30

Ser Ala Ser Val Gly Asp Arg Val Thr Ile Thr Cys Arg Ala Ser Gln
```

```
                35                  40                  45
Asp Ile Gly Ser Arg Leu Asn Trp Leu Gln Gln Lys Pro Gly Lys Ala
 50                  55                  60
Pro Lys Arg Leu Ile Tyr Ala Thr Ser Ser Leu Asp Ser Gly Val Pro
65                  70                  75                  80
Ser Arg Phe Ser Gly Ser Gly Ser Gly Thr Glu Phe Thr Leu Thr Ile
                85                  90                  95
Ser Ser Leu Gln Pro Glu Asp Phe Ala Thr Tyr Tyr Cys Leu Gln Tyr
            100                 105                 110
Ala Ser Ser Pro Phe Thr Phe Gly Gly Gly Thr Lys Val Glu Ile Lys
            115                 120                 125
Arg Thr Val Ala Ala Pro Ser Val Phe Ile Phe Pro Pro Ser Asp Glu
        130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
            195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235

<210> SEQ ID NO 63
<211> LENGTH: 470
<212> TYPE: PRT
<213> ORGANISM: Artificial Sequence
<220> FEATURE:
<223> OTHER INFORMATION: heavy chain AB3-LALA including leader sequence

<400> SEQUENCE: 63

Met Ala Cys Pro Gly Phe Leu Trp Ala Leu Val Ile Ser Thr Cys Leu
1               5                   10                  15
Glu Phe Ser Met Ala Ala Val Thr Leu Asp Glu Ser Gly Gly Gly Leu
                20                  25                  30
Gln Thr Pro Gly Gly Ala Leu Ser Leu Val Cys Lys Ala Ser Gly Phe
            35                  40                  45
Ile Phe Ser Asp Tyr Gly Met Asn Trp Val Arg Gln Ala Pro Gly Lys
 50                  55                  60
Gly Leu Glu Phe Val Ala Gln Ile Thr Ser Gly Ser Arg Thr Tyr Tyr
65                  70                  75                  80
Gly Ala Ala Val Lys Gly Arg Ala Thr Ile Ser Arg Asp Asn Arg Gln
                85                  90                  95
Ser Thr Val Lys Leu Gln Leu Asn Asn Leu Arg Ala Glu Asp Thr Gly
            100                 105                 110
Ile Tyr Phe Cys Ala Arg Asp Phe Gly Ser Gly Val Gly Ser Ile Asp
            115                 120                 125
Ala Trp Gly Asn Gly Thr Glu Val Ile Val Ser Ser Ala Ser Thr Lys
        130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
```

```
                165                 170                 175
Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly Lys
465                 470

<210> SEQ ID NO 64
<211> LENGTH: 230
<212> TYPE: PRT
<213> ORGANISM: Artificial Sequence
<220> FEATURE:
<223> OTHER INFORMATION: light chain AB3-LALA including leader sequence

<400> SEQUENCE: 64

Met Ala Cys Pro Gly Phe Leu Trp Ala Leu Val Ile Ser Thr Cys Leu
1               5                   10                  15

Glu Phe Ser Met Ala Ala Leu Thr Gln Pro Ala Ser Val Ser Ala Asn
                20                  25                  30

Leu Gly Gly Thr Val Lys Ile Thr Cys Ser Gly Ser Arg Gly Arg Tyr
            35                  40                  45

Gly Trp Tyr Gln Gln Arg Ser Pro Gly Ser Ala Pro Val Thr Val Ile
```

```
                50                  55                  60
Tyr Arg Asp Asn Gln Arg Pro Ser Asn Ile Pro Ser Arg Phe Ser Ser
 65                  70                  75                  80

Ser Thr Ser Gly Ser Thr Ser Leu Thr Ile Thr Gly Val Gln Ala
                 85                  90                  95

Asp Asp Glu Ser Val Tyr Phe Cys Gly Ser Tyr Asp Gly Ser Ile Asp
                100                 105                 110

Ile Phe Gly Ala Gly Thr Thr Leu Thr Val Leu Arg Thr Val Ala Ala
                115                 120                 125

Pro Ser Val Phe Ile Phe Pro Pro Ser Asp Glu Gln Leu Lys Ser Gly
                130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190

Ser Thr Leu Thr Leu Ser Lys Ala Asp Tyr Glu Lys His Lys Val Tyr
                195                 200                 205

Ala Cys Glu Val Thr His Gln Gly Leu Ser Ser Pro Val Thr Lys Ser
210                 215                 220

Phe Asn Arg Gly Glu Cys
225                 230

<210> SEQ ID NO 65
<211> LENGTH: 468
<212> TYPE: PRT
<213> ORGANISM: Artificial Sequence
<220> FEATURE:
<223> OTHER INFORMATION: heavy chain AB25-LALA including leader sequence

<400> SEQUENCE: 65

Met Ala Cys Pro Gly Phe Leu Trp Ala Leu Val Ile Ser Thr Cys Leu
  1               5                  10                  15

Glu Phe Ser Met Ala Asp Val Gln Leu Val Glu Ser Gly Gly Gly Val
                 20                  25                  30

Val Arg Pro Gly Glu Ser Leu Arg Leu Ser Cys Glu Ala Ser Gly Phe
                 35                  40                  45

Thr Phe Ser Ser Asn Ala Met Ser Trp Val Arg Gln Ala Pro Gly Lys
 50                  55                  60

Gly Leu Glu Trp Val Ala Gly Ile Ser Ser Gly Ser Asp Thr Tyr Tyr
 65                  70                  75                  80

Gly Asp Ser Val Lys Gly Arg Leu Thr Ile Ser Arg Asp Asn Ser Lys
                 85                  90                  95

Asn Ile Leu Tyr Leu Gln Met Asn Ser Leu Thr Ala Glu Asp Thr Ala
                100                 105                 110

Val Tyr Tyr Cys Ala Arg Glu Trp Asn His Leu Phe Asp Tyr Trp
                115                 120                 125

Gly Leu Gly Thr Leu Val Thr Val Ser Ser Ala Ser Thr Lys Gly Pro
                130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
```

```
            180                 185                 190
Ala Val Leu Gln Ser Ser Gly Leu Tyr Ser Leu Ser Val Val Thr
            195                 200                 205

Val Pro Ser Ser Leu Gly Thr Gln Thr Tyr Ile Cys Asn Val Asn
            210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Ala Ala
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 66
<211> LENGTH: 236
<212> TYPE: PRT
<213> ORGANISM: Artificial Sequence
<220> FEATURE:
<223> OTHER INFORMATION: light chain AB25-LALA including leader sequence

<400> SEQUENCE: 66

Met Ala Cys Pro Gly Phe Leu Trp Ala Leu Val Ile Ser Thr Cys Leu
1               5                   10                  15

Glu Phe Ser Met Ala Ser Tyr Glu Leu Thr Gln Pro Pro Ser Val Ser
            20                  25                  30

Val Ser Pro Gly Gln Thr Ala Arg Ile Thr Cys Ser Gly Gly Ser Tyr
            35                  40                  45

Ser Ser Tyr Tyr Tyr Ala Trp Tyr Gln Gln Lys Pro Gly Gln Ala Pro
            50                  55                  60

Val Thr Leu Ile Tyr Ser Asp Asp Lys Arg Pro Ser Asn Ile Pro Glu
```

```
                 65                  70                  75                  80
Arg Phe Ser Gly Ser Ser Ser Gly Thr Thr Val Thr Leu Thr Ile Ser
                 85                  90                  95

Gly Val Gln Ala Glu Asp Glu Ala Asp Tyr Tyr Cys Gly Gly Tyr Asp
                100                 105                 110

Gln Ser Ser Tyr Thr Asn Pro Phe Gly Gly Thr Lys Leu Thr Val
                115                 120                 125

Leu Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys
225                 230                 235

<210> SEQ ID NO 67
<211> LENGTH: 469
<212> TYPE: PRT
<213> ORGANISM: Artificial Sequence
<220> FEATURE:
<223> OTHER INFORMATION: heavy chain AB115-LALA including leader
      sequence

<400> SEQUENCE: 67

Met Ala Cys Pro Gly Phe Leu Trp Ala Leu Val Ile Ser Thr Cys Leu
1               5                   10                  15

Glu Phe Ser Met Ala Val Gln Leu Val Glu Ser Gly Gly Val Val
                20                  25                  30

Arg Pro Gly Glu Ser Leu Arg Leu Ser Cys Ala Ala Ser Gly Phe Ser
                35                  40                  45

Phe Ser Ser Tyr Ala Met Asn Trp Val Arg Gln Ala Pro Gly Glu Gly
                50                  55                  60

Leu Glu Trp Val Ser Arg Ile Asn Ser Gly Gly Gly Thr Asp Tyr
65                  70                  75                  80

Ala Glu Ser Val Lys Gly Arg Phe Thr Ile Ser Arg Asp Asn Ser Glu
                85                  90                  95

Asn Thr Leu Tyr Leu Gln Met Asn Ser Leu Arg Ala Glu Asp Thr Ala
                100                 105                 110

Val Tyr Tyr Cys Ala Lys Gln Tyr Asp Trp Asn Ser Phe Phe Asp Tyr
                115                 120                 125

Trp Gly Leu Gly Ala Leu Val Thr Val Ser Ser Ala Ser Thr Lys Gly
                130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190
```

-continued

```
Pro Ala Val Leu Gln Ser Ser Gly Leu Tyr Ser Leu Ser Val Val
            195                 200                 205

Thr Val Pro Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
    275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
    355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
450                 455                 460

Leu Ser Pro Gly Lys
465

<210> SEQ ID NO 68
<211> LENGTH: 236
<212> TYPE: PRT
<213> ORGANISM: Artificial Sequence
<220> FEATURE:
<223> OTHER INFORMATION: light chain AB115-LALA including leader
      sequence

<400> SEQUENCE: 68

Met Ala Cys Pro Gly Phe Leu Trp Ala Leu Val Ile Ser Thr Cys Leu
1               5                   10                  15

Glu Phe Ser Met Ala Glu Thr Val Leu Thr Gln Ser Pro Ala Thr Leu
            20                  25                  30

Ser Val Ser Pro Gly Glu Arg Ala Thr Leu Ser Cys Arg Ala Ser Gln
        35                  40                  45

Thr Val Gly Ser Lys Leu Ala Trp His Gln Gln Lys Pro Gly Gln Ala
    50                  55                  60

Pro Arg Leu Leu Ile Tyr Asp Ala Thr Asn Arg Ala Thr Gly Ile Ser
65                  70                  75                  80
```

```
Asp Arg Phe Ser Gly Ser Gly Ser Gly Thr Asp Phe Thr Leu Thr Ile
                85                  90                  95

Ser Ser Leu Gln Thr Glu Asp Ser Ala Val Tyr Tyr Cys Gln Gln Tyr
            100                 105                 110

Tyr Tyr Trp Pro Pro Tyr Arg Phe Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 69
<211> LENGTH: 470
<212> TYPE: PRT
<213> ORGANISM: Artificial Sequence
<220> FEATURE:
<223> OTHER INFORMATION: heavy chain AB119-LALA including leader
      sequence

<400> SEQUENCE: 69

Met Ala Cys Pro Gly Phe Leu Trp Ala Leu Val Ile Ser Thr Cys Leu
1               5                   10                  15

Glu Phe Ser Met Ala Val Gln Leu Leu Glu Ser Gly Gly Gly Val Val
            20                  25                  30

Gln Pro Gly Gly Ser Leu Arg Leu Ser Cys Ala Ala Ser Gly Phe Ser
        35                  40                  45

Phe Ser Asn Phe Ala Met Thr Trp Val Arg Gln Ala Pro Gly Glu Gly
    50                  55                  60

Leu Glu Trp Val Ser Thr Ile Gly Ser Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Lys Asp Ser Thr Val Ser Trp Ser Gly Asp Phe Phe Asp
        115                 120                 125

Tyr Trp Gly Leu Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
```

```
                195                 200                 205
Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly Lys
465                 470

<210> SEQ ID NO 70
<211> LENGTH: 236
<212> TYPE: PRT
<213> ORGANISM: Artificial Sequence
<220> FEATURE:
<223> OTHER INFORMATION: light chain AB119-LALA including leader
      sequence

<400> SEQUENCE: 70

Met Ala Cys Pro Gly Phe Leu Trp Ala Leu Val Ile Ser Thr Cys Leu
1               5                   10                  15

Glu Phe Ser Met Ala Glu Ile Val Leu Thr Gln Ser Pro Ala Thr Leu
                20                  25                  30

Ser Val Ser Pro Gly Glu Arg Ala Thr Phe Ser Cys Arg Ala Ser Gln
                35                  40                  45

Asn Val Lys Asn Asp Leu Ala Trp Tyr Gln Gln Arg Pro Gly Gln Ala
                50                  55                  60

Pro Arg Leu Leu Ile Tyr Ala Ala Arg Ile Arg Glu Thr Gly Ile Pro
65                  70                  75                  80
```

-continued

Glu Arg Phe Ser Gly Ser Gly Ser Gly Thr Glu Phe Thr Leu Thr Ile
                85              90                  95

Thr Ser Leu Gln Ser Glu Asp Phe Ala Val Tyr Tyr Cys Gln Gln Tyr
            100                 105                 110

Tyr Asp Trp Pro Pro Phe Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 71
<211> LENGTH: 470
<212> TYPE: PRT
<213> ORGANISM: Artificial Sequence
<220> FEATURE:
<223> OTHER INFORMATION: heavy chain AB136-LALA including leader
      sequence

<400> SEQUENCE: 71

Met Ala Cys Pro Gly Phe Leu Trp Ala Leu Val Ile Ser Thr Cys Leu
1               5                   10                  15

Glu Phe Ser Met Ala Asp Val Gln Leu Val Glu Ser Gly Gly Gly Val
            20                  25                  30

Val Arg Pro Gly Glu Ser Leu Arg Leu Ser Cys Ala Ala Ser Gly Phe
        35                  40                  45

Thr Phe Ser Ser Tyr Asp Met Asn Trp Val Arg Gln Ala Pro Gly Glu
    50                  55                  60

Gly Leu Glu Trp Val Ser Leu Ile Ser Gly Ser Gly Glu Ile Ile Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Glu Asn Asn Arg Tyr Arg Phe Phe Asp
        115                 120                 125

Asp Trp Gly Leu Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Ala Ala Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 72
<211> LENGTH: 236
<212> TYPE: PRT
<213> ORGANISM: Artificial Sequence
<220> FEATURE:
<223> OTHER INFORMATION: light chain AB136-LALA including leader
      sequence

<400> SEQUENCE: 72

Met Ala Cys Pro Gly Phe Leu Trp Ala Leu Val Ile Ser Thr Cys Leu
1               5                   10                  15

Glu Phe Ser Met Ala Glu Thr Val Leu Thr Gln Ser Pro Gly Thr Leu
            20                  25                  30

Thr Leu Ser Pro Gly Glu Arg Ala Thr Leu Thr Cys Arg Ala Ser Gln
        35                  40                  45

Ser Val Tyr Thr Tyr Leu Ala Trp Tyr Gln Glu Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Glu Phe Thr Leu Thr Ile

```
                85                  90                  95
Ser Ser Leu Gln Ser Glu Asp Phe Ala Val Tyr Tyr Cys Gln Gln Tyr
            100                 105                 110
Tyr Asp Arg Pro Pro Leu Thr Phe Gly Gly Gly Thr Lys Val Glu Ile
            115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
            195                 200                 205
Glu Lys His Lys Val Tyr Ala Cys Glu Val Thr His Gln Gly Leu Ser
            210                 215                 220
Ser Pro Val Thr Lys Ser Phe Asn Arg Gly Glu Cys
225                 230                 235

<210> SEQ ID NO 73
<211> LENGTH: 473
<212> TYPE: PRT
<213> ORGANISM: Artificial Sequence
<220> FEATURE:
<223> OTHER INFORMATION: heavy chain 3F9-LALA including leader sequence

<400> SEQUENCE: 73

Met Ala Cys Pro Gly Phe Leu Trp Ala Leu Val Ile Ser Thr Cys Leu
1               5                   10                  15
Glu Phe Ser Met Ala Glu Val Lys Leu Val Glu Ser Gly Gly Gly Leu
            20                  25                  30
Val Lys Pro Gly Gly Ser Leu Lys Leu Ser Cys Ala Ala Ser Gly Phe
        35                  40                  45
Thr Phe Ser Ser Tyr Ala Met Ser Trp Val Arg Gln Thr Pro Glu Lys
    50                  55                  60
Arg Leu Glu Trp Val Ala Thr Ile Ser Asp Tyr Gly Gly Ser Tyr Thr
65                  70                  75                  80
Tyr Tyr Pro Asp Ser Val Lys Gly Arg Phe Thr Ile Ser Arg Asp Asn
                85                  90                  95
Ala Lys Tyr Thr Leu Tyr Leu Gln Met Ser Ser Leu Arg Ser Glu Asp
            100                 105                 110
Thr Ala Leu Tyr Tyr Cys Ala Arg Pro Pro Tyr Asp Asp Tyr Tyr Gly
            115                 120                 125
Gly Phe Ala Tyr Trp Gly Gln Gly Thr Leu Val Thr Val Ser Ala Ala
            130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
```

```
                    210                 215                 220
Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 74
<211> LENGTH: 239
<212> TYPE: PRT
<213> ORGANISM: Artificial Sequence
<220> FEATURE:
<223> OTHER INFORMATION: light chain 3F9-LALA including leader sequence

<400> SEQUENCE: 74

Met Ala Cys Pro Gly Phe Leu Trp Ala Leu Val Ile Ser Thr Cys Leu
1               5                   10                  15

Glu Phe Ser Met Ala Asp Ile Val Leu Thr Gln Ser Pro Ala Ser Leu
            20                  25                  30

Ala Val Ser Leu Gly Gln Arg Ala Thr Ile Ser Cys Arg Ala Ser Lys
        35                  40                  45

Ser Val Ser Ser Ser Gly Tyr Ser Tyr Met His Trp Tyr Gln Gln Lys
    50                  55                  60

Pro Gly Gln Pro Pro Lys Leu Leu Ile Tyr Leu Ala Ser Asn Leu Glu
65                  70                  75                  80

Ser Gly Val Pro Ala Arg Phe Ser Gly Ser Gly Ser Gly Thr Asp Phe
                85                  90                  95

Thr Leu Asn Ile His Pro Val Glu Glu Glu Asp Ala Ala Thr Tyr Tyr
```

```
            100                 105                 110
Cys Gln His Asn Arg Glu Leu Pro Cys Thr Phe Gly Gly Gly Thr Lys
            115                 120                 125
Leu Glu Ile Lys Arg Thr Val Ala Ala Pro Ser Val Phe Ile Phe Pro
            130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
            180                 185                 190
Ser Lys Asp Ser Thr Tyr Ser Leu Ser Ser Thr Leu Thr Leu Ser Lys
            195                 200                 205
Ala Asp Tyr Glu Lys His Lys Val Tyr Ala Cys Glu Val Thr His Gln
            210                 215                 220
Gly Leu Ser Ser Pro Val Thr Lys Ser Phe Asn Arg Gly Glu Cys
225                 230                 235

<210> SEQ ID NO 75
<211> LENGTH: 468
<212> TYPE: PRT
<213> ORGANISM: Artificial Sequence
<220> FEATURE:
<223> OTHER INFORMATION: heavy chain 7H9-LALA including leader sequence

<400> SEQUENCE: 75

Met Ala Cys Pro Gly Phe Leu Trp Ala Leu Val Ile Ser Thr Cys Leu
1               5                   10                  15
Glu Phe Ser Met Ala Asp Val Gln Leu Gln Glu Ser Gly Pro Gly Leu
            20                  25                  30
Val Lys Pro Ser Gln Ser Leu Ser Leu Thr Cys Thr Val Thr Gly Phe
        35                  40                  45
Ser Ile Ser Arg Gly Tyr Asp Trp His Trp Ile Arg His Phe Pro Gly
50                  55                  60
Asn Ile Leu Glu Trp Met Gly Tyr Ile Thr Tyr Ser Gly Ile Ser Asn
65                  70                  75                  80
Tyr Asn Pro Ser Leu Lys Ser Arg Ile Ser Ile Thr His Asp Thr Ser
                85                  90                  95
Lys Asn His Phe Phe Leu Arg Leu Asn Ser Val Thr Ala Glu Asp Thr
            100                 105                 110
Ala Thr Tyr Tyr Cys Ala Arg Gly Gly Gly Ala Trp Phe Thr Tyr Trp
            115                 120                 125
Gly Gln Gly Thr Leu Val Thr Val Ser Ala Ala Ser Thr Lys Gly Pro
            130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
            195                 200                 205
Val Pro Ser Ser Ser Leu Gly Thr Gln Thr Tyr Ile Cys Asn Val Asn
            210                 215                 220
His Lys Pro Ser Asn Thr Lys Val Asp Lys Lys Val Glu Pro Lys Ser
```

```
                    225                 230                 235                 240

Cys Asp Lys Thr His Thr Cys Pro Pro Cys Pro Ala Pro Glu Ala Ala
                            245                 250                 255

Gly Gly Pro Ser Val Phe Leu Phe Pro Pro Lys Pro Lys Asp Thr Leu
                            260                 265                 270

Met Ile Ser Arg Thr Pro Glu Val Thr Cys Val Val Val Asp Val Ser
                            275                 280                 285

His Glu Asp Pro Glu Val Lys Phe Asn Trp Tyr Val Asp Gly Val Glu
                            290                 295                 300

Val His Asn Ala Lys Thr Lys Pro Arg Glu Glu Gln Tyr Asn Ser Thr
            305                 310                 315                 320

Tyr Arg Val Val Ser Val Leu Thr Val Leu His Gln Asp Trp Leu Asn
                            325                 330                 335

Gly Lys Glu Tyr Lys Cys Lys Val Ser Asn Lys Ala Leu Pro Ala Pro
                            340                 345                 350

Ile Glu Lys Thr Ile Ser Lys Ala Lys Gly Gln Pro Arg Glu Pro Gln
                            355                 360                 365

Val Tyr Thr Leu Pro Pro Ser Arg Asp Glu Leu Thr Lys Asn Gln Val
                            370                 375                 380

Ser Leu Thr Cys Leu Val Lys Gly Phe Tyr Pro Ser Asp Ile Ala Val
            385                 390                 395                 400

Glu Trp Glu Ser Asn Gly Gln Pro Glu Asn Asn Tyr Lys Thr Thr Pro
                            405                 410                 415

Pro Val Leu Asp Ser Asp Gly Ser Phe Phe Leu Tyr Ser Lys Leu Thr
                            420                 425                 430

Val Asp Lys Ser Arg Trp Gln Gln Gly Asn Val Phe Ser Cys Ser Val
                            435                 440                 445

Met His Glu Ala Leu His Asn His Tyr Thr Gln Lys Ser Leu Ser Leu
                            450                 455                 460

Ser Pro Gly Lys
            465

<210> SEQ ID NO 76
<211> LENGTH: 235
<212> TYPE: PRT
<213> ORGANISM: Artificial Sequence
<220> FEATURE:
<223> OTHER INFORMATION: light chain 7H9-LALA including leader sequence

<400> SEQUENCE: 76

Met Ala Cys Pro Gly Phe Leu Trp Ala Leu Val Ile Ser Thr Cys Leu
            1               5                   10                  15

Glu Phe Ser Met Ala Asp Ile Val Met Thr Gln Ser Pro Ala Thr Leu
                            20                  25                  30

Ser Val Thr Pro Gly Asp Arg Val Ser Leu Ser Cys Arg Ala Ser Gln
                            35                  40                  45

Ser Ile Ser Asp Ser Leu His Trp Tyr His Gln Lys Ser His Glu Ser
                            50                  55                  60

Pro Arg Leu Leu Ile Lys Tyr Ala Ser Gln Ser Ile Ser Gly Ile Pro
            65                  70                  75                  80

Ser Arg Phe Ser Ala Gly Gly Ser Gly Ser Asp Phe Thr Leu Thr Ile
                            85                  90                  95

Asn Ser Val Glu Pro Glu Asp Val Gly Val Tyr Tyr Cys Gln Asn Gly
                            100                 105                 110

His Ser Leu Pro Trp Thr Phe Gly Gly Gly Thr Lys Leu Glu Ile Lys
```

```
            115                 120                 125
Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 77
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: V or R or Q
<220> FEATURE:
<221> NAME/KEY: VARIANT
<222> LOCATION: (2)..(2)
<223> OTHER INFORMATION: Q or S
<220> FEATURE:
<221> NAME/KEY: VARIANT
<222> LOCATION: (3)..(3)
<223> OTHER INFORMATION: L or V
<220> FEATURE:
<221> NAME/KEY: VARIANT
<222> LOCATION: (4)..(4)
<223> OTHER INFORMATION: V or E
<220> FEATURE:
<221> NAME/KEY: VARIANT
<222> LOCATION: (9)..(9)
<223> OTHER INFORMATION: R or G
<220> FEATURE:
<221> NAME/KEY: VARIANT
<222> LOCATION: (11)..(11)
<223> OTHER INFORMATION: V or G
<220> FEATURE:
<221> NAME/KEY: VARIANT
<222> LOCATION: (15)..(15)
<223> OTHER INFORMATION: T or G
<220> FEATURE:
<221> NAME/KEY: VARIANT
<222> LOCATION: (16)..(16)
<223> OTHER INFORMATION: S or P
<220> FEATURE:
<221> NAME/KEY: VARIANT
<222> LOCATION: (18)..(18)
<223> OTHER INFORMATION: T or R
<220> FEATURE:
<221> NAME/KEY: VARIANT
<222> LOCATION: (22)..(22)
<223> OTHER INFORMATION: T or A
<220> FEATURE:
<221> NAME/KEY: VARIANT
<222> LOCATION: (23)..(23)
<223> OTHER INFORMATION: V or A

<400> SEQUENCE: 77

```
Xaa Xaa Xaa Xaa Glu Ser Gly Gly Xaa Leu Xaa Gln Pro Gly Xaa Xaa
1               5                   10                  15
```

```
Leu Xaa Leu Ser Cys Xaa Xaa Ser Gly Phe Ser Leu Ser
         20                  25

<210> SEQ ID NO 78
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: F or V
<220> FEATURE:
<221> NAME/KEY: VARIANT
<222> LOCATION: (12)..(12)
<223> OTHER INFORMATION: Y or W
<220> FEATURE:
<221> NAME/KEY: VARIANT
<222> LOCATION: (13)..(13)
<223> OTHER INFORMATION: I or V

<400> SEQUENCE: 78

Trp Xaa Arg Gln Ala Pro Gly Lys Gly Leu Glu Xaa Xaa Gly
 1               5                  10

<210> SEQ ID NO 79
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (4)..(4)
<223> OTHER INFORMATION: I or G
<220> FEATURE:
<221> NAME/KEY: VARIANT
<222> LOCATION: (9)..(9)
<223> OTHER INFORMATION: T or S
<220> FEATURE:
<221> NAME/KEY: VARIANT
<222> LOCATION: (11)..(11)
<223> OTHER INFORMATION: M or A
<220> FEATURE:
<221> NAME/KEY: VARIANT
<222> LOCATION: (12)..(12)
<223> OTHER INFORMATION: D or Y
<220> FEATURE:
<221> NAME/KEY: VARIANT
<222> LOCATION: (13)..(13)
<223> OTHER INFORMATION: L or M
<220> FEATURE:
<221> NAME/KEY: VARIANT
<222> LOCATION: (14)..(14)
<223> OTHER INFORMATION: K or Q or E
<220> FEATURE:
<221> NAME/KEY: VARIANT
<222> LOCATION: (15)..(15)
<223> OTHER INFORMATION: M or L
<220> FEATURE:
<221> NAME/KEY: VARIANT
<222> LOCATION: (16)..(16)
<223> OTHER INFORMATION: N or T or S
<220> FEATURE:
<221> NAME/KEY: VARIANT
<222> LOCATION: (18)..(18)
<223> OTHER INFORMATION: L or P
<220> FEATURE:
<221> NAME/KEY: VARIANT
<222> LOCATION: (19)..(19)
<223> OTHER INFORMATION: R or T
<220> FEATURE:
<221> NAME/KEY: VARIANT
<222> LOCATION: (20)..(20)
```

```
<223> OTHER INFORMATION: S or T or A
<220> FEATURE:
<221> NAME/KEY: VARIANT
<222> LOCATION: (25)..(25)
<223> OTHER INFORMATION: T or V
<220> FEATURE:
<221> NAME/KEY: VARIANT
<222> LOCATION: (27)..(27)
<223> OTHER INFORMATION: F or Y

<400> SEQUENCE: 79

Arg Phe Thr Xaa Ser Lys Thr Ser Xaa Thr Xaa Xaa Xaa Xaa Xaa
1               5                   10                  15

Ser Xaa Xaa Xaa Glu Asp Thr Ala Xaa Tyr Xaa Cys Ala Arg
            20                  25                  30

<210> SEQ ID NO 80
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: P or Q

<400> SEQUENCE: 80

Trp Gly Xaa Gly Thr Leu Val Thr Val Ser Ser
1               5                   10

<210> SEQ ID NO 81
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: Q or E or V
<220> FEATURE:
<221> NAME/KEY: VARIANT
<222> LOCATION: (11)..(11)
<223> OTHER INFORMATION: L or V
<220> FEATURE:
<221> NAME/KEY: VARIANT
<222> LOCATION: (21)..(21)
<223> OTHER INFORMATION: I or L

<400> SEQUENCE: 81

Asp Ile Xaa Met Thr Gln Ser Pro Ser Ser Xaa Ser Ala Ser Val Gly
1               5                   10                  15

Asp Arg Val Thr Xaa Thr Cys
            20

<210> SEQ ID NO 82
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (8)..(8)
<223> OTHER INFORMATION: K or Q

<400> SEQUENCE: 82

Trp Tyr Gln Gln Lys Pro Gly Xaa Ala Pro Lys Leu Leu Ile Tyr
1               5                   10                  15
```

```
<210> SEQ ID NO 83
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: Q or G

<400> SEQUENCE: 83

Phe Gly Xaa Gly Thr Lys Val Glu Ile Lys
1               5                   10
```